United States Patent
Ye et al.

(10) Patent No.: US 9,771,621 B2
(45) Date of Patent: *Sep. 26, 2017

(54) METHOD AND KIT FOR PERFORMING A COLORECTAL CANCER ASSAY

(71) Applicant: BIOMERIEUX, Marcy l'Etoile (FR)

(72) Inventors: Xun Ye, Shanghai (CN); Fei Wu, Shanghai (CN); Qinghua Xu, Hangzhou (CN); Xia Meng, Shanghai (CN); Bruno Mougin, Lyons (FR); Fang Liu, Shanghai (CN)

(73) Assignee: BIOMERIEUX, Marcy l'Etoile (FR)

(*) Notice: Subject to any disclaimer, the term of this patent is extended or adjusted under 35 U.S.C. 154(b) by 0 days.

This patent is subject to a terminal disclaimer.

(21) Appl. No.: 15/212,589

(22) Filed: Jul. 18, 2016

(65) Prior Publication Data

US 2016/0319371 A1   Nov. 3, 2016

Related U.S. Application Data

(62) Division of application No. 13/698,219, filed as application No. PCT/EP2010/057843 on Jun. 4, 2010, now Pat. No. 9,422,598.

(51) Int. Cl.
    *C07H 21/04* (2006.01)
    *C12Q 1/68* (2006.01)
    *C40B 40/06* (2006.01)

(52) U.S. Cl.
    CPC ......... *C12Q 1/6886* (2013.01); *C12Q 1/6837* (2013.01); *C40B 40/06* (2013.01); *C12Q 2600/112* (2013.01); *C12Q 2600/118* (2013.01); *C12Q 2600/158* (2013.01)

(58) Field of Classification Search
    None
    See application file for complete search history.

(56) References Cited

U.S. PATENT DOCUMENTS

| | | |
|---|---|---|
| 4,672,040 A | 6/1987 | Josephson |
| 4,683,195 A | 7/1987 | Mullis et al. |
| 4,683,202 A | 7/1987 | Mullis |
| 4,800,159 A | 1/1989 | Mullis et al. |
| 4,981,783 A | 1/1991 | Augenlicht |
| 5,234,809 A | 8/1993 | Boom et al. |
| 5,399,491 A | 3/1995 | Kacian et al. |
| 5,445,934 A | 8/1995 | Fodor et al. |
| 5,700,637 A | 12/1997 | Southern |
| 5,744,305 A | 4/1998 | Fodor et al. |
| 5,750,338 A | 5/1998 | Collins et al. |
| 5,807,522 A | 9/1998 | Brown et al. |
| 2004/0002082 A1 | 1/2004 | Feinberg |
| 2004/0033516 A1 | 2/2004 | Mougin |
| 2004/0265230 A1 | 12/2004 | Martinez et al. |
| 2005/0130170 A1 | 6/2005 | Harvey et al. |
| 2005/0287544 A1 | 12/2005 | Bertucci et al. |
| 2008/0311574 A1 | 12/2008 | Manne et al. |
| 2011/0117083 A1 | 5/2011 | Bais et al. |

FOREIGN PATENT DOCUMENTS

| | | |
|---|---|---|
| CN | 101068936 A | 11/2007 |
| CN | 101111604 A | 1/2008 |
| EP | 0 201 184 A2 | 12/1986 |
| EP | 2 169 078 A1 | 3/2010 |
| EP | 2 177 615 A1 | 4/2010 |
| FR | 14.691 E | 1/1912 |
| FR | 14.896 E | 3/1912 |
| FR | 2 780 059 A1 | 12/1999 |
| FR | 2 816 711 A1 | 5/2002 |
| FR | 2 816 958 A1 | 5/2002 |
| WO | 89/10977 A1 | 11/1989 |
| WO | 90/01069 A1 | 2/1990 |
| WO | 90/03382 A1 | 4/1990 |
| WO | 90/06995 A1 | 6/1990 |
| WO | 91/02818 A1 | 3/1991 |
| WO | 91/19812 A1 | 12/1991 |
| WO | 94/12670 A2 | 6/1994 |
| WO | 97/45202 A1 | 12/1997 |
| WO | 99/15321 A1 | 4/1999 |
| WO | 99/35500 A1 | 7/1999 |
| WO | 99/53304 A1 | 10/1999 |

(Continued)

OTHER PUBLICATIONS

Oct. 7, 2016 Office Action issued in U.S. Appl. No. 14/007,439.
Xu, Ye, et al., "Decrease in Natural Killer Cell Associated Gene Expression as a Major Characteristic of the Immune Status in the Bloodstream of Colorectal Cancer Patients." Cancer Biology & Therapy, http://dx.doi.org/10.4161/cbt.11.2.13670. vol. 11, Issue 2, p. 188-195, 2011.
Maglott et al., "Entrez Gene: Gene-Centered Information at NCBI," Nucleic Acids Research, 2007, vol. 35, pp. D26-D31.

(Continued)

*Primary Examiner* — Jeanine A Goldberg

(74) *Attorney, Agent, or Firm* — Oliff PLC

(57) ABSTRACT

The present invention relates to method and kit for performing a colorectal cancer assay. Especially a method including extracting total RNA from a peripheral blood sample obtained from a patient suspected of having or having colorectal cancer; contacting the total RNA, or cDNA or cRNA obtained from the total RNA, with one or more reagents specific for at least one target gene and no more than 100 target genes; and measuring the expression level of the at least one target gene and no more than 100 target genes. The at least one target gene and no more than 100 target genes includes one or more members selected from the group consisting of the KLRB1, KLRC2, KLRC3, KLRD1, KLRK1, CD247, RRAS2, SH2D1B, LCK, MRPS6, SPRY4, CYBB, DUSP2, PDE4D, SH2D2A, GZMB, INSR, ITGAM, VCAN, CD163, P2RY10, CD226, MRPL10, ITPRIPL2, CD2, and NUDT16 genes.

9 Claims, 1 Drawing Sheet

(56) References Cited

FOREIGN PATENT DOCUMENTS

| WO | 99/65926 A1 | 12/1999 |
|---|---|---|
| WO | 00/05338 A1 | 2/2000 |
| WO | 00/71750 A1 | 11/2000 |
| WO | 91/44506 A1 | 6/2001 |
| WO | 91/44507 A1 | 6/2001 |
| WO | 02/40711 A1 | 5/2002 |
| WO | 02/090319 A1 | 11/2002 |
| WO | 02/090584 A2 | 11/2002 |
| WO | 2005/054508 A2 | 6/2005 |
| WO | 2008063414 | 5/2008 |
| WO | 2009/049228 A2 | 4/2009 |
| WO | 2009/126804 A2 | 10/2009 |
| WO | 2010/040571 A2 | 4/2010 |
| WO | 2010/056374 A2 | 5/2010 |

OTHER PUBLICATIONS

Genbank, Accession No. NM_001031700, 2000.
Genbank, Accession No. NM_016613, 2000.
Genbank, Accession No. NM_001128424, 2000.
Oct. 1, 2013 International Preliminary Report on Patentability issued in International Patent Application No. PCT/CN2012/072931.
Jul. 5, 2012 International Search Report issued in International Patent Application No. PCT/CN2012/072931.
U.S. Appl. No. 14/007,439, filed Oct. 18, 2013 in the name of Ye et al.
Irizarry, R.A. et al., "Exploration, normalization, and summaries of high density oligonucleotide array probe level data," Biostatistics, 2003, pp. 249-264, vol. 4, No. 2.
Johnson, W.E. et al., "Adjusting batch effects in microarray expression data using empirical Bayes methods," Biostatistics, 2007, pp. 118-127, vol. 8, No. 1.
Tusher, V.G. et al., "Significance analysis of microarrays applied to the ionizing radiation response," PNAS, Apr. 24, 2001, pp. 5116-5121, vol. 98, No. 9.
Abstract of ComBat: 'Combatting' Batch Effects When Combining Batches of Gene Expression Microarray Data, Obtained from http://www.bu.edu/jlab/wp-assets/ComBat/Abstract.html on Feb. 14, 2013.
Nielsen, P.E. et al., "Sequence-Selective Recognition of DNA by Strand Displacement with a Thymine-Substituted Polyamide," Science, Dec. 6, 1991, pp. 1497-1500, vol. 254.
Kricka, L.J., "Nucleic Acid Detection Technologies-Labels, Strategies, and Formats," Clinical Chemistry, 1999, pp. 453-458, vol. 45, No. 4.
Chee, M. et al., "Accessing Genetic Information with High-Density DNA Arrays," Science, Oct. 25, 1996, pp. 610-614, vol. 274.
Pease, A.C. et al., "Light-generated oligonucleotide arrays for rapid DNA sequence analysis," Proc. Natl. Acad. Sci. USA, May 1994, pp. 5022-5026, vol. 91.
Ginot, F., "Oligonucleotide Micro-Arrays for Identification of Unknown Mutations: How Far from Reality?," Human Mutation, 1997, pp. 1-10, vol. 10.
Cheng, J. et al., "Microchip-based Devices for Molecular Diagnosis of Genetic Diseases," Molecular Diagnosis, 1996, vol. 1, No. 3.
Livache, T. et al., "Preparation of a DNA matrix via an electrochemically directed copolymerization of pyrrole and oligonucleotides bearing a pyrrole group," Nucleic Acids Research, 1994, pp. 2915-2921, vol. 22, No. 15.
Bustin, S.A., "Quantification of mRNA using real-time reverse transcription PCR (RT-PCR): trends and problems," Journal of Molecular Endocrinology, 2002, pp. 23-39, vol. 29.
Giulietti, A. et al, "An Overview of Real-Time Quantitative PCR: Applications to Quantify Cytokine Gene Expression," Methods, 2001, pp. 386-401, vol. 25.
Tachibana, T., et al., "Increased Intratumor Vα24-Positive Natural Killer T Cells: A Prognostic Factor for Primary Colorectal Carcinomas," Clin. Cancer Res., Oct. 15, 2005, pp. 7322-7327, vol. 11, No. 20.
Liu, J. et al., "Gene expression profiling for nitric oxide prodrug JS-K to kill HL-60 myeloid leukemia cells," Genomics, 2009, pp. 32-38, vol. 94.
Clemson, C.M. et al., "An Architectural Role for a Nuclear Noncoding RNA: NEAT1 RNA Is Essential for the Structure of Paraspeckles," Molecular Cell, Mar. 27, 2009, pp. 717-726, vol. 33.
Sheu, B., et al., "Up-regulation of Inhibitory Natural Killer Receptors CD94/NKG2A with Suppressed Intracellular Perforin Expression of Tumor-Infiltrating CD8+ T Lymphocytes in Human Cervical Carcinoma," Cancer Res., Apr. 1, 2005, pp. 2921-2929, vol. 65, No. 7.
McGilvray, R.W., et al., "NKG2D Ligand Expression in Human Colorectal Cancer Reveals Associations with Prognosis and Evidence for Immunoediting," Clin. Cancer Res., Nov. 15, 2009, pp. 6993-7002, vol. 15, No. 22.
Keller, G.H. et al., "Section 5 Non-Radioactive Labeling Procedures," DNA Probes, 2nd Ed., 1993, pp. 173-198.
Keller, G.H., et al., "Section 6 Hybridization Formats and Detection Procedures," DNA Probes, 2nd Ed., 1993, pp. 199-253.
Tyagi et al., "Molecular Beacons: Probes that Fluoresce upon Hybridization," Nature Biotechnology, Mar. 1996, pp. 303-308, vol. 14.
Ramsay, G., "DNA chips: State-of-the art," Nature Biotechnology, Jan. 1998, pp. 40-44, vol. 16.
Cheng, J. et al., "Preparation and hybridization analysis of DNA/RNA from E.coli on microfabricated bioelectronic chips," Nature Biotechnology, Jun. 1998, pp. 541-546, vol. 16.
Apr. 1, 2011 International Search Report issued in International Patent Application No. PCT/EP2010/057843.
Apr. 1, 2011 Written Opinion of the International Searching Authority issued in International Patent Application No. PCT/EP2010/057843.
Querying HG U133 Plus 2.0 Array Probe Set for Gene Symbols. Query results [online]. Affymetrix, 2014 [retrieved on Nov. 13, 2014]. Retrieved from the Internet: <https://www.affymetrix.com/analysis/netaffx/showresults.affx>.
Killer Cell Lectin-Like Receptor Subfamily K, Member 1. Datasheet [online]. Weizmann Institute of Science, Oct. 23, 2013 [retrieved on Apr. 4, 2014]. Retrieved from the Internet: <http://www.genecards.org/cgi-bin/carddisp.pl?gene=KLRK1>.
Killer Cell Lectin-Like Receptor Subfamily B, Member 1. Datasheet [online]. Weizmann Institure of Science, Oct. 23, 2013 [retrieved on Apr. 4, 2014]. Retrieved from the Internet: <http://genecards.org/cgi-bin/carddisp.pl?gene=KLRB1>.
Granzyme B (Granzyme 2, Cytotoxic T-Lymphocyte-Associated Serine Esterase 1). Datasheet [online]. Weizmann Institute of Science, Oct. 23, 2013 [retrieved on Apr. 4, 2014]. Retrieved from the Internet: <http://www.genecards.org/cgi-bin/carddisp.pl?gene=GZMB>.
Related RAS Viral (R-Ras) Onogene Homolog 2. Datasheet [online]. Weizmann Institute of Science, Oct. 23, 2013 [retrieved on Apr. 4, 2014]. Retrieved from the Internet: <http://www.genecards.org/cgi-bin/carddisp.pl?gene=RRAS2>.
U.S. Appl. No. 13/698,219, filed Nov. 15, 2012 in the name of Ye et al.
Apr. 18, 2016 Notice of Allowance issued in U.S. Appl. No. 13/698,219.
Nov. 19, 2015 Office Action issued in U.S. Appl. No. 13/689,219.
Jul. 9, 2015 Office Action issued in U.S. Appl. No. 13/698,219.
Dec. 19, 2014 Office Action issued in U.S. Appl. No. 13/698,219.
Apr. 16, 2014 Office Action issued in U.S. Appl. No. 13/698,219.
May 12, 2016 Office Action issued in U.S. Appl. No. 14/007,439.

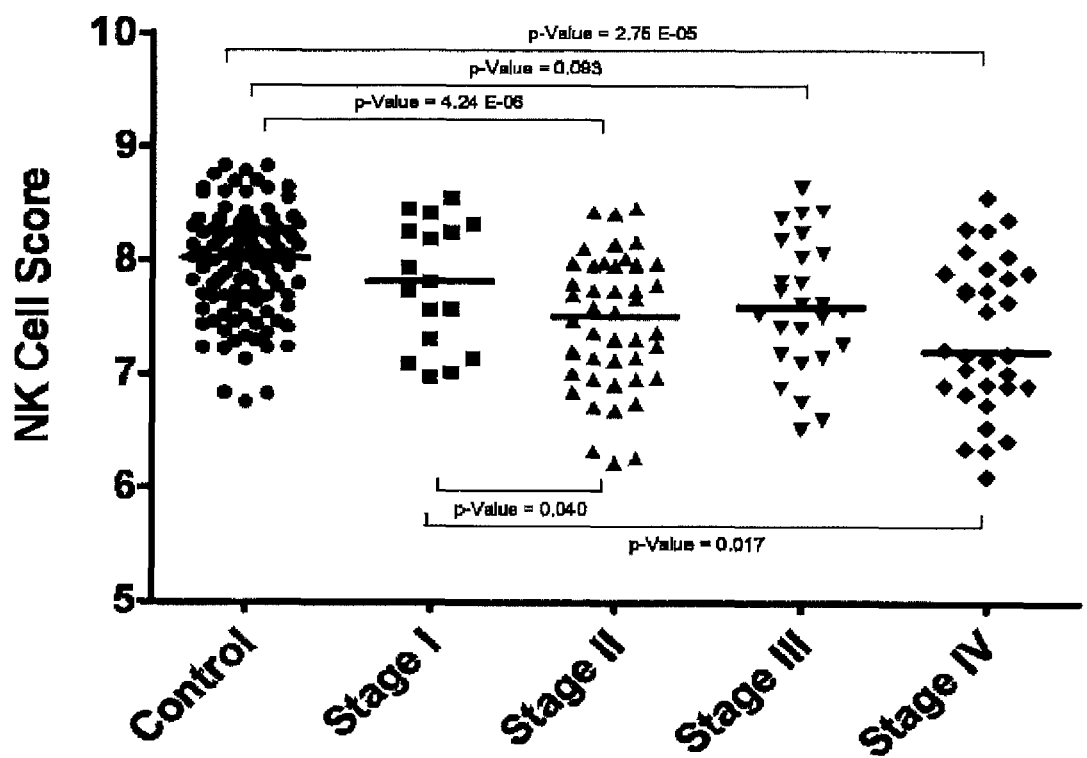

SEQUENCE LISTING

<160> NUMBER OF SEQ ID NOS: 59

<210> SEQ ID NO 1
<211> LENGTH: 1447
<212> TYPE: DNA
<213> ORGANISM: human

<400> SEQUENCE: 1

```
gagtttgttc ttacacacaa gtttaatgcc accttcctct gtctgccatg gaccaacaag      60
caatatatgc tgagttaaac ttacccacag actcaggccc agaaagttct tcaccttcat     120
ctcttcctcg ggatgtctgt cagggttcac cttggcatca atttgccctg aaacttagct     180
gtgctgggat tattctcctt gtcttggttg ttactgggtt gagtgtttca gtgacatcct     240
taatacagaa atcatcaata gaaaaatgca gtgtggacat tcaacagagc aggaataaaa     300
caacagagag accgggtctc ttaaactgcc caatatattg gcagcaactc cgagagaaat     360
```

```
gcttgttatt ttctcacact gtcaacccett ggaataacag tctagctgat tgttccacca      420
aagaatccag cctgctgctt attcgagata aggatgaatt gatacacaca cagaacctga      480
tacgtgacaa agcaattctg ttttggattg gattaaattt ttcattatca gaaaagaact      540
ggaagtggat aaacggctct tttttaaatt ctaatgactt agaaattaga ggtgatgcta      600
aagaaaacag ctgtatttcc atctcacaga catctgtgta ttctgagtac tgtagtacag      660
aaatcagatg gatctgccaa aaagaactaa cacctgtgag aaataaagtg tatcctgact      720
cttgactatg aatcccatct caatttattt gcttcccatt actgatctct gtacttgtag      780
ctgcacatac tattggtact acctaatagt gccacattta gtggcacaaa gtgaacaatt      840
ctgagaattg acaactgtta tgaatcttac agaagttcat gtttatcata ttcattctat      900
taaatgagga aacagagaca tagagaaaaa cgtgcatcgt tttaaagaaa cagtgatatt      960
ctatggtgaa ggagtgaagg atgtccccga atatgccaga ttggtatatg attgtttttgt     1020 gtttaaaaca gtggagaaat tgtagattca gaaagggaga gctgacctgt ctcttcccgc     1080
acgcggcaag ccgtgaagat tcctctggga gggctatccg agtcatacaa gggcaagaaa     1140
atagctctta tcgccagaga cctggaattg gatgctgcaa tgaacctgaa taaagatact     1200
taataaacac ctatctttca cctattttac agccccccgc aaccaatata tctcctagtg     1260
actcctctag aaaatttatt gccccctagcc agcttttctt catcctgtca tttcttttca     1320
aatttatcat tcttggtcta aaaagcataa aagcatcttg cttaggccac ttctatggat     1380
ttcactctct tgcgagttcc tcatgtacat gcaaaacgaa taaaatgtgt atacttttat     1440
tttgttc                                                               1447
```

<210> SEQ ID NO 2
<211> LENGTH: 1209
<212> TYPE: DNA
<213> ORGANISM: human

<400> SEQUENCE: 2

```
tgcagagatg aataaacaaa gaggaaccett ctcagaagtg agtctggccc aggacccaaa       60
gcggcagcaa aggaaaccta aaggcaataa aagctccatt tcaggaaccg aacaggaaat      120
attccaagta gaattaaatc ttcaaaatcc ttccctgaat catcaaggga ttgataaaat      180
atatgactgc caaggtttac tgccacctcc agagaagctc actgccgagg tcctaggaat      240
catttgcatt gtcctgatgg ccactgtgtt aaaaacaata gttcttattc ctttcctgga      300
gcagaacaat tcttccccaa atacaagaac ccagaaaaca cgtcattgtg gccattgtcc      360
tgaggagtgg attacatatt ccaacagttg ttattacatt ggtaaggaaa gaagaacttg      420
ggaagagagt ttgctggcct gtacttcgaa gaactccagt ctgctttcta tagataatga      480
agaagaaatg aaatttctgg ccagcatttt accttcctca tggattggtg tgtttcgtaa      540
cagcagtcat catccatggg tgacaataaa tggtttggct ttcaaacata agataaaaga      600
ctcagataat gctgaactta actgtgcagt gctacaagta aatcgactta atcagccca       660 gtgtggatct tcaatgatat atcattgtaa gcataagctt tagaagtaaa gcatttgcgt      720
ttgcagtgca tcagatacat tttatatttc ttaaaataga aatattatga ttgcataaat      780
ctgaaaatga attatgttat ttgctctgat acaaaaattc taaatcaatt attgaaatag      840
gatgcacaca attactaaag tacagacatc ctagcatttg tgtcgggctc attttgctca      900
acatggtatt tgtggttttc agcctttcta aaagttgcat gttatgtgag tcagcttata      960
```

```
ggaagtacca agaacagtca aacccatgga gacagaaagt agaatagtgg ttgccaatgt      1020
ctcagggagg ttgaaatagg agatgaccac taattgatag aacgttttctt tgtgtcgtga     1080 tgaaaacttt ctaaatttca gtagtggtga tggttgtaac tctgcgaata tactaaacat     1140
cattgatttt taatcatttt aagtgcatga aatgtatgct ttgtacatga cacttcaata     1200
aagctatcc                                                              1209

<210> SEQ ID NO 3
<211> LENGTH: 1209
<212> TYPE: DNA
<213> ORGANISM: human

<400> SEQUENCE: 3
tgcagagatg aataaacaaa gaggaacctt ctcagaagtg agtctggccc aggacccaaa        60
gcggcagcaa aggaaaccta aaggcaataa aagctccatt tcaggaaccg aacaggaaat      120
attccaagta gaattaaatc ttcaaaatcc ttccctgaat catcaaggga ttgataaaat      180
atatgactgc caaggtttac tgccacctcc agagaagctc actgccgagg tcctaggaat      240
catttgcatt gtcctgatgg ccactgtgtt aaaaacaata gttcttattc ctttcctgga      300
gcagaacaat ttttccccga atacaagaac gcagaaagca cgtcattgtg gccattgtcc      360
tgaggagtgg attacatatt ccaacagttg ttattacatt ggtaaggaaa gaagaacttg      420
ggaagagagt ttgctggcct gtacttcgaa gaactccagt ctgctttcta tagataatga      480
agaagaaatg aaatttctgg ccagcatttt accttcctca tggattggtg tgtttcgtaa      540
cagcagtcat catccatggg tgacaataaa tggtttggct ttcaaacata agataaaaga      600
ctcagataat gctgaactta actgtgcagt gctacaagta aatcgactta aatcagccca      660
gtgtggatct tcaatgatat atcattgtaa gcataagctt tagaagtaaa gcatttgcgt      720
ttgcagtgca tcagatacat tttatattc ttaaaataga aatattatga ttgcataaat      780
ctgaaaatga attatgttat ttgctctgat acaaaaattc taaatcaatt attgaaaatag     840 gatgcacaca attactaaag tacagacatc ctagcatttg tgtcgggctc attttgctca      900
acatggtatt tgtggttttc agcctttcta aaagttgcat gttatgtgag tcagcttata      960
ggaagtacca agaacagtca aacccatgga gacagaaagt agaatagtgg ttgccaatgt     1020
ctcagggagg ttgaaatagg agatgaccac taattgatag aacgtttctt tgtgtcgtga     1080
tgaaaacttt ctaaatttca gtagtggtga tggttgtaac tctgcgaata tactaaacat     1140
cattgatttt taatcatttt aagtgcatga aatgtatgct ttgtacatga cacttcaata     1200
aagctatcc                                                              1209

<210> SEQ ID NO 4
<211> LENGTH: 881
<212> TYPE: DNA
<213> ORGANISM: human

<400> SEQUENCE: 4
atgataccaa cacgtcattg tggccattgt cctgaggagt ggattacata ttccaacagt        60
tgttattaca ttggtaagga aagaagaact tgggaagaga gtttgctggc ctgtacttcg      120
aagaactcca gtctgctttc tatagataat gaagaagaaa tgaaatttct ggccagcatt      180
ttaccttcct catggattgg tgtgtttcgt aacagcagtc atcatccatg ggtgacaata      240
aatggtttgg ctttcaaaca taagataaaa gactcagata atgctgaact taactgtgca      300
gtgctacaag taaatcgact taaatcagcc cagtgtggat cttcaatgat atatcattgt      360
```

```
aagcataagc tttagaagta aagcatttgc gtttgcagtg catcagatac attttatatt    420
tcttaaaata gaaatattat gattgcataa atctgaaaat gaattatgtt atttgctctg    480
atacaaaaat tctaaatcaa ttattgaaat aggatgcaca caattactaa agtacagaca    540
tcctagcatt tgtgtcgggc tcattttgct caacatggta tttgtggttt tcagcctttc    600
taaaagttgc atgttatgtg agtcagctta taggaagtac caagaacagt caaacccatg    660
gagacagaaa gtagaatagt ggttgccaat gtctcaggga ggttgaaata ggagatgacc    720
actaattgat agaacgtttc tttgtgtcgt gatgaaaact ttctaaattt cagtagtggt    780
gatggttgta actctgcgaa tatactaaac atcattgatt tttaatcatt ttaagtgcat    840
gaaatgtatg ctttgtacat gacacttcaa taaagctatc c                       881
```

<210> SEQ ID NO 5
<211> LENGTH: 843
<212> TYPE: DNA
<213> ORGANISM: human

<400> SEQUENCE: 5

```
gcagttatca tagagcacag tccctcacat cacacagctg cagagatgag taaacaaaga     60
ggaaccttct cagaagtgag tctggcccag gacccaaagt ggcagcaaag gaaacctaaa    120
ggcaataaaa gctccatttc aggaaccgaa caggaaatat ccaagtagaa attaaacctt    180
caaaatgctt ctctgaatca tcaagggatt gataaaatat atgactgcca aggtttactg    240
ccacctccag aaaagctcac tgccgaggtc ctaggaatca tttgcattgt cctgatggcc    300
actgtgttaa aaacaatagt tcttattcct ttcctggagc agaacaattc ttccccgaat    360
gcaagaaccc agaaagcacg tcattgtggc cattgtcctg aggagtggat tacatattcc    420
aacagttgtt attacattgg taaggaaaga agaacttggg aagagagttt gcaggcctgt    480
gcttcaaaga actcttctag tctgctttgt atagataatg aagaagaaat gaaatttctg    540
gccagcattt taccttcctc atggattggt gtgtttcgta acagcagtca tcatccatgg    600
gtgacaataa atggtttggc tttcaaacat gagataaaag actcagatca tgctgaacgt    660
aactgtgcaa tgctacatgt acgtggactt atatcagacc agtgtggatc ttcaagaatc    720
attgtgagca taagctttag aattaaagcg cttgagcttg cagtgcatca gataaaattt    780
tatatttgtt caaacagaaa tgatattatg attgcataag ccttaaaatg aattgtgtta    840
ttt                                                                 843
```

<210> SEQ ID NO 6
<211> LENGTH: 1018
<212> TYPE: DNA
<213> ORGANISM: human

<400> SEQUENCE: 6

```
gcagttatca tagagcacag tccctcacat cacacagctg cagagatgag taaacaaaga     60
ggaaccttct cagaagtgag tctggcccag gacccaaagt ggcagcaaag gaaacctaaa    120
ggcaataaaa gctccatttc aggaaccgaa caggaaatat ccaagtagaa attaaacctt    180
caaaatgctt ctctgaatca tcaagggatt gataaaatat atgactgcca aggtttactg    240
ccacctccag aaaagctcac tgccgaggtc ctaggaatca tttgcattgt cctgatggcc    300
actgtgttaa aaacaatagt tcttattcct ttcctggagc agaacaattc ttccccaaat    360
acaagaaccc agaaaacacg tcattgtggc cattgtcctg aggagtggat tacatattcc    420
```

```
aacagttgtt attacattgg taaggaaaga agaacttggg aagagagttt gcaggcctgt      480
gcttcaaaga actcttctag tctgctttgt atagataatg aagaagaaat gaaatttctg      540
gccagcattt taccttcctc atggattggt gtgtttcgta acagcagtca tcatccatgg      600
gtgacaataa atggtttggc tttcaaacat gagataaaag actcagatca tgctgaacgt      660
aactgtgcaa tgctacatgt acgtggactt atatcagacc agtgtggatc ttcaagaatc      720
attagacggg gtttcatcat gttgaccagg ctggtcttga actcctgagc tcaagaaatc      780
aacacatctt ggcctcccaa gttgctggga ttactgacac aagccaccgc ccctgagtgc      840
tcatgtacca tttagcttgt gttttaaaaa tctactttt  ctgccctccc tattttaac       900 tagatgatgt tttaaaaatt acttttccct ctctatatag tttgatttaa gcattagtca      960
tttacaacaa atattaatat taaaatgcag accgttatga ttggaaaata aatcaatg      1018

<210> SEQ ID NO 7
<211> LENGTH: 1018
<212> TYPE: DNA
<213> ORGANISM: human

<400> SEQUENCE: 7
gcagttatca tagagcacag tccctcacat cacacagctg cagagatgag taaacaaaga       60
ggaaccttct cagaagtgag tctggcccag gacccaaagt ggcagcaaag gaaacctaaa      120
ggcaataaaa gctccatttc aggaaccgaa caggaaatat tccaagtaga attaaacctt      180
caaaatgctt ctctgaatca tcaagggatt gataaaatat atgactgcca aggtttactg      240
ccacctccag aaaagctcac tgccgaggtc ctaggaatca tttgcattgt cctgatggcc      300
actgtgttaa aaacaatagt tcttattcct ttcctggagc agaacaattc ttccccgaat      360
gcaagaaccc agaaagcacg tcattgtggc cattgtcctg aggagtggat tacatattcc      420
aacagttgtt attacattgg taaggaaaga agaacttggg aagagagttt gcaggcctgt      480
gcttcaaaga actcttctag tctgctttgt atagataatg aagaagaaat gaaatttctg      540
gccagcattt taccttcctc atggattggt gtgtttcgta acagcagtca tcatccatgg      600
gtgacaataa atggtttggc tttcaaacat gagataaaag actcagatca tgctgaacgt      660
aactgtgcaa tgctacatgt acgtggactt atatcagacc agtgtggatc ttcaagaatc      720
attagacggg gtttcatcat gttgaccagg ctggtcttga actcctgagc tcaagaaatc      780
aacacatctt ggcctcccaa gttgctggga ttactgacac aagccaccgc ccctgagtgc      840
tcatgtacca tttagcttgt gttttaaaaa tctactttt  ctgccctccc tattttaac       900 tagatgatgt tttaaaaatt acttttccct ctctatatag tttgatttaa gcattagtca      960
tttacaacaa atattaatat taaaatgcag accgttatga ttggaaaata aatcaatg      1018

<210> SEQ ID NO 8
<211> LENGTH: 3258
<212> TYPE: DNA
<213> ORGANISM: human

<400> SEQUENCE: 8
ctgtattgtg gttcctggaa cacttcagag gcttgtgatt ctactgcttc ttattcacac       60
tataatacat gtctcaccaa tagatgattc aagaacatca tttaaataca caatttttca      120
ttctctattt ttgctaaatt tcttcatact caactttcag attctttaat ctccagctca      180
gcttcaacaa ttcaacgctg ttcttttctga aaaagtacac atcgtgcctt ctctacttcg      240
ctcttggaac ataatttctc atggcagtgt ttaagaccac tctgtggagg ttaatttctg      300
```

```
ggaccttagg gataatatgc ctttcgttga tgtctacgtt gggaattttg ttgaaaaatt      360
cttttactaa actgagtatt gagccagcat ttactccagg acccaacata gaactccaga      420
aagactctga ctgctgttct tgccaagaaa aatgggttgg gtaccggtgc aactgttact      480
tcatttccag tgaacagaaa acttggaacg aaagtcggca tctctgtgct tctcagaaat      540
ccagcctgct tcagcttcaa aacacagatg aactggattt tatgagctcc agtcaacaat      600
tttactggat tggactctct tacagtgagg agcacaccgc ctggttgtgg gagaatggct      660
ctgcactctc ccagtatcta tttccatcat ttgaaacttt taatacaaag aactgcatag      720
cgtataatcc aaatggaaat gctttagatg aatcctgtga agataaaaat cgttatatct      780
gtaagcaaca gctcatttaa atgtttcttg gggcagagaa ggtggagagt aaagacccaa      840
cattactaac aatgatacag ttgcatgtta tattattact aattgtctac ttctggagtc      900
tataaaatgt ttttaaacag tgtcatatac aattgtcatg tatgtgaaac aatgtgtttt      960
aaaattgatg aaattcgttc acctacattt gagaattata aaattaacat aaagaatttt     1020 gtatttcat ttaatgtata tatttaatgt taaattcaat gtagttttat tacacattta      1080
tgtaatttta tttacattct tgctaattct cagcagaaat ttaaataaga tttaattcac      1140
atcaaataaa atttagaaaa taaaatttaa ctcacactgc ccaggctgga gcatagtggc      1200
aagatcatag ctcattgcaa gctcaagtga tcctcctgac tcagcctccc aagtagctag      1260
gactgcaggc accatgtcac tatgcccgac taattttaa ttttttaattt tttgtcaaga      1320 caaggtcttg ctatgttgcc caggctggtc ttgaactcct ggcctcaagg gattctccca      1380
ccttggattc ccaaagtgct gggattatag gtgtgaacca ccatccctgg ccctcttcac      1440
attcttgtat gaagattgat ttgggaaaaa tgcatttcag gtaactgaca aaagatatag      1500
gatgaaaaat aatatctttc aaatgtttaa tttgaactaa gagagcttat gcattgcact      1560
ttctggagat ttgtaatgtt ttggttttgt tgtccatgtg actacaaaat aatatatttt      1620
ttaattaaaa aatttaaaat aatacaggca agcatgtaat gattatcaat attttttttcc     1680 accaactatc ctatacccct gacctccttt cattaggcat tatcttctgt tttgatttta      1740
acacttagag tggttttctc tgttatgaat caaagctgat ctattttcat cattttttgtg     1800 atgaaaaaat taattttgat tgacttagga tggaaggatt tggactgggt gtggtggttt      1860
atgcctgtaa tcgcagcact ttgggaggcc aaggcgggtg gatcacttga ggtcaggagt      1920
ttgagaccag cctggccaac atggtgaaac cctgtctcta ctaaaaatac aaaaattggc      1980
tgggtgtggt agtgcacacc tgtaatccca gctatttggg aggctgagtc gagaggatcg      2040
cttgaaccta ggaggtggag gttgcagtga gtcgagattg caccactgca ctccagcctg      2100
ggtgacagag ccagactcct ctccaaaaaa aaaaaaaaa aaaaagatg aaaggatttg       2160 gaaccttaat tgcatctgaa aaactgcctc acctttgtta tttagtgtac tccaaccacg      2220
gagtaacatc ccatcataat cccaaatcct actcaaacaa aaggggaagg gattatgcag      2280
gtgtacacta ggccactggt gtaccaatta gaaaccactt tagagttatg cctactgtac      2340
ccacataatc ctaaaaatat gttacaactg ctacttcata gtttatgcca cttattttat      2400
tttttacttt tattattttt ttttctgaga cacggtttca ttcccattgc ccaggctgta      2460
gtgcaatgat gcaatcatgg ttcactgcag cttcaacttc ccaggctcaa gggatcctcc      2520
cacctcagcc ttctgagtac ttgggactca ggtgcgagcc atcatgctca gctaattttt      2580 tgtatcatt gtagaaatgg ggttttgtat tgttgcccag gctgatcttg aactcctggg       2640
```

| | |
|---|---|
| gtcaaggatt ctgcccgcct tggcctccta aagggctgga attacaggca taagccactg | 2700 |
| tgcccggcca gtttatataa tttaaacact gccttttggt tccttgattc ccatatgcta | 2760 |
| ggacaagtaa ttattatttt attttatttt actttaagtt ctgggttaca tgtgcagaac | 2820 |
| ctgcaggttt gttacatagg tatacatgtt ccaaggtggt tgctgcacc tattgaccca | 2880 |
| tcatctaggt tttaagtccc acatgcatta ggtatttgtc ctaatgctct tcctccctt | 2940 |
| gccccccacc cccgacagg ccttggtctg tgatgttcac ctccctgtgt ccatgtgttc | 3000 |
| tcattgttca actcccactt attagtaaga acatgtggtg tttggttttc tgttcctgtg | 3060 |
| ttagtttgct gagaatgatg gtttccagct tcatccatgt cgctgcaaag gacatgaact | 3120 |
| cattctttt atggctgcat agtattccat ggtgtatatg tgccatattt tctttatcca | 3180 |
| gtctatcact gatgggcatt tgggttggtt ccaagtcttt gctatggtaa atagtgctgc | 3240 |
| aataaacata cgtgtgca | 3258 |

<210> SEQ ID NO 9
<211> LENGTH: 292
<212> TYPE: DNA
<213> ORGANISM: human

<400> SEQUENCE: 9

| | |
|---|---|
| caattcaacg ctgttctttc tgaaaaagta cacatcgtgc cttctctact tcgctcttgg | 60 |
| aacataattt ctcatggcag tgtttaagac cactctgtgg aggttaattt ctgggacctt | 120 |
| agggataata tgcctttcgt tgatgtctac gttgggaatt tgttgaaaa attcttttac | 180 |
| taaactgagt attgagccag catttactcc aggacccaac atagaactcc agaaagcagg | 240 |
| attttatgag ctccagtcaa caattttact ggattggact ctcttacagt ga | 292 |

<210> SEQ ID NO 10
<211> LENGTH: 3165
<212> TYPE: DNA
<213> ORGANISM: human

<400> SEQUENCE: 10

| | |
|---|---|
| ctgtattgtg gttcctggaa cacttcagag gcttgtgatt ctactgcttc ttattcacac | 60 |
| tataatacat gtctcaccaa tagatgattc aagaacatca tttaaataca caattttca | 120 |
| ttctctattt ttgctaaatt tcttcatact caactttcag attctttaat ctccagctca | 180 |
| gcttcaacaa ttcaacgctg ttctttctga aaaagtacac atcgtgcctt ctctacttcg | 240 |
| ctcttggaac ataatttctc atggcagctt ttactaaact gagtattgag ccagcattta | 300 |
| ctccaggacc caacatagaa ctccagaaag actctgactg ctgttcttgc caagaaaaat | 360 |
| gggttgggta ccggtgcaac tgttacttca tttccagtga acagaaaact tggaacgaaa | 420 |
| gtcggcatct ctgtgcttct cagaaatcca gcctgcttca gcttcaaaac acagatgaac | 480 |
| tggattttat gagctccagt caacaatttt actggattgg actctcttac agtgaggagc | 540 |
| acaccgcctg gttgtgggag aatggctctg cactctccca gtatctattt ccatcatttg | 600 |
| aaactttaa tacaaagaac tgcatagcgt ataatccaaa tggaaatgct ttagatgaat | 660 |
| cctgtgaaga taaaaatcgt tatatctgta agcaacagct catttaaatg tttcttgggg | 720 |
| cagagaaggt ggagagtaaa gacccaacat tactaacaat gatacagttg catgttatat | 780 |
| tattactaat tgtctacttc tggagtctat aaaatgtttt taaacagtgt catatacaat | 840 |
| tgtcatgtat gtgaaacaat gtgttttaaa attgatgaaa ttcgttcacc tacatttgag | 900 |
| aattataaaa ttaacataaa gaattttgta ttttcattta atgtatatat ttaatgttaa | 960 |

```
attcaatgta gttttattac acatttatgt aattttattt acattcttgc taattctcag    1020
cagaaattta aataagattt aattcacatc aaataaaatt tagaaaataa aatttaactc    1080
acactgccca ggctggagca tagtggcaag atcatagctc attgcaagct caagtgatcc    1140
tcctgactca gcctcccaag tagctaggac tgcaggcacc atgtcactat gcccgactaa    1200
ttttaatttt ttaattttt gtcaagacaa ggtcttgcta tgttgcccag gctggtcttg    1260
aactcctggc tcaagggat tctcccacct tggattccca aagtgctggg attataggtg    1320
tgaaccacca tccctggccc tcttcacatt cttgtatgaa gattgatttg gaaaaatgc    1380 atttcaggta actgacaaaa gatataggat gaaaaataat atcttttcaaa tgtttaattt    1440 gaactaagag agcttatgca ttgcactttc tggagatttg taatgttttg gttttgttgt    1500
ccatgtgact acaaaataat atatttttta attaaaaaat ttaaataat acaggcaagc    1560 atgtaatgat tatcaatatt ttttccacc aactatccta taccctgac ctccttttcat    1620 taggcattat cttctgtttt gatttaaca cttagagtgg ttttctctgt tatgaatcaa    1680
agctgatcta ttttcatcat ttttgtgatg aaaaaattaa ttttgattga cttaggatgg    1740 aaggattgg actgggtgtg gtggtttatg cctgtaatcg cagcactttg ggaggccaag    1800
gcgggtggat cacttgaggt caggagtttg agaccagcct ggccaacatg gtgaaaccct    1860
gtctctacta aaatacaaa aattggctgg gtgtggtagt gcacacctgt aatcccagct    1920
atttgggagg ctgagtcgag aggatcgctt gaacctagga ggtggaggtt gcagtgagtc    1980
gagattgcac cactgcactc cagcctgggt gacagagcca gactcctctc caaaaaaaaa    2040 aaaaaaaaa aagatgaaa ggatttggaa ccttaattgc atctgaaaaa ctgcctcacc    2100
tttgttattt agtgtactcc aaccacggag taacatccca tcataatccc aaatcctact    2160
caaacaaaag gggaagggat tatgcaggtg tacactaggc cactggtgta ccaattagaa    2220
accactttag agttatgcct actgtaccca cataatccta aaaatatgtt acaactgcta    2280
cttcatagtt tatgccactt attttatttt ttacttttat tatttttttt tctgagacac    2340
ggtttcattc ccattgccca ggctgtagtg caatgatgca atcatggttc actgcagctt    2400
caacttccca ggctcaaggg atcctcccac ctcagccttc tgagtacttg ggactcaggt    2460
gcgagccatc atgctcagct aattttttgt atcatttgta gaaatggggt tttgtattgt    2520
tgcccaggct gatcttgaac tcctggggtc aaggattctg cccgccttgg cctcctaaag    2580
ggctggaatt acaggcataa gccactgtgc ccggccagtt tatataattt aaacactgcc    2640
ttttggttcc ttgattccca tatgctagga caagtaatta ttattttatt ttattttact    2700
ttaagttctg ggttacatgt gcagaacctg caggtttgtt acataggtat acatgttcca    2760
aggtggtttg ctgcacctat tgacccatca tctaggtttt aagtcccaca tgcattaggt    2820
atttgtccta atgctcttcc tcccccttgcc ccccacccc cgacaggcct ggtctgtga    2880 tgttcacctc cctgtgtcca tgtgttctca ttgttcaact cccacttatt agtaagaaca    2940
tgtggtgttt ggttttctgt tcctgtgtta gtttgctgag aatgatggtt tccagcttca    3000
tccatgtcgc tgcaaaggac atgaactcat tctttttatg gctgcatagt attccatggt    3060
gtatatgtgc catattttct ttatccagtc tatcactgat gggcatttgg gttggttcca    3120
agtctttgct atggtaaata gtgctgcaat aaacatacgt gtgca                    3165
```

<210> SEQ ID NO 11
<211> LENGTH: 3195
<212> TYPE: DNA

<213> ORGANISM: human

<400> SEQUENCE: 11

```
ctgtattgtg gttcctggaa cacttcagag gcttgtgatt ctactgcttc ttattcacac      60
tataatacat gtctcaccaa tagatgattc aagaacatca tttaaataca caattttttca   120
ttctctattt ttgctaaatt tcttcatact caactttcag attctttaat ctccagctca    180
gcttcaacaa ttcaacgctg ttctttctga aaaagtacac atcgtgcctt ctctacttcg    240
ctcttggaac ataatttctc atggcagtgt ttaagaccac tctgtggagg ttaatttctg    300
ggacccttagg gataatatgc ctttcgttga tgtctacgtt gggaattttg ttgaaaaatt   360
actctgactg ctgttcttgc caagaaaaat gggttgggta ccggtgcaac tgttacttca    420
tttccagtga acagaaaact tggaacgaaa gtcggcatct ctgtgcttct cagaaatcca    480
gcctgcttca gcttcaaaac acagatgaac tggattttat gagctccagt caacaatttt   540
actggattgg actctcttac agtgaggagc acaccgcctg ttgtgggag aatggctctg     600
cactctccca gtatctattt ccatcatttg aaactttaa tacaaagaac tgcatagcgt      660
ataatccaaa tggaaatgct ttagatgaat cctgtgaaga taaaaatcgt tatatctgta    720
agcaacagct catttaaatg tttcttgggg cagagaaggt ggagagtaaa gacccaacat    780
tactaacaat gatacagttg catgttatat tattactaat tgtctacttc tggagtctat    840
aaaatgttt taaacagtgt catatacaat tgtcatgtat gtgaaacaat gtgttttaaa      900
attgatgaaa ttcgttcacc tacatttgag aattataaaa ttaacataaa gaattttgta   960
ttttcattta atgtatatat ttaatgttaa attcaatgta gttttattac acatttatgt   1020
aattttattt acattcttgc taattctcag cagaaattta ataagatttt aattcacatc  1080
aaataaaatt tagaaaataa aatttaactc acactgccca ggctggagca tagtggcaag  1140
atcatagctc attgcaagct caagtgatcc tcctgactca gcctcccaag tagctaggac  1200
tgcaggcacc atgtcactat gcccgactaa ttttttaattt ttaattttttt gtcaagacaa 1260
ggtcttgcta tgttgcccag gctggtcttg aactcctggc tcaagggat tctcccacct   1320
tggattccca aagtgctggg attataggtg tgaaccacca tccctggccc tcttcacatt  1380
cttgtatgaa gattgatttg ggaaaaatgc atttcaggta actgacaaaa gatataggat  1440
gaaaaataat atctttcaaa tgtttaattt gaactaagag agcttatgca ttgcactttc 1500
tggagatttg taatgttttg gttttgttgt ccatgtgact acaaaataat atattttta    1560
attaaaaaat ttaaaataat acaggcaagc atgtaatgat tatcaatatt ttttttccacc 1620
aactatccta taccctgac ctcctttcat taggcattat cttctgtttt gattttaaca   1680
cttagagtgg ttttctctgt tatgaatcaa agctgatcta ttttcatcat ttttgtgatg  1740
aaaaaattaa ttttgattga cttaggatgg aaggatttgg actgggtgtg gtggtttatg  1800
cctgtaatcg cagcactttg ggaggccaag gcgggtggat cacttgaggt caggagtttg  1860
agaccagcct ggccaacatg gtgaaaccct gtctctacta aaaatacaaa aattggctgg  1920
gtgtggtagt gcacacctgt aatcccagct atttgggagg ctgagtcgag aggatcgctt  1980
gaacctagga ggtggaggtt gcagtgagtc gagattgcac cactgcactc cagcctgggt   2040
gacagagcca gactcctctc caaaaaaaaa aaaaaaaaa aaagatgaaa ggatttggaa    2100
ccttaattgc atctgaaaaa ctgcctcacc tttgttattt agtgtactcc aaccacggag   2160
taacatccca tcataatccc aaatcctact caaacaaaag gggaagggat tatgcaggtg   2220
tacactaggc cactggtgta ccaattagaa accactttag agttatgcct actgtaccca   2280
```

-continued

```
cataatccta aaaatatgtt acaactgcta cttcatagtt tatgccactt attttatttt    2340
ttacttttat tatttttttt tctgagacac ggtttcattc ccattgccca ggctgtagtg    2400
caatgatgca atcatggttc actgcagctt caacttccca ggctcaaggg atcctcccac    2460
ctcagccttc tgagtacttg ggactcaggt gcgagccatc atgctcagct aattttttgt    2520
atcatttgta gaaatggggt tttgtattgt tgcccaggct gatcttgaac tcctggggtc    2580
aaggattctg cccgccttgg cctcctaaag gctggaatt acaggcataa gccactgtgc    2640
ccggccagtt tatataattt aaacactgcc ttttggttcc ttgattccca tatgctagga    2700
caagtaatta ttattttatt ttattttact ttaagttctg ggttacatgt gcagaacctg    2760 caggttttgtt acataggtat acatgttcca aggtggtttg ctgcacctat tgacccatca    2820
tctaggtttt aagtcccaca tgcattaggt atttgtccta atgctcttcc tccccttgcc    2880 ccccacccc cgacaggcct tggtctgtga tgttcacctc cctgtgtcca tgtgttctca    2940
ttgttcaact cccacttatt agtaagaaca tgtggtgttt ggttttctgt tcctgtgtta    3000
gtttgctgag aatgatggtt ccagcttca tccatgtcgc tgcaaaggac atgaactcat    3060 tcttttatg gctgcatagt attccatggt gtatatgtgc catattttct ttatccagtc    3120
tatcactgat gggcatttgg gttggttcca agtctttgct atggtaaata gtgctgcaat    3180
aaacatacgt gtgca                                                     3195
```

<210> SEQ ID NO 12
<211> LENGTH: 3261
<212> TYPE: DNA
<213> ORGANISM: human

<400> SEQUENCE: 12

```
ctgtattgtg gttcctggaa cacttcagag gcttgtgatt ctactgcttc ttattcacac      60
tataatacat gtctcaccaa tagatgattc aagaacatca tttaaataca caattttttca    120 ttctctattt ttgctaaatt tcttcatact caactttcag attctttaat ctccagctca    180
gcttcaacaa ttcaacgctg ttcttctga aaagtacac atcgtgcctt ctctacttcg       240
ctcttggaac ataatttctc atggcagtgt ttaagaccac tctgtggagg ttaatttctg    300
ggaccttagg gataatatgc ctttcgttga tgtctacgtt gggaattttg ttgaaaaatt    360 ctttactaa actgagtatt gagccagcat ttactccagg acccaacata gaactccaga    420
aagactctga ctgctgttct tgccaagaaa aatgggttgg gtaccggtgc aactgttact    480
tcatttccag tgaacagaaa acttggaacg aaagtcggca tctctgtgct ctcagaaat    540 ccagcctgct tcagcttcaa aacacagatg aactgcagga ttttatgagc tccagtcaac    600
aattttactg gattggactc tcttacagtg aggagcacac cgcctggttg tgggagaatg    660
gctctgcact ctcccagtat ctatttccat catttgaaac ttttaataca aagaactgca    720
tagcgtataa tccaaatgga aatgctttag atgaatcctg tgaagataaa aatcgttata    780
tctgtaagca acagctcatt taaatgtttc ttggggcaga gaaggtggag agtaaagacc    840
caacattact aacaatgata cagttgcatg ttatattatt actaattgtc tacttctgga    900
gtctataaaa tgttttaaa cagtgtcata tacaattgtc atgtatgtga acaatgtgt     960 tttaaaattg atgaaattcg ttcacctaca tttgagaatt ataaaattaa cataaagaat   1020
tttgtatttt catttaatgt atatatttaa tgttaaattc aatgtagttt tattacacat   1080
ttatgtaatt ttatttacat tcttgctaat tctcagcaga aatttaaata agatttaatt   1140
```

```
cacatcaaat aaaatttaga aaataaaatt taactcacac tgcccaggct ggagcatagt    1200
ggcaagatca tagctcattg caagctcaag tgatcctcct gactcagcct cccaagtagc    1260
taggactgca ggcaccatgt cactatgccc gactaatttt taatttttaa ttttttgtca    1320
agacaaggtc ttgctatgtt gcccaggctg gtcttgaact cctggcctca agggattctc    1380
ccaccttgga ttcccaaagt gctgggatta taggtgtgaa ccaccatccc tggccctctt    1440
cacattcttg tatgaagatt gatttgggaa aaatgcattt caggtaactg acaaaagata    1500
taggatgaaa ataatatatct ttcaaatgtt taatttgaac taagagagct tatgcattgc    1560
actttctgga gatttgtaat gttttggttt tgttgtccat gtgactacaa aataatatat    1620
tttttaatta aaaaatttaa aataatacag gcaagcatgt aatgattatc aatatttttt    1680
tccaccaact atcctatacc cctgacctcc tttcattagg cattatcttc tgttttgatt    1740
ttaacactta gagtggtttt ctctgttatg aatcaaagct gatctatttt catcattttt    1800
gtgatgaaaa aattaattttt gattgactta ggatggaagg atttggactg ggtgtggtgg    1860
tttatgcctg taatcgcagc actttgggag gccaaggcgg gtggatcact tgaggtcagg    1920
agtttgagac cagcctggcc aacatggtga accctgtctc tactaaaaaa tacaaaaatt    1980
ggctgggtgt ggtagtgcac acctgtaatc ccagctattt gggaggctga gtcgagagga    2040
tcgcttgaac ctaggaggtg gaggttgcag tgagtcgaga ttgcaccact gcactccagc    2100
ctgggtgaca gagccagact cctctccaaa aaaaaaaaa aaaaaaaaag atgaaaggat    2160
ttggaacctt aattgcatct gaaaaactgc ctcacctttg ttatttagtg tactccaacc    2220
acggagtaac atcccatcat aatcccaaat cctactcaaa caaaagggga agggattatg    2280
caggtgtaca ctaggccact ggtgtaccaa ttagaaacca ctttagagtt atgcctactg    2340
tacccacata atcctaaaaa tatgttacaa ctgctacttc atagtttatg ccacttattt    2400
tattttttac ttttattatt ttttttttctg agacacggtt tcattcccat tgcccaggct    2460
gtagtgcaat gatgcaatca tggttcactg cagcttcaac ttcccaggct caagggatcc    2520
tcccacctca gccttctgag tacttgggac tcaggtgcga gccatcatgc tcagctaatt    2580
ttttgtatca tttgtagaaa tggggttttg tattgttgcc caggctgatc ttgaactcct    2640
ggggtcaagg attctgcccg ccttggcctc ctaaagggct ggaattacag gcataagcca    2700
ctgtgcccgg ccagtttata taatttaaac actgccttttt ggttccttga ttcccatatg    2760
ctaggacaag taattattat tttatttttat tttactttaa gttctgggtt acatgtgcag    2820
aacctgcagg tttgttacat aggtatacat gttccaaggt ggtttgctgc acctattgac    2880
ccatcatcta ggttttaagt cccacatgca ttaggtattt gtcctaatgc tcttcctccc    2940
cttgcccccc accccccgac aggccttggt ctgtgatgtt cacctccctg tgtccatgtg    3000
ttctcattgt tcaactccca cttattagta agaacatgtg gtgtttggtt ttctgttcct    3060
gtgttagttt gctgagaatg atggtttcca gcttcatcca tgtcgctgca aaggacatga    3120
actcattctt tttatggctg catagtattc catggtgtat atgtgccata tttctcttat    3180
ccagtctatc actgatgggc atttggggttg gttccaagtc tttgctatgg taaatagtgc    3240
tgcaataaac atacgtgtgc a                                              3261
```

<210> SEQ ID NO 13
<211> LENGTH: 1575
<212> TYPE: DNA
<213> ORGANISM: human

<400> SEQUENCE: 13

```
actttcaatt ctagatcagg aactgaggac atatctaaat tttctagttt tatagaaggc      60 tttatccac aagaatcaag atcttccctc tctgagcagg aatcctttgt gcattgaaga      120
ctttagattc ctctctgcgg tagacgtgca cttataagta tttgatgggg tggattcgtg    180
gtcggaggtc tcgacacagc tgggagatga gtgaatttca taattataac ttggatctga    240
agaagagtga ttttcaaca cgatggcaaa agcaaagatg tccagtagtc aaaagcaaat     300
gtagagaaaa tgcatctcca ttttttttct gctgcttcat cgctgtagcc atgggaatcc    360
gtttcattat tatggtaaca atatggagtg ctgtattcct aaactcatta ttcaaccaag    420
aagttcaaat tcccttgacc gaaagttact gtgggcccatg tcctaaaaac tggatatgtt   480
acaaaaataa ctgctaccaa ttttttgatg agagtaaaaa ctggtatgag agccaggctt    540
cttgtatgtc tcaaaatgcc agccttctga agtatacag caaagaggac caggatttac     600
ttaaactggt gaagtcatat cattggatgg gactagtaca cattccaaca aatggatctt    660
ggcagtggga agatggctcc attctctcac ccaacctact aacaataatt gaaatgcaga    720
agggagactg tgcactctat gcctcgagct ttaaaggcta tatagaaaac tgttcaactc    780
caaatacgta catctgcatg caaaggactg tgtaaagatg atcaaccatc tcaataaaag    840
ccaggaacag agaagagatt acaccagcgg taacactgcc aactgagact aaaggaaaca    900
aacaaaaaca ggacaaaatg accaaagact gtcagatttc ttagactcca caggaccaaa    960
ccatagaaca atttcactgc aaacatgcat gattctccaa gacaaaagaa gagagatcct   1020
aaaggcaatt cagatatccc caaggctgcc tctcccacca caagcccaga gtggatgggc   1080
tgggggaggg gtgctgtttt aatttctaaa ggtaggacca cacccaggg gatcagtgaa    1140 ggaagagaag gccagcagat cactgagagt gcaaccccac cctccacagg aaattgcctc   1200
atgggcaggg ccacagcaga gagacacagc atgggcagtg ccttccctgc ctgtgggggt   1260
catgctgcca cttttaatgg gtcctccacc caacggggtc agggaggtgg tgctgcccca   1320
gtgggccatg attatcttaa aggcattatt ctccagcctt aagtaagatc ttaggacgtt   1380
tcctttgcta tgatttgtac ttgcttgagt cccatgactg tttctcttcc tctctttctt   1440
ccttttggaa tagtaatatc catcctatgt ttgtcccact attgtatttt ggaagcacat   1500
aacttgtttg gtttcacagg ttcacagtta agaaggaatt ttgcctctga ataaatagaa   1560
tcttgagtct catgc                                                    1575
```

<210> SEQ ID NO 14
<211> LENGTH: 967
<212> TYPE: DNA
<213> ORGANISM: human

<400> SEQUENCE: 14

```
ggaacatgaa gtcactgagc ctgctccacc tctttcctct cccaagagct aaaagagagc     60
aaggaggaaa caacagcagc tccaaccagg gcagccttcc tgagaagatg caaccaatcc    120
tgcttctgct ggccttcctc ctgctgccca gggcagatgc aggggagatc atcggggac    180 atgaggccaa gccccactcc cgcccctaca tggcttatct tatgatctgg gatcagaagt    240
ctctgaagag gtgcggtggc ttcctgatac gagacgactt cgtgctgaca gctgctcact    300
gttggggaag ctccataaat gtcaccttgg ggcccacaa tatcaaagaa caggagccga    360
cccagcagtt tatccctgtg aaaagaccca tcccccatcc agcctataat cctaagaact    420
tctccaacga catcatgcta ctgcagctgg agagaaaggc caagcggacc agagctgtgc    480
```

| | |
|---|---|
| agcccctcag gctacctagc aacaaggccc aggtgaagcc agggcagaca tgcagtgtgg | 540 |
| ccggctgggg gcagacggcc cccctgggaa acactcaca cacactacaa gaggtgaaga | 600 |
| tgacagtgca ggaagatcga aagtgcgaat ctgacttacg ccattattac gacagtacca | 660 |
| ttgagttgtg cgtgggggac ccagagatta aaaagacttc ctttaagggg gactctggag | 720 |
| gccctcttgt gtgtaacaag gtggcccagg gcattgtctc ctatggacga acaatggca | 780 |
| tgcctccacg agcctgcacc aaagtctcaa gctttgtaca ctggataaag aaaaccatga | 840 |
| aacgctacta actacaggaa gcaaactaag cccccgctgt aatgaaacac cttctctgga | 900 |
| gccaagtcca gatttacact gggagaggtg ccagcaactg aataaatacc tcttagctga | 960 |
| gtggaaa | 967 |

<210> SEQ ID NO 15
<211> LENGTH: 559
<212> TYPE: DNA
<213> ORGANISM: human

<400> SEQUENCE: 15

| | |
|---|---|
| atgcaaccaa tcctgcttct gctggccttc ctcctgctgc ccagggcaga tcagctggag | 60 |
| agaaaggcca agcggaccag agctgtgcag cccctcaggc tacctagcaa caaggcccag | 120 |
| gtgaagccag gcagacatg cagtgtggcc ggctgggggc agacggcccc cctgggaaaa | 180 |
| cactcacaca cactacaaga ggtgaagatg acagtgcagg aagatcgaaa gtgcgaatct | 240 |
| gacttacgcc attattacga cagtaccatt gagttgtgcg tggggaccc agagattaaa | 300 |
| aagacttcct ttaagggga ctctggaggc cctcttgtgt gtaacaaggt ggcccagggc | 360 |
| attgtctcct atggacgaaa caatggcatg cctccacgag cctgcaccaa agtctcaagc | 420 |
| tttgtacact ggataaagaa aaccatgaaa cgctactaac tacaggaagc aaactaagcc | 480 |
| cccgctgtaa tgaaacacct tctctggagc caagtccaga tttacactgg gagaggtgcc | 540 |
| agcaactgaa taaatacct | 559 |

<210> SEQ ID NO 16
<211> LENGTH: 816
<212> TYPE: DNA
<213> ORGANISM: human

<400> SEQUENCE: 16

| | |
|---|---|
| ggaacatgaa gtcactgagc ctgctccacc tctttcctct cccaagagct aaaagagagc | 60 |
| aaggaggaaa caacagcagc tccaaccagg gcagccttcc tgagaagatg caaccaatcc | 120 |
| tgcttctgct ggccttcctc ctgctgccca gggcagatgc aggggagatc atcggggac | 180 |
| atgaggccaa gccccactcc cgcccctaca tggcttatct tatgatctgg gatcagaagt | 240 |
| ctctgaagag gtgcggtggc ttcctgatac gagacgactt cgtgctgaca gctgctcact | 300 |
| gttgggaag actggagaga aaggccaagc ggaccagagc tgtgcagccc tcaggctac | 360 |
| ctagcaacaa ggcccaggtg aagccagggc agacatgcag tgtggccggc tgggggcaga | 420 |
| cggcccccct gggaaaacac tcacacacac tacaagaggt gaagatgaca gtgcaggaag | 480 |
| atcgaaagtg cgaatctgac ttacgccatt attacgacag taccattgag ttgtgcgtgg | 540 |
| gggacccaga gattaaaaag acttccttta agggggactc tggaggccct cttgtgtgta | 600 |
| acaaggtggc ccagggcatt gtctcctatg gacgaaacaa tggcatgcct ccacgagcct | 660 |
| gcaccaaagt ctcaagcttt gtacactgga taagaaaac catgaaacgc tactaactac | 720 |
| aggaagcaaa ctaagccccc gctgtaatga aacaccttct ctggagccaa gtccagattt | 780 | acactgggag aggtgccagc aactgaataa atacct 816

<210> SEQ ID NO 17
<211> LENGTH: 951
<212> TYPE: DNA
<213> ORGANISM: human

<400> SEQUENCE: 17

| | | | | | |
|---|---|---|---|---|---|
| ggaacatgaa | gtcactgagc | ctgctccacc | tctttcctct | cccaagagct | aaaagagagc | 60
| aaggaggaaa | caacagcagc | tccaaccagg | gcagccttcc | tgagaagatg | caaccaatcc | 120
| tgcttctgct | ggccttcctc | ctgctgccca | gggcagatgc | aggggagatc | atcgggggac | 180
| atgaggccaa | gccccactcc | cgcccctaca | tggcttatct | tatgatctgg | gatcagaagt | 240
| ctctgaagag | gtgcggtggc | ttcctgatac | gagacgactt | cgtgctgaca | gctgctcact | 300
| gttgggaag | ctccataaat | gtcaccttgg | gggcccacaa | tatcaaagaa | caggagccga | 360
| cccagcagtt | tatccctgtg | aaaagaccca | tcccccatcc | agcctataat | cctaagaact | 420
| tctccaacga | catcatgcta | ctgcagctgg | agagaaaggc | caagcggacc | agagctgtgc | 480
| agcccctcag | gctacctagc | aacaaggccc | aggtgaagcc | agggcagaca | tgcagtgtgg | 540
| ccggctgggg | gcagacggcc | ccctgggaa | acactcaca | cacactacaa | gaggtgaaga | 600
| tgacagtgca | ggaagatcga | aagtgcgaat | ctgacttacg | ccattattac | gacagtacca | 660
| ttgagttgtg | cgtgggggac | ccagagatta | aaaagacttc | ctttaagggg | gactctggag | 720
| gccctcttgt | gtgtaacaag | gtggcccagg | gcattgtctc | ctatgacga | aacaatggca | 780
| tgcctccacg | agcctgcacc | aaagtctcaa | gctttgtaca | ctggataaag | aaaaccatga | 840
| aacgctacta | actacaggaa | gcaaactaag | cccccgctgt | aatgaaacac | cttctctgga | 900
| gccaagtcca | gatttacact | gggagaggtg | ccagcaactg | aataaatacc | t | 951

<210> SEQ ID NO 18
<211> LENGTH: 6854
<212> TYPE: DNA
<213> ORGANISM: human

<400> SEQUENCE: 18

| | | | | | |
|---|---|---|---|---|---|
| agtgctgaag | aaagagggca | ctagtgtaca | gcccagatcg | catccttgca | ccgtctggat | 60
| tagagctgag | gcgtctgcaa | gccgagcgtg | gccacggtcc | tctggccccg | ggaccatagc | 120
| gctgtctacc | ccgactcagg | tactcagcag | catctagctc | accgctgcca | acacgacttc | 180
| cactgtactc | ttgatcaatt | taccttgatg | cactaccggt | gaagaacggg | gactcgaatt | 240
| cccttacaaa | cgcctccagc | ttgtagaggc | ggtcgtggag | gacccagagg | aggagacgaa | 300
| ggggaaggag | gcggtggtgg | aggaggcaaa | ggccttggac | gaccattgtt | ggcgaggggc | 360
| accactccgg | gagaggcggc | gctgggcgtc | ttggggggtgc | gcgccgggag | cctgcagcgg | 420
| gaccagcgtg | ggaacgcggc | tggcaggctg | tggacctcgt | cctcaccacc | atggtcgggc | 480
| tcctttttgtt | tttttttccca | gcgatctttt | tggaggtgtc | ccttctcccc | agaagccccg | 540
| gcaggaaagt | gttgctggca | ggagcgtcgt | ctcagcgctc | ggtggccaga | atggacggag | 600
| atgtcatcat | tggagccctc | ttctcagtcc | atcaccagcc | tccggccgag | aaagtgcccg | 660
| agaggaagtg | tggggagatc | agggagcagt | atggcatcca | gagggtggag | gccatgttcc | 720
| acacgttgga | taagatcaac | gcggaccggg | tcctcctgcc | caacatcacc | ctgggcagtg | 780
| agatccggga | ctcctgctgg | cactcttccg | tggctctgga | acagagcatt | gagttcatta | 840

```
gggactctct gatttccatt cgagatgaga aggatgggat caaccggtgt ctgcctgacg    900
gccagtccct ccccccaggc aggactaaga agcccattgc gggagtgatc ggtcccggct    960
ccagctctgt agccattcaa gtgcagaacc tgctccagct cttcgacatc ccccagatcg   1020
cttattcagc cacaagcatc gacctgagtg acaaaacttt gtacaaatac ttcctgaggg   1080
ttgtcccttc tgacactttg caggcaaggg ccatgcttga catagtcaaa cgttacaatt   1140
ggacctatgt ctctgcagtc cacacggaag ggaattatgg ggagagcgga atggacgctt   1200
tcaaagagct ggctgcccag gaaggcctct gtatcgccca ttctgacaaa atctacagca   1260
acgctgggga gaagagcttt gaccgactct tgcgcaaact ccgagagagg cttcccaagg   1320
ctagagtggt ggtctgcttc tgtgaaggca tgacagtgcg aggactcctg agcgccatgc   1380
ggcgccttgg cgtcgtgggc gagttctcac tcattggaag tgatggatgg gcagacagag   1440
atgaagtcat tgaaggttat gaggtggaag ccaacggggg aatcacgata aagctgcagt   1500
ctccagaggt caggtcattt gatgattatt tcctgaaact gaggctggac actaacacga   1560
ggaatccctg gttccctgag ttctggcaac atcggttcca gtgccgcctt ccaggacacc   1620
ttctggaaaa tcccaacttt aaacgaatct gcacaggcaa tgaaagctta aagaaaaact   1680
atgtccagga cagtaagatg gggttttgtca tcaatgccat ctatgccatg gcacatgggc   1740
tgcagaacat gcaccatgcc ctctgccctg ccacgtggg cctctgcgat gccatgaagc   1800
ccatcgacgc cagcaagctg ctggacttcc tcatcaagtc ctcattcatt ggagtatctg   1860
gagaggaggt gtggtttgat gagaaaggag acgctcctgg aaggtatgat atcatgaatc   1920
tgcagtacac tgaagctaat cgctatgact atgtgcacgt tggaacctgg catgaaggag   1980
tgctgaacat tgatgattac aaaatccaga tgaacaagag tggagtggtg cggtctgtgt   2040
gcagtgagcc ttgcttaaag ggccagatta aggttatacg gaaaggagaa gtgagctgct   2100
gctggatttg cacggcctgc aaagagaatg aatatgtgca agatgagttc acctgcaaag   2160
cttgtgactt gggatggtgg cccaatgcag atcaacagg ctgtgagccc attcctgtgc   2220
gctatcttga gtggagcaac atcgaatcca ttatagccat cgccttttca tgcctgggaa   2280
tccttgttac cttgtttgtc accctaatct ttgtactgta ccgggacaca ccagtggtca   2340
aatcctccag tcgggagctc tgctacatca tcctagctgg catcttcctt ggttatgtgt   2400
gcccattcac tctcattgcc aaacctacta ccacctcctg ctacctccag cgcctcttgg   2460
ttggcctctc ctctgcgatg tgctactctg ctttagtgac taaaaccaat cgtattgcac   2520
gcatcctggc tggcagcaag aagaagatct gcacccggaa gcccaggttc atgagtgcct   2580
gggctcaggt gatcattgcc tcaattctga ttagtgtgca actaaccctg gtggtaaccc   2640
tgatcatcat ggaaccccct atgcccattc tgtcctaccc aagtatcaag gaagtctacc   2700
ttatctgcaa taccagcaac ctgggtgtgg tggcccctttt gggctacaat ggactcctca   2760
tcatgagctg tacctactat gccttcaaga cccgcaacgt gcccgccaac ttcaacgagg   2820
ccaaatatat cgcgttcacc atgtacacca cctgtatcat ctggctagct tttgtgccca   2880
tttactttgg gagcaactac aagatcatca aacttgctt tgcagtgagt ctcagtgtaa   2940
cagtggctct ggggtgcatg ttcactccca agatgtacat cattattgcc aagcctgaga   3000
ggaatgtccg cagtgccttc accacctctg atgttgtccg catgcatgtt ggcgatggca   3060
agctgccctg ccgctccaac actttcctca acatcttccg aagaaagaag gcaggggcag   3120
ggaatgccaa ttctaatggc aagtctgtgt catggtctga accaggtgga ggacaggtgc   3180
ccaagggaca gcatatgtgg caccgcctct ctgtgcacgt gaagaccaat gagacggcct   3240
```

```
gcaaccaaac agccgtcatc aagcccctca ctaaaagtta ccaaggctct ggcaagagcc    3300 tgacctttc agataccagc accaagaccc tttacaacgt agaggaggag gaggatgccc    3360
agccgattcg ctttagcccg cctggtagcc cttccatggt ggtgcacagg cgcgtgccaa    3420
gcgcggcgac cactccgcct ctgccgtccc acctgaccgc agaggagacc ccctcttcc    3480 tggccgaacc agccctcccc aagggcttgc cccctcctct ccagcagcag cagcaacccc    3540
ctccacagca gaaatcgctg atggaccagc tccagggagt ggtcagcaac ttcagtaccg    3600
cgatcccgga ttttcacgcg gtgctggcag gccccggtgg tcccgggaac gggctgcggt    3660
ccctgtaccc gccccgcca cctccgcagc acctgcagat gctgccgctg cagctgagca    3720
cctttgggga ggagctggtc tccccgcccg cggacgacga cgacgacagc gagaggttta    3780
agctcctcca ggagtacgtg tatgagcacg agcgggaagg gaacacggaa gaagacgaac    3840
tggaagagga ggaggaggac ctgcaggcgg ccagcaaact gaccccggat gattcgcctg    3900
cgctgacgcc tccgtcgcct ttccgcgact cggtggcctc gggcagctcg gtgcccagct    3960
cccccgtgtc cgagtcggtg ctctgcaccc ctcccaacgt atcctacgcc tctgtcattc    4020
tgcgggacta caagcaaagc tcttccaccc tgtaaggggg aagggtccac atagaaaagc    4080
aagacaagcc agagatctcc cacacctcca gagatgtgca acagctggga aggaaaagcc    4140
tgggagtggg gggcctcgtc ggggaggacag gagaccgctg ctgctgctgc cgctactgct    4200
gctgctgcct taagtaggaa gagagggaag gacaccaagc aaaaaatgtt ccaggccagg    4260
attcggattc ttgaattact cgaagccttc tctgggaaga aagggaattc tgacaaagca    4320
caattccata tggtatgtaa cttttatcac aaatcaaata gtgacatcac aaacataatg    4380
tcctcttttg cacaattgtg catagatata tatgcccca cacacactgg gccatgcttg    4440
ccaaggaaca gcccacgtgg acatgccagt cggatcatga gttcacctga tggcattcgg    4500
agtgagctgg tggagccaga cagagcaggt gcggggaagg gaagggccca ggccagaccc    4560
atcccaaacg gatgatggga tgatgggaca gcagctcctt gctcagaagc ccttctcccc    4620
gctgggctga cagactcctc atcttcagga gactcaggaa tggagcggca caggggtctc    4680
tcttcatcca ctgcaaccca tccagtgcca gctttgagat tgcacttgaa gaaaggtgca    4740 tggacccct gctgctctgc agattccctt tatttaggaa aacaggaata agagcaaaat    4800
tatcaccaaa aagtgcttca tcaggcgtgc tacaggagga aggagctaga aatagaacaa    4860
tccatcagca tgagactttg aaaaaaaaaac acatgatcag cttctcatgt tccatattca    4920
cttattggcg atttggggaa aaggccgaa caagagattg ttacgagagt ggcagaaacc    4980 ctttttgtaga ttgacttgtg tttgtgccaa gcgggctttc cattgacctt cagttaaaga    5040 acaaccatg tgacaaaatt gttaccttcc acttactgta gcaaataata cctacaagtt    5100
gaacttctaa gatgcgtata tgtacaattt ggtgccatta tttctcctac gtattagaga    5160
aacaaatcca tctttgaatc taatggtgta ctcatagcaa ctattactgg tttaaatgac    5220
aaataattct atcctattgt cactgaagtc cttgtaacta gcgagtgaat gtgttcctgt    5280
gtccttgtat atgtgcgatc gtaaaatttg tgcaatgtaa tgtcaaattg actggtcaat    5340
gtcaacctag tagtcaatct aactgcaatt agaaattgtc ttttgaatat actatatata    5400
ttttttatgt tccaataatg ttttgtacat cattgtcatc aatatctaca gaagctcttt    5460
gacggtttga atactatggc tcaaggtttt catatgcagc tcggatggac attttcttc    5520 taagatggaa cttattttc agatattttc tgatgtggag atatgttatt aatgaagtgg    5580
```

```
tttgaaaatt tgttatatta aaagtgcaca aaaactgaga gtgaaaataa aaggtacatt    5640
ttataagctt gcacacatta ttaacacata agattgaaca aagcatttag attattccag    5700
gttatatcat tttttttaaag attttccaca gctacttgag tgtctaacat acagtaacat   5760
ctaactcagc taataatttg taaaatcttt atcaatcaca ttttgccttc ttttaatttt    5820
tatgttcatg gacttttatt cctgtgtctt ggctgtcata acttttatt tctgctattt     5880 gctgttgtgt aatatccatg gacatgtaat ccacttactc catctttaca atccctttt     5940 accaccaata aaaggatttt tcttgctgtt ttgatttctt ctattatttg tggaatgaat    6000 tataccccccc ttaaatatct ttgtttatgc cttatgttca gtcatatttt aatatgcttc   6060
cttcatattg aagctgctga tttctcagcc aaaaatcatc ttagaatctt taaatatcca   6120
ttgcatcatt tgttcagaat ttaacatcca ttccaatgtt ggaggcttgt attacttata   6180
tttcatcata ttctattgcc aagtttagtc agttccacac caagaatgaa ctgcatttcc   6240
tttaaaaatt attttaaaac cctttattg aaaagatctc atgactgaga tgtggacttt    6300
ggttccatgt tttcattgta agaaagcaga gagcggaaaa tcaatggctc cagtgattaa   6360
tagatgggtt tttagtaatt gacaaattca tgagggaaag catatgatct ctttattagt   6420
gaatcatgct tattttttac tcttaatgcc actaatatac atccctaata tcacagggct   6480
tgtgcattca gattttttaaa aaattaggat agataaggaa acaacttata ttcaagtgta   6540
agatgatatc aggttggtct aagacttttg gtgaacacgt tcattcaact gtgatcactt   6600
tattactctg aatgcctact attatcctga ttatggggtc tcctgaataa atagagtatt   6660
agtccttatg tcatcattgt tcaaaattgg agatgtacac atacataccc tataccaaga   6720
gggccgaaac tcttcacctt gatgtatgtt ctgatacaag ttgttcagct tcttgtaaat   6780
gtgttttcct tcggcttgtt actgcctttt gtcaaataat cttgacaatg ctgtataata   6840
aatattttct attt                                                     6854
```

<210> SEQ ID NO 19
<211> LENGTH: 1609
<212> TYPE: DNA
<213> ORGANISM: human

<400> SEQUENCE: 19

```
ttttctcccta accgtcccgg ccaccgctgc ctcagcctct gcctcccagc ctctttctga    60
gggaaaggac aagatgaagt ggaaggcgct tttcaccgcg gccatcctgc aggcacagtt    120
gccgattaca gaggcacaga gctttggcct gctggatccc aaactctgct acctgctgga   180
tggaatcctc ttcatctatg gtgtcattct cactgccttg ttcctgagag tgaagttcag   240
caggagcgca gacgccccccg cgtaccagca gggcccagaac cagctctata cgagctcaa   300 tctaggacga agagaggagt acgatgtttt ggacaagaga cgtggccggg accctgagat   360 gggggggaaag ccgcagagaa ggaagaaccc tcaggaaggc ctgtacaatg aactgcagaa   420
agataagatg gcgaggcct acagtgagat tgggatgaaa ggcgagcgcc ggaggggcaa    480
ggggcacgat ggcctttacc agggtctcag tacagccacc aaggacacct acgacgccct   540
tcacatgcag gccctgcccc ctcgctaaca gccaggggat tcaccactc aaaggccaga   600 cctgcagacg cccagattat gagacacagg atgaagcatt acaacccgg ttcactcttc   660 tcagccactg aagtattccc ctttatgtac aggatgcttt ggttatattt agctccaaac   720
cttcacacac agactgttgt ccctgcactc tttaagggag tgtactccca gggcttacgg   780
ccctggcctt gggccctctg gtttgccggt ggtgcaggta gacctgtctc ctggcggttc   840
```

-continued

```
ctcgttctcc ctgggaggcg ggcgcactgc ctctcacagc tgagttgttg agtctgtttt      900
gtaaagtccc cagagaaagc gcagatgcta gcacatgccc taatgtctgt atcactctgt      960
gtctgagtgg cttcactcct gctgtaaatt tggcttctgt tgtcaccttc acctcctttc     1020
aaggtaactg tactgggcca tgttgtgcct ccctggtgag agggccgggc agaggggcag     1080
atggaaagga gcctaggcca ggtgcaacca gggagctgca ggggcatggg aaggtgggcg     1140
ggcaggggag ggtcagccag ggcctgcgag gcagcgggag cctccctgc ctcaggcctc      1200
tgtgccgcac cattgaactg taccatgtgc tacaggggcc agaagatgaa cagactgacc     1260
ttgatgagct gtgcacaaag tggcataaaa aacatgtggt tacacagtgt gaataaagtg     1320
ctgcggagca agaggaggcc gttgattcac ttcacgcttt cagcgaatga caaaatcatc     1380
tttgtgaagg cctcgcagga agacccaaca catgggacct ataactgccc agcggacagt     1440
ggcaggacag gaaaaacccg tcaatgtact aggatactgc tgcgtcatta cagggcacag     1500
gccatggatg gaaaacgctc tctactctgc tttttttcta ctgttttaat ttatactggc     1560
atgctaaagc cttcctattt tgcataataa atgcttcagt gaaaatgca               1609

<210> SEQ ID NO 20
<211> LENGTH: 1678
<212> TYPE: DNA
<213> ORGANISM: human

<400> SEQUENCE: 20
tgctttctca aaggccccac agtcctccac ttcctgggga ggtagctgca gaataaaacc       60
agcagagact cctttttctcc taaccgtccc ggccaccgct gcctcagcct ctgcctccca      120
gcctctttct gagggaaagg acaagatgaa gtggaaggcg cttttcaccg cggccatcct      180
gcaggcacag ttgccgatta cagaggcaca gagctttggc ctgctggatc ccaaactctg      240
ctacctgctg gatggaatcc tcttcatcta tggtgtcatt ctcactgcct tgttcctgag      300
agtgaagttc agcaggagcg cagacgcccc cgcgtaccag cagggccaga ccagctcta      360
taacgagctc aatctaggac gaagagagga gtacgatgtt ttggacaaga acgtggccg      420
ggaccctgag atgggggga agccgagaag gaagaaccct caggaaggcc tgtacaatga      480
actgcagaaa gataagatgg cggaggccta cagtgagatt gggatgaaag gcgagcgccg      540
gaggggcaag gggcacgatg gcctttacca gggtctcagt acagccacca aggacaccta      600
cgacgccctt cacatgcagg ccctgccccc tcgctaacag ccagggatt tcaccactca      660
aaggccagac ctgcagacgc ccagattatg agacacagga tgaagcattt acaacccggt      720
tcactcttct cagccactga agtattcccc tttatgtaca ggatgctttg gttatattta      780
gctccaaacc ttcacacaca gactgttgtc cctgcactct ttaagggagt gtactcccag      840
ggcttacggc cctggccttg ggccctctgg tttgccggtg gtgcaggtag acctgtctcc      900
tggcggttcc tcgttctccc tgggaggcg gcgcactgcc tctcacagct gagttgttga      960
gtctgttttg taaagtcccc agagaaagcg cagatgctag cacatgccct aatgtctgta     1020
tcactctgtg tctgagtggc ttcactcctg ctgtaaattt ggcttctgtt gtcaccttca     1080
cctcctttca aggtaactgt actgggcatt gttgtgcctc cctggtgaga gggccgggca     1140
gaggggcaga tggaaaggag cctaggccag gtgcaaccag ggagctgcag gggcatggga     1200
aggtgggcgg gcaggggagg gtcagccagg gcctgcgagg cagcgggag cctccctgcc      1260
tcaggcctct gtgccgcacc attgaactgt accatgtgct acaggggcca agagatgaac     1320
```

```
agactgacct tgatgagctg tgcacaaagt ggcataaaaa acatgtggtt acacagtgtg    1380
aataaagtgc tgcggagcaa gaggaggccg ttgattcact tcacgctttc agcgaatgac    1440
aaaatcatct tgtgaaggc ctcgcaggaa acccaacac atgggaccta taactgccca    1500
gcggacagtg gcaggacagg aaaaacccgt caatgtacta ggatactgct gcgtcattac    1560
agggcacagg ccatggatgg aaaacgctct ctactctgct ttttttctac tgttttaatt    1620
tatactggca tgctaaagcc ttcctatttt gcataataaa tgcttcagtg aaaatgca     1678
```

```
<210> SEQ ID NO 21
<211> LENGTH: 2209
<212> TYPE: DNA
<213> ORGANISM: human

<400> SEQUENCE: 21
```

```
gggagggcgg agctggaagg gtgggaagca ccgatccacc ttattgctct ggccgaggcc      60
agagacctcc gggagaggct gggccaccga gccgggcttt actgctccga gggtccgggc     120
gtggggctgg agctggagcc ccgcgcgctg cttttccagc cgcctgcggc cgcgccttca     180
ccgtcggggc gatagcggtg caacttggc cgcggctccg cgtggtctcc gggcttcccc      240
gcgccgcctg agccggagct gcccgcttca atcctatttt gtaacggatt atgatccaac     300
cattgaagat tcttacacaa agcagtgtgt gatagatgac agagcagccc ggctagatat     360
tttggataca gcaggacaag aagagtttgg agccatgaga aacagtata tgaggactgg      420 cgaaggcttc ctgttggtct tttcagtcac agatagaggc agtttgaag aaatctataa      480 gtttcaaaga cagattctca gagtaaagga tcgtgatgag ttcccaatga ttttaattgg    540
taataaagca gatctggatc atcaaagaca ggtaacacag gaagaaggac aacagttagc     600
acggcagctt aaggtaacat acatggaggc atcagcaaag attaggatga atgtagatca     660 agcttccat gaacttgtcc gggttatcag gaaatttcaa gagcaggaat gtcctccttc      720
accagaacca acacggaaag aaaaagacaa gaaaggctgc cattgtgtca ttttctagaa     780
tcccttcagt tttagctacc aacggccagg aaaagccctc atcttctctt tctctcctca     840
gtttacatct tgttggtacc tttctagcct tagacaaatg atcaccatgt tagccttaga     900
cgaagaagct ggctagtcct ttctgtgaag ctaatacaat ggtcatttcc agacaaattt     960
aaaggaaaca ctaaggctgc ttcaaagatt atctgattcc tttaaaatat atgtctatat    1020
acacagacat gctctttttt taagtgctta cattttaata gagatgaatc agttttggaa    1080
tctaagctgt ttgccaagct gaagctacag gttgtgaaat aattttttaac ttttggaatc   1140 atactgccta ctgttactct aaatagaaat ataggttttt ttttaatgtg aatttttgcc    1200
tatctttaaa catttcaatg tcagcctttg ttaaccttaa atacactgaa ttgaatctac   1260
aaaagtgaac catctcagac ctttactgat actacaactt ttgttttctg atggccaaaa    1320
taccaaatgc ctgttgtatt tatggattaa aaactgctta taaaaccctg tgttactact    1380
cctactcttg gagatgataa tattctatgt ggtcaaatat ttggactcat ttaggactta    1440
gatatttcag tgtacttgat ttttaatt aactctttt cacagccacg ctaagggtaa      1500
aaaggaataa tttccttctg tcttcctttt caagtatttc tgggtaaggg attcaaaaaa    1560
ctaaaactgt ttttgtttgt aatataaaat atggaattga tctttccagg gtcagagatg    1620
attaatgttt ttgctatata cttttataca ttatttttctt atcaaactag ttaacaagta   1680 ttttatatg tttgtaagca gatatgcttt catagcatac cttgtgtata tgtaaagata    1740
agtatttaat tctcactgtt cacttttaac tgacaaagaa aaacaagtgg aaactacaga    1800
```

```
aactgtggta gaacttttac ttgctggtct ggtcttggtt gtacccatct ttggccagtc    1860
acataactac tcaagaaacc ttcccaatag agtacaacag gatgagactc tgaaatcact    1920
ttcagtattc cctgctagat attgattgtt atttcaagta ttaagtgtaa gcttttaatg    1980
gataattagt ataactgtgg atggcatctg attttgtttt taattctgtg gattgtgttt    2040
aagcaattca atagtatgtt cctgattttg agatgctaag tggtattgca cagttgtcac    2100
tttatcaagt gtgtacaaca gtcccatgaa gtttatagag catacccttg tatagcttca    2160
ggtgctagaa ttaaaattga tctgttatca aagaaaaaa aaaaaaaaa                 2209
```

<210> SEQ ID NO 22
<211> LENGTH: 2360
<212> TYPE: DNA
<213> ORGANISM: human

<400> SEQUENCE: 22

```
cagacggcca tttgtggcgg cgctggaggc tgcgttcggc aggcgctgcg gagacgcgta      60
gaggagcgcg ccccccggcc gctgccgccc ctggcccgtg ccgtcacccc gcttctccgc     120
gcctcgggcg gtacccagcc agtccccagc gccgcgctac cgcgctgacc ggccctccag     180
acgcctcccg gtacccggga ccccagcccg gccgctcgcc cgcagcccgc cggccgcaca     240
cgtccccgga gccgggccta gggcgggcgg cagcggcggc tcggcgcagt caggctgggc     300
tctgtagcgt ccccatggcc gcggccggct ggcgggacgg ctccggccag gagaagtacc     360
ggctcgtggt ggtcggcggg ggcggcgtgg gcaagtcggc gctcaccatc cagttcatcc     420
agtcctattt tgtaacggat tatgatccaa ccattgaaga ttcttacaca aagcagtgtg     480
tgatagatga cagagcagcc cggctagata ttttggatac agcaggacaa gaagagtttg     540
gagccatgag agaacagtat atgaggactg gcgaaggctt cctgttggtc ttttcagtca     600
cagatagagg cagttttgaa gaaatctata agtttcaaag acagattctc agagtaaagg     660
atcgtgatga gttcccaatg atttttaattg gtaataaagc agatctggat catcaaagac     720
aggtaacaca ggaagaagga caacagttag cacggcagct taaggtaaca tacatggagg     780
catcagcaaa gattaggatg aatgtagatc aagctttcca tgaacttgtc cgggttatca     840
ggaaatttca agagcaggaa tgtcctcctt caccagaacc aacacggaaa gaaaaagaca     900
agaaaggctg ccattgtgtc attttctaga atcccttcag ttttagctac caacggccag     960
gaaaagccct catcttctct ttctctcctc agtttacatc ttgttggtac ctttctagcc    1020
ttagacaaat gatcaccatg ttagccttag acgaagaagc tggctagtcc tttctgtgaa    1080
gctaatacaa tggtcatttc cagacaaatt taaggaaac actaaggctg cttcaaagat    1140
tatctgattc ctttaaaata tatgtctata tacacagaca tgctctttt ttaagtgctt    1200 acatttttaat agagatgaat cagttttgga atctaagctg tttgccaagc tgaagctaca    1260
ggttgtgaaa taatttttaa cttttggaat catactgcct actgttactc taaatagaaa    1320
tataggtttt ttttaatgt gaatttttgc ctatctttaa acatttcaat gtcagccttt    1380 gttaaccttta aatacactga attgaatcta caaagtgaa ccatctcaga cctttactga    1440
tactacaact tttgtttct gatggccaaa ataccaaatg cctgttgtat ttatggatta    1500
aaaactgctt ataaaaccct gtgttactac tcctactctt ggagatgata atattctatg    1560
tggtcaaata tttggactca tttaggactt agatatttca gtgtacttga ttttttaatt    1620
taactctttt tcacagccac gctaagggta aaaaggaata atttccttct gtcttccttt    1680
```

```
tcaagtatttt ctgggtaagg gattcaaaaa actaaaactg ttttttgtttg taatataaaa    1740 tatggaattg atcttttccag ggtcagagat gattaatgtt tttgctatat acttttatac    1800
attattttct tatcaaacta gttaacaagt attttttatat gtttgtaagc agatatgctt    1860
tcatagcata ccttgtgtat atgtaaagat aagtatttaa ttctcactgt tcactttttaa    1920 ctgacaaaga aaacaagtg gaaactacag aaactgtggt agaacttta cttgctggtc       1980 tggtcttggt tgtacccatc tttggccagt cacataacta ctcaagaaac cttcccaata    2040
gagtacaaca ggatgagact ctgaaatcac tttcagtatt ccctgctaga tattgattgt    2100
tatttcaagt attaagtgta agcttttaat ggataattag taactgtg gatggcatct      2160 gatttttgttt ttaattctgt ggattgtgtt taagcaattc aatagtatgt tcctgatttt    2220
gagatgctaa gtggtattgc acagttgtca ctttatcaag tgtgtacaac agtcccatga   2280
agtttataga gcatacccttt gtatagcttc aggtgctaga attaaaattg atctgttatc   2340
acaagaaaaa aaaaaaaaaa                                                 2360

<210> SEQ ID NO 23
<211> LENGTH: 2041
<212> TYPE: DNA
<213> ORGANISM: human

<400> SEQUENCE: 23
gtagctccac aggaggtaca gctgcttaca catctctcct cagagctgtc ccttgacttg      60
ggggtgaatt tcaggccaac agggcttcct gggatacaag agcgttctcc atggatctgc    120
cttactacca tggacgtctg accaagcaag actgtgagac cttgctgctc aaggaagggg    180
tggatggcaa ctttcttttta agagacagcg agtcgatacc aggagtcctg tgcctctgtg    240
tctcgtttaa aaatattgtc tacacatacc gaatcttcag agagaaacac gggtattaca    300
ggatacagaa cagtaacagc gattatgtgg atgtcttgcc ttgaagataa ggctgccgga    360
caaagcaagt tgaagagatg agtaacagtt ctcactgatg acccacttct gcaggcatag    420
gtccagagca ccaaactcta gtggacaatt cagactctcc tggttgtgta actgaagatg    480
ttctgcccac cagcaccaga ggtcactctc cacatccccg cctcccagac atataccagg    540
agcaatttca aaccctctc cagtttcact cttctttctt ggaatgggac agcctgaaca     600
ttttcccttt gacttgttaa aggtaccacc ctacatcatg gttgacaccc tcctttggac    660
catgcagtca gaggggcagc tttatacaga ggaggggcac acttgtctgt gagtttgaag   720
ccctgagttc cagtcctgtg gctgtgtgac tttgaacacg tttctgccca tctccaggtc   780 ttagttttctt tgtctctgtg gttgggtggg atgataaaca ttgccccagt ctctctgttg   840
agcctgcttg tgtcaggtga aggtgaggga tcgggagtga tggagatgca tacagatcag   900
caccttctct gtacctgctg gaccccccatg tgcacccttc tcctccagc ctgggctact    960 ctcctcctgg ttcttttctaa tcttaaactt cctggtgagc attgccccag ccacactttc   1020
tccctggttt tgcttaattc cacttatgca tcagtcattt caacagcatg aatgtggttc    1080
tgtacagtga tgtatgtgga gatttctaaa atattctatg tgtgatttct gttcccaact    1140
aggttctaag tgccatcaaa gcacggttgg gtctccttg tatcttccac agtgtgtaga   1200
aatttgtgct gcccagagct gtgcctagtt catagaaact gactggaagc acattgctga   1260
gggaggtttg ttgaattggt ttttaaggtt tactgaaatt gatttgctga attttttctgc  1320 tagttcaaaa tgtgaattag gacctggtca gtttgaaata taccaaattc tatgcccttt   1380 ctccttaccta tcatcaaatt gtagtaatgt atttcacccc actggactta tcttcagagt   1440
```

```
tttaaaagag aggagctctc gacttagagg taatatgaac agatgaacag acactgtggc    1500
tggagcccca aagtgtggag cattgtgaga tttggggtca cagcaattta tggctactat    1560
tccctgggtc tggtaggtag gacaaatgtc ctctttact tttcaaaact ggcttaggta     1620
ttcatggacc ttgattcttc tatatacatt ttataataaa tacgtgaaat tgcttaaaac    1680
ctctttttgg aattttaat gaacttgcaa caaatttgta aataggagag aactgacgtt     1740
cttgtgatgt tttcccatgc ataaacatgc cacatccatg ttcttgggtc atctttttg    1800 cccttcatg gagtcataaa tttcccaac tgaagtcttg tatattctgt tagattaatt     1860
cctatttcta gttgctgtaa atgatatctt atgttttatt acatttctaa taggatatgg    1920
tgttggtgaa atgttaaccc tctcattaga tctactagtt tacctgttga ttctattgtg    1980
ttttctatgt aaatgatttt gtcagctata aataataaca tttattttc ctttccttg     2040 c                                                                    2041

<210> SEQ ID NO 24
<211> LENGTH: 2523
<212> TYPE: DNA
<213> ORGANISM: human

<400> SEQUENCE: 24
gtagctccac aggaggtaca gctgcttaca catctctcct cagagctgtc ccttgacttg      60
ggggtgaatt tcaggccaac agggcttcct gggatacaag agcgttctcc atggatctgc    120
cttactacca tggacgtctg accaagcaag actgtgagac cttgctgctc aaggaagggg    180
tggatggcaa ctttctttta agagacagcg agtcgatacc aggagtcctg tgcctctgtg    240
tctcgtttaa aaatattgtc tacacatacc gaatcttcag agagaaacac gggtattaca    300
ggatacagac tgcagaaggt tctccaaaac aggtctttcc aagcctaaag gaactgatct    360
ccaaatttga aaaccaaat caggggatgg tggttcacct tttaaagcca ataagagaa      420 ccagccccag cttgagatgg agaggattga aattagagtt ggaaacattt gtgaacagta    480
acagcgatta tgtggatgtc ttgccttgaa gataaggctg ccggacaaag caagttgaag    540
agatgagtaa cagttctcac tgatgaccca cttctgcagg cataggtcca gagcaccaaa    600
ctctagtgga caattcagac ctcctggtt gtgtaactga agatgttctg cccaccagca     660
ccagaggtca ctctccacat ccccgcctcc cagacatata ccaggagcaa tttcaaaacc    720
ctctccagtt tcactcttct ttcttggaat gggacagcct gaacatttc cctttgactt     780 gttaaaggta ccaccctaca tcatggttga caccctcctt tggaccatgc agtcagaggg    840
gcagctttat acagaggagg ggcacacttg tctgtgagtt tgaagccctg agttccagtc    900
ctgtggctgt gtgactttga acacgtttct gcccatctcc aggtcttagt ttctttgtct    960
ctgtggttgg gtgggatgat aaacattgcc ccagtctctc tgttgagcct gcttgtgtca   1020
ggtgaaggtg agggatcggg agtgatggag atgcatacag atcagcacct tctctgtacc   1080
tgctggaccc ccatgtgcac ccttctccct ccagcctggg ctactctcct cctggttctt   1140
tctaatctta aacttcctgg tgagcattgc cccagccaca ctttctccct ggttttgctt   1200
aattccactt atgcatcagt catttcaaca gcatgaatgt ggttctgtac agtgatgtat   1260
gtggagattt ctaaaatatt ctatgtgtga tttctgttcc caactaggtt ctaagtgcca   1320
tcaaagcacg gttgggtctc ccttgtatct tccacagtgt gtagaaattt gtgctgccca   1380
gagctgtgcc tagttcatag aaactgactg gaagcacatt gctgagggag gtttgttgaa   1440
```

```
ttggttttta aggtttactg aaattgattt gctgaatttt tctgctagtt caaaatgtga    1500
attaggacct ggtcagtttg aaatatacca aattctatgc cctttctctt acctatcatc    1560
aaattgtagt aatgtatttc accccactgg acttatcttc agagttttaa aagagaggag    1620
ctctcgactt agaggtaata tgaacagatg aacagacact gtggctggag ccccaaagtg    1680
tggagcattg tgagatttgg ggtcacagca atttatggct actattccct gggtctggta    1740
ggtaggacaa atgtcctctt ttacttttca aaactggctt aggtattcat ggaccttgat    1800
tcttctatat acattttata ataaatacgt gaaattgctt aaaacctctt tttggaattt    1860
ttaatgaact tgcaacaaat tgtaaatag gagagaactg acgttcttgt gatgttttcc    1920
catgcataaa catgccacat ccatgttctt gggtcatctt ttttgccctt tcatggagtc    1980
ataaattttc ccaactgaag tcttgtatat tctgttagat taattcctat ttctagttgc    2040
tgtaaatgat atcttatgtt ttattacatt tctaatagga tatggtgttg gtgaaatgtt    2100
aaccctctca ttagatctac tagtttacct gttgattcta ttgtgttttc tatgtaaatg    2160
attttgtcag ctataaataa taacatttta ttttctcttt ccttgcaata cctatgctca    2220 tttattttt atgtttaccc attggttagg gcctcctgta tacattaaac agttcatagt    2280
catgatagtg agtattctta cactgttccc agtattacag ggaatgctta gaaattttct    2340
ttatttaaac attatgtttg ttgtagcctt gttaaaggct attttataat ttttactaga    2400 aatatttga catttattgt gattttttc tatctctaat ctattgagat agtcacattc    2460
cttttgtctt cactccatta taaaggtaag ttaccttaat aaaattgttg atatcatttc    2520
atc                                                                 2523

<210> SEQ ID NO 25
<211> LENGTH: 2166
<212> TYPE: DNA
<213> ORGANISM: human

<400> SEQUENCE: 25
gagggctcag agggagcacc ggtttggagc tgggaccccc tattttagct tttctgtggc      60
tggtgaatgg ggatcccagg atctcacaat ctcagggacc atgggctgtg ctgcagctc     120 acacccggaa gatgactgga tggaaaacat cgatgtgtgt gagaactgcc attatcccat    180
agtcccactg gatggcaagg gcacgctgct catccgaaat ggctctgagg tgcgggaccc    240
actggttacc tacgaaggct ccaatccgcc ggcttcccca ctgcaagaca acctggttat    300
cgctctgcac agctatgagc cctctcacga cggagatctg gctttgaga gggggaaca    360 gctccgcatc ctggagcaga gcggcgagtg gtggaaggcg cagtccctga ccacgggcca    420
ggaaggcttc atcccttca attttgtggc caaagcgaac agcctggagc cgaaccctg    480 gttcttcaag aacctgagcc gcaaggacgc ggagcggcag ctcctggcgc ccgggaacac    540
tcacggctcc ttcctcatcc gggagagcga agcaccgcg ggatcgtttt cactgtcggt    600
ccgggacttc gaccagaacc agggagaggt ggtgaaacat acaagatcc gtaatctgga    660 caacggtggc ttctacatct cccctcgaat cacttttccc ggcctgcatg aactggtccg    720
ccattacacc aatgcttcag atgggctgtg cacacgttg agccgcccct gccagaccca    780
gaagccccag aagccgtggt gggaggacga gtgggaggtt cccagggaga cgctgaagct    840
ggtggagcgg ctgggggctg gacagttcgg ggaggtgtgg atggggtact acaacgggca    900
cacgaaggtg gcggtgaaga gcctgaagca gggcagcatg tccccggacg ccttcctggc    960
cgaggccaac ctcatgaagc agctgcaaca ccagcggctg gttcggctct acgctgtggt   1020
```

-continued

```
cacccaggag cccatctaca tcatcactga atacatggag aatgacacac ttctagactc    1080
ccagttggag gagaaaggtc tgggggcctc ccctgggc aacttgggcc agcaactctt    1140
gcttctgccc acagggagtc tagtggattt tctcaagacc ccttcaggca tcaagttgac    1200
catcaacaaa ctcctggaca tggcagccca aattgcagaa ggcatggcat tcattgaaga    1260
gcggaattat attcatcgtg accttcgggc tgccaacatt ctggtgtctg cacccctgag    1320
ctgcaagatt gcagactttg cctagcacg cctcattgag acaacgagt acacagccag    1380 ggagggggcc aagtttccca ttaagtggac agcgccagaa gccattaact acgggacatt    1440
caccatcaag tcagatgtgt ggtcttttgg gatcctgctg acggaaattg tcacccacgg    1500
ccgcatccct acccaggga tgaccaaccc ggaggtgatt cagaacctgg agcgaggcta    1560
ccgcatggtg cgccctgaca actgtccaga ggagctgtac caactcatga ggctgtgctg    1620
gaaggagcgc ccagaggacc ggcccacctt tgactacctg cgcagtgtgc tggaggactt    1680
cttcacggcc acagagggcc agtaccagcc tcagccttga gaggcttga gaggccctgg    1740 ggttctcccc ctttctctcc agcctgactt ggggagatgg agttcttgtg ccatagtcac    1800
atggcctatg cacatatgga ctctgcacat gaatcccacc cacatgtgac acatatgcac    1860
cttgtgtctg tacacgtgtc ctgtagttgc gtggactctg cacatgtctt gtacatgtgt    1920
agcctgtgca tgtatgtctt ggacactgta caaggtaccc ctttctggct ctcccatttc    1980
ctgagaccac agagagaggg gagaagcctg ggattgacag aagcttctgc ccacctactt    2040
ttctttcctc agatcatcca gaagttcctc aagggccagg actttatcta atacctctgt    2100
gtgctcctcc ttggtgcctg gcctggcaca catcaggagt tcaataaatg tctgttgatg    2160
actgtt                                                              2166
```

<210> SEQ ID NO 26
<211> LENGTH: 2116
<212> TYPE: DNA
<213> ORGANISM: human

<400> SEQUENCE: 26

```
aagtcagggt gggacgtggg cgcggggaga caggtggtgg ctacgacggc gaagggagct     60
gagactgtcc aggcagccag gttaggccag gaggaccatg tgaatgggc cagagggctc    120 ccgggctggg cagggaccat gggctgtggc tgcagctcac acccggaaga tgactggatg    180
gaaaacatcg atgtgtgtga aactgccat tatcccatag tcccactgga tggcaagggc    240
acgctgctca tccgaaatgg ctctgaggtg cgggaccca tggttaccta cgaaggctcc    300
aatccgccgg cttccccact gcaagacaac ctggttatcg ctctgcacag ctatgagccc    360
tctcacgacg gagatctggg ctttgagaag ggggaacagc tccgcatcct ggagcagagc    420
ggcgagtggt ggaaggcgca gtccctgacc acgggccagg aaggcttcat cccttcaat    480 tttgtggcca aagcgaacag cctggagccc gaaccctggt tcttcaagaa cctgagccgc    540
aaggacgcgg agcggcagct cctggcgccc gggaacactc acggctcctt cctcatccgg    600
gagagcgaga gcaccgcggg atcgttttca ctgtcggtcc gggacttcga ccagaaccag    660
ggagaggtgg tgaaacatta caagatccgt aatctgaca acgtggcttt ctacatctcc    720
cctcgaatca ctttccccgg cctgcatgaa ctggtccgcc attacaccaa tgcttcagat    780
gggctgtgca cacggttgag ccgccctgc cagacccaga agcccagaa gccgtggtgg    840 gaggacgagt gggaggttcc cagggagacg ctgaagctgg tggagcggct gggggctgga    900
```

```
cagttcgggg aggtgtggat ggggtactac aacgggcaca cgaaggtggc ggtgaagagc    960
ctgaagcagg gcagcatgtc cccggacgcc ttcctggccg aggccaacct catgaagcag   1020
ctgcaacacc agcggctggt tcggctctac gctgtggtca cccaggagcc catctacatc   1080
atcactgaat acatggagaa tgggagtcta gtggattttc tcaagacccc ttcaggcatc   1140
aagttgacca tcaacaaact cctggacatg gcagcccaaa ttgcagaagg catggcattc   1200
attgaagagc ggaattatat tcatcgtgac cttcgggctg ccaacattct ggtgtctgac   1260
accctgagct gcaagattgc agactttggc ctagcacgcc tcattgagga caacgagtac   1320
acagccaggg aggggccaa gtttcccatt aagtggacag cgccagaagc cattaactac   1380
gggacattca ccatcaagtc agatgtgtgg tcttttggga tcctgctgac ggaaattgtc   1440
acccacggcc gcatccctta cccagggatg accaacccgg aggtgattca gaacctggag   1500
cgaggctacc gcatggtgcg ccctgacaac tgtccagagg agctgtacca actcatgagg   1560
ctgtgctgga aggagcgccc agaggaccgg cccacctttg actacctgcg cagtgtgctg   1620
gaggacttct tcacggccac agagggccag taccagcctc agccttgaga ggccttgaga   1680
ggccctgggg ttctccccct ttctctccag cctgacttgg ggagatggag ttcttgtgcc   1740
atagtcacat ggcctatgca catatggact ctgcacatga atcccaccca catgtgacac   1800
atatgcacct tgtgtctgta cacgtgtcct gtagttgcgt ggactctgca catgtcttgt   1860
acatgtgtag cctgtgcatg tatgtcttgg acactgtaca aggtacccct ttctggctct   1920
cccatttcct gagaccacag agagagggga gaagcctggg attgacagaa gcttctgccc   1980
acctactttt ctttcctcag atcatccaga agttcctcaa gggccaggac tttatctaat   2040
acctctgtgt gctcctcctt ggtgcctggc ctggcacaca tcaggagttc aataaatgtc   2100
tgttgatgac tgttgt                                                   2116

<210> SEQ ID NO 27
<211> LENGTH: 2064
<212> TYPE: DNA
<213> ORGANISM: human

<400> SEQUENCE: 27
gggagctgag actgtccagg cagccaggtt aggccaggag gaccatgtga atggggccag     60
agggctcccg ggctgggcag ggaccatggg ctgtggctgc agctcacacc cggaagatga    120
ctggatggaa acatcgatg tgtgtgagaa ctgccattat cccatagtcc cactggatgg    180
caagggcacg ctgctcatcc gaaatggctc tgaggtgcgg gacccactgg ttacctacga    240
aggctccaat ccgccggctt ccccactgca agacaacctg gttatcgctc tgcacagcta    300
tgagccctct cacgacggag atctgggctt tgagaagggg gaacagctcc gcatcctgga    360
gcagagcggc gagtggtgga aggcgcagtc cctgaccacg ggccaggaag gcttcatccc    420 cttcaattt gtggccaaag cgaacagcct ggagcccgaa ccctggttct tcaagaacct    480
gagccgcaag gacgcggagc ggcagctcct ggcgcccggg aacactcacg ctccttcct    540 catccgggag agcgagagca ccgcgggatc gttttcactg tcggtccggg acttcgacca    600
gaaccaggga gaggtggtga acattacaa gatccgtaat ctggacaacg gtggcttcta    660
catctcccct cgaatcactt ttcccggcct gcatgaactg gtccgccatt acaccaatgc    720
ttcagatggg ctgtgcacac ggttgagccg cccctgccag acccagaagc cccagaagcc    780
gtggtgggag gacgagtggg aggttcccag ggagacgctg aagctggtgg agcggctggg    840
ggctggacag ttcggggagg tgtggatggg gtactacaac gggcacacga aggtggcggt    900
```

```
gaagagcctg aagcagggca gcatgtcccc ggacgccttc ctggccgagg ccaacctcat    960
gaagcagctg caacaccagc ggctggttcg gctctacgct gtggtcaccc aggagcccat   1020
ctacatcatc actgaataca tggagaatgg gagtctagtg gattttctca agacccccttc  1080
aggcatcaag ttgaccatca acaaactcct ggacatggca gcccaaattg cagaaggcat   1140
ggcattcatt gaagagcgga attatattca tcgtgacctt cgggctgcca acattctggt   1200
gtctgacacc ctgagctgca agattgcaga ctttggccta gcacgcctca ttgaggacaa   1260
cgagtacaca gccagggagg gggccaagtt tcccattaag tggacagcgc cagaagccat   1320
taactacggg acattcacca tcaagtcaga tgtgtggtct tttgggatcc tgctgacgga   1380
aattgtcacc cacggccgca tcccttaccc agggatgacc aacccggagg tgattcagaa   1440
cctggagcga ggctaccgca tggtgcgccc tgacaactgt ccagaggagc tgtaccaact   1500
catgaggctg tgctggaagg agcgcccaga ggaccggccc acctttgact acctgcgcag   1560
tgtgctggag gacttcttca cggccacaga gggccagtac cagcctcagc cttgagaggc   1620
cttgagaggc cctggggttc tccccctttc tctccagcct gacttgggga gatggagttc   1680
ttgtgccata gtcacatggc ctatgcacat atggactctg cacatgaatc ccacccacat   1740
gtgacacata tgcaccttgt gtctgtacac gtgtcctgta gttgcgtgga ctctgcacat   1800
gtcttgtaca tgtgtagcct gtgcatgtat gtcttggaca ctgtacaagg tacccctttc   1860
tggctctccc atttcctgag accacagaga gaggggagaa gcctgggatt gacagaagct   1920
tctgcccacc tacttttctt tcctcagatc atccagaagt tcctcaaggg ccaggacttt   1980
atctaatacc tctgtgtgct cctccttggt gcctggcctg gcacacatca ggagttcaat   2040
aaatgtctgt tgatgactgt tgta                                          2064

<210> SEQ ID NO 28
<211> LENGTH: 2189
<212> TYPE: DNA
<213> ORGANISM: human

<400> SEQUENCE: 28
gtgtgaattt acttgtagcc tgagggctca gagggagcac cggtttggag ctgggacccc     60
ctattttagc ttttctgtgg ctggtgaatg gggatcccag gatctcacaa tctcagggac    120
catgggctgt ggctgcagct cacacccgga agatgactgg atggaaaaca tcgatgtgtg    180
tgagaactgc cattatccca tagtcccact ggatggcaag ggcacgctgc tcatccgaaa    240
tggctctgag gtgcgggacc cactggttac ctacgaaggc tccaatccgc ggcttccccc    300
actgcaagac aacctggtta tcgctctgca cagctatgag ccctctcacg acggagatct    360
gggctttgag aagggggaac agctccgcat cctggagcag agcggcgagt ggtggaaggc    420
gcagtccctg accacgggcc aggaaggctt catcccccttc aattttgtgg ccaaagcgaa    480
cagcctggag cccgaaccct ggttcttcaa gaacctgagc cgcaaggacg cggagcggca    540
gctcctggcg cccgggaaca ctcacggctc cttcctcatc cgggagagcg agagcaccgc    600
gggatcgttt tcactgtcgg tccgggactt cgaccagaac cagggagagg tggtgaaaca    660
ttacaagatc cgtaatctgg acaacggtgg cttctacatc tccccctcgaa tcacttttcc    720
cggcctgcat gaactggtcc gccattacac caatgcttca gatgggctgt gcacacggtt    780
gagccgcccc tgccagaccc agaagcccca gaagccgtgg tgggaggacg agtgggaggt    840
tcccagggag acgctgaagc tggtggagcg gctggggggct ggacagttcg gggaggtgtg    900
```

```
gatgggtac tacaacgggc acacgaaggt ggcggtgaag agcctgaagc agggcagcat    960
gtccccggac gccttcctgg ccgaggccaa cctcatgaag cagctgcaac accagcggct   1020
ggttcggctc tacgctgtgg tcacccagga gcccatctac atcatcactg aatacatgga   1080
gaatgacaca cttctagact cccagttgga ggagaaaggt ctgggggcct cccctgggg    1140
caacttgggc cagcaactct tgcttctgcc cacagggagt ctagtggatt ttctcaagac   1200
cccttcaggc atcaagttga ccatcaacaa actcctggac atggcagccc aaattgcaga   1260
aggcatggca ttcattgaag agcggaatta tattcatcgt gaccttcggg ctgccaacat   1320
tctggtgtct gacaccctga gctgcaagat tgcagacttt ggcctagcac gcctcattga   1380
ggacaacgag tacacagcca gggaggggc caagtttccc attaagtgga cagcgccaga   1440
agccattaac tacgggacat tcaccatcaa gtcagatgtg tggtcttttg ggatcctgct   1500
gacggaaatt gtcacccacg gccgcatccc ttacccaggg atgaccaacc cggaggtgat   1560
tcagaacctg gagcgaggct accgcatggt gcgccctgac aactgtccag aggagctgta   1620
ccaactcatg agggctgtgc tggaaggagcg cccagaggac cggcccacct ttgactacct   1680
gcgcagtgtg ctggaggact tcttcacggc cacagagggc cagtaccagc tcagccttg    1740
agaggccttg agaggccctg ggttctcccc cttctctc cagcctgact ggggagatg     1800
gagttcttgt gccatagtca catggcctat gcacatatgg actctgcaca tgaatcccac   1860
ccacatgtga cacatatgca ccttgtgtct gtacacgtgt cctgtagttg cgtggactct   1920
gcacatgtct tgtacatgtg tagcctgtgc atgtatgtct tggacactgt acaaggtacc   1980
cctttctggc tctcccattt cctgagacca cagagagagg ggagaagcct gggattgaca   2040
gaagcttctg cccacctact tttctttcct cagatcatcc agaagttcct caagggccag   2100
gactttatct aataccctg tgtgctcctc cttggtgcct ggcctggcac acatcaggag   2160
ttcaataaat gtctgttgat gactgttgt                                     2189
```

<210> SEQ ID NO 29
<211> LENGTH: 2120
<212> TYPE: DNA
<213> ORGANISM: human

<400> SEQUENCE: 29

```
gtgtgaattt acttgtagcc tgagggctca gagggagcac cggtttggag ctggaccccc    60
ctattttagc ttttctgtgg ctggtgaatg gggatcccag gatctcacaa tctcagggac   120
catgggctgt ggctgcagct cacacccgga agatgactgg atggaaaaca tcgatgtgtg   180
tgagaactgc cattatccca tagtcccact ggatggcaag ggcacgctgc tcatccgaaa   240
tggctctgag gtgcgggacc cactggttac ctacgaaggc tccaatccgc cggcttcccc   300
actgcaaggt gacccccaggc agcagggcct gaaagacaag gcctgcggat ccctggctgt   360
tggcttccac ctctccccca cctactttct ccccggtctt gccttccttg tccccaccc    420
tgtaactcca ggcttcctgc cgatcccagc tcggttctcc ctgatgcccc ttgtctttac   480
agacaacctg gttatcgctc tgcacagcta tgagccctct cacgacggag atctgggctt   540
tgagaagggg gaacagctcc gcatcctgga gcagagcggc gagtggtgga aggcgcagtc   600
cctgaccacg ggccaggaag gcttcatccc cttcaatttt gtggccaaag cgaacagcct   660
ggagcccgaa ccctggttct tcaagaacct gagccgcaag gacgcgggagc ggcagctcct   720
ggcgcccggg aacactcacg gctccttcct catccgggag agcgagagca ccgcgggatc   780
gttttcactg tcggtccggg acttcgacca gaaccaggga gaggtggtga acattacaa    840
```

```
gatccgtaat ctggacaacg gtggcttcta catctcccct cgaatcactt ttcccggcct       900
gcatgaactg gtccgccatt acaccaggta ctacaacggg cacacgaagg tggcggtgaa       960
gagcctgaag cagggcagca tgtccccgga cgccttcctg gccgaggcca acctcatgaa      1020
gcagctgcaa caccagcggc tggttcggct ctacgctgtg gtcacccagg agcccatcta      1080
catcatcact gaatacatgg agaatgggag tctagtggat tttctcaaga ccccttcagg      1140
catcaagttg accatcaaca aactcctgga catggcagcc caaattgcag aaggcatggc      1200
attcattgaa gagcggaatt atattcatcg tgaccttcgg gctgccaaca ttctggtgtc      1260
tgacaccctg agctgcaaga ttgcagactt tggcctagca cgcctcattg aggacaacga      1320
gtacacagcc agggaggggg ccaagtttcc cattaagtgg acagcgccag aagccattaa      1380
ctacgggaca ttcaccatca agtcagatgt gtggtctttt gggatcctgc tgacggaaat      1440
tgtcacccac ggccgcatcc cttacccagg gatgaccaac ccggaggtga ttcagaacct      1500
ggagcgaggc taccgcatgg tgcgcccctg caactgtcca gaggagctgt accaactcat      1560
gaggctgtgc tggaaggagc gcccagagga ccggcccacc tttgactacc tgcgcagtgt      1620
gctggaggac ttcttcacgg ccacagaggg ccagtaccag cctcagcctt gagaggcctt      1680
gagaggccct ggggttctcc ccctttctct ccagcctgac ttggggagat ggagttcttg      1740
tgccatagtc acatggccta tgcacatatg gactctgcac atgaatccca cccacatgtg      1800
acacatatgc accttgtgtc tgtacacgtg tcctgtagtt gcgtggactc tgcacatgtc      1860
ttgtacatgt gtagcctgtg catgtatgtc ttggacactg tacaaggtac ccctttctgg      1920
ctctcccatt tcctgagacc acagagagag gggagaagcc tgggattgac agaagcttct      1980
gcccacctac ttttctttcc tcagatcatc cagaagttcc tcaagggcca ggactttatc      2040
taatacctct gtgtgctcct ccttggtgcc tggcctggca cacatcagga gttcaataaa      2100
tgtctgttga tgactgttgt                                                  2120
```

<210> SEQ ID NO 30
<211> LENGTH: 2099
<212> TYPE: DNA
<213> ORGANISM: human

<400> SEQUENCE: 30

```
gtgtgaattt acttgtagcc tgagggctca gagggagcac cggtttggag ctgggacccc        60
ctattttagc ttttctgtgg ctggtgaatg gggatcccag gatctcacaa tctcagggac       120
catgggctgt ggctgcagct cacacccgga agatgactgg atggaaaaca tcgatgtgtg       180
tgagaactgc cattatccca tagtcccact ggatggcaag ggcacgctgc tcatccgaaa       240
tggctctgag gtgcgggacc cactggttac ctacgaaggc tccaatccgc ggcttcccc       300 actgcaagac aacctggtta tcgctctgca cagctatgag ccctctcacg acggagatct       360
gggctttgag aaggggggaac agctccgcat cctggagcag agcggcgagt ggtgaaggc      420 gcagtccctg accacgggcc aggaaggctt catccccttc aattttgtgg ccaaagcgaa       480
cagcctggag cccgaaccct ggttcttcaa gaacctgagc cgcaaggacg cggagcggca       540
gctcctggcg cccgggaaca ctcacggctc cttcctcatc cggagagcg agagcaccgc       600 gggatcgttt tcactgtcgg tccgggactt cgaccagaac cagggagagg tggtgaaaca       660
ttacaagatc cgtaatctgg acaacggtgg cttctacatc tccccctcgaa tcactttttcc     720 cggcctgcat gaactggtcc gccattacac caatgcttca gatgggctgt gcacacggtt       780
```

| | |
|---|---|
| gagccgcccc tgccagaccc agaagcccca gaagccgtgg tgggaggacg agtgggaggt | 840 |
| tcccagggag acgctgaagc tggtggagcg gctgggggct ggacagttcg gggaggtgtg | 900 |
| gatggggtac tacaacgggc acacgaaggt ggcggtgaag agcctgaagc agggcagcat | 960 |
| gtccccggac gccttcctgg ccgaggccaa cctcatgaag cagctgcaac accagcggct | 1020 |
| ggttcggctc tacgctgtgg tcacccagga gcccatctac atcatcactg aatacatgga | 1080 |
| gaatgggagt ctagtggatt ttctcaagac cccttcaggc atcaagttga ccatcaacaa | 1140 |
| actcctggac atggcagccc aaattgcaga aggcatggca ttcattgaag agcggaatta | 1200 |
| tattcatcgt gaccttcggg ctgccaacat tctggtgtct gacaccctga gctgcaagat | 1260 |
| tgcagacttt ggcctagcac gcctcattga ggacaacgag tacacagcca gggaggggc | 1320 |
| caagtttccc attaagtgga cagcgccaga agccattaac tacgggacat tcaccatcaa | 1380 |
| gtcagatgtg tggtcttttg ggatcctgct gacggaaatt gtcacccacg ccgcatccc | 1440 |
| ttacccaggg atgaccaacc cggaggtgat tcagaacctg gagcgaggct accgcatggt | 1500 |
| gcgccctgac aactgtccag aggagctgta ccaactcatg aggctgtgct ggaaggagcg | 1560 |
| cccagaggac cggcccacct ttgactacct cgcagtgtg ctggaggact tcttcacggc | 1620 |
| cacagagggc cagtaccagc ctcagccttg agaggccttg agaggccctg ggttctccc | 1680 |
| cctttctctc cagcctgact tggggagatg gagttcttgt gccatagtca catggcctat | 1740 |
| gcacatatgg actctgcaca tgaatcccac ccacatgtga cacatatgca ccttgtgtct | 1800 |
| gtacacgtgt cctgtagttg cgtggactct gcacatgtct tgtacatgtg tagcctgtgc | 1860 |
| atgtatgtct tggacactgt acaaggtacc cctttctggc tctcccattt cctgagacca | 1920 |
| cagagagagg ggagaagcct gggattgaca gaagcttctg cccacctact tttctttcct | 1980 |
| cagatcatcc agaagttcct caagggccag gactttatct aatacctctg tgtgctcctc | 2040 |
| cttggtgcct ggcctggcac acatcaggag ttcaataaat gtctgttgat gactgttgt | 2099 |

<210> SEQ ID NO 31
<211> LENGTH: 641
<212> TYPE: DNA
<213> ORGANISM: human

<400> SEQUENCE: 31

| | |
|---|---|
| ggagccgtcc ggcgcagcag tttctaggtc cccactgtcc ccgccgtccc gcccttcgc | 60 |
| gtcccgggaa ccggctggct tccgagccgc actcgccgat cctccaggca tgccccgcta | 120 |
| cgagctggct ttaatcctga aagccatgca gcggccagag actgctgcta ctttgaaacg | 180 |
| tacgatagag gccctgatgg acagaggagc aatagtgagg gacttggaaa acctgggtga | 240 |
| acgagcgctt ccttatagga tctctgccca cagtcagcag cacaacagag gcggttgcaa | 300 |
| gtggatggca agcttccttg tgacttctca tcctggcaat tttctggagt gtttgtgact | 360 |
| ggactttaac atttccaaaa tgtggcgaca gtgactgtta agtcttccca agacgagg | 420 |
| ttcctgggag cccagggct gcaagcatca ggacagcaga gaccaaattc atcattgaat | 480 |
| cctcaacatc tagcacaata tgcctggcat aagatatatc aaggtgtaca gactatattt | 540 |
| ttgctgattt ataattcaac tgcattgtag taatggaacc cagtctacat aaagctgata | 600 |
| tttaaaaatt tggttggact tcttttgtga cccagcacat g | 641 |

<210> SEQ ID NO 32
<211> LENGTH: 370
<212> TYPE: DNA
<213> ORGANISM: human

<400> SEQUENCE: 32

```
catgccccgc tataagctgg ctttaatcct gaaagccatg ccgcggccag actgctgctg      60
ctttgaaaca tacgatagag gttctgatgg aaaaaggagc aatagtgagg aacttggaaa     120
acctgggtga gtgagcgctt ccttgtaaga tctccaccca caatcagtgg cacaacagag     180
gcgggtattt cctggtgaat ttttatgcac caaccacaac tgttgaaagc atgatggagc     240
acttctccaa acgtagatgt gattagaccg aatattgtca aacaccctct gacccaggaa     300
ctaaaagaat gtgaagggat tgtcccaatc ccacttaaag gaaaattata ttacacaaag     360
aagaggaaga                                                            370
```

<210> SEQ ID NO 33
<211> LENGTH: 990
<212> TYPE: DNA
<213> ORGANISM: human

<400> SEQUENCE: 33

```
cggcgtctgc gcagctgcca gcgcctttaa gcccgggctc gcgctctcgg accgtgcttt      60
cgccgcctgg gagccgtccg gcgcagcagt ttctaggtcc ccactgtccc cgccgtcccg     120
cccccttcgcg tcccgggaac cggctggctt ccgagccgca ctcgccgatc ctccaggcat     180
gccccgctac gagctggctt taatcctgaa agccatgcag cggccagaga ctgctgctac     240
tttgaaacgt acgatagagg ccctgatgga cagaggagca atagtgaggg acttggaaaa     300
cctgggtgaa cgagcgcttc cttataggat ctctgcccac agtcagcagc acaacagagg     360
cgggtatttc ttggtggatt tttatgcacc accgcagct gttgaaagca tggtggagca     420
cttgtctcga gatatagatg tgattagagg gaatattgtc aaacaccctc tgacccagga     480
actaaaagaa tgtgaaggga ttgtcccagt cccactcgca gaaaaattat attccacaaa     540
gaagaggaag aagtgagaag attgccagat ttttagcctt atatgtaatt ccttcacatt     600
tgggcagcat ggacgagaag gaagaatttg caagtttggc ctttatataa gcatgtgttg     660
caggtgctgt ttgatttttc taaggtattt ttagcccttg atccccttg cttgcgagag      720
gtggggaact gctcactgac agcttctctg taacctgcag taccagtgga tcgttcttga     780
ttttgttttc attagtgtca tttctttgtc attgaggact tttcccctta caacagtaac     840
accatttttt gaagagcaaa acttataata cctcctggga ttgtgagcta gtcattcagc     900
ctgtgtaacc atgtggaaat aaaaattgac gaccaatgta ttatatggac aacttttgct     960
ttgagtaata aacttgattg taggaatgtg                                      990
```

<210> SEQ ID NO 34
<211> LENGTH: 7053
<212> TYPE: DNA
<213> ORGANISM: human

<400> SEQUENCE: 34

```
gcgagctgag ctgacagcgc ggagctggcg ctgtggagcg cagggagcct tgccggttcc      60
tccgaccggc gtctgcgagt acagcggcgg ctaacctgcc ccggcttcag gatttacaca     120
gacgtggggc gatgcttgtg accctgcagc tcctcaaagg cccctagaag cctgtttctc     180
cgtacagtcc aggacctcca gccccatgga gccccgatc ccacagagcg ccccccttgac     240
tcccaactca gtcatggtcc agccccttct tgacagccgg atgtcccaca gccggctcca     300
gcacccactc accatcctac ccattgacca ggtgaagacc agccatgtgg agaatgacta     360
```

```
catagacaac cctagcctgg ccctgaccac cggcccaaag cggacccggg gcggggcccc      420
agagctggcc ccgacgcccg cccgctgtga ccaggatgtc acccaccatt ggatctcctt      480
cagcgggcgc ccctgctctg ctacctgcct gccaccggct gcgtgaagct ggcccagcgt      540
ggctacgacc gtctgcgccg ccctggttgc cgctgcaagc acacgaacag cgtcatctgc      600
aaagcagcca gcggggatgc caagaccagc aggcccgaca agcctttctg acagtttgtg      660
tcgaagcccc agtgctctgc ctggaaacct ggttctcttc tgacatctaa gaagactgca      720
gcaaggtcag aggttttagc ctcctgaggc tgaccttgct agtctgccca ctccctaccc      780
ccagcttcgg aaaatacaga gaccaccacc acgtaccctg tattcccaa ggtgatgaag       840 aagcactttg gggcttttttt tcagggtcct gaaactttgt gtcaaacaga caatgcaggg     900
gcagggtgtg gtttgggggg aaattttttct ttttcagaag acagaacaca gatgtggaca    960
catatccgga aactgcagct gcttgaatgc cttcccagcc cctccttctc cctccctccc     1020 tccgccccc ccttcctctt tttccattgtc tttggctctc acaggagcta gctgcctggg     1080
aggaattgtt aactgagtac cagggtacct ttaaagaaga cccttggagt cttctatacc     1140
ttcttctcct tccccatctc actccacccc actttgtccc tgatgtcttg gggaaggtgt     1200
agaacaccct agcagttcct attgtatata cttgggagcc actgagaaca gaggacggcc     1260
agtgagtcca agcctcgttc ctccttctgc ctccccggag ccacaggatg gatttaggag     1320
ccactgctca gtgcacttct cccttccaac tgcatcaact aactctcggg ggtgttctgc     1380
tcaccacacc gtccttcggt tcttactgag tcacagactc gcctgcccac tacgtgtcct     1440
gggttctcta ctcagatccc ttccagaaac tttatatggg tagaggaagc cagggcggca    1500
aatgcgagac caaatatcat tttgccaatg agtctgaggc tgtggtctct ggatccagtc     1560
attatgtttt tatagaataa ttaaaccgga tgctaacggt gttttaaaaa ataataataa     1620
aacaacttgt ttcctttttgg ccacccccag gaagggctga tttcaaaatc tgggggcgag    1680
caacctcaag gaacacaatt tccctcccta tcaacaagag gattttaaca gcaaagaaga    1740
gaggcagcac ctcccattgg cagaatgacc gctgagccag gctgggtttg ggtttcttct    1800
cttctgattc tgctgctcac tgtcatagcc ttttgtgtat agtgatgtgt ctgtatcttt    1860
aatgtaaata gagagatgat gaaaaaagag tctattttag tgttaggaag ccccagcagg    1920
ggagtcggaa gagcttggaa gagctgggga gagggtaggg gaaaggtttt tccaggggcc    1980
actgggtttg agccctgctt ctgtgcacag ccacaccacc ctctcccgac agccctcaaa    2040
gacgtagcaa ctcttttctct caaggtgcta aaggactcag aaggtgcagc acgtccagtg    2100
ggtaggtact tgttgcatgc aaaagctgta gtgtatctgg tccttcctcc ccagcttttg    2160 tgtgggttc ttgctttgtg tggtattttg ttttcccctc taatgagagg gcatggcctg    2220
agtcagaaga gctaccccag gtgaaactgg aagtgcatga ggcagagcgt ccgtagcatt    2280
tccagtttgt tctgtatagg acagaggtgc ctccgggaag gaggcagcga ggtaggtagc    2340
tatgataggc acctaatgct tctcaaggac ttatttttttc cttcttgaag actagtagta    2400
acatcttatg atttagagta agttgattgt aaccataggt atttattgat tggaggaagg    2460
gagggtcata ttattttcgg cttttattat gtaacatttg ctagcttata aaaggcgaat    2520
gtgaaatatt gcatctgcat tttccaaggc tgattcgtgt agctaccctt gccacagttg    2580
tgacggatgt atggatgttc ttgaacattt cagaaggagt ggtagaaaaa aacacacatt    2640
cagccaacca cttatatgaa ttgaatgtat cagaagtgta ctgaagggac tggagatggt    2700
tttcctcaga tgaggggggcc ccaaaattga tagtgcacat ctgcacgctt tctgcgaggc    2760
```

```
ctcagaactt ttcccagggc ccctccctca aattgtctcc atgggaaact tgacccagtg    2820
gcaagttgca ctttggtgat cttggtggtc tacacacccg ttctgtggag agtcgattta    2880
cataagctgt gtatacacac acacacacac acacacacac acaccccctac              2940 cccacactga ctgtctaccg acagagaccc tatttcctgg caaacggcct cctgaaccct    3000 gacttttttgt gtacatactt gtaaacacgg attttttctgg gttttggttt gcttttttcct 3060 tttttccccc tgcccctgtt ctagcttgtt cttcttggtt tgctttcaac ctgcttgatg    3120
gatgtctgca gagtgctctc taagagtcca cctcagtgcc tcgtgtgctc agtggtcatg    3180
ggaaggagcg aaggaaccat ccttggttct cccagcttgg ttgtgtagca atccctcagc    3240 attgttttttc tcagcttctt ggcaaaaatt aaaacaacaa caacaacaac aacaacaaca   3300
acaaacagaa ggataaactg gcttgcctgt ggaccctccc cggctctggg gccagtcgag   3360
agccactgag ggacccagca ctcagagaca caacacacat gtgtagctgc ttctggctga    3420
gtgtgtttcc tgtcaccaat ggcctgtttg gctggacgat gcctcggctt gacctttttt    3480
gaaaagtgct ggttagttcc cgccccctgg taaacctggg gtaggtgggg gttctgtctt    3540
aactcgaggg gcacctggga tccaggacgc ttctagggg ctctggctgc ccgtgttaat     3600
gaaggacagc gcttccgcga gcaccctggg aactgggtct tgggtagcaa agccctccca    3660
gagaaaagat gggcacaact aaggcttttcc tgagcaggaa gggggtgaag accaatccct   3720
tcctttggtc ctttggtacg caccccctca gagctgagat ggaagacatg gctagttctt    3780
ttcagccttg tggagcctgt cagtcgccat catacctcga gtgaggccca gctagataat    3840
gacttgtcca agatggcaca cgtggaaagt tgatctgcac cagaacccgg atgactgtca    3900
ccttgaagcg tcctgttctc cttctgtgct gtcccaggaa gtgtctggcg ggcgtgggca    3960
gcacagctct acactgtacg attcactagg gcatcctgcg agcctcacta gccttctggt    4020
tcatgccttt gacaagcatt tttgtgcccc ctctgcttac tgtgacagtc gatgatgaat    4080
cttgcgttgc cattttctgc tgtgggtaac tgcgtgcagt gtcttgcctt gctttctctt    4140
cttactgtcc cacagcttgg tttcatgtta caaacagaaa agctcgaggc tccaccccg     4200 ccacatccca acttcatttc cccctcactg tagcccattt ccaccccacc acaaagttgc    4260
cacaggtttt ctttgtatag aatatttatt ttgaagctct attttaatag tatttatttt    4320
agaaagtcta ctattgtaag agttcttctg tttgtgaaga aaaaaacaag ttaaaaactg    4380
aatgtactga tttagaaaat atatataaat atatattgtt aaatatactt tgattgcgcc    4440
actgcactcc agccttggcg accagactaa gacgctgtct caaaaaaaaa caaaacgac    4500 aaaaaaaaa caaaacagaa aaaataaact aaggcaatga cagtccctgg caaatgctgg    4560
gagggaggca gcagtggtca gggaaggtaa ccctgaagca ggacttgtaa agcaaataag    4620
attgggaggc caaggtgggt ggatcacgag gtcaggagtt cgagaccagc ctggccaaca    4680
tagtgaaacc ccgtctttac taaaaataca aaaaaattag ccaggtgtgg tggtgggtgc    4740
ctgtagtccc agctacttgg gaggctgagg caggagaatc tcgaacccag gaggcggagg    4800
ttacagtcag ctgagaccgc accattgcac tccagcctgg gtgacagagc aagattccgt    4860
ctcaaaaaaa aaaaaaaaaa aaaaaccaa gaagaaaagg aatgaattag aacttcttct    4920
gcttggactt aagggcatca tcaggcaggt tttgggtagg atagcagggg aggcagagac    4980
atagtcgggg tcagtggtca tgagtgtggc tttgagccca aaaacttggt ttctgttccc    5040
tactttgcca ctcagtagtg catgactttg gccaaatttc ttaaattcat gaagcaagtt    5100
```

| | | | | | |
|---|---|---|---|---|---|
| tccgggtgaa | tgaaatgggg | ataaaaatag | tgttcaaacc | tatccgttgg | tttgtgtgaa | 5160 |
| actgaaatga | atagtatcgt | gcaggtactt | gtgagcaagg | ggagctgctg | tttcctgtcc | 5220 |
| ctttatgatg | ggaaatatct | agacaagttc | ccaaccctct | gcactgcagg | ctgcatggca | 5280 |
| cggagggtct | tgtaacacag | ctggggctgg | ccttctttta | ggagcttcag | tggttctgaa | 5340 |
| aacttttatt | tgtttgtttg | ttttagtaga | tgtggggtct | ttctgtgttg | tccggactgg | 5400 |
| tctcaaactt | ctggactcaa | gtgatcctcc | cccgctcaac | ctcccaaagt | gttgggatta | 5460 |
| caggtgtgag | ccactgtgcc | cagccttgaa | aacttttca | ggttcttcca | gggttactgg | 5520 |
| gcaattaaat | atttctattt | cattataagt | cagttttca | aagttatatt | atcttaatta | 5580 |
| cctttttat | atgtattagt | gtagagtagc | attttatatt | ttgatatcct | ccttatgcat | 5640 |
| agttttcac | tttttattcc | tagttttcg | ttttaataa | gactttcaag | aaatttattt | 5700 |
| tattggcctt | ttgaaaaaag | cagctttaga | taaagtaagc | agttctgctt | tcattttata | 5760 |
| atttatttct | actttgttt | cattaatctt | ttcctccggc | atgccttgga | ttttgttgtg | 5820 |
| ttactctttt | tctagaggct | cgcattgtgt | gtctggttca | cttatgatca | cgcttgccta | 5880 |
| cttttaagaa | tggaagaggg | gaggtggagg | gtggctgcac | agtcgagggt | gtgaggcagt | 5940 |
| cttgctctag | ccccaccatg | ccctcagccc | gctgtggcca | cgctggttcc | tcaattgctg | 6000 |
| gggcgtgcag | tgtctgtaag | ggaggctact | gatgccatcc | gaggaagatg | taaggtttcg | 6060 |
| tgtgggcagc | gagagcctag | caggcatgtg | gggtgcccag | caaagggtaa | cagtggacag | 6120 |
| ttgttgcctc | attccacaga | gttttgattt | ttttttttt | tttaatggtc | actccatcaa | 6180 |
| catcccccat | ggccagagcc | tgagctggtc | cccagagaca | caggcattca | gctgacagcc | 6240 |
| tcgccttcac | gctgctgctg | ttctcatggg | ggacaggcct | caggtggcaa | tgcacaaatc | 6300 |
| attagttaag | ggcagttgtg | acagttacca | aggagtgtag | cccccgcccg | agtgaaaaca | 6360 |
| gccctaacca | ggggtgggga | ccttggggct | ctgacccgaa | gggtaggaga | agctggaagg | 6420 |
| acagcattcc | tgtctgcgaa | ggcaggagca | aagctgccag | gctatgaagg | aaatggctgg | 6480 |
| agcctgaagt | catgcaagct | ggggctggca | gggacagggc | caacttccag | gcctggggc | 6540 |
| caccatgagg | attcaggacg | tgaccccccag | ggcacatgaa | ggccttccat | ctgtatttaa | 6600 |
| gaaaagactt | tatcagacga | gtatggtgct | cacgcctgta | atcttagcac | tttgggaggc | 6660 |
| tgaggcaggt | ggatcacgag | gtcaggagtt | caagaccagc | ctggccaata | tggtaaaccc | 6720 |
| catctctact | aaaactacaaa | atagccaggc | atggtggcgc | acgcctgtag | tcccagctac | 6780 |
| tcgggaggct | gaggcagaag | aatcacttga | acccgggagg | tggaggttac | agtgagccaa | 6840 |
| gatcgcgcca | ctacactcca | gcctgggtga | cagagtgaga | ctccgtctca | aaaaaaccaa | 6900 |
| aagactttat | cttatttcct | atatgttgt | ggtttcagtc | ctgatgtata | atttgaccct | 6960 |
| agttagaatg | gttatctgag | gaagtggcct | gtacgatttc | tgcttttta | aatgtgtggc | 7020 |
| tcccttcttt | cattgattaa | cgtatgatta | ttt | | | 7053 |

<210> SEQ ID NO 35
<211> LENGTH: 3756
<212> TYPE: DNA
<213> ORGANISM: human

<400> SEQUENCE: 35

| | | | | | |
|---|---|---|---|---|---|
| ggagttagcg | acagggaggg | atgcgcgcct | gggtgtagtt | gtgggggagg | aagtggctag | 60 |
| ctcagggctt | caggggacag | acaggagag | atgactgagt | tagatgagac | gaggggcgg | 120 |
| gctgggggtg | cgagaaggaa | gcttggcaag | gagactaggt | ctaggggac | cacagtgggg | 180 |

```
caggctgcat ggaaaatatc cgcagggtcc cccaggcaga acagccacgc tccaggccag      240
gctgtcccta ctgcctggtg gagggggaac ttgacctctg ggagggcgcc gctcttgcat      300
agctgagcga gcccgggtgc gctggtctgt gtggaaggag gaaggcaggg agaggtagaa      360
ggggtggagg agtcaggagg aataggccgc agcagccctg gaaatgatca ggaaggcagg      420
cagtgggtgc agggctgcag gagggccggg agggctaatc ttcaacttgt ccatgccagc      480 agccccttt tttccagacc aagggctgtg aacccgcctg gggatgaggc ctggtcttgt      540
ggaactgaac ttagctcgac ggggctgacc gctctggccc agggtggtat gtaattttcg      600
ctcggcctgg gacggggccc aggccggcc cagcctggtg gagcgtccag gtctgggtgc      660
gaagccaggc ccctgggcgg aggtgagggg tggtctgagg agtgatgtgg agttaaggcg      720
ccatcctcac cggtgactgg tgcggcacct agcatgtttg acaggcgggg actgcgaggc      780
acgctgctcg ggtgttgggg acaacattga ccaacgcttt attttccagg tggcagtgct      840
ccttttggac ttttctctag gtttggcgct aaactcttct tgtgagctca ctccaccct      900 tcttcctccc tttaacttat ccattcactt aaaacattac ctggtcatct ggtaagcccg      960
ggacagtaag ccgagtggct gttggagtcg gtattgttgg taatggtgga ggaagagagg     1020
ccttcccgct gaggctgggg tggggcggat cggtgttgct tgcctgcaga gagggtgggg     1080
agtgaatgtg cacccttggg tgggcctgca gccatccagc tgaaagttac aaaaatgctt     1140
catggaccgt ggtttgttac tatagtgttc ctcatggcga gcagatggaa ccgggagaca     1200
tggagtccct ggccagtgtg agtcctagca ttgcaggagg ggagaccctg gaggagagag     1260
cccgcctcaa ttgatgcctg cagattgaat ttccagaggc ttaggaggag gaagttctcc     1320
aatgttctgt ttccaggcct tgctcaggaa gccctgtatt caggaggcta ccatttaaag     1380
tttgcagatg agcttatggg gggcaatctt aaaaagtcca cagcagatgc atccggctcg     1440
aggggccatc agctttgaat aaatgcttgt tccagagccc atgaatgcca gcaggcaccc     1500 ctccttcct ggggtaaagg ttttcagatg ctgcatcttc taaattgagc ctccggtcat     1560
actagttttg tgcttggaac cttgcttcaa gaagatccct aagctgtaga acattttaac     1620
gttgatgcca caacgcagat tgatgccttg tagatggagc ttgcagatgg agccccgtga     1680
cctctcacct acccacctgt ttgcctgcct tcttgtgcgt ttctcggaga agttcttagc     1740
ctgatgaaat aacttgggc gttgaagagc tgtttaattt taaatgcctt agactgggga     1800
tatattagag gaagcagatt gtcaaattaa gggtgtcatt gtgttgtgct aaacgctggg     1860
agggtacaag ttggtcattc ctaaatctgt gtgtgagaaa tggcaggtct agtttgggca     1920
ttgtgattgc attgcagatt actaggagaa gggaatggtg ggtacaccgg tagtgctctt     1980
ttgttcttgc ttcgtttttt taaacttgaa ctttacttcg ttagatttca taatactttc     2040
ttggcattct agtaagagga ccctgaggtg ggagttgtgg gggacgggga aaggggaca     2100 gcttggcacc ggtcccgtgg gcgttgcagt gtggggatg gggtatgca gcttggcact     2160 ggtactggga gggatgaggg tgaagaaggg gagagggttg gttagagata cagtgtgggt     2220
ggtgggggtg gtaggaaatg caggttgaag ggaattctct ggggctttgg ggaatttagt     2280
gcgtgggtga gccaagaaaa tactaattaa taatagtaag ttgttagtgt ggttaagtt      2340 gttgcttgga agtgagaagt tgcttagaaa cttttccaaag tgcttagaac tttaagtgca      2400
aacagacaaa ctaacaaaca aaaattgttt tgctttgcta caaggtgggg aagactgaag     2460
aagtgttaac tgaaaacagg tgacacagag tcaccagttt tccgagaacc aaagggaggg     2520
```

```
gtgtgtgatg ccatctcaca ggcaggggaa atgtctttac cagcttcctc ctggtggcca    2580
agacagcctg tttcagaggg ttgttttgtt tggggtgtgg gtgttatcaa gtgaattagt    2640
cacttgaaag atgggcgtca gacttgcata cgcagcagat cagcatcctt cgctgcccct    2700
tagcaactta ggtggttgat ttgaaactgt gaaggtgtga ttttttcagg agctggaagt    2760
cttagaaaag ccttgtaaat gcctatattg tgggctttta acgtatttaa gggaccactt    2820
aagacgagat tagatgggct cttctggatt tgttcctcat ttgtcacagg tgtcttgtga    2880
ttgaaaatca tgagcgaagt gaaattgcat tgaatttcaa gggaatttag tatgtaaatc    2940
gtgccttaga aacacatctg ttgtctttc tgtgtttggt cgatattaat aatggcaaaa     3000
tttttgccta tctagtatct tcaaattgta gtctttgtaa caaccaaata accttttgtg    3060
gtcactgtaa aattaatatt tggtagacag aatccatgta cctttgctaa ggttagaatg    3120
aataatttat tgtattttta atttgaatgt ttgtgctttt taaatgagcc aagactagag    3180
gggaaactat cacctaaaat cagtttggaa aacaagacct aaaagggaa ggggatgggg     3240 attgtgggga gagagtgggc gaggtgcctt tactacatgt gtgatctgaa aaccctgctt    3300
ggttctgagc tgcgtctatt gaattggtaa agtaatacca atggcttttt atcatttcct    3360
tcttcccttt aagtttcact tgaaatttta aaaatcatgg ttattttat cgttgggatc     3420 tttctgtctt ctgggttcca ttttttaaat gtttaaaaat atgttgacat ggtagttcag    3480
ttcttaacca atgacttggg gatgatgcaa acaattactg tcgttgggat ttagagtgta    3540
ttagtcacgc atgtatgggg aagtagtctc gggtatgctg ttgtgaaatt gaaactgtaa    3600
aagtagatgg ttgaaagtac tggtatgttg ctctgtatgg taagaactaa ttctgttacg    3660
tcatgtacat aattactaat cacttttctt ccccttaca gcacaaataa agtttgagtt     3720
ctaaactcat tagaaaaaaa aaaaaaaaaa aaaaaa                              3756

<210> SEQ ID NO 36
<211> LENGTH: 4324
<212> TYPE: DNA
<213> ORGANISM: human

<400> SEQUENCE: 36
ttcctcattg gaagaagaag catagtatag aagaaaggca aacacaacac attcaacctc      60
tgccaccatg gggaactggg ctgtgaatga ggggctctcc attttgtca ttctggtttg      120 gctggggttg aacgtcttcc tctttgtctg gtattaccgg gtttatgata ttccacctaa     180 gttctttac acaagaaaac ttcttgggtc agcactggca ctggccaggg ccctgcagc      240 ctgcctgaat tcaactgca tgctgattct cttgccagtc tgtcgaaatc tgctgtcctt     300
cctcaggggt tccagtgcgt gctgctcaac aagagttcga agacaactgg acaggaatct    360 caccttcat aaaatggtgg catggatgat tgcacttcac tctgcgattc acaccattgc     420
acatctattt aatgtggaat ggtgtgtgaa tgcccgagtc aataattctg atccttattc     480
agtagcactc tctgaacttg gagacaggca aaatgaaagt tatctcaatt ttgctcgaaa    540
gagaataaag aaccctgaag gaggcctgta cctggctgtg accctgttgg caggcatcac     600
tggagttgtc atcacgctgt gcctcatatt aattatcact tcctccacca aaaccatccg    660
gaggtcttac tttgaagtct tttggtacac acatcatctc tttgtgatct tcttcattgg    720
ccttgccatc catggagctg aacgaattgt acgtgggcag accgcagaga gtttggctgt    780
gcataatata acagtttgtg aacaaaaaat ctcagaatgg ggaaaaataa aggaatgccc    840
aatccctcag tttgctggaa accctcctat gacttggaaa tggatagtgg gtcccatgtt    900
```

```
tctgtatctc tgtgagaggt tggtgcggtt ttggcgatct caacagaagg tggtcatcac    960
caaggtggtc actcaccctt tcaaaaccat cgagctacag atgaagaaga aggggttcaa   1020
aatggaagtg ggacaataca tttttgtcaa gtgcccaaag gtgtccaagc tggagtggca   1080
cccttttaca ctgacatccg cccctgagga agacttcttt agtatccata tccgcatcgt   1140
tggggactgg acagaggggc tgttcaatgc ttgtggctgt gataagcagg agtttcaaga   1200
tgcgtggaaa ctacctaaga tagcggttga tgggcccttt ggcactgcca gtgaagatgt   1260
gttcagctat gaggtggtga tgttagtggg agcagggatt ggggtcacac ccttcgcatc   1320
cattctcaag tcagtctggt acaaatattg caataacgcc accaatctga agctcaaaaa   1380
gatctacttc tactggctgt gccgggacac acatgccttt gagtggtttg cagatctgct   1440
gcaactgctg gagagccaga tgcaggaaag gaacaatgcc ggcttcctca gctacaacat   1500
ctacctcact ggctgggatg agtctcaggc caatcacttt gctgtgcacc atgatgagga   1560
gaaagatgtg atcacaggcc tgaaacaaaa gactttgtat ggacggccca actgggataa   1620
tgaattcaag acaattgcaa gtcaacaccc taataccaga ataggagttt tcctctgtgg   1680
acctgaagcc ttggctgaaa ccctgagtaa acaaagcatc tccaactctg agtctggccc   1740
tcggggagtg catttcattt tcaacaagga aaacttctaa cttgtctctt ccatgaggaa   1800
ataaatgtgg gttgtgctgc caaatgctca aataatgcta attgataata taaataccccc  1860 ctgcttaaaa atgacaaaaa agaaactata atgtaatggt tttcccttaa aggaatgtca   1920
aagattgttt gatagtgata agttacattt atgtggagct ctatggtttt gagagcactt   1980
ttacaaacat tatttcattt ttttcctctc agtaatgtca gtggaagtta gggaaaagat   2040
tcttggactc aattttagaa tcaaagggaa aggatcaaa aggttcagta acttccctaa    2100
gattatgaaa ctgtgaccag atctagccca tcttactcca ggtttgatac tctttccaca   2160
atactgagct gcctcagaat cctcaaaatc agttttata ttccccaaaa gaagaaggaa    2220
accaaggagt agctatatat ttctactttg tgtcattttt gccatcatta ttatcatact   2280
gaaggaaatt ttccagatca ttaggacata atacatgttg agagtgtctc aacacttatt   2340
agtgacagta ttgacatctg agcatactcc agtttactaa tacagcaggg taactgggcc   2400
agatgttctt tctacagaag aatattggat tgattggagt taatgtaata ctcatcatt    2460 accactgtgc ttggcagaga gcggatactc aagtaagttt tgttaaatga atgaatgaat   2520
ttagaaccac acaatgccaa gatagaatta atttaaagcc ttaaacaaaa tttatctaaa   2580
gaaataactt ctattactgt catagaccaa aggaatctga ttctccctag ggtcaagaac   2640
aggctaagga tactaaccaa taggattgcc tgaagggttc tgcacattct tatttgaagc   2700
atgaaaaaag agggttggag gtggagaatt aacctcctgc catgactctg gctcatctag   2760
tcctgctcct tgtgctataa aataaatgca gactaatttc ctgcccaaag tggtcttctc   2820
cagctagccc ttatgaatat tgaacttagg aattgtgaca aatatgtatc tgatatggtc   2880
atttgtttta aataacaccc accccttatt ttccgtaaat acacacacaa aatggatcgc   2940
atctgtgtga ctaatggttt atttgtatta tatcatcatc atcatcctaa aattaacaac   3000
ccagaaacaa aaatctctat acagagatca aattcacact caatagtatg ttctgaatat   3060
atgttcaaga gagagtctct aaatcactgt tagtgtggcc aagagcaggg ttttcttttt   3120
gttcttagaa ctgctcccat ttctgggaac taaaaccagt tttatttgcc ccaccccttg   3180
gagccacaaa tgtttagaac tcttcaactt cggtaatgag gaagaaggag aaagagctgg   3240
```

-continued

| | |
|---|---|
| gggaagggca gaagactggt ttaggaggaa aaggaaataa ggagaaaaga gaatgggaga | 3300 |
| gtgagagaaa ataaaaaagg caaaagggag agagaggggga aggggtctc atattggtca | 3360 |
| ttccctgccc cagatttctt aaagtttgat atgtatagaa tataattgaa ggaggtatac | 3420 |
| acatattgat gttgttttga ttatctatgg tattgaatct tttaaaatct ggtcacaaat | 3480 |
| tttgatgctg aggggggatta ttcaagggac taggatgaac taaataagaa ctcagttgtt | 3540 |
| ctttgtcata ctactattcc tttcgtctcc cagaatcctc agggcactga gggtaggtct | 3600 |
| gacaaataag gcctgctgtg cgaatatagc ctttctgaaa tgtaccagga tggtttctgc | 3660 |
| ttagagacac ttaggtccag cctgttcaca ctgcacctca ggtatcaatt catctattca | 3720 |
| acagatattt attgtgttat tactatgagt caggctctgt ttattgtttc aattctttac | 3780 |
| accaaagtat gaactggaga gggtacctca gttataagga gtctgagaat attggccctt | 3840 |
| tctaacctat gtgcataatt aaaaccagct tcatttgttg ctccgagagt gtttctccaa | 3900 |
| ggttttctat cttcaaaacc aactaagtta tgaaagtaga gagatctgcc ctgtgttatc | 3960 |
| cagttatgag ataaaaaatg aatataagag tgcttgtcat tataaaagtt tcctttttta | 4020 |
| ttctctcaag ccaccagctg ccagccacca gcagccagct gccagcctag cttttttttt | 4080 |
| ttttttttt ttttagcact tagtatttag catttattaa caggtactct aagaatgatg | 4140 |
| aagcattgtt tttaatctta agactatgaa ggttttctt agttcttctg cttttgcaat | 4200 |
| tgtgtttgtg aaatttgaat acttgcaggc tttgtatgtg aataattcta gcgggggacc | 4260 |
| tgggagataa ttcctacggg gaattcttaa aactgtgctc aactattaaa atgaatgagc | 4320 |
| tttc | 4324 |

<210> SEQ ID NO 37
<211> LENGTH: 1688
<212> TYPE: DNA
<213> ORGANISM: human

<400> SEQUENCE: 37

| | |
|---|---|
| ggagtcgacc gctcgggcag cgccaccgcc acgagagccc gggacgcggg aaagaccgaa | 60 |
| aggaagagga agaggcaccg gtggccatgg ggctggaggc ggcgcgcgag ctggagtgcg | 120 |
| cggcgctggg cacgctgctg cgggatccgc gggaggcgga acgcacgctg ctgctggact | 180 |
| gccgccccttt cctggccttc tgccggcgcc acgtgcgcgc cgcgcggcca gtgccttgga | 240 |
| acgcgctgct gcggcgccgc gcgcgcggcc ctcctgccgc cgttctcgcc tgcctgctgc | 300 |
| ccgaccgcgc gctgcggacg cgcctggtcc gcggggagct ggcgcgggcc gtggtgctgg | 360 |
| acgagggcag tgcctcggtg gcggagctcc ggcccgacag cccggctcat gtgctgctgg | 420 |
| ccgcgctgct gcacgagacc cgcgcggggc ccactgccgt gtacttcctg cgaggaggct | 480 |
| tcgacggctt ccagggctgc tgtcccgatc tgtgctctga ggcccccgcc cctgcgctgc | 540 |
| cgccaacagg ggacaaaacc agccgctccg actccagggc tcctgtctac gaccagggtg | 600 |
| gccctgtgga gatcttgccc tacctgttcc tgggcagctg cagtcactcg tcagacctgc | 660 |
| aggggctgca ggcctgtggc atcacagccg tcctcaacgt gtccgccagc tgccccaacc | 720 |
| actttgaggg ccttttccgc tacaagagta tccctgtgga ggacaaccag atggtggaga | 780 |
| tcagtgcctg gttccaggag gccataggct tcattgactg ggtgaagaac agcggaggcc | 840 |
| gggtgctggt gcactgccag gcgggtatct cgcgctctgc caccatctgt ctggcatacc | 900 |
| tcatgcagag tcgccgtgtg cggctggacg aggcctttga cttcgttaag cagcgccggg | 960 |
| gggtcatctc ccccaacttc agtttcatgg ggcagctgct gcagtttgag acccaggtgc | 1020 |

```
tgtgtcactg aggtggtgcc cctctgcctg cctgccccac tgtgctggca ggagctgact    1080
gtggactggt gggctcccct ctgggccagc acagtcccct cacctctggc agggctgcta    1140
cctcctcaga gtttcagaag cccccacatg ggggctctag gaatgccggc atgctggtct    1200
ttccgacctg tgtgctcttct gctggggggac tgaggctggc cctcattcgg ggtcgggaac    1260
caagggtgtg tctgctcttt ccctccccat cctctggcag aaatcagcta gacgctatac    1320
cgtggactct ccctggtcca ccaccatgtt gaagcccttg gcagcctgag agctccaagg    1380
aacaagctgt gacaaccagg agccctgtct gtgggttcgt ctgcccaggg cctggagccc    1440
aagccctgtg ttcctgggga agctggggac ttgggaagtg atgggtgtgt catgttgcgt    1500
gtgtctgtct gtgagccttt cacacctgtg ctggcgctgg aaaattattt gtgctcagct    1560
gacatttaac actccctccc ccgcttcctc ctagccctgt gggcaggggt tggaaactta    1620
gcactttata tttatacaga acattcagga tatgtcaata aatattgtt atatttaaaa    1680 aacaacaa                                                             1688

<210> SEQ ID NO 38
<211> LENGTH: 7783
<212> TYPE: DNA
<213> ORGANISM: human

<400> SEQUENCE: 38
aatacttgtt gcaataattg cccacgatag ctgctcaaac aagagagttg gaattcatct      60
gtaaaaatca ctacatgtaa cgtaggagac aagaaaaata ttaatgacag aagatctgcg     120
aacatgatgc acgtgaataa ttttcccttt agaaggcatt cctggatatg ttttgatgtg     180
gacaatggca catctgcggg acggagtccc ttggatccca tgaccagccc aggatccggg     240
ctaattctcc aagcaaattt tgtccacagt caacgacggg agtccttcct gtatcgatcc     300
gacagcgatt atgacctctc tccaaagtct atgtcccgga actcctccat tgccagtgat     360
atacacggag atgacttgat tgtgactcca tttgctcagg tcttggccag tctgcgaact     420
gtacgaaaca actttgctgc attaactaat ttgcaagatc gagcacctag caaaagatca     480
cccatgtgca accaaccatc catcaacaaa gccaccataa cagaggaggc ctaccagaaa     540
ctggccagcg agaccctgga ggagctggac tggtgtctgg accagctaga gaccctacag     600
accaggcact ccgtcagtga gatggcctcc aacaagtta aaaggatgct taatcgggag     660
ctcacccatc tctctgaaat gagtcggtct ggaaatcaag tgtcagagtt tatatcaaac     720
acattcttag ataagcaaca tgaagtgaa attccttctc caactcagaa ggaaaaggag     780
aaaaagaaaa gaccaatgtc tcagatcagt ggagtcaaga attgatgca cagctctagt     840 ctgactaatt caagtatccc aaggtttgga gttaaaactg aacaagaaga tgtccttgcc     900
aaggaactag aagatgtgaa caaatggggt cttcatgttt tcagaatagc agagttgtct     960
ggtaaccggc ccttgactgt tatcatgcac accattttc aggaacggga tttattaaaa    1020
acatttaaaa ttccagtaga tactttaatt acatatctta tgactctcga agaccattac    1080
catgctgatg tggcctatca caacaatatc catgctgcag atgttgtcca gtctactcat    1140
gtgctattat ctacacctgc tttggaggct gtgtttacag atttggagat tcttgcagca    1200
atttttgcca gtgcaataca tgatgtagat catcctggtg tgtccaatca atttctgatc    1260
aatacaaact ctgaacttgc cttgatgtac aatgattcct cagtcttaga gaaccatcat    1320
ttggctgtgg gctttaaatt gcttcaggaa gaaaactgtg acattttcca gaatttgacc    1380
```

```
aaaaaacaaa gacaatctttt aaggaaaatg gtcattgaca tcgtacttgc aacagatatg    1440
tcaaaacaca tgaatctact ggctgatttg aagactatgg ttgaaactaa gaaagtgaca    1500
agctctggag ttcttcttct tgataattat tccgatagga ttcaggttct tcagaatatg    1560
gtgcactgtg cagatctgag caacccaaca aagcctctcc agctgtaccg ccagtggacg    1620
gaccggataa tggaggagtt cttccgccaa ggagaccgag agagggaacg tggcatggag    1680
ataagcccca tgtgtgacaa gcacaatgct tccgtggaaa aatcacaggt gggcttcata    1740
gactatattg ttcatcccct ctgggagaca tgggcagacc tcgtccaccc tgacgcccag    1800
gatattttgg acactttgga ggacaatcgt gaatggtacc agagcacaat ccctcagagc    1860
ccctctcctg cacctgatga cccagaggag ggccggcagg gtcaaactga gaaattccag    1920
tttgaactaa ctttagagga agatggtgag tcagacacgg aaaaggacag tggcagtcaa    1980
gtggaagaag acactagctg cagtgactcc aagactcttt gtactcaaga ctcagagtct    2040
actgaaattc cccttgatga acaggttgaa gaggaggcag taggggaaga agaggaaagc    2100
cagcctgaag cctgtgtcat agatgatcgt tctcctgaca cgtaacagtg caaaaacttt    2160
catgcctttt ttttttttaa gtagaaaaat tgtttccaaa gtgcatgtca catgccacaa    2220
ccacggtcac acctcactgt catctgccag gacgtttgtt gaacaaaact gaccttgact    2280
actcagtcca gcgctcagga atatcgtaac cagttttttc acctccatgt catccgagca    2340
aggtggacat cttcacgaac agcgtttta acaagatttc agcttggtag agctgacaaa    2400
gcagataaaa tctactccaa attattttca agagagtgtg actcatcagg cagcccaaaa    2460
gtttattgga cttggggttt ctattccttt ttatttgttt gcaatatttt cagaagaaag    2520
gcattgcaca gagtgaactt aatggacgaa gcaacaaata tgtcaagaac aggacatagc    2580
acgaatctgt taccagtagg aggaggatga gccacagaaa ttgcataatt ttctaatttc    2640
aagtcttcct gatacatgac tgaatagtgt ggttcagtga gctgcactga cctctacatt    2700
ttgtatgata tgtaaaacag attttttgta gagcttactt ttattattaa atgtattgag    2760
gtattatatt taaaaaaaac tatgttcaga acttcatctg ccactggtta ttttttttcta    2820 aggagtaact tgcaagtttt cagtacaaat ctgtgctaca ctggataaaa atctaattta    2880
tgaattttac ttgcacctta tagttcatag caattaactg atttgtagtg attcattgtt    2940
tgttttatat accaatgact tccatatttt aaaagagaaa aacaacttta tgttgcagga    3000 aaccctttt gtaagtcttt attatttact ttgcattttg tttcactctt tccagataag    3060
cagagttgct cttcaccagt gttttttcttc atgtgcaaag tgactatttg ttctataata    3120 ctttatgtg tgttatatca aatgtgtctt aagcttcatg caaactcagt catcagttcg    3180
tgttgtctga agcaagtggg agatatataa atacccagta gctaaaatgg tcagtctttt    3240
ttagatgttt tcctacttag tatctcctaa taacgttttg ctgtgtcact agatgttcat    3300
ttcacaagtg catgtctttc taataatcca cacatttcat gctctaataa tccacacatt    3360
tcatgctcat ttttattgtt tttacagcca gttatagtaa gaaaaaggtt tttccccttg    3420
tgctgcttta taatttagcg tgtgtctgaa ccttatccat gtttgctaga tgaggtcttg    3480
tcaaatatat cactaccatt gtcaccggtg aaaagaaaca ggtagttaag ttagggttaa    3540
cattcatttc aaccacgagg ttgtatatca tgactagctt ttactcttgg tttacagaga    3600
aaagttaaac agccaactag gcagttttta agaatattaa caatatatta acaaacacca    3660
atacaactaa tcctatttgg ttttaatgat ttcaccatgg gattaagaac tatatcagga    3720
acatccctga gaaacggttt taagtgtagc aactactctt ccttaatgga cagccacata    3780
```

```
acgtgtagga agtcctttat cacttatcct cgatccataa gcatatcttg cagaggggaa    3840
ctacttcttt aaacacatgg agggaaagaa gatgatgcca ctggcaccag agggttagta    3900
ctgtgatgca tcctaaaata tttattatat tggtaaaaat tctggttaaa taaaaaatta    3960
gagatcactc ttggctgatt tcagcaccag gaactgtatt acagttttag agattaattc    4020
ctagtgttta cctgattata gcagttggca tcatggggca tttaattctg actttatccc    4080
cacgtcagcc ttaataaagt cttctttacc ttctctatga agactttaaa gcccaaataa    4140 tcattttttca cattgatatt caagaattga gatagataga agccaaagtg ggtatctgac    4200
aagtggaaaa tcaaacgttt aagaagaatt acaactctga aaagcattta tatgtggaac    4260
ttctcaagga gcctcctggg gactggaaag taagtcatca gccaggcaaa tgactcatgc    4320
tgaagagagt ccccatttca gtcccctgag atctagctga tgcttagatc ctttgaaata    4380
aaaattatgt ctttataact ctgatctttt acataaagca gaagaggaat caactagtta    4440
attgcaaggt ttctactctg tttcctctgt aaagatcaga tggtaatctt tcaaataaga    4500
aaaaaataaa gacgtatgtt tgaccaagta gtttcacaag aatatttggg aacttgtttc    4560
ttttaatttt atttgtccct gagtgaagtc tagaaagaaa ggtaaagagt ctagagttta    4620
ttcctctttc caaaacattc tcattcctct cctccctaca cttagtattt cccccacaga    4680
gtgcctagaa tcttaataat gaataaaata aaaagcagca atatgtcatt aacaaatcca    4740
gacctgaaag ggtaaagggt ttataactgc actaataaag agaggctctt ttttttttctt    4800 ccagtttgtt ggttttttaat ggtaccgtgt tgtaaagata cccactaatg gacaatcaaa    4860
ttgcagaaaa ggctcaatat ccaagagaca gggactaatg cactgtacaa tctgcttatc    4920
cttgcccttc tctcttgcca aagtgtgctt cagaaatata tactgcttta aaaaagaata    4980
aaagaatatc cttttacaag tggctttaca tttcctaaaa tgccataaga aaatgcaata    5040
tctgggtact gtatggggaa aaaaatgtcc aagtttgtgt aaaaccagtg catttcagct    5100
tgcaagttac tgaacacaat aatgctgttt taattttgtt ttatatcagt taaaattcac    5160
aataatgtag atagaacaaa ttacagacaa ggaaagaaaa aacttgaatg aaatggattt    5220
tacagaaagc tttatgataa ttttttgaatg cattatttat tttttgtgcc atgcattttt    5280
tttctcacca aatgacctta cctgtaatac agtcttgttt gtctgtttac aaccatgtat    5340
ttattgcaat gtacatactg taatgttaat tgtaaattat ctgttcttat taaaacatca    5400
tcccatgatg ggatggtgtt gatatatttg gaaactcttg gtgagagaat gaatggtgtg    5460
tatacatact ctgtacattt ttcttttctc ctgtaatata gtcttgtcac cttagagctt    5520
gtttatggaa gattcaagaa aactataaaa tacttaaaga tatataaatt taaaaaaaca    5580
tagctgcagg tctttggtcc cagggctgtg ccttaacttt aaccaatatt tcttctgtt     5640 ttgctgcatt tgaaaggtaa cagtggagct agggctgggc attttacatc caggctttta    5700
attgattaga attctgccaa taggtggatt ttacaaaacc acagacaacc tctgaaagat    5760
tctgagaccc ttttgagaca gaagctctta agtacttctt gccagggagc agcactgcat    5820
gtgtgatggt tgtttgccat ctgttgatca ggaactactt cagctacttg catttgatta    5880
tttccttttt ttttttttttt aactcggaaa cacaactggg gaaatatatt ctttcccagt    5940
gattataaac aatctttttc tttttttttaa gtcctttttgg cttctagagc tcataggaaa    6000
atggacttga tttgaaattg gagccagagt ttactcgtgt tggttatcta ttcatcagct    6060
tcctgacatg ttaagagaat acattaaaga gaaaatactg ttttttaatc ctaaaattttt   6120
```

| | |
|---|---:|
| tcttccacta agataaacca aatgtcctta catatatgta aacccatcta tttaaacgca | 6180 |
| aaggtgggtt gatgtcagtt tacatagcag aaagcattca ctatcctcta agatttgttt | 6240 |
| ctgcaaaact ttcattgctt tagaatttta aaatttcacc ttgtacaatg gccagcccct | 6300 |
| aaagcaggaa acatttataa tggattatat ggaaacatcc tcccagtact tgcccagccc | 6360 |
| ttgaatcatg tggcttttca gtgaaaggaa agattctttt tctaggaaaa atgagcctat | 6420 |
| tttattttat tttattttat tttttgacac aaactgtaga ttttagcagc cctggcccaa | 6480 |
| aggaatttga ttacttttgt tttaaacagt acaaggggga cactataatt acaaaaacat | 6540 |
| ccttaactga tttgagttgt ttttatttct ttggatatat tttcagagtg gtaaattgtg | 6600 |
| tgtgagaatt acaaatgatt attcttttag tggtttctta gcctctctta cagcccacgg | 6660 |
| ggatagtact gtacatcaat accttcatat gaattttta tatgcaatga aaataaaagc | 6720 |
| atgggttgat tctgcctatt tatgactcaa tcttttacaa ataaaagatt attcattta | 6780 |
| aattatagtt caatcagcat gtctcttagg atactgaacg tggttgaaat gaaaggatag | 6840 |
| tgacatcata agttagtact gatattcata accaaataaa gccaacttga gtaattttgc | 6900 |
| tacattaaaa attaccaaaa ttacttagat ggcctataag attaagcatg gtgttttcta | 6960 |
| agcaagcttt gaaaggggcc ttccatactt acttaattga atattctggg atattgaaaa | 7020 |
| ttattcagat acttgacaat tatttttggt tacctactcc gcaaactaca agttttaag | 7080 |
| gactcaacaa taagttaatg agacacagtg tttgctttca tggagcttac agtctggagg | 7140 |
| ggacaaaggc ttaaacaata ctcatataat tatatatgtg atcagtacaa tgaaggagct | 7200 |
| cagtggggta aataagcagg aacctgaact tgatctgttc cggagggcca cagaaggctt | 7260 |
| ccttgaggcc ttgagaaagt gatttgcatc tgagttctga aggattgtaa gaggtaacta | 7320 |
| gggaaaaagt tgacaggaag aggaagggga tccagacaag aaacatttgc aaagatcttg | 7380 |
| aggcataaat gagcttgaga catctggaga aactgaggaa aagtgagaga gtaggcaggg | 7440 |
| cctggagccg cagagccatt gctaaccatc ctgtgtgaga tatcccccat tctgtagctt | 7500 |
| tattctcata accctgctca attttctta taacacttct cacagattta tatacgtgtt | 7560 |
| tgttttttgtt atctgtctct cccaccagac cacagctcca tgagagcaag gtctttgctt | 7620 |
| accaatatat cactagcact taaaactatg cctggtacac agtaggttct taatatgtgt | 7680 |
| tgaatatagc catcaaattg atattggata taattcaatc tgataagata ttttgagata | 7740 |
| ttaaagagtt tttaacttga taccataaaa aaaaaaaaaa aaa | 7783 |

<210> SEQ ID NO 39
<211> LENGTH: 8240
<212> TYPE: DNA
<213> ORGANISM: human

<400> SEQUENCE: 39

| | |
|---|---:|
| cccctctcgg tagccctgag gctctggcgc cttcaagtga gaagctaagc accagcctct | 60 |
| gctgggctgc agaagcggcg gcggcggcag cagcagcagc agcatcagga aggcgctcgg | 120 |
| gccagcgcgg tgaacccggg ctgggcagca ggtcgcggag ccgcgagcca ggatggaggc | 180 |
| agagggcagc agcgcgccgg cccggcgggg cagcggagag ggcagcgaca cgcgcggcgg | 240 |
| ggccacgctc aaagcccccca agcatctctg gaggcacgag cagcaccacc agtacccgct | 300 |
| ccggcagccc cagttccgcc tcctgcatcc ccatcaccac ctgccccgc cgccgccacc | 360 |
| ctcgccccag cccagccccc agtgtccgct acagccgccg ccgccgcccc cctgccgcc | 420 |
| gcccccgccg ccgcccgggg ctgcccgcgg ccgctacgcc tcgagcgggg ccaccggccg | 480 |

```
cgtccggcat cgcggctact cggacaccga gcgctacctg tactgtcgcg ccatggaccg      540
cacctcctac gcggtggaga ccggccaccg gcccggcctg aagaaatcca ggatgtcctg      600
gccctcctcg ttccagggac tcaggcgttt tgatgtggac aatggcacat ctgcgggacg      660
gagtcccttg gatcccatga ccagcccagg atccgggcta attctccaag caaattttgt      720
ccacagtcaa cgacgggagt ccttcctgta tcgatccgac agcgattatg acctctctcc      780
aaagtctatg tcccggaact cctccattgc cagtgatata cacggagatg acttgattgt      840
gactccattt gctcaggtct tggccagtct gcgaactgta cgaaacaact ttgctgcatt      900
aactaatttg caagatcgag cacctagcaa aagatcaccc atgtgcaacc aaccatccat      960
caacaaagcc accataacag aggaggccta ccagaaactg ccagcgaga ccctggagga     1020 gctggactgg tgtctggacc agctagagac cctacagacc aggcactccg tcagtgagat     1080
ggcctccaac aagtttaaaa ggatgcttaa tcgggagctc acccatctct ctgaaatgag     1140
tcggtctgga aatcaagtgt cagagtttat atcaaacaca ttcttagata agcaacatga     1200
agtggaaatt ccttctccaa ctcagaagga aaaggagaaa aagaaaagac caatgtctca     1260
gatcagtgga gtcaagaaat tgatgcacag ctctagtctg actaattcaa gtatcccaag     1320
gtttggagtt aaaactgaac aagaagatgt ccttgccaag gaactagaag atgtgaacaa     1380
atggggtctt catgttttca gaatagcaga gttgtctggt aaccggccct tgactgttat     1440
catgcacacc attttcagg aacgggattt attaaaaaca tttaaaattc cagtagatac      1500
tttaattaca tatcttatga ctctcgaaga ccattaccat gctgatgtgg cctatcacaa     1560
caatatccat gctgcagatg ttgtccagtc tactcatgtg ctattatcta cacctgcttt     1620
ggaggctgtg tttacagatt tggagattct tgcagcaatt tttgccagtg caatacatga     1680
tgtagatcat cctggtgtgt ccaatcaatt tctgatcaat acaaactctg aacttgcctt     1740
gatgtacaat gattcctcag tcttagagaa ccatcatttg gctgtgggct ttaaattgct     1800
tcaggaagaa aactgtgaca ttttccagaa tttgaccaaa aaacaaagac aatctttaag     1860
gaaaatggtc attgacatcg tacttgcaac agatatgtca aaacacatga atctactggc     1920
tgatttgaag actatggttg aaactaagaa agtgacaagc tctggagttc ttcttcttga     1980
taattattcc gataggattc aggttcttca gaatatggtg cactgtgcag atctgagcaa     2040
cccaacaaag cctctccagc tgtaccgcca gtggacggac cggataatgg aggagttctt     2100
ccgccaagga gaccgagaga gggaacgtgg catggagata agccccatgt gtgacaagca     2160
caatgcttcc gtgaaaaaat cacaggtggg cttcatagac tatattgttc atcccctctg     2220
ggagacatgg gcagacctcg tccaccctga cgcccaggat attttggaca ctttggagga     2280
caatcgtgaa tggtaccaga gcacaatccc tcagagcccc tctcctgcac ctgatgaccc     2340
agaggagggc cggcagggtc aaactgagaa attccagttt gaactaactt tagaggaaga     2400
tggtgagtca gacacggaaa aggacagtgg cagtcaagtg aagaagaca ctagctgcag     2460 tgactccaag actctttgta ctcaagactc agagtctact gaaattcccc ttgatgaaca     2520
ggttgaagag gaggcagtag gggaagaaga ggaaagccag cctgaagcct gtgtcataga     2580
tgatcgttct cctgacacgt aacagtgcaa aaactttcat gcctttttt ttttaagta      2640 gaaaaattgt ttccaaagtg catgtcacat gccacaacca cggtcacacc tcactgtcat     2700
ctgccaggac gtttgttgaa caaaactgac cttgactact cagtccagcg ctcaggaata     2760
tcgtaaccag ttttttcacc tccatgtcat ccgagcaagg tggacatctt cacgaacagc     2820
```

```
gttttaaca agatttcagc ttggtagagc tgacaaagca gataaaatct actccaaatt    2880
attttcaaga gagtgtgact catcaggcag cccaaaagtt tattggactt ggggtttcta    2940
ttccttttta tttgtttgca atattttcag aagaaaggca ttgcacagag tgaacttaat    3000
ggacgaagca acaaatatgt caagaacagg acatagcacg aatctgttac cagtaggagg    3060
aggatgagcc acagaaattg cataattttc taatttcaag tcttcctgat acatgactga    3120
atagtgtggt tcagtgagct gcactgacct ctacattttg tatgatatgt aaaacagatt    3180
ttttgtagag cttactttta ttattaaatg tattgaggta ttatatttaa aaaaaactat    3240
gttcagaact tcatctgcca ctggttattt ttttctaagg agtaacttgc aagttttcag    3300
tacaaatctg tgctacactg gataaaaatc taatttatga attttacttg caccttatag    3360
ttcatagcaa ttaactgatt tgtagtgatt cattgtttgt tttatatacc aatgacttcc    3420
atattttaaa agagaaaaac aactttatgt tgcaggaaac cctttttgta agtctttatt    3480
atttactttg cattttgttt cactctttcc agataagcag agttgctctt caccagtgtt    3540
tttcttcatg tgcaaagtga ctatttgttc tataatactt ttatgtgtgt tatatcaaat    3600
gtgtcttaag cttcatgcaa actcagtcat cagttcgtgt tgtctgaagc aagtgggaga    3660
tatataaata cccagtagct aaaatggtca gtcttttta gatgttttcc tacttagtat    3720
ctcctaataa cgttttgctg tgtcactaga tgttcatttc acaagtgcat gtctttctaa    3780
taatccacac atttcatgct ctaataatcc acacatttca tgctcatttt tattgttttt    3840
acagccagtt atagtaagaa aaaggttttt ccccttgtgc tgctttataa tttagcgtgt    3900
gtctgaacct tatccatgtt tgctagatga ggtcttgtca aatatatcac taccattgtc    3960
accggtgaaa agaaacaggt agttaagtta gggttaacat tcatttcaac cacgaggttg    4020
tatatcatga ctagcttta ctcttggttt acagagaaaa gttaaacagc caactaggca    4080 gttttaaga atattaacaa tatattaaca aacaccaata caactaatcc tatttggttt    4140
taatgatttc accatgggat taagaactat atcaggaaca tccctgagaa acggttttaa    4200
gtgtagcaac tactcttcct taatggacag ccacataacg tgtaggaagt cctttatcac    4260
ttatcctcga tccataagca tatcttgcag aggggaacta cttcttaaaa cacatggagg    4320
gaaagaagat gatgccactg gcaccagagg gttagtactg tgatgcatcc taaaatattt    4380
attatattgg taaaaattct ggttaaataa aaaattagag atcactcttg gctgatttca    4440
gcaccaggaa ctgtattaca gttttagaga ttaattccta gtgtttacct gattatagca    4500
gttggcatca tggggcattt aattctgact ttatccccac gtcagcctta ataaagtctt    4560
ctttaccttc tctatgaaga ctttaaagcc caaataatca ttttttcacat tgatattcaa    4620 gaattgagat agatagaagc caaagtgggt atctgacaag tggaaaatca aacgtttaag    4680
aagaattaca actctgaaaa gcatttatat gtggaacttc tcaaggagcc tcctggggac    4740
tggaaagtaa gtcatcagcc aggcaaatga ctcatgctga agagagtccc catttcagtc    4800
ccctgagatc tagctgatgc ttagatcctt tgaaataaaa attatgtctt tataactctg    4860
atcttttaca taaagcagaa gaggaatcaa ctagttaatt gcaaggtttc tactctgttt    4920
cctctgtaaa gatcagatgg taatctttca aataagaaaa aaataaagac gtatgtttga    4980
ccaagtagtt tcacaagaat atttgggaac ttgtttcttt taattttatt tgtccctgag    5040
tgaagtctag aaagaaaggt aaagagtcta gagtttattc ctctttccaa acattctca    5100 ttcctctcct ccctacactt agtatttccc ccacagagtg cctagaatct taataatgaa    5160
taaaataaaa agcagcaata tgtcattaac aaatccagac ctgaaagggt aaagggttta    5220
```

```
taactgcact aataaagaga ggctctttt ttttcttcca gtttgttggt ttttaatggt    5280
accgtgttgt aaagataccc actaatggac aatcaaattg cagaaaaggc tcaatatcca    5340
agagacaggg actaatgcac tgtacaatct gcttatcctt gcccttctct cttgccaaag    5400
tgtgcttcag aaatatatac tgctttaaaa aagaataaaa gaatatcctt ttacaagtgg    5460
ctttacattt cctaaaatgc cataagaaaa tgcaatatct gggtactgta tggggaaaaa    5520
aatgtccaag tttgtgtaaa accagtgcat ttcagcttgc aagttactga acacaataat    5580
gctgttttaa ttttgtttta tatcagttaa aattcacaat aatgtagata gaacaaatta    5640
cagacaagga aagaaaaaac ttgaatgaaa tggattttac agaaagcttt atgataattt    5700
ttgaatgcat tatttatttt ttgtgccatg catttttttt ctcaccaaat gaccttacct    5760
gtaatacagt cttgtttgtc tgtttacaac catgtatttta ttgcaatgta catactgtaa    5820
tgttaattgt aaattatctg ttcttattaa aacatcatcc catgatggga tggtgttgat    5880
atatttggaa actcttggtg agagaatgaa tggtgtgtat acatactctg tacattttc    5940 ttttctcctg taatatagtc ttgtcacctt agagcttgtt tatggaagat tcaagaaaac    6000
tataaaatac ttaagatat ataaatttaa aaaaacatag ctgcaggtct ttggtcccag    6060
ggctgtgcct taactttaac caatattttc ttctgttttg ctgcatttga aaggtaacag    6120
tggagctagg gctgggcatt ttacatccag gctttaatt gattagaatt ctgccaatag    6180
gtggatttta caaaccaca gacaacctct gaaagattct gagacccttt tgagacagaa    6240
gctcttaagt acttcttgcc agggagcagc actgcatgtg tgatggttgt ttgccatctg    6300
ttgatcagga actacttcag ctacttgcat ttgattattt cctttttttt ttttttaac    6360 tcggaaacac aactggggaa atatattctt tcccagtgat tataaacaat cttttctttt    6420
tttttaagtc ctttggctt ctagagctca taggaaaatg gacttgattt gaaattggag    6480
ccagagttta ctcgtgttgg ttatctattc atcagcttcc tgacatgtta agagaataca    6540
ttaaagagaa aatactgttt tttaatccta aaattttct tccactaaga taaaccaaat    6600
gtccttacat atatgtaaac ccatctattt aaacgcaaag gtgggttgat gtcagtttac    6660
atagcagaaa gcattcacta tcctctaaga tttgttctg caaaactttc attgctttag    6720
aattttaaaa tttcacccttg tacaatggcc agccctaaa gcaggaaaca tttataatgg    6780
attatatgga aacatcctcc cagtacttgc ccagcccttg aatcatgtgg cttttcagtg    6840
aaaggaaaga ttcttttttct aggaaaaatg agcctatttt atttattttt atttttttt    6900 ttgacacaaa ctgtagattt tagcagcect ggcccaaagg aatttgatta cttttgtttt    6960
aaacagtaca aaggggacac tataattaca aaaacatcct taactgattt gagttgtttt    7020
tatttctttg gatatatttt cagagtggta aattgtgtgt gagaattaca aatgattatt    7080
cttttagtgg tttcttagcc tctcttacag cccacgggga tagtactgta catcaatacc    7140
ttcatatgaa attttatat gcaatgaaaa taaaagcatg ggttgattct gcctatttat    7200
gactcaatct tttacaaata aaagattatt catttaaat tatagttcaa tcagcatgtc    7260
tcttaggata ctgaacgtgg ttgaaatgaa aggatagtga catcataagt tagtactgat    7320
attcataacc aaataaagcc aacttgagta attttgctac attaaaaatt accaaaatta    7380
cttagatggc ctataagatt aagcatggtg ttttctaagc aagctttgaa agggccttc    7440 catacttact taattgaata ttctgggata ttgaaaatta ttcagatact tgacaattat    7500
ttttggttac ctactccgca aactacaaag ttttaaggac tcaacaataa gttaatgaga    7560
```

-continued

| | |
|---|---|
| cacagtgttt gctttcatgg agcttacagt ctggagggga caaaggctta aacaatactc | 7620 |
| atataattat atatgtgatc agtacaatga aggagctcag tggggtaaat aagcaggaac | 7680 |
| ctgaacttga tctgttccgg agggccacag aaggcttcct tgaggccttg agaaagtgat | 7740 |
| ttgcatctga gttctgaagg attgtaagag gtaactaggg aaaaagttga caggaagagg | 7800 |
| aaggggatcc agacaagaaa catttgcaaa gatcttgagg cataaatgag cttgagacat | 7860 |
| ctggagaaac tgaggaaaag tgagagagta ggcagggcct ggagccgcag agccattgct | 7920 |
| aaccatcctg tgtgagatat cccccattct gtagctttat tctcataacc ctgctcaatt | 7980 |
| ttctttataa cacttctcac agatttatat acgtgtttgt ttttgttatc tgtctctccc | 8040 |
| accagaccac agctccatga gagcaaggtc tttgcttacc aatatatcac tagcacttaa | 8100 |
| aactatgcct ggtacacagt aggttcttaa tatgtgttga atatagccat caaattgata | 8160 |
| ttggatataa ttcaatctga taagatattt tgagatatta aagagttttt aacttgatac | 8220 |
| cataaaaaaa aaaaaaaaaa | 8240 |

<210> SEQ ID NO 40
<211> LENGTH: 1599
<212> TYPE: DNA
<213> ORGANISM: human

<400> SEQUENCE: 40

| | |
|---|---|
| gggtaaggcg acatttcctg cccccggggc cagggtgaga ggagagatga tgagttgctg | 60 |
| agtgtgcaca cctttccgga acacatacac acaccctgct ctgggatccc ttgtgaggct | 120 |
| gccctcatgg agttcccect ggcccagata tgtccccaag caccttccag atcacagaca | 180 |
| tgacccgcag gagctgccag aacctgggct acactgcggc atctccccag gccccggagg | 240 |
| ctgcctccaa cacagggaat gctgagaggg cagaggaggt gcctggagaa ggaagcctgt | 300 |
| tcctgcaggc cgagacccgg gcttggttcc agaagaccca ggcccactgg ctcctgcagc | 360 |
| acggggcagc ccctgcctgg ttccatggct tcatcacccg gagggaggca gagaggctgc | 420 |
| tggagcccaa gcctcagggg tgctacttgg tgcggttcag cgagagcgcg gtgaccttcg | 480 |
| tgctgactta caggagccgg acttgctgcc gccacttcct gctggcccag ctcagggacg | 540 |
| gcgccacgt ggtgctgggc gaggacagcg cccacgcgcg gctgcaggac ctgctgctgc | 600 |
| actacaccgc gcacccgctc agccctacg gggagacgct caccgagccc ctcgcccgac | 660 |
| agactcctga gcctgcagga ctttccctga ggaccgaaga atcaaacttt ggaagcaaaa | 720 |
| gccaggaccc aaaccccag tacagcccaa tcatcaaaca ggggcaagcc ccagtcccga | 780 |
| tgcagaaaga gggggccggg gagaaggagc cctcccagct gctcaggccc aagcctccca | 840 |
| tccccgccaa acctcagctg cccccagaag tctacacaat ccctgttcca cgacaccgcc | 900 |
| cggccccacg ccccaagccc tccaatccta tctacaatga gcctgatgaa cccatagctt | 960 |
| tctatgccat gggccgggc agccctgggg aagcccccag caacatctat gtggaagtgg | 1020 |
| aagatgaggg cctacccgcc acccttgggc accctgtcct acggaagagc tggtccaggc | 1080 |
| ctgtcccagg aggccagaat acaggtggct cccagctgca ttctgagaac tctgtgattg | 1140 |
| ggcaaggccc tcccctgccc caccagcccc caccgcctg gagacacacc ctcccccaca | 1200 |
| atctttctag acaggtgctt caggacagag acaggcatg gcttcccctt gggcctcctc | 1260 |
| agtaggcggt ctggcctgac ccccaacaaa gaagcctgga ggtcagagaa gcaaatgcgg | 1320 |
| agcctgctcc ctcctaagaa gatcccaaga atccaatggc tcagtccttg gtgatctaag | 1380 |
| acagcaaaga agtgtgcaag gagggccctg ttagctccca ctgtcctggt ttctcctcct | 1440 |

```
ggagtctaat tccttggcc ctctgagcct tttgagtctg ggccctggtc caatgctgct    1500
gttgtctgag aatggtttg gtgagaacag atgttagaac ttgtttgttg attcttgtct    1560
ggctaataaa tcatcaccaa ctgccttctc ctacaggga                          1599
```

<210> SEQ ID NO 41
<211> LENGTH: 1658
<212> TYPE: DNA
<213> ORGANISM: human

<400> SEQUENCE: 41

```
cgtgagtcct cgccagaact aaggctgtgg gtaaggcgac atttcctgcc cccggggcca     60
gggtgagagg agagatgatg agttgctgag tgtgcacacc tttccggaac acatacacac    120
accctgctct gggatccctt gtgaggctgc cctcatggag ttcccctgg cccagatatg     180 tccccaaggg agtcacgaag ccccatccc aaccttcagc accttccaga tcacagacat     240
gacccgcagg agctgccaga acctgggcta cactgcggca tctccccagg ccccggaggc    300
tgcctccaac acagggaatg ctgagagggc agaggaggtg cctggagaag gaagcctgtt    360
cctgcaggcc gagacccggg cttggttcca gaagacccag gcccactggc tcctgcagca    420
cggggcagcc cctgcctggt tccatggctt catcacccgg agggaggcag agaggctgct    480
ggagcccaag cctcagggt gctacttggt gcggttcagc gagagcgcgg tgaccttcgt    540
gctgacttac aggagccgga cttgctgccg ccacttcctg ctggcccagc tcaggacgg    600 gcgccacgtg gtgctgggcg aggacagcgc ccacgcgcgg ctgcaggacc tgctgctgca    660
ctacaccgcg cacccgctca gcccctacgg ggagacgctc accgagcccc tcgcccgaca    720
gactcctgag cctgcaggac tttccctgag gaccgaagaa tcaaactttg gaagcaaaag    780
ccaggaccca aaccccagt acagcccaat catcaaacag gggcaagccc cagtcccgat    840
gcagaaagag ggggccgggg agaaggagcc ctcccagctg tcaggcccca gcctcccat    900 ccccgccaaa cctcagctgc cccagaagt ctacacaatc cctgttccac acaccgccc     960 ggcccccacgc cccaagccct caatcctat ctacaatgag cctgatgaac ccatagcttt    1020
ctatgccatg ggccggggca gccctgggga agccccagc aacatctatg tggaagtgga    1080
agatgagggc ctaccccgcca cccttgggca ccctgtccta cggaagagct ggtccaggcc    1140
tgtcccagga ggcagaata caggtggctc ccagctgcat tctgagaact ctgtgattgg    1200 gcaaggcct cccctgcccc accagccccc accgcctgg agacacaccc tcccccacaa    1260
tctttctaga caggtgcttc aggacagagg acaggcatgg cttcccttg ggcctcctca    1320 gtaggcggtc tggcctgacc cccaacaaag aagcctggag gtcagagaag caaatgcgga    1380
gcctgctccc tcctaagaag atcccaagaa tccaatggct cagtccttgg tgatctaaga    1440
cagcaaagaa gtgtgcaagg agggccctgt tagctcccac tgtcctggtt tctcctcctg    1500
gagtctaatt tccttggccc tctgagcctt ttgagtctgg ccctggtcc aatgctgctg    1560 ttgtctgagg aatggttttgg tgagaacaga tgttagaact tgtttgttga ttcttgtctg    1620
gctaataaat catcaccaac tgccttctcc tacaggga                          1658
```

<210> SEQ ID NO 42
<211> LENGTH: 1635
<212> TYPE: DNA
<213> ORGANISM: human

<400> SEQUENCE: 42

-continued

| | |
|---|---|
| cggggccagg gtgagaggag agatgatgag ttgctgagtg tgcacacctt tccggaacac | 60 |
| atacacacac cctgctctgg gatcccttgt gaggctgccc tcatggagtt cccccctggcc | 120 |
| cagatatgtc cccaagggag tcacgaagcc cccatcccaa ccttcagcac cttccagatc | 180 |
| acagacatga cccgcaggag ctgccagaac ctgggctaca ctgcggcatc tccccaggcc | 240 |
| ccggaggctg cctccaacac agggaatgct gagagggcag aggaggtgcc tggagaagga | 300 |
| agcctgttcc tgcaggccga gacccgggct tggttccaga agaccaggc ccactggctc | 360 |
| ctgcagcacg gggcagcccc tgcctggttc catggcttca tcacccggag ggttcggccc | 420 |
| cctctctccg tcacccacag ggaggcagag aggctgctgg agcccaagcc tcaggggtgc | 480 |
| tacttggtgc ggttcagcga gagcgcggtg accttcgtgc tgacttacag gagccggact | 540 |
| tgctgccgcc acttcctgct ggcccagctc agggacgggc gccacgtggt gctgggcgag | 600 |
| gacagcgccc acgcgcggct gcaggacctg ctgctgcact acaccgcgca cccgctcagc | 660 |
| ccctacgggg agacgctcac cgagcccctc gcccgacaga ctcctgagcc tgcaggactt | 720 |
| tccctgagga ccgaagaatc aaactttgga agcaaaagcc aggacccaaa cccccagtac | 780 |
| agcccaatca tcaaacaggg gcaagcccca gtcccgatgc agaaagaggg ggccggggag | 840 |
| aaggagccct cccagctgct caggcccaag cctcccatcc ccgccaaacc tcagctgccc | 900 |
| ccagaagtct acacaatccc tgttccacga caccgcccgg ccccacgccc caagccctcc | 960 |
| aatcctatct acaatgagcc tgatgaaccc atagctttct atgccatggg ccggggcagc | 1020 |
| cctggggaag cccccagcaa catctatgtg gaagtggaag atgagggcct acccgccacc | 1080 |
| cttgggcacc ctgtcctacg gaagagctgg tccaggcctg tcccaggagg ccagaataca | 1140 |
| ggtggctccc agctgcattc tgagaactct gtgattgggc aaggccctcc cctgccccac | 1200 |
| cagcccccac ccgcctggag acacaccctc ccccacaatc tttctagaca ggtgcttcag | 1260 |
| gacagaggac aggcatggct tccccttggg cctcctcagt aggcggtctg gcctgacccc | 1320 |
| caacaaagaa gcctggaggt cagagaagca aatgcggagc ctgctccctc ctaagaagat | 1380 |
| cccaagaatc caatggctca gtccttggtg atctaagaca gcaagaagt gtgcaaggag | 1440 |
| ggccctgtta gctcccactg tcctggtttc tcctcctgga gtctaatttc cttggccctc | 1500 |
| tgagccttttt gagtctgggc cctggtccaa tgctgctgtt gtctgaggaa tggtttggtg | 1560 |
| agaacagatg ttagaacttg tttgttgatt cttgtctggc taataaatca tcaccaactg | 1620 |
| ccttctccta caggg | 1635 |

<210> SEQ ID NO 43
<211> LENGTH: 9059
<212> TYPE: DNA
<213> ORGANISM: human

<400> SEQUENCE: 43

| | |
|---|---|
| gagaaggacg cgcggccccc agcgcctctt gggtggccgc ctcggagcat gaccccgcg | 60 |
| ggccagcgcc gcgcgctctg atccgaggag accccgcgct cccgcagcca tggccaccgg | 120 |
| gggccggcgg ggggcggcgg ccgcgccgct gctggtggcg gtggccgcgc tgctactggg | 180 |
| cgccgcgggc cacctgtacc ccggagaggt gtgtccggc atggatatcc ggaacaacct | 240 |
| cactaggttg catgagctgg agaattgctc tgtcatcgaa ggacacttgc agatactctt | 300 |
| gatgttcaaa acgaggcccg aagatttccg agacctcagt ttccccaaac tcatcatgat | 360 |
| cactgattac ttgctgctct tccgggtcta tgggctcgag agcctgaagg acctgttccc | 420 |
| caacctcacg gtcatccggg gatcacgact gttctttaac tacgcgctgg tcatcttcga | 480 |

```
gatggttcac ctcaaggaac tcggcctcta caacctgatg aacatcaccc ggggttctgt      540
ccgcatcgag aagaacaatg agctctgtta cttggccact atcgactggt cccgtatcct      600
ggattccgtg gaggataatt acatcgtgtt gaacaaagat gacaacgagg agtgtggaga      660
catctgtccg ggtaccgcga agggcaagac caactgcccc gccaccgtca tcaacgggca      720
gtttgtcgaa cgatgttgga ctcatagtca ctgccagaaa gtttgcccga ccatctgtaa      780
gtcacacggc tgcaccgccg aaggcctctg ttgccacagc gagtgcctgg caactgttc       840 tcagcccgac gaccccacca agtgcgtggc ctgccgcaac ttctacctgg acggcaggtg      900
tgtggagacc tgcccgcccc cgtactacca cttccaggac tggcgctgtg tgaacttcag      960
cttctgccag gacctgcacc acaaatgcaa gaactcgcgg aggcagggct gccaccagta     1020
cgtcattcac aacaacaagt gcatccctga gtgtccctcc gggtacacga tgaattccag     1080
caacttgctg tgcaccccat gcctgggtcc ctgtcccaag gtgtgccacc tctagaagg     1140 cgagaagacc atcgactcgg tgacgtctgc ccaggagctc cgaggatgca ccgtcatcaa     1200
cgggagtctg atcatcaaca ttcgaggagg caacaatctg gcagctgagc tagaagccaa     1260
cctcggcctt attgaagaaa tttcagggta tctaaaaatc cgccgatcct acgtctggt      1320 gtcactttcc ttcttccgga agttacgtct gattcgagga gagaccttgg aaattgggaa     1380
ctactccttc tatgccttgg acaaccagaa cctaaggcag ctctgggact ggagcaaaca     1440
caacctcacc atcactcagg ggaaactctt cttccactat aaccccaaac tctgcttgtc     1500
agaaatccac aagatggaag aagtttcagg aaccaagggg cgccaggaga gaaacgacat     1560
tgccctgaag accaatgggg accaggcatc ctgtgaaaat gagttactta aattttctta     1620
cattcggaca tcttttgaca agatcttgct gagatgggag ccgtactggc cccccgactt     1680
ccgagacctc ttggggttca tgctgttcta caaagaggcc cttatcaga atgtgacgga      1740 gttcgacggg caggatgcgt gtggttccaa cagttggacg gtggtagaca ttgacccacc     1800
cctgaggtcc aacgacccca atcacagaa ccacccaggg tggctgatgc ggggtctcaa      1860
gccctggacc cagtatgcca tctttgtgaa gaccctggtc acctttcgg atgaacgccg      1920 gacctatggg gccaagagtg acatcattta tgtccagaca gatgccacca cccctctgt      1980 gccctggat ccaatctcag tgtctaactc atcatcccag attattctga agtggaaacc      2040
accctccgac cccaatggca acatcaccca ctacctggtt ttctgggaga ggcaggcgga     2100
agacagtgag ctgttcgagc tggattattg cctcaaaggg ctgaagctgc cctcgaggac     2160
ctggtctcca ccattcgagt ctgaagattc tcagaagcac aaccagagtg agtatgagga     2220
ttcggccggc gaatgctgct cctgtccaaa gacagactct cagatcctga aggagctgga     2280
ggagtcctcg tttaggaaga cgtttgagga ttacctgcac aacgtggttt cgtccccag      2340 aaaaacctct tcaggcactg gtgccgagga ccctaggcca tctcggaaac gcaggtccct     2400
tggcgatgtt gggaatgtga cggtggccgt gccacggtg gcagctttcc ccaacacttc      2460
ctcgaccagc gtgcccacga gtccggagga gcacaggcct tttgagaagg tggtgaacaa     2520
ggagtcgctg gtcatctccg gcttgcgaca cttcacgggc tatcgcatcg agctgcaggc     2580
ttgcaaccag gacacccctg aggaacggtg cagtgtggca gcctacgtca gtgcgaggac     2640
catgcctgaa gccaaggctg atgacattgt tggccctgtg acgcatgaaa tctttgagaa     2700
caacgtcgtc cacttgatgt ggcaggagcc gaaggagccc aatggtctga tcgtgctgta     2760
tgaagtgagt tatcggcgat atggtgatga ggagctgcat ctctgcgtct cccgcaagca     2820
```

```
cttcgctctg gaacggggct gcaggctgcg tgggctgtca ccggggaact acagcgtgcg    2880
aatccgggcc acctcccttg cgggcaacgg ctcttggacg gaacccacct atttctacgt    2940
gacagactat ttagacgtcc cgtcaaatat tgcaaaaatt atcatcggcc ccctcatctt    3000
tgtctttctc ttcagtgttg tgattggaag tatttatcta ttcctgagaa agaggcagcc    3060
agatgggccg ctgggaccgc tttacgcttc ttcaaaccct gagtatctca gtgccagtga    3120 tgtgttttcca tgctctgtgt acgtgccgga cgagtgggag gtgtctcgag agaagatcac    3180
cctccttcga gagctggggc agggctcctt cggcatggtg tatgagggca atgccaggga    3240
catcatcaag ggtgaggcag agacccgcgt ggcggtgaag acggtcaacg agtcagccag    3300
tctccgagag cggattgagt tcctcaatga ggcctcggtc atgaagggct tcacctgcca    3360
tcacgtggtg cgcctcctgg gagtggtgtc caagggccag cccacgctgg tggtgatgga    3420
gctgatggct cacggagacc tgaagagcta cctccgttct ctgcggccag aggctgagaa    3480
taatcctggc cgcccctccc ctaccccttca agagatgatt cagatggcgg cagagattgc    3540
tgacgggatg gcctacctga cgccaagaa gtttgtgcat cgggacctgg cagcgagaaa    3600
ctgcatggtc gcccatgatt ttactgtcaa aattggagac tttggaatga ccagagacat    3660
ctatgaaacg gattactacc ggaaagggg caagggtctg ctccctgtac ggtggatggc    3720
accggagtcc ctgaaggatg gggtcttcac cacttcttct gacatgtggt cctttggcgt    3780
ggtcctttgg gaaatcacca gcttggcaga acagccttac caaggcctgt ctaatgaaca    3840
ggtgttgaaa tttgtcatgg atggagggta tctggatcaa cccgacaact gtccagagag    3900
agtcactgac ctcatgcgca tgtgctggca attcaaccccc aagatgaggc caaccttcct    3960
ggagattgtc aacctgctca aggacgacct gcaccccagc tttccagagg tgtcgttctt    4020
ccacagcgag gagaacaagg ctcccgagag tgaggagctg gagatggagt ttgaggacat    4080
ggagaatgtg cccctggacc gttcctcgca ctgtcagagg gaggaggcgg ggggccggga    4140 tgagggtcc tcgctgggtt tcaagcggag ctacgaggaa cacatccctt acacacacat    4200
gaacggaggc aagaaaaacg ggcggattct gaccttgcct cggtccaatc cttcctaaca    4260
gtgcctaccg tggcggggc gggcagggggt tcccattttc gctttcctct ggtttgaaag    4320
cctctggaaa actcaggatt ctcacgactc taccatgtcc aatggagttc agagatcgtt    4380
cctatacatt tctgttcatc ttaaggtgga ctcgttggt taccaattta actagtcctg    4440
cagaggattt aactgtgaac ctggagggca aggggtttcc acagttgctg ctccttgggg    4500
gcaacgacgg tttcaaaccca ggattttgtg tttttcgtt ccccccaccc gcccccagca    4560
gatggaaaga aagcacctgt ttttacaaat tcttttttttt tttttttttt tttgctggtg    4620
tctgagcttc agtataaag acaaaacttc ctgtttgtgg aacaaagttt cgaaagaaaa    4680
aacaaaacaa aaacacccag ccctgttcca ggagaatttc aagttttaca ggttgagctt    4740
caagatggtt tttttggttt ttttttttc tctcatccag gctgaaggat ttttttttc    4800 tttacaaaat gagttcctca aattgaccaa tagctgctgc tttcatattt tggataaggg    4860
tctgtggtcc cggcgtgtgc tcacgtgtgt atgcacgtgt gtgtgtccat tagacacggc    4920
tgatgtgtgt gcaaagtatc catgcggagt tgatgctttg ggaattggct catgaaggtt    4980
cttctcaagg gtgcgagctc atcccctct ctccttcctt cttattgact gggagactgt    5040
gctctcgaca gattcttctt gtgtcagaag tctagcctca ggtttctacc ctccctccc    5100 attggtggcc aagggaggag catttcattt ggagtgatta tgaatctttt caagaccaaa    5160
ccaagctagg acattaaaaa aaaaaaaga aaagaaaga aaaacaaaa tggaaaaagg    5220
```

```
aaaaaaaaaa agaactgaga tgacagagtt ttgagaatat atttgtacca tatttaattt      5280
ttaaagtctc tggtattagc ctcataagtt attgactatt ccccgggtt ggcggggagt       5340 ggggacatga gttggtctgc ctgttgtggg gccgggaagg ggagggagtc aggcacaagt      5400
ggcctctttg tttggtctta aaggcatcca tttctgggaa tgaagccatg ttcgctgcta     5460
acacttttgg atgttgtgag gccacgtgga gtgtgtgaga gactaggttt tatggatggt     5520
ctggttcagg taccaggtct gctggaaggt tcctgttcgg ataagctggt agctacctag     5580
ctctgagcct gccttcaaga acacctgtgt tcatcctctg attctctgtg tgtacctctt     5640
gtggcgtttc ctctcccggg tgtgaacatc ctaaccgtta ttgtgcaaac ccaagaacgt     5700
cagatcccaa agcacaacaa cctggatgga cttttgggaac atctaagcaa tgtaagagag   5760
aggtgcactg agagtacgtc ttggtcccct ccacccctgag agcatctgac ggtcctcagt   5820
actgaactcc cggaagctgc tctgagcccg gtgacctcat ctgggccagg tgtggtgcct    5880
gagctgaatg ctcaggtgct tacagtgttg caatccctaa gagagtagag tctggaggag    5940
aaaccgtgaa aaagacctta cacaccacca agaacttccg aatgggcgtg aatccaccgt    6000
ttcttctctt tgcaaaaaga accaccacag ctgctcaaag aacacagtga actcatcact    6060
ttggttcatc aaaaaatcat cgcccatgcg ttattcctga gtgcattttc ttacaacttt    6120
ttgactgctt ccttttcttc ttctcttaag agttgtgggc ttaagaatgg gatagagtca    6180
taatggcaac ctccaagccc tctcaattct tgattaagaa cacaggtaga catgaatccc    6240
aattgtctat tgctatctta tttatatgat tcgggaaaat acagcatgta aaaatattgc    6300
tgaggagcct cagtgattgg gtacaagaag caagagtaca gaaattattt ttgccaaatt    6360
tattttgtaa atatgagggt ctgtacctaa atttaaaaaa aaaacacgta gaactaggta    6420
ttttgttctc ttcttagtaa atttgtagtg gttgtatact acactagctg caattttcac    6480 attttctaa ttcagaaagg tttttcttat attaggggaa aaagtattta ttttaatata     6540
taaaatcact ctgaaaatca ctctcataaa aaatggagcg catgtaaatt tttatcaaag    6600
aaaaataaac aggtgaatgg gggatagtga ttttctttt tcagcacagt ctacctcagt     6660
gtattgttaa gatgtgattc aatcatggac atctttgaga tttcagaatt ctacctggaa    6720
ccggtctgaa tcagggaacg tgtgtatcag ctgattcgaa tgccagggac cagtaagaat    6780
tttgagggag ggagttggga tggagaaggt atggcccttta tgcgagcata gatccttttc   6840
ttcctggctg gtaatattct tctctgaatt taatcttcct ttaaaaaaaa atcctccatc    6900
tattgtcact atgttcccca aacataaact aagttccagg ctgtcatgat gtatctgata    6960
tatggggtaa cccagcaagg tgtaccttcc tttggtgaga gatggctgcc ggggcaaaga   7020
cgggctttga ttcagagcaa gcattccac ctgttccatg gaatcccct gaagtgagca     7080 caaaggtgcc ctgggctccc tgatggttta tgcccactcc tttcaggctg gtgatgcacc   7140
ttacacacaa acacctaatg caatgtcttt ttaaattctc caagtgggat gggagcatgt   7200
gagggaaatt ccaatccaaa acccattaat gtgctgaacg cttttttttt tttttttttt   7260 tttttgcaa caacaccttg gacctctgtg ttggggtttg actgacctca agctgatatt    7320
attggacctt gtgcagcttt gataacccat gtgagagtct aggcaggacc agtgggccc    7380 aaatcttgct gctcttgtac ttttaggcac tgcccttgca gactcacctt tctccacctg   7440
ccctggagaa aggtagggtg tgctgggcct gcccttgca aatgggattc accagtttca    7500
tttatttgac tctactgcca cagtgaaaag agcaaacagc tattggggttg caaacctcct   7560
```

```
ttgacattag gaaatgttga ctttgtaaca ataaaacttt ggtcctagaa agacacggtt    7620
gtcctgggag tttgtagtgt taagttgcaa caacaacaac aaaaagcaac aaaaccagct    7680
taggataaca cttttgttg cttgttctta aagatgtctc actatgatta aaacccttt    7740 cattaatgta gtgaaagcca cacaggagtt ccttcttcca ggaggagaat accaagcaca    7800
tcactttctc tctgcatcag tgatgtcaaa tacgcatcag aaaatgttca ggttttagga    7860
gctgtcctag gtgctgtttc atcattggaa gcagtgagaa agagaagcac tgctgcttgt    7920
ctggatatag gctgaggatg attgagagaa gctgtgggaa ctgacacaag ggtctgcata    7980
ggtcatcctg tgaccctggg gactatgtta ccaactgaca gacagatctt tcactgtatc    8040
ctagcagggc aggtagtcca ccaagaaatg tgcttattgg attgggaggt gtttatttgt    8100
agtctgctgt aacacgtgtg aaagagcagg agcgtcatca gcatatgact tgcgctggtc    8160
atccggtaaa tggatgtgct gtagtcccag tgctaatcat ttctctcctt cacagtgggt    8220
ggaagtttag ggttaaatgt cctttgaatg tcacctggtg agtccttgac accttaggct    8280
cttcagaaac aatggttttg ttgaggatgg ggaacaggga atgccgattt tatatacatg    8340
gtacacagag aggggtgtca cttcagaaaa tcttccagca tgttcttcag aatattaatt    8400
tatatgcgag gtgaggttgg gaatgaaaag aacaggtcag cactttttt tttcctagaa    8460 catacaaaag aacatggtgg actttcaggg agtgcaatgg aaggtgaata tttccttaag    8520
ggtccccgag aaatgggagt gagggagggg gacacaatgc ttttgagc ttacttttac    8580 cttctgatac tagtcaaggt ccagaaccag ccaccagcca aatttctatc tgggtgcggg    8640
ccactgaaaa tccttgttaa aaaccagatc acaaatctgg ggctcttggt cccattggag    8700
aaggaaggaa gagcctcaaa ataagtgtgc acccatgcac atattcagga acagcttgtt    8760
tagtctttac actttgcctg aaagttgctt ctcctcgtcc ctttgtgtgc ctgggtggcc    8820
tcggccctgt gcgttggcaa cgcaggatca aatgtgctgc agcttttgca gaaaacaact    8880
cagaaacaca aaacccccca acagctcaat tattatttt tcaatgtttt cctacaagag    8940
ccaagtagca ccatgtacag aagacgcctt tttttttgga atattgaaat cgttctgcat    9000
gtaaaatatg ggataatgac ctgtttatat taaaattctg attaaattat ctgagaata    9059
```

<210> SEQ ID NO 44
<211> LENGTH: 9023
<212> TYPE: DNA
<213> ORGANISM: human

<400> SEQUENCE: 44

```
gagaaggacg cgcggccccc agcgcctctt gggtggccgc ctcggagcat gaccccgcg     60 ggccagcgcc gcgcgctctg atccgaggag accccgcgct cccgcagcca tggccaccgg    120
gggccggcgg ggggcggcgg ccgcgccgct gctggtggcg gtggccgcgc tgctactggg    180
cgccgcgggc cacctgtacc ccggagaggt gtgtccggc atggatatcc ggaacaacct    240
cactaggttg catgagctgg agaattgctc tgtcatcgaa ggacacttgc agatactctt    300
gatgttcaaa acgaggcccg aagatttccg agacctcagt ttccccaaac tcatcatgat    360
cactgattac ttgctgctct tccgggtcta tgggctcgag agcctgaagg acctgttccc    420
caacctcacg gtcatccggg gatcacgact gttctttaac tacgcgctgg tcatcttcga    480
gatggttcac ctcaaggaac tcggcctcta caacctgatg aacatcaccc ggggttctgt    540
ccgcatcgag aagaacaatg agctctgtta cttggccact atcgactggt cccgtatcct    600
ggattccgtg gaggataatt acatcgtgtt gaacaaagat gacaacgagg agtgtggaga    660
```

-continued

```
catctgtccg ggtaccgcga agggcaagac caactgcccc gccaccgtca tcaacgggca    720
gtttgtcgaa cgatgttgga ctcatagtca ctgccagaaa gtttgcccga ccatctgtaa    780
gtcacacggc tgcaccgccg aaggcctctg ttgccacagc gagtgcctgg gcaactgttc    840
tcagcccgac gaccccacca agtgcgtggc ctgccgcaac ttctacctgg acggcaggtg    900
tgtggagacc tgcccgcccc cgtactacca cttccaggac tggcgctgtg tgaacttcag    960
cttctgccag gacctgcacc acaaatgcaa gaactcgcgg aggcagggct gccaccagta   1020
cgtcattcac aacaacaagt gcatccctga gtgtccctcc gggtacacga tgaattccag   1080
caacttgctg tgcaccccat gcctgggtcc ctgtcccaag gtgtgccacc tcctagaagg   1140
cgagaagacc atcgactcgg tgacgtctgc ccaggagctc cgaggatgca ccgtcatcaa   1200
cgggagtctg atcatcaaca ttcgaggagg caacaatctg cagctgagc tagaagccaa    1260 cctcggcctc attgaagaaa tttcagggta tctaaaaatc cgccgatcct acgctctggt   1320
gtcactttcc ttcttccgga agttacgtct gattcgagga gagaccttgg aaattgggaa   1380
ctactccttc tatgccttgg acaaccagaa cctaaggcag ctctgggact ggagcaaaca   1440
caacctcacc atcactcagg ggaaactctt cttccactat aaccccaaac tctgcttgtc   1500
agaaatccac aagatggaag aagtttcagg aaccaagggg cgccaggaga gaaacgacat   1560
tgccctgaag accaatgggg accaggcatc ctgtgaaaat gagttactta aattttctta   1620
cattcggaca tctttttgaca agatcttgct gagatgggag ccgtactggc cccccgactt   1680
ccgagacctc ttggggttca tgctgttcta caaagaggcc ccttatcaga atgtgacgga   1740
gttcgacggg caggatgcgt gtggttccaa cagttggacg gtggtagaca ttgacccacc   1800
cctgaggtcc aacgacccca aatcacagaa ccacccaggg tggctgatgc ggggtctcaa   1860
gccctggacc cagtatgcca tctttgtgaa gaccctggtc accttttcgg atgaacgccg   1920
gacctatggg gccaagagtg acatcattta tgtccagaca gatgccacca ccccctctgt   1980
gcccctggat ccaatctcag tgtctaactc atcatcccag attattctga agtggaaacc   2040
accctccgac cccaatggca acatcaccca ctacctggtt ttctgggaga ggcaggcgga   2100
agacagtgag ctgttcgagc tggattattg cctcaaaggg ctgaagctgc cctcgaggac   2160
ctggtctcca ccattcgagt ctgaagattc tcagaagcac aaccagagtg agtatgagga   2220
ttcggccggc gaatgctgct cctgtccaaa gacagactct cagatcctga aggagctgga   2280
ggagtcctcg tttaggaaga cgtttgagga ttacctgcac aacgtggttt cgtccccag    2340 gccatctcgg aaacgcaggt cccttggcga tgttgggaat gtgacggtgg ccgtgccac    2400 ggtggcagct tccccaaca cttcctcgac cagcgtgccc acgagtccgg aggagcacag    2460
gccttttgag aagtggtga acaaggagtc gctggtcatc tccggcttgc gacacttcac    2520
gggctatcgc atcgagctgc aggcttgcaa ccaggacacc cctgaggaac ggtgcagtgt   2580
ggcagcctac gtcagtgcga ggaccatgcc tgaagccaag gctgatgaca ttgttggccc   2640
tgtgacgcat gaaatctttg agaacaacgt cgtccacttg atgtggcagg agccgaagga   2700
gcccaatggt ctgatcgtgc tgtatgaagt gagttatcgg cgatatggtg atgaggagct   2760
gcatctctgc gtctcccgca agcacttcgc tctggaacgg gctgcaggc tgcgtgggct   2820 gtcaccgggg aactacagcg tgcgaatccg ggccacctcc cttgcgggca acggctcttg   2880
gacggaaccc acctatttct acgtgacaga ctatttagac gtcccgtcaa atattgcaaa   2940
aattatcatc ggccccctca tctttgtctt tctcttcagt gttgtgattg gaagtattta   3000
```

```
tctattcctg agaaagaggc agccagatgg gccgctggga ccgctttacg cttcttcaaa    3060
ccctgagtat ctcagtgcca gtgatgtgtt tccatgctct gtgtacgtgc cggacgagtg    3120
ggaggtgtct cgagagaaga tcaccctcct tcgagagctg gggcagggct ccttcggcat    3180
ggtgtatgag ggcaatgcca gggacatcat caagggtgag gcagagaccc gcgtggcggt    3240
gaagacggtc aacgagtcag ccagtctccg agagcggatt gagttcctca atgaggcctc    3300
ggtcatgaag ggcttcacct gccatcacgt ggtgcgcctc ctgggagtgg tgtccaaggg    3360
ccagcccacg ctggtggtga tggagctgat ggctcacgga gacctgaaga gctacctccg    3420
ttctctgcgg ccagaggctg agaataatcc tggccgccct ccccctaccc ttcaagagat    3480
gattcagatg gcggcagaga ttgctgacgg gatggcctac ctgaacgcca gaagtttgt     3540 gcatcgggac ctggcagcga gaaactgcat ggtcgcccat gattttactg tcaaaattgg    3600
agactttgga atgaccagag acatctatga aacggattac taccggaaag ggggcaaggg    3660
tctgctccct gtacggtgga tggcaccgga gtccctgaag gatggggtct caccacttc     3720 ttctgacatg tggtcctttg gcgtggtcct ttgggaaatc accagcttgg cagaacagcc    3780
ttaccaaggc ctgtctaatg aacaggtgtt gaaatttgtc atggatggag ggtatctgga    3840
tcaacccgac aactgtccag agagagtcac tgacctcatg cgcatgtgct ggcaattcaa    3900
ccccaagatg aggccaacct tcctggagat tgtcaacctg ctcaaggacg acctgcaccc    3960
cagctttcca gaggtgtcgt tcttccacag cgaggagaac aaggctcccg agagtgagga    4020
gctggagatg gagtttgagg acatggagaa tgtgcccctg accgttcct cgcactgtca     4080 gagggaggag gcgggggggcc gggatggagg gtcctcgctg ggtttcaagc ggagctacga    4140
ggaacacatc ccttacacac acatgaacgg aggcaagaaa acgggcgga ttctgacctt     4200 gcctcggtcc aatccttcct aacagtgcct accgtggcgg gggcgggcag gggttcccat    4260
tttcgctttc ctctggtttg aaagcctctg gaaaactcag gattctcacg actctaccat    4320
gtccaatgga gttcagagat cgttcctata catttctgtt catcttaagg tggactcgtt    4380
tggttaccaa tttaactagt cctgcagagg atttaactgt gaacctggag ggcaagggt     4440 ttccacagtt gctgctcctt tggggcaacg acggtttcaa accaggattt tgtgtttttt    4500
cgttcccccc acccgccccc agcagatgga agaaagcac ctgttttac aaattctttt      4560 tttttttttt tttttttgct ggtgtctgag cttcagtata aaagacaaaa cttcctgttt    4620
gtggaacaaa agttcgaaag aaaaaacaaa acaaaaacac ccagccctgt tccaggagaa    4680
tttcaagttt tacaggttga gcttcaagat ggtttttttg gtttttttt tttctctcat     4740 ccaggctgaa ggattttttt tttctttaca aaatgagttc ctcaaattga ccaatagctg    4800
ctgctttcat attttggata agggtctgtg gtcccggcgt gtgctcacgt gtgtatgcac    4860
gtgtgtgtgt ccattagaca cggctgatgt gtgtgcaaag tatccatgcg gagttgatgc    4920
tttgggaatt ggctcatgaa ggttcttctc aagggtgcga gctcatcccc ctctctcctt    4980
ccttcttatt gactgggaga ctgtgctctc gacagattct tcttgtgtca gaagtctagc    5040
ctcaggtttc taccctcccct tcacattggt ggccaaggga ggagcatttc atttggagtg   5100
attatgaact ttttcaagac caaaccaagc taggacatta aaaaaaaaa aagaaaaaga    5160 aagaaaaaac aaaatggaaa aaggaaaaaa aaaagaact gagatgacag agttttgaga     5220
atatatttgt accatattta attttttaaag tctctggtat tagcctcata agttattgac    5280
tattccccgg ggttggcggg gagtggggac atgagttggg ctgcctgttg tggggccggg    5340
aaggggaggg agtcaggcac aagtggcctc tttgtttggt cttaaaggca tccatttctg    5400
```

```
ggaatgaagc catgttcgct gctaacactt ttggatgttg tgaggccacg tggagtgtgt    5460
gagagactag gttttatgga tggtctggtt caggtaccag gtctgctgga aggttcctgt    5520
tcggataagc tggtagctac ctagctctga gcctgccttc aagaacacct gtgttcatcc    5580
tctgattctc tgtgtgtacc tcttgtggcg tttcctctcc cgggtgtgaa catcctaacc    5640
gttattgtgc aaacccaaga acgtcagatc ccaaagcaca caacctggga tggactttgg    5700
gaacatctaa gcaatgtaag agagaggtgc actgagagta cgtcttggtc ccctccaccc    5760
tgagagcatc tgacggtcct cagtactgaa ctcccggaag ctgctctgag cccggtgacc    5820
tcatctgggc caggtgtggt gcctgagctg aatgctcagg tgcttacagt gttgcaatcc    5880
ctaagagagt agagtctgga ggagaaaccg tgaaaaagac cttacacacc accaagaact    5940
tccgaatggg cgtgaatcca ccgtttcttc tctttgcaaa aagaaccacc acagctgctc    6000
aaagaacaca gtgaactcat cactttggtt catcaaaaaa tcatcgccca tgcgttattc    6060
ctgagtgcat tttcttacaa cttttttgact gcttcctttt cttcttctct taagagttgt    6120
gggcttaaga atgggataga gtcataatgg caacctccaa gccctctcaa ttcttgatta    6180
agaacacagg tagacatgaa tcccaattgt ctattgctat cttatttata tgattcggga    6240
aaatacagca tgtaaaaata ttgctgagga gcctcagtga ttgggtacaa gaagcaagag    6300
tacagaaatt attttttgcca aatttatttt gtaaatatga gggtctgtac ctaaatttaa    6360
aaaaaaaaca cgtagaacta ggtattttgt tctcttctta gtaaatttgt agtggttgta    6420
tactacacta gctgcaattt tcacattttt ctaattcaga aaggttttttc ttatattagg    6480 ggaaaaagta tttattttaa tatataaaat cactctgaaa atcactctca taaaaaatgg    6540
agcgcatgta aatttttatc aaagaaaaat aaacaggtga atgggggata gtgattttct    6600
tttttcagca cagtctacct cagtgtattg ttaagatgtg attcaatcat ggacatcttt    6660
gagatttcag aattctacct ggaaccggtc tgaatcaggg aacgtgtgta tcagctgatt    6720
cgaatgccag ggaccagtaa gaattttgag ggagggagtt gggatggaga aggtatggcc    6780
tttatgcgag catagatcct ttttcttcctg gctggtaata ttcttctctg aatttaatct    6840
tcctttaaaa aaaaatcctc catctattgt cactatgttc cccaaacata aactaagttc    6900
caggctgtca tgatgtatct gatatatggg gtaacccagc aaggtgtacc ttcctttggt    6960
gagagatggc tgccggggca aagacgggct ttgattcaga gcaagcattc ccacctgttc    7020
catggaatcc ccctgaagtg agcacaaagg tgccctgggc tccctgatgg tttatgccca    7080
ctcctttcag gctggtgatg caccttacac acaaacacct aatgcaatgt ctttttaaat    7140
tctccaagtg ggatgggagc atgtgaggga aattccaatc caaaacccat taatgtgctg    7200
aacgcttttt ttttttttt ttttttttt gcaacaacac cttggacctc tgtgttgggg    7260
tttgactgac ctcaagctga tattattgga ccttgtgcag cttttgataac ccatgtgaga    7320 gtctaggcag gaccagtggg gcccaaatct tgctgctctt gtacttttag gcactgccct    7380
tgcagactca cctttctcca cctgccctgg agaaggtag ggtgtgctgg gcctgcccct    7440
tgcaaatggg attcaccagt ttcatttatt tgactctact gccacagtga aaagagcaaa    7500
cagctattgg gttgcaaacc tcctttgaca ttaggaaatg ttgactttgt aacaataaaa    7560
ctttggtcct agaaagacac ggttgtcctg ggagtttgta gtgttaagtt gcaacaacaa    7620
caacaaaaag caacaaaacc agcttaggat aacacttttt gttgcttgtt cttaaagatg    7680
tctcactatg attaaaaccc ttttcattaa tgtagtgaaa gccacacagg agttccttct    7740
```

| | |
|---|---|
| tccaggagga gaataccaag cacatcactt tctctctgca tcagtgatgt caaatacgca | 7800 |
| tcagaaaatg ttcaggtttt aggagctgtc ctaggtgctg tttcatcatt ggaagcagtg | 7860 |
| agaaagagaa gcactgctgc ttgtctggat ataggctgag gatgattgag agaagctgtg | 7920 |
| ggaactgaca caagggtctg cataggtcat cctgtgaccc tggggactat gttaccaact | 7980 |
| gacagacaga tctttcactg tatcctagca gggcaggtag tccaccaaga aatgtgctta | 8040 |
| ttggattggg aggtgtttat ttgtagtctg ctgtaacacg tgtgaaagag caggagcgtc | 8100 |
| atcagcatat gacttgcgct ggtcatccgg taaatggatg tgctgtagtc ccagtgctaa | 8160 |
| tcatttctct ccttcacagt gggtggaagt ttagggttaa atgtcctttg aatgtcacct | 8220 |
| ggtgagtcct tgacacctta ggctcttcag aaacaatggt tttgttgagg atggggaaca | 8280 |
| gggaatgccg attttatata catggtacac agagaggggt gtcacttcag aaaatcttcc | 8340 |
| agcatgttct tcagaatatt aatttatatg cgaggtgagg ttgggaatga aaagaacagg | 8400 |
| tcagcacttt ttttttttcct agaacataca aagaacatg gtggactttc agggagtgca | 8460 |
| atggaaggtg aatatttcct taagggtccc cgagaaatgg gagtgagggg aggggacaca | 8520 |
| atggcttttt gagcttactt ttaccttctg atactagtca aggtccagaa ccagccacca | 8580 |
| gccaaatttc tatctgggtg cgggccactg aaaatccttg ttaaaaacca gatcacaaat | 8640 |
| ctggggctct tggtcccatt ggagaaggaa ggaagagcct caaaataagt gtgcacccat | 8700 |
| gcacatattc aggaacagct tgtttagtct ttacactttg cctgaaagtt gcttctcctc | 8760 |
| gtcccttgt gtgcctgggt ggcctcggcc ctgtgcgttg gcaacgcagg atcaaatgtg | 8820 |
| ctgcagcttt tgcagaaaac aactcagaaa cacaaaaccc cccaacagct caattattat | 8880 |
| tttttcaatg ttttcctaca agagccaagt agcaccatgt acagaagacg cctttttttt | 8940 |
| tggaatattg aaatcgttct gcatgtaaaa tatgggataa tgacctgttt atattaaaat | 9000 |
| tctgattaaa ttatctgaga ata | 9023 |

```
<210> SEQ ID NO 45
<211> LENGTH: 4742
<212> TYPE: DNA
<213> ORGANISM: human

<400> SEQUENCE: 45
```

| | |
|---|---|
| ttttctgccc ttctttgctt tggtggcttc cttgtggttc ctcagtggtg cctgcaaccc | 60 |
| ctggttcacc tccttccagg ttctggctcc ttccagccat ggctctcaga gtccttctgt | 120 |
| taacagcctt gacctatgt catgggttca acttggacac tgaaaacgca atgaccttcc | 180 |
| aagagaacgc aagggcttc gggcagagcg tggtccagct tcagggatcc agggtggtgg | 240 |
| ttggagcccc ccaggagata gtggctgcca ccaaagggg cagcctctac cagtgcgact | 300 |
| acagcacagg ctcatgcgag cccatccgcc tgcaggtccc cgtggaggcc gtgaacatgt | 360 |
| ccctgggcct gtccctggca gccaccacca gccccctca gctgctggcc tgtggtccca | 420 |
| ccgtgcacca gacttgcagt gagaacacgt atgtgaaagg gctctgcttc ctgtttggat | 480 |
| ccaacctacg gcagcagccc cagaagttcc agaggccct ccgagggtgt cctcaagagg | 540 |
| atagtgacat tgccttcttg attgatggct ctggtagcat catcccacat gactttcggc | 600 |
| ggatgaagga gtttgtctca actgtgatgg agcaattaaa aaagtccaaa accttgttct | 660 |
| ctttgatgca gtactctgaa gaattccgga ttcactttac cttcaaagag ttccagaaca | 720 |
| accctaaccc aagatcactg gtgaagccaa taacgcagct gcttgggcgg acacacacgg | 780 |
| ccacgggcat ccgcaaagtg gtacgagagc tgtttaacat caccaacgga gcccgaaaga | 840 |

-continued

```
atgcctttaa gatcctagtt gtcatcacgg atggagaaaa gtttggcgat cccttgggat    900
atgaggatgt catccctgag gcagacagag agggagtcat tcgctacgtc attggggtgg    960
gagatgcctt ccgcagtgag aaatcccgcc aagagcttaa taccatcgca tccaagccgc   1020
ctcgtgatca cgtgttccag gtgaataact ttgaggctct gaagaccatt cagaaccagc   1080
ttcgggagaa gatctttgcg atcgagggta ctcagacagg aagtagcagc tcctttgagc   1140
atgagatgtc tcaggaaggc ttcagcgctg ccatcacctc taatgcccc ttgctgagca    1200
ctgtggggag ctatgactgg gctggtggag tctttctata tacatcaaag gagaaaagca   1260
ccttcatcaa catgaccaga gtggattcag acatgaatga tgcttacttg ggttatgctg   1320
ccgccatcat cttacggaac cgggtgcaaa gcctggttct gggggcacct cgatatcagc   1380
acatcggcct ggtagcgatg ttcaggcaga acactggcat gtgggagtcc aacgctaatg   1440
tcaagggcac ccagatcggc gcctacttcg gggcctccct ctgctccgtg gacgtggaca   1500
gcaacggcag caccgacctg gtcctcatcg gggcccccca ttactacgag cagacccgag   1560
ggggccaggt gtccgtgtgc cccttgccca gggggagggc tcggtggcag tgtgatgctg   1620
ttctctacgg ggagcagggc caaccctggg ccgctttgg ggcagcccta acagtgctgg    1680
gggacgtaaa tggggacaag ctgacggacg tggccattgg ggccccagga gaggaggaca   1740
accggggtgc tgtttacctg tttcacggaa cctcaggatc tggcatcagc ccctcccata   1800
gccagcggat agcaggctcc aagctctctc ccaggctcca gtattttggt cagtcactga   1860
gtgggggcca ggacctcaca atggatggac tggtagacct gactgtagga gcccaggggc   1920
acgtgctgct gctcaggtcc cagccagtac tgagagtcaa ggcaatcatg gagttcaatc   1980
ccagggaagt ggcaaggaat gtatttgagt gtaatgatca ggtggtgaaa ggcaaggaag   2040
ccggagaggt cagagtctgc ctccatgtcc agaagagcac acgggatcgg ctaagagaag   2100
gacagatcca gagtgttgtg acttatgacc tggctctgga ctccggccgc ccacattccc   2160
gcgccgtctt caatgagaca aagaacagca cacgcagaca gacacaggtc ttggggctga   2220
cccagacttg tgagaccctg aaactacagt tgccgaattg catcgaggac ccagtgagcc   2280
ccattgtgct gcgcctgaac ttctctctgg tgggaacgcc attgtctgct ttcgggaacc   2340
tccggccagt gctggcggag gatgctcaga gactcttcac agccttgttt ccctttgaga   2400
agaattgtgg caatgacaac atctgccagg atgacctcag catcaccttc agtttcatga   2460
gcctggactg cctcgtggtg ggtgggcccc gggagttcaa cgtgacagtg actgtgagaa   2520
atgatggtga ggactcctac aggacacagg tcaccttctt cttcccgctt gacctgtcct   2580
accggaaggt gtccacgctc cagaaccagc gctcacagcg atcctggcgc ctggcctgtg   2640
agtctgcctc ctccaccgaa gtgtctgggg ccttgaagag caccagctgc agcataaacc   2700
acccatctt cccggaaaac tcagaggtca cctttaatat cacgtttgat gtagactcta   2760
aggcttccct tggaaacaaa ctgctcctca aggccaatgt gaccagtgag aacaacatgc   2820
ccagaaccaa caaaaccgaa ttccaactgg agctgccggt gaaatatgct gtctacatgg   2880
tggtcaccag ccatggggtc tccactaaat atctcaactt cacggcctca gagaatacca   2940
gtcgggtcat gcagcatcaa tatcaggtca gcaacctggg gcagaggagc ctccccatca   3000
gcctggtgtt cttggtgccc gtccggctga accagactgt catatgggac cgcccccagg   3060
tcaccttctc cgagaacctc tcgagtacgt gccacaccaa ggagcgcttg ccctctcact   3120
ccgactttct ggctgagctt cggaaggccc ccgtggtgaa ctgctccatc gctgtctgcc   3180
```

-continued

| | |
|---|---|
| agagaatcca gtgtgacatc ccgttctttg gcatccagga agaattcaat gctaccctca | 3240 |
| aaggcaacct ctcgtttgac tggtacatca agacctcgca taaccacctc ctgatcgtga | 3300 |
| gcacagctga gatcttgttt aacgattccg tgttcaccct gctgccggga caggggggcgt | 3360 |
| ttgtgaggtc ccagacggag accaaagtgg agccgttcga ggtccccaac cccctgccgc | 3420 |
| tcatcgtggg cagctctgtc gggggactgc tgctcctggc cctcatcacc gccgcgctgt | 3480 |
| acaagctcgg cttcttcaag cggcaataca aggacatgat gagtgaaggg ggtccccgg | 3540 |
| gggccgaacc ccagtagcgg ctccttcccg acagagctgc ctctcggtgg ccagcaggac | 3600 |
| tctgcccaga ccacacgtag cccccaggct gctggacacg tcggacagcg aagtatcccc | 3660 |
| gacaggacgg gcttgggctt ccatttgtgt gtgtgcaagt gtgtatgtgc gtgtgtgcaa | 3720 |
| gtgtctgtgt gcaagtgtgt gcacatgtgt gcgtgtgcgt gcatgtgcac ttgcacgccc | 3780 |
| atgtgtgagt gtgtgcaagt atgtgagtgt gtccaagtgt gtgtgcgtgt gtccatgtgt | 3840 |
| gtgcaagtgt gtgcatgtgt gcgagtgtgt gcatgtgtgt gctcaggggc gtgtggctca | 3900 |
| cgtgtgtgac tcagatgtct ctggcgtgtg ggtaggtgac ggcagcgtag cctctccggc | 3960 |
| agaagggaac tgcctgggct cccttgtgcg tgggtgaagc cgctgctggg ttttcctccg | 4020 |
| ggagagggga cggtcaatcc tgtgggtgaa gacagaggga aacacagcag cttctctcca | 4080 |
| ctgaaagaag tgggacttcc cgtcgcctgc gagcctgcgg cctgctggag cctgcgcagc | 4140 |
| ttggatggag actccatgag aagccgtggg tggaaccagg aacctcctcc acaccagcgc | 4200 |
| tgatgcccaa taaagatgcc cactgaggaa tgatgaagct tcctttctgg attcatttat | 4260 |
| tatttcaatg tgactttaat ttttttggatg gataagcttg tctatggtac aaaaatcaca | 4320 |
| aggcattcaa gtgtacagtg aaaagtctcc ctttccagat attcaagtca cctccttaaa | 4380 |
| ggtagtcaag attgtgtttt gaggtttcct tcagacagat tccaggcgat gtgcaagtgt | 4440 |
| atgcacgtgt gcacacacac cacacataca cacacacaag cttttttaca caaatggtag | 4500 |
| catactttat attggtctgt atcttgcttt ttttcaccaa tatttctcag acatcggttc | 4560 |
| atattaagac ataaattact ttttcattct tttataccgc tgcatagtat tccattgtgt | 4620 |
| gagtgtacca taatgtattt aaccagtctt cttttgatat actattttca ttctcttgtt | 4680 |
| attgcatcaa tgctgagtta ataaatcaaa tatatgtcat ttttgcatat atgtaaggat | 4740 |
| aa | 4742 |

<210> SEQ ID NO 46
<211> LENGTH: 12625
<212> TYPE: DNA
<213> ORGANISM: human

<400> SEQUENCE: 46

| | |
|---|---|
| gctgtcccca agccgattgg tacttcttgt caggaagaaa cgccaagagg tgggagtgcc | 60 |
| tggggaggga ggcaggcggt ccctaccgca ggcgcgggga gctgcctttc cgcccctccg | 120 |
| cctgctttcc aagcctggac tcttaggagt ggctgaagct gcggagcgct tttgagcct | 180 |
| gtgaatgaac cctcctcctc tccctcctcc ttcttctcgc tgagtctcct cctcggctct | 240 |
| gacggtacag tgatataatg atgatgggtg tcacaacccg catttgaact tgcaggcgag | 300 |
| ctgccccgag cctttctggg gaagaactcc aggcgtgcgg acgcaacagc cgagaacatt | 360 |
| aggtgttgtg gacaggagct gggaccaaga tcttcggcca gccccgcatc ctcccgcatc | 420 |
| ttccagcacc gtcccgcacc ctccgcatcc ttccccgggc caccacgctt cctatgtgac | 480 |
| ccgcctgggc aacgccgaac ccagtcgcgc agcgctgcag tgaatttcc ccccaaactg | 540 |

```
caataagccg ccttccaagg ccaagatgtt cataaatata aagagcatct tatggatgtg    600 ttcaaccttaa atagtaaccc atgcgctaca taaagtcaaa gtgggaaaaaa gcccaccggt    660 gaggggctcc ctctctggaa aagtcagcct accttgtcat ttttcaacga tgcctacttt    720
gccacccagt tacaacacca gtgaatttct ccgcatcaaa tggtctaaga ttgaagtgga    780
caaaaatgga aaagatttga aagagactac tgtccttgtg gcccaaaatg gaaatatcaa    840
gattggtcag gactacaaag ggagagtgtc tgtgcccaca catcccgagg ctgtgggcga    900
tgcctccctc actgtggtca agctgctggc aagtgatgcg ggtctttacc gctgtgacgt    960
catgtacggg attgaagaca cacaagacac ggtgtcactg actgtggatg gggttgtgtt   1020
tcactacagg gcggcaacca gcaggtacac actgaattt gaggctgctc agaaggcttg   1080
tttggacgtt ggggcagtca tagcaactcc agagcagctc tttgctgcct atgaagatgg   1140
atttgagcag tgtgacgcag gctggctggc tgatcagact gtcagatatc ccatccgggc   1200
tcccagagta ggctgttatg gagataagat gggaaaggca ggagtcagga cttatggatt   1260
ccgttctccc caggaaactt acgatgtgta ttgttatgtg gatcatctgg atggtgatgt   1320
gttccacctc actgtcccca gtaaattcac cttcgaggag gctgcaaaag agtgtgaaaa   1380
ccaggatgcc aggctggcaa cagtggggga actccaggcg gcatggagga acggctttga   1440
ccagtgcgat tacgggtggc tgtcggatgc cagcgtgcgc caccctgtga ctgtggccag   1500
ggcccagtgt ggaggtggtc tacttggggt gagaaccctg tatcgttttg agaaccagac   1560
aggcttccct ccccctgata gcagatttga tgcctactgc tttaaaccta aagaggctac   1620
aaccatcgat ttgagtatcc tcgcagaaac tgcatcaccc agtttatcca agaaccaca   1680 aatggtttct gatagaacta caccaatcat ccctttagtt gatgaattac ctgtcattcc   1740
aacagagttc cctcccgtgg gaaatattgt cagttttgaa cagaaagcca cagtccaacc   1800
tcaggctatc acagatagtt tagccaccaa attacccaca cctactgca gtaccaagaa   1860 gccctgggat atggatgact actcaccttc tgcttcagga cctcttggaa agctagacat   1920
atcagaaatt aaggaagaag tgctccagag tacaactggc gtctctcatt atgctacgga   1980
ttcatgggat ggtgtcgtgg aagataaaca aacacaagaa tcggttacac agattgaaca   2040
aatagaagtg ggtcctttgg taacatctat ggaaatctta aagcacattc cttccaagga   2100
attccctgta actgaaacac cattggtaac tgcaagaatg atcctggaat ccaaaactga   2160
aaagaaaatg gtaagcactg tttctgaatt ggtaaccaca ggtcactatg gattcacctt   2220
gggagaagag gatgatgaag acagaacact tacagttgga tctgatgaga gcaccttgat   2280
ctttgaccaa attcctgaag tcattacggt gtcaaagact tcagaagaca ccatccacac   2340
tcatttagaa gacttggagt cagtctcagc atccacaact gtttcccctt taattatgcc   2400
tgataataat ggatcatcca tggatgactg ggaagagaga caaactagtg gtaggataac   2460
ggaagagttt cttggcaaat atctgtctac tacacctttt ccatcacagc atcgtacaga   2520
aatagaattg tttccttatt ctggtgataa aatattagta gagggaattt ccacagttat   2580
ttatccttct ctacaaacag aaatgacaca tagaagagaa agaacagaaa cactaatacc   2640
agagatgaga acagatactt atacagatga aatacaagaa gagatcacta aaagtccatt   2700
tatgggaaaa acagaagaag aagtcttctc tgggatgaaa ctctctacat ctctctcaga   2760
gccaattcat gttacagagt cttctgtgga aatgaccaag tcttttgatt tcccaacatt   2820
gataacaaag ttaagtgcag agccaacaga agtaagagat atggaggaag actttacagc   2880
```

-continued

```
aactccaggt actacaaaat atgatgaaaa tattacaaca gtgcttttgg cccatggtac    2940
tttaagtgtt gaagcagcca ctgtatcaaa atggtcatgg gatgaagata atacaacatc    3000
caagccttta gagtctacag aaccttcagc ctcttcaaaa ttgccccctg ccttactcac    3060
aactgtgggg atgaatggaa aggataaaga catcccaagt ttcactgaag atggagcaga    3120
tgaatttact cttattccag atagtactca aaagcagtta gaggaggtta ctgatgaaga    3180
catagcagcc catggaaaat tcacaattag atttcagcca actacatcaa ctggtattgc    3240
agaaaagtca actttgagag attctacaac tgaagaaaaa gttccaccta tcacaagcac    3300
tgaaggccaa gtttatgcaa ccatggaagg aagtgctttg ggtgaagtag aagatgtgga    3360
cctctctaag ccagtatcta ctgttcccca atttgcacac acttcagagg tggaaggatt    3420
agcatttgtt agttatagta gcacccaaga gcctactact tatgtagact cttcccatac    3480
cattcctctt tctgtaattc ccaagacaga ctggggagtg ttagtaccttt ctgttccatc    3540 agaagatgaa gttctaggtg aaccctctca agacatactt gtcattgatc agactcgcct    3600
tgaagcgact atttctccag aaactatgag aacaacaaaa atcacagagg gaacaactca    3660
ggaagaattc ccttggaaag aacagactgc agagaaacca gttcctgctc tcagttctac    3720
agcttggact cccaaggagg cagtaacacc actggatgaa caagagggcg atggatcagc    3780
atatacagtc tctgaagatg aattgttgac aggttctgag agggtcccag ttttagaaac    3840
aactccagtt ggaaaaattg atcacagtgt gtcttatcca ccaggtgctg taactgagca    3900
caaagtgaaa acagatgaag tggtaacact aacaccacgc attgggccaa agtatctttt    3960
aagtccaggg cctgaacaaa aatatgaaac agaaggtagt agtacaacag gatttacatc    4020
atctttgagt ccttttagta cccacattac ccagcttatg aagaaaacca ctactgagaa    4080
aacatcccta gaggatattg atttaggctc aggattattt gaaaagccca agccacaga    4140 actcatagaa ttttcaacaa tcaaagtcac agttccaagt gatattacca ctgccttcag    4200
ttcagtagac agacttcaca caacttcagc attcaagcca tcttccgcga tcactaagaa    4260
accacctctc atcgacaggg aacctggtga agaaacaacc agtgacatgg taatcattgg    4320
agaatcaaca tctcatgttc ctcccactac ccttgaagat attgtagcca aggaaacaga    4380
aaccgatatt gatagagagt atttcacgac ttcaagtcct cctgctacac agccaacaag    4440
accacccact gtggaagaca aagaggcctt tggaccctcag gcgctttcta cgccacagcc    4500
cccagcaagc acaaaatttc accctgacat taatgtttat attattgagg tcagagaaaa    4560
taagacaggt cgaatgagtg atttgagtgt aattggtcat ccaatagatt cagaatctaa    4620
agaagatgaa ccttgtagtg aagaaacaga tccagtgcat gatctaatgg ctgaaatttt    4680
acctgaattc cctgacataa ttgaaataga cctataccac agtgaagaaa atgaagaaga    4740
agaagaagag tgtgcaaatg ctactgatgt gacaaccacc ccatctgtgc agtacataaa    4800
tgggaagcat ctcgttacca ctgtgcccaa ggacccagaa gctgcagaag ctaggcgtgg    4860
ccagtttgaa agtgttgcac cttctcagaa tttctcggac agctctgaaa gtgatactca    4920
tccatttgta atagccaaaa cggaattgtc tactgctgtg caacctaatg aatctacaga    4980
aacaactgag tctcttgaag ttacatggaa gcctgagact accctgaaa catcagaaca    5040 tttttcaggt ggtgagcctg atgttttccc cacagtccca ttccatgagg aatttgaaag    5100
tggaacagcc aaaaaagggg cagaatcagt cacagagaga gatactgaag ttggtcatca    5160
ggcacatgaa catactgaac ctgtatctct gtttcctgaa gagtcttcag gagagattgc    5220
cattgaccaa gaatctcaga aaatagcctt tgcaagggct acagaagtaa catttggtga    5280
```

```
agaggtagaa aaaagtactt ctgtcacata cactcccact atagttccaa gttctgcatc    5340
agcatatgtt tcagaggaag aagcagttac cctaatagga aatccttggc cagatgacct    5400
gttgtctacc aaagaaagct gggtagaagc aactcctaga caagttgtag agctctcagg    5460
gagttcttcg attccaatta cagaaggctc tggagaagca gaagaagatg aagatacaat    5520
gttcaccatg gtaactgatt tatcacagag aaatactact gatacactca ttactttaga    5580
cactagcagg ataatcacag aaagcttttt tgaggttcct gcaaccacca tttatccagt    5640
ttctgaacaa ccttctgcaa aagtggtgcc taccaagttt gtaagtgaaa cagacacttc    5700
tgagtggatt tccagtacca ctgttgagga aaagaaaagg aaggaggagg agggaactac    5760
aggtacggct tctacatttg aggtatattc atctcacacag agatcggatc aattaatttt    5820 acccttttgaa ttagaaagtc caaatgtagc tacatctagt gattcaggta ccaggaaaag    5880
ttttatgtcc ttgacaacac caacacagtc tgaaagggaa atgacagatt ctactcctgt    5940
ctttacagaa acaaatacat tagaaaaattt gggggcacag accactgagc acagcagtat    6000
ccatcaacct ggggttcagg aagggctgac cactctccca cgtagtcctg cctctgtctt    6060
tatggagcag ggctctggag aagctgctgc cgacccagaa accaccactg tttcttcatt    6120
ttcattaaac gtagagtatg caattcaagc cgaaaaggaa gtagctggca cttttgtctcc    6180 gcatgtggaa actacattct ccactgagcc aacaggactg gttttgagta cagtaatgga    6240
cagagtagtt gctgaaaata taacccaaaac atccagggaa atagtgattt cagagcgatt    6300
aggagaacca aattatgggg cagaaataag gggcttttcc acaggttttc ctttggagga    6360
agatttcagt ggtgacttta gagaatactc aacagtgtct catcccatag caaaagaaga    6420
aacggtaatg atggaaggct ctggagatgc agcatttagg gacacccaga cttcaccatc    6480
tacagtacct acttcagttc acatcagtca catatctgac tcagaaggac ccagtagcac    6540
catggtcagc acttcagcct tccccctggga agagtttaca tcctcagctg agggctcagg    6600
tgagcaactg gtcacagtca gcagctctgt tgttccagtg cttcccagtg ctgtgcaaaa    6660
gttttctggt acagcttcct ccattatcga cgaaggattg ggagaagtgg gtactgtcaa    6720
tgaaattgat agaagatcca ccattttacc aacagcagaa gtgaaggta cgaaagctcc    6780 agtagagaag gaggaagtaa aggtcagtgg cacagtttca acaaactttc cccaaactat    6840
agagccagcc aaattatggt ctaggcaaga agtcaaccct gtaagacaag aaattgaaag    6900
tgaaacaaca tcagaggaac aaattcaaga agaaaagtca tttgaatccc ctcaaaactc    6960
tcctgcaaca gaacaaacaa tctttgattc acagacattt actgaaactg aactcaaaac    7020
cacagattat tctgtactaa caacaaagaa aacttacagt gatgataaag aaatgaagga    7080
ggaagacact tctttagtta acatgtctac tccagatcca gatgcaaatg gcttggaatc    7140
ttacacaact ctccctgaag ctactgaaaa gtcacatttt ttcttagcta ctgcattagt    7200
aactgaatct ataccagctg aacatgtagt cacagattca ccaatcaaaa aggaagaaag    7260
tacaaaacat tttccgaaag gcatgagacc aacaattcaa gagtcagata ctgagctctt    7320
attctctgga ctgggatcag gagaagaagt tttacctact ctaccaacag agtcagtgaa    7380
ttttactgaa gtgaacaaa tcaataacac attatatccc cacacttctc aagtggaaag    7440
tacctcaagt gacaaaattg aagactttaa cagaatggaa aatgtggcaa agaagttgg    7500 accactcgta tctcaaacag acatctttga aggtagtggg tcagtaacca gcacaacatt    7560
aatagaaatt ttaagtgaca ctggagcaga aggacccacg gtggcacctc tcccttttctc    7620
```

```
cacggacatc ggacatcctc aaaatcagac tgtcaggtgg gcagaagaaa tccagactag    7680
tagaccacaa accataactg aacaagactc taacaagaat tcttcaacag cagaaattaa    7740
cgaaacaaca acctcatcta ctgattttct ggctagagct tatggttttg aaatggccaa    7800
agaatttgtt acatcagcac caaaaccatc tgacttgtat tatgaacctt ctggagaagg    7860
atctggagaa gtggatattg ttgattcatt tcacacttct gcaactactc aggcaaccag    7920
acaagaaagc agcaccacat ttgtttctga tgggtccctg gaaaacatc ctgaggtgcc     7980 aagcgctaaa gctgttactg ctgatggatt cccaacagtt tcagtgatgc tgcctcttca    8040
ttcagagcag aacaaaagct cccctgatcc aactagcaca ctgtcaaata cagtgtcata    8100
tgagaggtcc acagacggta gtttccaaga ccgtttcagg gaattcgagg attccacctt    8160
aaaacctaac agaaaaaaac ccactgaaaa tattatcata gacctggaca agaggacaa     8220 ggatttaata ttgacaatta cagagagtac catccttgaa attctacctg agctgacatc    8280
ggataaaaat actatcatag atattgatca tactaaacct gtgtatgaag acattcttgg    8340
aatgcaaaca gatatagata cagaggtacc atcagaacca catgacagta atgatgaaag    8400
taatgatgac agcactcaag ttcaagagat ctatgaggca gctgtcaacc tttcttttaac   8460 tgaggaaaca tttgagggct ctgctgatgt tctggctagc tacactcagg caacacatga    8520
tgaatcaatg acttatgaag atagaagcca actagatcac atgggctttc acttcacaac    8580
tgggatccct gctcctagca cagaaacaga attagacgtt ttacttccca cggcaacatc    8640
cctgccaatt cctcgtaagt ctgccacagt tattccagag attgaaggaa taaaagctga    8700
agcaaaagcc ctgatgaca tgtttgaatc aagcactttg tctgatggtc aagctattgc     8760
agaccaaagt gaaataatac caacattggg ccaatttgaa aggactcagg aggagtatga    8820
agacaaaaaa catgctggtc cttcttttca gccagaattc tcttcaggag ctgaggaggc    8880
attagtagac catactccct atctaagtat tgctactacc caccttatgg atcagagtgt    8940
aacagaggtg cctgatgtga tggaaggatc caatccccca tattcactg atacaacatt     9000 agcagtttca acatttgcga agttgtcttc tcagacacca tcatctcccc tcactatcta    9060
ctcaggcagt gaagcctctg gacacacaga gatcccccag cccagtgctc tgccaggaat    9120
agacgtcggc tcatctgtaa tgtccccaca ggattctttt aaggaaattc atgtaaatat    9180
tgaagcgact ttcaaaccat caagtgagga ataccttcac ataactgagc ctccctcttt    9240
atctcctgac acaaaattag aaccttcaga agatgatggt aaacctgagt tattagaaga    9300
aatggaagct tctcccacag aacttattgc tgtggaagga actgagattc tccaagattt    9360
ccaaaacaaa accgatggtc aagtttctgg agaagcaatc aagatgtttc ccaccattaa    9420
aacacctgag gctggaactg ttattacaac tgccgatgaa attgaattag aaggtgctac    9480
acagtggcca cactctactt ctgcttctgc cacctatggg gtcgaggcag gtgtggtgcc    9540
ttggctaagt ccacagactt ctgagaggcc cacgctttct tcttctccag aaataaaccc    9600
tgaaactcaa gcagctttaa tcagagggca ggattccacg atagcagcat cagaacagca    9660
agtggcagcg agaattcttg attccaatga tcaggcaaca gtaaaccctg tggaatttaa    9720
tactgaggtt gcaacaccac catttttccct tctggagact tctaatgaaa cagatttcct   9780
gattggcatt aatgaagagt cagtggaagg cacggcaatc tatttaccag gacctgatcg    9840
ctgcaaaatg aacccgtgcc ttaacggagg cacctgttat cctactgaaa cttcctacgt    9900
atgcacctgt gtgccaggat acagcggaga ccagtgtgaa cttgattttg atgaatgtca    9960
ctctaatccc tgtcgtaatg gagccacttg tgttgatggt tttaacacat tcaggtgcct   10020
```

```
ctgccttcca agttatgttg gtgcactttg tgagcaagat accgagacat gtgactatgg   10080
ctggcacaaa ttccaagggc agtgctacaa atactttgcc catcgacgca catgggatgc   10140
agctgaacgg gaatgccgtc tgcagggtgc ccatctcaca agcatcctgt ctcacgaaga   10200
acaaatgttt gttaatcgtg tgggccatga ttatcagtgg ataggcctca atgacaagat   10260
gtttgagcat gacttccgtt ggactgatgg cagcacactg caatacgaga attggagacc   10320
caaccagcca gacagcttct tttctgctgg agaagactgt gttgtaatca tttggcatga   10380
gaatggccag tggaatgatg ttccctgcaa ttaccatctc acctatacgt gcaagaaagg   10440
aacagtcgct tgcggccagc ccctgttgt agaaaatgcc aagacctttg gaaagatgaa   10500
acctcgttat gaaatcaact ccctgattag ataccactgc aaagatggtt tcattcaacg   10560
tcaccttcca actatccggt gcttaggaaa tggaagatgg gctataccta aaattacctg   10620
catgaaccca tctgcatacc aaaggactta ttctatgaaa tactttaaaa attcctcatc   10680
agcaaaggac aattcaataa atacatccaa acatgatcat cgttggagcc ggaggtggca   10740
ggagtcgagg cgctgatccc taaaatggcg aacatgtgtt ttcatcattt cagccaaagt   10800
cctaacttcc tgtgcctttc ctatcacctc gagaagtaat tatcagttgg tttggatttt   10860
tggaccaccg ttcagtcatt ttgggttgcc gtgctcccaa aacattttaa atgaaagtat   10920
tggcattcaa aaagacagca gacaaaatga aagaaaatga gagcagaaag taagcatttc   10980
cagcctatct aatttcttta gttttctatt tgcctccagt gcagtccatt tcctaatgta   11040
taccagccta ctgtactatt taaaatgctc aatttcagca ccgatggcca tgtaaataag   11100
atgatttaat gttgatttta atcctgtata taaaataaaa agtcacaatg agtttgggca   11160
tatttaatga tgattatgga gccttagagg tctttaatca ttggttcggc tgcttttatg   11220
tagtttaggc tggaaatggt ttcacttgct ctttgactgt cagcaagact gaagatggct   11280
tttcctggac agctagaaaa cacaaaatct gtaggtcat tgcacctatc tcagccatag    11340
gtgcagtttg cttctacatg atgctaaagg ctgcgaatgg gatcctgatg gaactaagga   11400
ctccaatgtc gaactcttct ttgctgcatt ccttttttctt cacttacaag aaaggcctga   11460
atggaggact tttctgtaac caggaacatt ttttaggggt caaagtgcta ataattaact   11520
caaccaggtc tactttttaa tggctttcat aacactaact cataaggtta ccgatcaatg   11580
catttcatac ggatatagac ctagggctct ggagggtggg ggattgttaa aacacatgca   11640 aaaaaaaaa aaaaaaaaaa aaaagaaatt ttgtatatat aaccatttta atctttata    11700 aagttttgaa tgttcatgta tgaatgctgc agctgtgaag catacataaa taatgaagt    11760 aagccatact gatttaattt attggatgtt atttccccta agacctgaaa atgaacatag   11820
tatgctagtt attttcagt gttagccttt tactttcctc acacaatttg gaatcatata    11880
atataggtac tttgtccctg attaaataat gtgacggata gaatgcatca agtgtttatt   11940
atgaaaagag tggaaaagta tatagctttt agcaaaggt gtttgcccat tctaagaaat    12000
gagcgaatat atagaaatag tgtgggcatt tcttcctgtt aggtggagtg tatgtgttga   12060
catttctccc catctcttcc cactctgttt tctccccatt atttgaataa agtgactgct   12120
gaagatgact ttgaatcctt atccacttaa tttaatgttt aaagaaaaac ctgtaatgga   12180
aagtaagact ccttccctaa tttcagttta gagcaacttg aagaagagta gacaaaaaat   12240
aaaatgcaca tagaaaaaga gaaaagggc acaagggat tggcccaata ttgattcttt     12300
ttttataaaa cctcctttgg cttagaagga atgactctag ctacaataat acacagtatg   12360
```

```
tttaagcagg ttcccttggt tgttgcatta aatgtaatcc acctttaggt attttagagc   12420
acagaacaac actgtgttga tctagtaggt ttctattttt cctttctctt tacaatgcac   12480
ataatacttt cctgtattta tatcataacg tgtatagtgt aaaatgtgaa tgactttttt   12540
tgtgaatgaa aatctaaaat cttttgtaact ttttatatct gcttttgttt caccaaagaa   12600
acctaaaatc cttcttttac tacac                                          12625

<210> SEQ ID NO 47
<211> LENGTH: 6795
<212> TYPE: DNA
<213> ORGANISM: human

<400> SEQUENCE: 47
acagtgatat aatgatgatg ggtgtcacaa cccgcatttg aacttgcagg cgagctgccc     60 cgagccttc tggggaagaa ctccaggcgt gcggacgcaa cagccgagaa cattaggtgt     120
tgtggacagg agctgggacc aagatcttcg gccagcccg catcctcccg catcttccag     180
caccgtcccg caccctccgc atccttcccc gggccaccac gcttcctatg tgacccgcct    240
gggcaacgcc gaacccagtc gcgcagcgct gcagtgaatt ttccccccaa actgcaataa   300
gccgccttcc aaggccaaga tgttcataaa tataaagagc atcttatgga tgtgttcaac   360
cttaatagta acccatgcgc tacataaagt caaagtggga aaaagcccac cggtgagggg   420
ctccctctct ggaaaagtca gcctaccttg tcatttttca acgatgccta ctttgccacc   480
cagttacaac accagtgaat ttctccgcat caaatggtct aagattgaag tggacaaaaa   540
tggaaaagat ttgaaagaga ctactgtcct tgtgggccaa aatggaaata tcaagattgg   600
tcaggactac aaagggagag tgtctgtgcc cacacatccc gaggctgtgg gcgatgcctc   660
cctcactgtg gtcaagctgc tggcaagtga tgcgggtctt taccgctgtg acgtcatgta   720
cgggattgaa gacacacaag acacggtgtc actgactgtg gatggggttg tgtttcacta   780
cagggcggca accagcaggt acacactgaa ttttgaggct gctcagaagg cttgtttgga   840
cgttggggca gtcatagcaa ctccagagca gctctttgct gcctatgaag atggatttga   900
gcagtgtgac gcaggctggc tggctgatca gactgtcaga tatcccatcc gggctcccag   960
agtaggctgt tatggagata agatgggaaa ggcaggagtc aggacttatg gattccgttc    1020 tcccaggaa acttacgatg tgtattgtta tgtggatcat ctggatggtg atgtgttcca    1080
cctcactgtc cccagtaaat tcaccttcga ggaggctgca aaagagtgtg aaaaccagga    1140
tgccaggctg gcaacagtgg gggaactcca ggcggcatgg aggaacggct ttgaccagtg    1200
cgattacggg tggctgtcgg atgccagcgt gcgccaccct gtgactgtgg ccagggccca    1260
gtgtggaggt ggtctacttg gggtgagaac cctgtatcgt tttgagaacc agacaggctt    1320
ccctccccct gatagcagat ttgatgccta ctgctttaaa cctaaagagg ctacaaccat    1380
cgatttgagt atcctcgcag aaactgcatc acccagttta tccaaagaac cacaaatggt    1440
ttctgataga actacaccaa tcatcccttt agttgatgaa ttacctgtca ttccaacaga    1500
gttccctccc gtgggaaata ttgtcagttt tgaacagaaa gccacagtcc aacctcaggc    1560
tatcacagat agtttagcca ccaaattacc cacacctact ggcagtacca agaagccctg    1620
ggatatggat gactactcac cttctgcttc aggacctctt ggaaagctag acatatcaga    1680
aattaaggaa gaagtgctcc agagtacaac tggcgtctct cattatgcta cggattcatg    1740
ggatggtgtc gtggaagata acaaaacaca agaatcggtt acacagattg aacaaatga   1800 agtgggtcct ttggtaacat ctatggaaat cttaaagcac attccttcca aggaattccc    1860
```

```
tgtaactgaa acaccattgg taactgcaag aatgatcctg gaatccaaaa ctgaaaagaa      1920
aatggtaagc actgtttctg aattggtaac cacaggtcac tatggattca ccttgggaga      1980
agaggatgat gaagacagaa cacttacagt tggatctgat gagagcacct tgatctttga      2040
ccaaattcct gaagtcatta cggtgtcaaa gacttcagaa gacaccatcc acactcattt      2100
agaagacttg gagtcagtct cagcatccac aactgtttcc cctttaatta tgcctgataa      2160
taatggatca tccatggatg actgggaaga gagacaaact agtggtagga taacggaaga      2220
gtttcttggc aaatatctgt ctactacacc ttttccatca cagcatcgta cagaaataga      2280 attgttttcct tattctggtg ataaaatatt agtagaggga atttccacag ttatttatcc      2340
ttctctacaa acagaaatga cacatagaag agaaagaaca gaaacactaa taccagagat      2400
gagaacagat acttatacag atgaaataca agaagagatc actaaaagtc catttatggg      2460
aaaaacagaa gaagaagtct tctctgggat gaaactctct acatctctct cagagccaat      2520
tcatgttaca gagtcttctg tggaaatgac caagtctttt gatttcccaa cattgataac      2580
aaagttaagt gcagagccaa cagaagtaag agatatggag gaagacttta cagcaactcc      2640
aggtactaca aatatgatg aaaatattac aacagtgctt ttggcccatg gtactttaag      2700
tgttgaagca gccactgtat caaaatggtc atgggatgaa gataatacaa catccaagcc      2760
tttagagtct acagaacctt cagcctcttc aaaattgccc cctgccttac tcacaactgt      2820
ggggatgaat ggaaaggata agacatccc aagtttcact gaagatggag cagatgaatt      2880
tactcttatt ccagatagta ctcaaaagca gttagaggag gttactgatg aagacatagc      2940
agcccatgga aaattcacaa ttagatttca gccaactaca tcaactggta ttgcagaaaa      3000
gtcaactttg agagattcta caactgaaga aaaagttcca cctatcacaa gcactgaagg      3060
ccaagtttat gcaaccatgg aaggaagtgc tttgggtgaa gtagaagatg tggacctctc      3120
taagccagta tctactgttc cccaatttgc acacacttca gaggtggaag gattagcatt      3180
tgttagttat agtagcaccc aagagcctac tacttatgta gactcttccc ataccattcc      3240
tctttctgta attcccaaga cagactgggg agtgttagta ccttctgttc catcagaaga      3300
tgaagttcta ggtgaaccct ctcaagacat acttgtcatt gatcagactc gccttgaagc      3360
gactatttct ccagaaacta tgagaacaac aaaaatcaca gagggaacaa ctcaggaaga      3420
attcccttgg aaagaacaga ctgcagaaa accagttcct gctctcagtt ctacagcttg      3480
gactcccaag gaggcagtaa caccactgga tgaacaagag ggcgatggat cagcatatac      3540
agtctctgaa gatgaattgt tgacaggttc tgagagggtc ccagttttag aaacaactcc      3600
agttggaaaa attgatcaca gtgtgtctta tccaccaggt gctgtaactg agcacaaagt      3660
gaaaacagat gaagtggtaa cactaacacc acgcattggg ccaaaagtat ctttaagtcc      3720
agggcctgaa caaaaatatg aaacagaagg tagtagtaca acaggattta catcatcttt      3780
gagtcctttt agtacccaca ttacccagct tatggaagaa accactactg agaaaacatc      3840
cctagaggat attgatttag gctcaggatt atttgaaaag cccaaagcca cagaactcat      3900
agaattttca acaatcaaag tcacagttcc aagtgatatt accactgcct tcagttcagt      3960
agacagactt cacacaactt cagcattcaa gccatcttcc gcgatcacta agaaaccacc      4020
tctcatcgac agggaacctg gtgaagaaac aaccagtgac atggtaatca ttggagaatc      4080
aacatctcat gttcctccca ctaccccttga agatattgta gccaaggaaa cagaaaccga      4140
tattgataga gagtattca cgacttcaag tcctcctgct acacagccaa caagaccacc      4200
```

```
cactgtggaa gacaaagagg cctttggacc tcaggcgctt tctacgccac agccccagc    4260
aagcacaaaa tttcaccctg acattaatgt ttatattatt gaggtcagag aaaataagac   4320
aggacctgat cgctgcaaaa tgaacccgtg ccttaacgga ggcacctgtt atcctactga   4380
aacttcctac gtatgcacct gtgtgccagg atacagcgga gaccagtgtg aacttgattt   4440
tgatgaatgt cactctaatc cctgtcgtaa tggagccact tgtgttgatg gttttaacac   4500
attcaggtgc ctctgccttc caagttatgt tggtgcactt tgtgagcaag ataccgagac   4560
atgtgactat ggctggcaca aattccaagg gcagtgctac aaatactttg cccatcgacg   4620
cacatgggat gcagctgaac gggaatgccg tctgcagggt gcccatctca caagcatcct   4680
gtctcacgaa gaacaaatgt tgttaatcg tgtgggccat gattatcagt ggataggcct    4740
caatgacaag atgtttgagc atgacttccg ttggactgat ggcagcacac tgcaatacga   4800
gaattggaga cccaaccagc cagacagctt ctttttctgct ggagaagact gtgttgtaat  4860
catttggcat gagaatggcc agtggaatga tgttccctgc aattaccatc tcacctatac   4920
gtgcaagaaa ggaacagtcg cttgcggcca gcccctgtt gtagaaaatg ccaagacctt    4980
tggaaagatg aaacctcgtt atgaaatcaa ctccctgatt agataccact gcaaagatgg   5040
tttcattcaa cgtcacccttc caactatccg gtgcttagga aatggaagat gggctatacc  5100
taaaattacc tgcatgaacc catctgcata ccaaaggact tattctatga aatactttaa   5160
aaattcctca tcagcaaagg acaattcaat aaatacatcc aaacatgatc atcgttggag   5220
ccggaggtgg caggagtcga ggcgctgatc cctaaaatgg cgaacatgtg ttttcatcat   5280
ttcagccaaa gtcctaactt cctgtgcctt tcctatcacc tcgagaagta attatcagtt   5340
ggtttggatt tttggaccac cgttcagtca ttttgggttg ccgtgctccc aaaacatttt   5400
aaatgaaagt attggcattc aaaaagacag cagacaaaat gaaagaaaat gagagcagaa   5460
agtaagcatt tccagcctat ctaatttctt tagttttcta tttgcctcca gtgcagtcca   5520
tttcctaatg tataccagcc tactgtacta tttaaaatgc tcaatttcag caccgatggc   5580
catgtaaata agatgattta atgttgattt taatcctgta tataaaataa aaagtcacaa   5640
tgagtttggg catatttaat gatgattatg gagccttaga ggtctttaat cattggttcg   5700
gctgctttta tgtagtttag gctggaaatg gtttcacttg ctctttgact gtcagcaaga   5760
ctgaagatgg cttttcctgg acagctagaa aacacaaaat cttgtaggtc attgcaccta   5820
tctcagccat aggtgcagtt tgcttctaca tgatgctaaa ggctgcgaat gggatcctga   5880
tggaactaag gactccaatg tcgaactctt ctttgctgca ttcctttttc ttcacttaca   5940
agaaaggcct gaatggagga cttttctgta accaggaaca tttttaggg gtcaaagtgc    6000
taataattaa ctcaaccagg tctacttttt aatggctttc ataacactaa ctcataaggt   6060
taccgatcaa tgcatttcat acggatatag acctagggct ctggagggtg ggggattgtt   6120
aaaacacatg caaaaaaaaa aaaaaaaaa aaaaagaaa ttttgtatat ataaccatt     6180
taatcttta taaagttttg aatgttcatg tatgaatgct gcagctgtga agcatacata   6240
aataaatgaa gtaagccata ctgatttaat ttattggatg ttattttccc taagacctga   6300
aaatgaacat agtatgctag ttattttttca gtgttagcct tttactttcc tcacacaatt  6360
tggaatcata taatataggt actttgtccc tgattaaata atgtgacgga tagaatgcat   6420
caagtgttta ttatgaaaag agtggaaaag tatatagctt ttagcaaaag gtgtttgccc   6480
attctaagaa atgagcgaat atatagaaat agtgtgggca tttcttcctg ttaggtggag   6540
tgtatgtgtt gacatttctc cccatctctt cccactctgt tttctcccca ttatttgaat   6600
```

| | | |
|---|---|---|
| aaagtgactg ctgaagatga ctttgaatcc ttatccactt aatttaatgt ttaaagaaaa | 6660 |
| acctgtaatg gaaagtaaga ctccttccct aatttcagtt tagagcaact tgaagaagag | 6720 |
| tagacaaaaa ataaaatgca catagaaaaa gagaaaaagg gcacaagggg attggcccaa | 6780 |
| tattgattct ttttt | 6795 |

<210> SEQ ID NO 48
<211> LENGTH: 9096
<212> TYPE: DNA
<213> ORGANISM: human

<400> SEQUENCE: 48

| | |
|---|---|
| acagtgatat aatgatgatg ggtgtcacaa cccgcatttg aacttgcagg cgagctgccc | 60 |
| cgagcctttc tggggaagaa ctccaggcgt gcggacgcaa cagccgagaa cattaggtgt | 120 |
| tgtggacagg agctgggacc aagatcttcg gccagccccg catcctcccg catcttccag | 180 |
| caccgtcccg caccctccgc atccttcccc gggccaccac gcttcctatg tgacccgcct | 240 |
| gggcaacgcc gaacccagtc gcgcagcgct gcagtgaatt ttccccccaa actgcaataa | 300 |
| gccgccttcc aaggccaaga tgttcataaa tataaagagc atcttatgga tgtgttcaac | 360 |
| cttaatagta acccatgcgc tacataaagt caaagtggga aaaagcccac cggtgagggg | 420 |
| ctccctctct ggaaaagtca gcctaccttg tcattttca acgatgccta ctttgccacc | 480 |
| cagttacaac accagtgaat ttctccgcat caaatggtct aagattgaag tggacaaaaa | 540 |
| tggaaaagat ttgaaagaga ctactgtcct tgtggcccaa aatggaaata tcaagattgg | 600 |
| tcaggactac aaagggagag tgtctgtgcc cacacatccc gaggctgtgg gcgatgcctc | 660 |
| cctcactgtg gtcaagctgc tggcaagtga tgcgggtctt taccgctgtg acgtcatgta | 720 |
| cgggattgaa gacacacaag acacggtgtc actgactgtg gatggggttg tgtttcacta | 780 |
| cagggcggca accagcaggt acacactgaa ttttgaggct gctcagaagg cttgtttgga | 840 |
| cgttggggca gtcatagcaa ctccagagca gctctttgct gcctatgaag atggatttga | 900 |
| gcagtgtgac gcaggctggc tggctgatca gactgtcaga tatcccatcc gggctcccag | 960 |
| agtaggctgt tatggagata agatgggaaa ggcaggagtc aggacttatg gattccgttc | 1020 |
| tccccaggaa acttacgatg tgtattgtta tgtggatcat ctggatggtg atgtgttcca | 1080 |
| cctcactgtc cccagtaaat tcaccttcga ggaggctgca aaagagtgtg aaaaccagga | 1140 |
| tgccaggctg gcaacagtgg gggaactcca ggcggcatgg aggaacggct tgaccagtg | 1200 |
| cgattacggg tggctgtcgg atgccagcgt gcgccaccct gtgactgtgg ccagggccca | 1260 |
| gtgtggaggt ggtctacttg gggtgagaac cctgtatcgt tttgagaacc agacaggctt | 1320 |
| ccctcccct gatagcagat tgatgcctac tgctttaaa cgtcgaatga gtgatttgag | 1380 |
| tgtaattggt catccaatag attcagaatc taaagaagat gaaccttgta gtgaagaaac | 1440 |
| agatccagtg catgatctaa tggctgaaat tttacctgaa ttccctgaca taattgaaat | 1500 |
| agacctatac cacagtgaag aaaatgaaga agaagaagaa gagtgtgcaa atgctactga | 1560 |
| tgtgacaacc accccatctg tgcagtacat aaatgggaag catctcgtta ccactgtgcc | 1620 |
| caaggaccca gaagctgcag aagctaggcg tggccagttt gaaagtgttg caccttctca | 1680 |
| gaatttctcg gacagctctg aaagtgatac tcatccattt gtaatagcca aaacggaatt | 1740 |
| gtctactgct gtgcaaccta tgaatctac agaaacaact gagtctcttg aagttacatg | 1800 |
| gaagcctgag acttaccctg aaacatcaga acatttttca ggtggtgagc ctgatgtttt | 1860 |

```
ccccacagtc ccattccatg aggaatttga aagtggaaca gccaaaaaag gggcagaatc    1920
agtcacagag agagatactg aagttggtca tcaggcacat gaacatactg aacctgtatc    1980
tctgtttcct gaagagtctt caggagagat tgccattgac caagaatctc agaaaatagc    2040
ctttgcaagg gctacagaag taacatttgg tgaagaggta gaaaaaagta cttctgtcac    2100
atacactccc actatagttc caagttctgc atcagcatat gtttcagagg aagaagcagt    2160
taccctaata ggaaatcctt ggccagatga cctgttgtct accaaagaaa gctgggtaga    2220
agcaactcct agacaagttg tagagctctc agggagttct tcgattccaa ttacagaagg    2280
ctctggagaa gcagaagaag atgaagatac aatgttcacc atggtaactg atttatcaca    2340
gagaaatact actgatacac tcattacttt agacactagc aggataatca cagaaagctt    2400
ttttgaggtt cctgcaacca ccatttatcc agtttctgaa caaccttctg caaaagtggt    2460
gcctaccaag tttgtaagtg aaacagacac ttctgagtgg atttccagta ccactgttga    2520
ggaaaagaaa aggaaggagg aggagggaac tacaggtacg gcttctacat ttgaggtata    2580
ttcatctaca cagagatcgg atcaattaat tttaccctttt gaattagaaa gtccaaatgt    2640
agctacatct agtgattcag gtaccaggaa aagttttatg tccttgacaa caccaacaca    2700
gtctgaaagg gaaatgacag attctactcc tgtctttaca gaaacaaata cattagaaaa    2760
tttgggggca cagaccactg agcacagcag tatccatcaa cctggggttc aggaagggct    2820
gaccactctc ccacgtagtc ctgcctctgt ctttatggag cagggctctg gagaagctgc    2880
tgccgaccca gaaaccacca ctgtttcttc attttcatta aacgtagagt atgcaattca    2940
agccgaaaag gaagtagctg gcactttgtc tccgcatgtg gaaactacat ctccactga    3000 gccaacagga ctggttttga gtacagtaat ggacagagta gttgctgaaa atataaccca    3060
aacatccagg gaaatagtga tttcagagcg attaggagaa ccaaattatg gggcagaaat    3120 aagggcttt tccacaggtt ttcctttgga ggaagatttc agtggtgact ttagagaata    3180
ctcaacagtg tctcatccca tagcaaaaga agaaacggta atgatggaag gctctggaga    3240
tgcagcattt agggacaccc agacttcacc atctacagta cctacttcag ttcacatcag    3300
tcacatatct gactcagaag gacccagtag caccatggtc agcacttcag ccttccctg    3360 ggaagagttt acatcctcag ctgagggctc aggtgagcaa ctggtcacag tcagcagctc    3420
tgttgttcca gtgcttccca gtgctgtgca aaagtttttct ggtacagctt cctccattat    3480
cgacgaagga ttgggagaag tgggtactgt caatgaaatt gatagaagat ccaccatttt    3540
accaacagca gaagtggaag gtacgaaagc tccagtagag aaggaggaag taaaggtcag    3600
tggcacagtt tcaacaaact ttccccaaac tatagagcca gccaaattat ggtctaggca    3660
agaagtcaac cctgtaagac aagaaattga aagtgaaaca acatcagagg aacaaattca    3720
agaagaaaag tcatttgaat cccctcaaaa ctctcctgca acagaacaaa caatctttga    3780
ttcacagaca tttactgaaa ctgaactcaa aaccacagat tattctgtac taacaacaaa    3840
gaaaacttac agtgatgata agaaatgaa ggaggaagac acttctttag ttaacatgtc    3900
tactccagat ccagatgcaa atggcttgga atcttacaca actctccctg aagctactga    3960
aaagtcacat ttttcttag ctactgcatt agtaactgaa tctataccag ctgaacatgt    4020
agtcacagat tcaccaatca aaaggaaga agtacaaaa cattttccga aaggcatgag    4080
accaacaatt caagagtcag atactgagct cttattctct ggactgggat caggagaaga    4140
agttttacct actctaccaa cagagtcagt gaatttact gaagtggaac aaatcaataa    4200
cacattatat ccccacactt ctcaagtgga aagtacctca agtgacaaaa ttgaagactt    4260
```

```
taacagaatg gaaaatgtgg caaaagaagt tggaccactc gtatctcaaa cagacatctt    4320
tgaaggtagt gggtcagtaa ccagcacaac attaatagaa attttaagtg acactggagc    4380
agaaggaccc acggtggcac ctctcccttt ctccacggac atcggacatc ctcaaaatca    4440
gactgtcagg tgggcagaag aaatccgaca tagtagacca caaaccataa ctgaacaaga    4500
ctctaacaag aattcttcaa cagcagaaat taacgaaaca acaacctcat ctactgattt    4560
tctggctaga gcttatggtt ttgaaatggc caaagaattt gttacatcag caccaaaacc    4620
atctgacttg tattatgaac cttctggaga aggatctgga gaagtggata ttgttgattc    4680
atttcacact tctgcaacta ctcaggcaac cagacaagaa agcagcacca catttgtttc    4740
tgatgggtcc ctggaaaaac atcctgaggt gccaagcgct aaagctgtta ctgctgatgg    4800
attcccaaca gtttcagtga tgctgcctct tcattcagag cagaacaaaa gctcccctga    4860
tccaactagc acactgtcaa atacagtgtc atatgagagg tccacagacg gtagtttcca    4920
agaccgtttc agggaattcg aggattccac cttaaaacct aacagaaaaa acccactga    4980 aaatattatc atagacctgg acaaagagga caaggattta atattgacaa ttacagagag    5040
taccatcctt gaaattctac ctgagctgac atcggataaa aatactatca tagatattga    5100
tcatactaaa cctgtgtatg aagacattct tggaatgcaa acagatatag atacagaggt    5160
accatcagaa ccacatgaca gtaatgatga aagtaatgat gacagcactc aagttcaaga    5220
gatctatgag gcagctgtca ccttctcttt aactgaggaa catttgagg ctctgctga    5280 tgttctggct agctacactc aggcaacaca tgatgaatca atgacttatg aagatagaag    5340
ccaactagat cacatgggct ttcacttcac aactgggatc cctgctccta gcacagaaac    5400
agaattagac gttttacttc ccacggcaac atccctgcca attcctcgta agtctgccac    5460
agttattcca gagattgaag gaataaaagc tgaagcaaaa gccctggatg acatgtttga    5520
atcaagcact ttgtctgatg gtcaagctat tgcagaccaa agtgaaataa taccaacatt    5580
gggccaattt gaaaggactc aggaggagta tgaagacaaa aaacatgctg gtccttcttt    5640
tcagccagaa ttctcttcag gagctgagga ggcattagta gaccatactc cctatctaag    5700
tattgctact acccacctta tggatcagag tgtaacagag gtgcctgatg tgatggaagg    5760
atccaatccc ccatattaca ctgatacaac attagcagtt tcaacatttg cgaagttgtc    5820
ttctcagaca ccatcatctc ccctcactat ctactcaggc agtgaagcct ctggacacac    5880
agagatcccc cagcccagtg ctctgccagg aatagacgtc ggctcatctg taatgtcccc    5940
acaggattct tttaaggaaa ttcatgtaaa tattgaagcg acttcaaac catcaagtga    6000 ggaatacctt cacataactg agcctccctc tttatctcct gacacaaaat tagaaccttc    6060
agaagatgat ggtaaacctg agttattaga agaaatggaa gcttctccca cagaacttat    6120
tgctgtggaa ggaactgaga ttctccaaga tttccaaaac aaaaccgatg gtcaagtttc    6180
tggagaagca atcaagatgt ttcccaccat taaaacacct gaggctggaa ctgttattac    6240
aactgccgat gaaattgaat tagaaggtgc tacacagtgg ccacactcta cttctgcttc    6300
tgccacctat ggggtcgagg caggtgtggt gccttggcta agtccacaga cttctgagag    6360
gcccacgctt tcttcttctc cagaaataaa ccctgaaact caagcagctt taatcagagg    6420
gcaggattcc acgatagcag catcagaaca gcaagtggca gcgagaattc ttgattccaa    6480
tgatcaggca acagtaaacc ctgtggaatt taatactgag gttgcaacac caccattttc    6540
ccttctggag acttctaatg aaacagattt cctgattggc attaatgaag agtcagtgga    6600
```

```
aggcacggca atctatttac caggacctga tcgctgcaaa atgaacccgt gccttaacgg      6660
aggcacctgt tatcctactg aaacttccta cgtatgcacc tgtgtgccag gatacagcgg      6720
agaccagtgt gaacttgatt ttgatgaatg tcactctaat ccctgtcgta atggagccac      6780
ttgtgttgat ggttttaaca cattcaggtg cctctgcctt ccaagttatg ttggtgcact      6840
ttgtgagcaa gataccgaga catgtgacta tggctggcac aaattccaag gcagtgcta       6900
caaatacttt gcccatcgac gcacatggga tgcagctgaa cgggaatgcc gtctgcaggg      6960
tgcccatctc acaagcatcc tgtctcacga agaacaaatg tttgttaatc gtgtgggcca     7020
tgattatcag tggataggcc tcaatgacaa gatgtttgag catgacttcc gttggactga     7080
tggcagcaca ctgcaatacg agaattggag acccaaccag ccagacagct tcttttctgc     7140
tggagaagac tgtgttgtaa tcatttggca tgagaatggc cagtggaatg atgttccctg     7200
caattaccat ctcacctata cgtgcaagaa aggaacagtc gcttgcggcc agccccctgt     7260
tgtagaaaat gccaagacct ttggaaagat gaaacctcgt tatgaaatca actccctgat     7320
tagataccac tgcaaagatg gtttcattca acgtcacctt ccaactatcc ggtgcttagg     7380
aaatggaaga tgggctatac ctaaaattac ctgcatgaac ccatctgcat accaaaggac     7440
ttattctatg aaatacttta aaaattcctc atcagcaaag gacaattcaa taatacatc      7500
caaacatgat catcgttgga gccggaggtg gcaggagtcg aggcgctgat ccctaaaatg     7560
gcgaacatgt gttttcatca tttcagccaa agtcctaact tcctgtgcct ttcctatcac     7620
ctcgagaagt aattatcagt tggtttggat ttttggacca ccgttcagtc attttgggtt     7680
gccgtgctcc caaacatttt aaatgaaag tattggcatt caaaaagaca gcagacaaaa      7740
tgaaagaaaa tgagagcaga aagtaagcat ttccagccta tctaatttct ttagtttctt     7800
atttgcctcc agtgcagtcc atttcctaat gtataccagc ctactgtact atttaaaatg     7860
ctcaatttca gcaccgatgg ccatgtaaat aagatgattt aatgttgatt ttaatcctgt     7920
atataaaata aaaagtcaca atgagtttgg gcatatttaa tgatgattat ggagccttag     7980
aggtctttaa tcattggttc ggctgctttt atgtagttta ggctggaaat ggtttcactt     8040
gctctttgac tgtcagcaag actgaagatg cttttcctg dacagctaga aaacacaaa      8100
tcttgtaggt cattgcacct atctcagcca taggtgcagt ttgcttctac atgatgctaa     8160
aggctgcgaa tgggatcctg atggaactaa ggactccaat gtcgaactct tctttgctgc     8220
attccttttt cttcacttac aagaaaggcc tgaatggagg acttttctgt aaccaggaac     8280
atttttagg ggtcaaagtg ctaataatta actcaaccag gtctacttt taatggcttt      8340
cataacacta actcataagg ttaccgatca atgcatttca tacggatata gacctagggc     8400
tctggagggt gggggattgt taaaacacat gcaaaaaaaa aaaaaaaaaa aaaaaagaa      8460
attttgtata tataaccatt ttaatctttt ataaagtttt gaatgttcat gtatgaatgc     8520
tgcagctgtg aagcatacat aaataaatga agtaagccat actgatttaa tttattggat    8580
gttatttcc ctaagacctg aaaatgaaca tagtatgcta gttattttc agtgttagcc      8640
ttttactttc ctcacacaat ttggaatcat ataatatagg tactttgtcc ctgattaaat    8700
aatgtgacgg atagaatgca tcaagtgttt attatgaaaa gagtggaaaa gtatatagct    8760
tttagcaaaa ggtgtttgcc cattctaaga aatgagcgaa tatatagaaa tagtgtgggc    8820
atttcttcct gttaggtgga gtgtatgtgt tgacatttct ccccatctct tcccactctg    8880
ttttctcccc attatttgaa taaagtgact gctgaagatg actttgaatc cttatccact    8940
taatttaatg tttaaagaaa aacctgtaat ggaaagtaag actccttccc taatttcagt    9000
```

| | | | |
|---|---|---|---|
| ttagagcaac | ttgaagaaga | gtagacaaaa aataaaatgc acatagaaaa agagaaaaag | 9060 |
| ggcacaaagg | gattggccca | atattgattc tttttt | 9096 |

<210> SEQ ID NO 49
<211> LENGTH: 3834
<212> TYPE: DNA
<213> ORGANISM: human

<400> SEQUENCE: 49

| | | | | | |
|---|---|---|---|---|---|
| acagtgatat | aatgatgatg | ggtgtcacaa | cccgcatttg | aacttgcagg | cgagctgccc | 60 |
| cgagcctttc | tggggaagaa | ctccaggcgt | gcggacgcaa | cagccgagaa | cattaggtgt | 120 |
| tgtggacagg | agctgggacc | aagatcttcg | gccagccccg | catcctcccg | catcttccag | 180 |
| caccgtcccg | caccctccgc | atccttcccc | gggccaccac | gcttcctatg | tgacccgcct | 240 |
| gggcaacgcc | gaacccagtc | gcgcagcgct | gcagtgaatt | ttccccccaa | actgcaataa | 300 |
| gccgccttcc | aaggccaaga | tgttcataaa | tataaagagc | atcttatgga | tgtgttcaac | 360 |
| cttaatagta | acccatgcgc | tacataaagt | caaagtggga | aaaagcccac | cggtgagggg | 420 |
| ctccctctct | ggaaaagtca | gcctaccttg | tcattttca | acgatgccta | ctttgccacc | 480 |
| cagttacaac | accagtgaat | ttctccgcat | caaatggtct | aagattgaag | tggacaaaaa | 540 |
| tggaaaagat | ttgaaagaga | ctactgtcct | tgtggcccaa | aatggaaata | tcaagattgg | 600 |
| tcaggactac | aaagggagag | tgtctgtgcc | cacacatccc | gaggctgtgg | gcgatgcctc | 660 |
| cctcactgtg | gtcaagctgc | tggcaagtga | tgcgggtctt | taccgctgtg | acgtcatgta | 720 |
| cgggattgaa | gacacacaag | acacggtgtc | actgactgtg | gatggggttg | tgtttcacta | 780 |
| cagggcggca | accagcaggt | acacactgaa | ttttgaggct | gctcagaagg | cttgtttgga | 840 |
| cgttgggca | gtcatagcaa | ctccagagca | gctctttgct | gcctatgaag | atggatttga | 900 |
| gcagtgtgac | gcaggctggc | tggctgatca | gactgtcaga | tatcccatcc | gggctcccag | 960 |
| agtaggctgt | tatggagata | agatgggaaa | ggcaggagtc | aggacttatg | gattccgttc | 1020 |
| tccccaggaa | acttacgatg | tgtattgtta | tgtggatcat | ctggatggtg | atgtgttcca | 1080 |
| cctcactgtc | cccagtaaat | tcaccttcga | ggaggctgca | aaagagtgtg | aaaaccagga | 1140 |
| tgccaggctg | gcaacagtgg | gggaactcca | ggcggcatgg | aggaacggct | tgaccagtg | 1200 |
| cgattacggg | tggctgtcgg | atgccagcgt | gcgccaccct | gtgactgtgg | ccagggccca | 1260 |
| gtgtggaggt | ggtctacttg | gggtgagaac | cctgtatcgt | tttgagaacc | agacaggctt | 1320 |
| ccctcccct | gatagcagat | tgatgcctta | ctgctttaaa | cgacctgatc | gctgcaaaat | 1380 |
| gaacccgtgc | cttaacggag | gcacctgtta | tcctactgaa | acttcctacg | tatgcacctg | 1440 |
| tgtgccagga | tacagcggag | accagtgtga | acttgatttt | gatgaatgtc | actctaatcc | 1500 |
| ctgtcgtaat | ggagccactt | gtgttgatgg | ttttaacaca | ttcaggtgcc | tctgccttcc | 1560 |
| aagttatgtt | ggtgcacttt | gtgagcaaga | taccgagaca | tgtgactatg | gctggcacaa | 1620 |
| attccaaggg | cagtgctaca | aatactttgc | ccatcgacgc | acatgggatg | cagctgaacg | 1680 |
| ggaatgccgt | ctgcagggtg | cccatctcac | aagcatcctg | tctcacgaag | aacaaatgtt | 1740 |
| tgttaatcgt | gtgggccatg | attatcagtg | gataggcctc | aatgacaaga | tgtttgagca | 1800 |
| tgacttccgt | tggactgatg | gcagcacact | gcaatacgag | aattggagac | caaccagcc | 1860 |
| agacagcttc | ttttctgctg | gagaagactg | tgttgtaatc | atttggcatg | agaatggcca | 1920 |
| gtggaatgat | gttccctgca | attaccatct | cacctatacg | tgcaagaaag | gaacagtcgc | 1980 |

```
ttgcggccag cccoctgttg tagaaaatgc caagacctt ggaaagatga aacctcgtta    2040
tgaaatcaac tccctgatta gataccactg caaagatggt ttcattcaac gtcaccttcc   2100
aactatccgg tgcttaggaa atggaagatg ggctatacct aaaattacct gcatgaaccc   2160
atctgcatac caaggactt attctatgaa atactttaaa aattcctcat cagcaaagga    2220
caattcaata aatacatcca aacatgatca tcgttggagc cggaggtggc aggagtcgag   2280
gcgctgatcc ctaaaatggc gaacatgtgt tttcatcatt tcagccaaag tcctaacttc   2340
ctgtgccttt cctatcacct cgagaagtaa ttatcagttg gtttggattt ttggaccacc   2400
gttcagtcat tttgggttgc cgtgctccca aaacatttta aatgaaagta ttggcattca    2460
aaaagacagc agacaaaatg aaagaaaatg agagcagaaa gtaagcattt ccagcctatc   2520
taatttcttt agttttctat ttgcctccag tgcagtccat ttcctaatgt ataccagcct   2580
actgtactat ttaaaatgct caatttcagc accgatggcc atgtaaataa gatgatttaa   2640
tgttgatttt aatcctgtat ataaaataaa aagtcacaat gagtttgggc atatttaatg    2700
atgattatgg agccttagag gtcttaatc attggttcgg ctgcttttat gtagtttagg    2760
ctggaaatgg tttcacttgc tctttgactg tcagcaagac tgaagatggc ttttcctgga   2820
cagctagaaa acacaaaatc ttgtaggtca ttgcacctat ctcagccata ggtgcagttt   2880
gcttctacat gatgctaaag gctgcgaatg ggatcctgat ggaactaagg actccaatgt   2940
cgaactcttc tttgctgcat tcctttttct tcacttacaa gaaaggcctg aatggaggac   3000
ttttctgtaa ccaggaacat ttttaggggg tcaaagtgct aataattaac tcaaccaggt   3060 ctactttta atggctttca taacactaac tcataaggtt accgatcaat gcatttcata    3120
cggatataga cctagggctc tggagggtgg gggattgtta aaacacatgc aaaaaaaaaa   3180
aaaaaaaaaa aaaagaaat tttgtatata taaccatttt aatcttttat aaagttttga    3240
atgttcatgt atgaatgctg cagctgtgaa gcatacataa ataaatgaag taagccatac   3300 tgattaatt tattggatgt tatttttccct aagacctgaa aatgaacata gtatgctagt    3360
tatttttcag tgttagcctt ttactttcct cacacaattt ggaatcatat aatataggta   3420
ctttgtccct gattaaataa tgtgacggat agaatgcatc aagtgtttat tatgaaaaga   3480 gtggaaagt atatagcttt tagcaaaagg tgtttgccca ttctaagaaa tgagcgaata    3540
tatagaaata gtgtgggcat tcttcctgt taggtggagt gtatgtgttg acatttctcc    3600
ccatctcttc ccactctgtt ttctccccat tatttgaata aagtgactgc tgaagatgac   3660
tttgaatcct tatccactta atttaatgtt taaagaaaaa cctgtaatgg aaagtaagac    3720
tccttcccta atttcagttt agagcaactt gaagaagagt agacaaaaaa taaaatgcac    3780
atagaaaaag agaaaaggg cacaagggaa ttggcccaat attgattctt tttt          3834
```

<210> SEQ ID NO 50
<211> LENGTH: 4060
<212> TYPE: DNA
<213> ORGANISM: human

<400> SEQUENCE: 50

```
atgagcaaac tcagaatggt gctacttgaa gactctggat ctgctgactt cagaagacat     60
tttgtcaact tgagtcccct caccattact gtggtcttac ttctcagtgc ctgttttgtc   120
accagttctc ttggaggaac agacaaggag ctgaggctag tggatggtga aaacaagtgt    180
agcgggagag tggaagtgaa agtccaggag gagtggggaa cggtgtgtaa taatggctgg    240
agcatggaag cggtctctgt gatttgtaac cagctgggat gtccaactgc tatcaaagcc    300
```

```
cctggatggg ctaattccag tgcaggttct ggacgcattt ggatggatca tgtttcttgt      360
cgtgggaatg agtcagctct ttgggattgc aaacatgatg gatggggaaa gcatagtaac      420
tgtactcacc aacaagatgc tggagtgacc tgctcagatg gatccaattt ggaaatgagg      480
ctgacgcgtg gagggaatat gtgttctgga agaatagaga tcaaattcca aggacggtgg      540
ggaacagtgt gtgatgataa cttcaacata gatcatgcat ctgtcatttg tagacaactt      600
gaatgtggaa gtgctgtcag tttctctggt tcatctaatt ttggagaagg ctctggacca      660
atctggtttg atgatcttat atgcaacgga aatgagtcag ctctctggaa ctgcaaacat      720
caaggatggg gaaagcataa ctgtgatcat gctgaggatg ctggagtgat ttgctcaaag      780
ggagcagatc tgagcctgag actggtagat ggagtcactg aatgttcagg aagattagaa      840
gtgagattcc aaggagaatg ggggacaata tgtgatgacg gctgggacag ttacgatgct      900
gctgtggcat gcaagcaact gggatgtcca actgccgtca cagccattgg tcgagttaac      960
gccagtaagg gatttggaca catctggctt gacagcgttt cttgccaggg acatgaacct     1020
gctatctggc aatgtaaaca ccatgaatgg ggaaagcatt attgcaatca caatgaagat     1080
gctggcgtga catgttctga tggatcagat ctggagctaa gacttagagg tggaggcagc     1140
cgctgtgctg gacagttgag ggtggagatt cagagactgt tagggaaggt gtgtgacaga     1200
ggctggggac tgaaagaagc tgatgtggtt tgcaggcagc tgggatgtgg atctgcactc     1260
aaaacatctt atcaagtgta ctccaaaatc caggcaacaa acacatggct gttcctaagt     1320
agctgtaacg gaaatgaaac ttctctttgg gactgcaaga actggcaatg gggtggactt     1380
acctgtgatc actatgaaga agccaaaatt acctgctcag cccacaggga acccagactg     1440
gttggagggg acattccctg ttctggacgt gttgaagtga gcatggtgga cacgtggggc     1500
tccatctgtg attcggactt ctctctggaa gctgccagcg ttctatgcag ggaattacag     1560
tgtggcacag ttgtctctat cctgggggga gctcactttg agagggaaa tggacagatc     1620 tgggctgaag aattccagtg tgagggacat gagtcccatc tttcactctg cccagtagca     1680
ccccgcccag aaggaacttg tagccacagc agggatgttg gagtagtctg ctcaagatac     1740
acagaaattc gcttggtgaa tggcaagacc ccgtgtgagg gcagagtgga gctcaaaacg     1800
cttggtgcct ggggatccct ctgtaactct cactgggaca tagaagatgc ccatgttctt     1860
tgccagcagc ttaaatgtgg agttgccctt tctaccccag gaggagcacg ttttggaaaa     1920
ggaaatggtc agatctggag gcatatgttt cactgcactg ggactgagca gcacatggga     1980
gattgtcctg taactgctct aggtgcttca ttatgtcctt cagagcaagt ggcctctgta     2040
atctgctcag gaaaccagtc ccaaacactg tcctcgtgca attcatcgtc tttgggccca     2100
acaaggccta ccattccaga gaaagtgctg tggcctgca tagagagtgg tcaacttcgc     2160
ctggtaaatg gaggaggtcg ctgtgctggg agagtagaga tctatcatga gggctcctgg     2220
ggcaccatct gtgatgacag ctgggaccctg agtgatgccc acgtggtttg cagacagctg     2280
ggctgtggag aggccattaa tgccactggt tctgctcatt ttggggaagg aacagggccc     2340
atctggctgg atgagatgaa atgcaatgga aagaatccc gcatttggca gtgccattca     2400
cacggctggg ggcagcaaaa ttgcaggcac aaggaggatg cggagttat ctgctcagaa     2460 ttcatgtctc tgagactgac cagtgaagcc agcagagagg cctgtgcagg gcgtctggaa     2520 gtttttttaca atggagcttg gggcactgtt ggcaagagta gcatgtctga aaccactgtg     2580
ggtgtggtgt gcaggcagct gggctgtgca gacaaaggga aaatcaaccc tgcatcttta     2640
```

| | | | | |
|---|---|---|---|---|
| gacaaggcca | tgtccattcc | catgtgggtg | gacaatgttc | agtgtccaaa | aggacctgac | 2700 |
| acgctgtggc | agtgcccatc | atctccatgg | gagaagagac | tggccagccc | ctcggaggag | 2760 |
| acctggatca | catgtgacaa | caagataaga | cttcaggaag | gacccacttc | ctgttctgga | 2820 |
| cgtgtggaga | tctggcatgg | aggttcctgg | gggacagtgt | gtgatgactc | ttgggacttg | 2880 |
| gacgatgctc | aggtggtgtg | tcaacaactt | ggctgtggtc | cagctttgaa | agcattcaaa | 2940 |
| gaagcagagt | ttggtcaggg | gactggaccg | atatggctca | atgaagtgaa | gtgcaaaggg | 3000 |
| aatgagtctt | ccttgtggga | ttgtcctgcc | agacgctggg | gccatagtga | gtgtgggcac | 3060 |
| aaggaagacg | ctgcagtgaa | ttgcacagat | atttcagtgc | agaaaacccc | acaaaaagcc | 3120 |
| acaacaggtc | gctcatcccg | tcagtcatcc | tttattgcag | tcgggatcct | tggggttgtt | 3180 |
| ctgttggcca | ttttcgtcgc | attattcttc | ttgactaaaa | agcgaagaca | gagacagcgg | 3240 |
| cttgcagttt | cctcaagagg | agagaactta | gtccaccaaa | ttcaataccg | ggagatgaat | 3300 |
| tcttgcctga | atgcagatga | tctggaccta | atgaattcct | cagaaaattc | ccatgagtca | 3360 |
| gctgatttca | gtgctgctga | actaatttct | gtgtctaaat | ttcttcctat | ttctggaatg | 3420 |
| gaaaaggagg | ccattctgag | ccacactgaa | aaggaaaatg | ggaatttata | acccagtgag | 3480 |
| ttcagccttt | aagataccct | tgatgaagacc | tggactattg | aatggagcag | aaattcacct | 3540 |
| ctctcactga | ctattacagt | tgcatttta | tggagttctt | cttctcctag | gattcctaag | 3600 |
| actgctgctg | aatttataaa | aattaagttt | gtgaatgtga | ctacttagtg | gtgtatatga | 3660 |
| gactttcaag | ggaattaaat | aaataaataa | gaatgttatt | gatttgagtt | tgctttaatt | 3720 |
| acttgtcctt | aattctatta | atttctaaat | gggcttccta | attttttgta | gagtttccta | 3780 |
| gatgtattat | aatgtgtttt | atttgacagt | gtttcaattt | gcatatacag | tactgtatat | 3840 |
| tttttcttat | ttggtttgaa | taattttcct | attaccaaat | aaaaataaat | ttattttac | 3900 |
| tttagttttt | ctaagacagg | aaaagttaat | gatattgaag | ggtctgtaaa | taatatatgg | 3960 |
| ctaactttat | aaggcatgac | tcacaacgat | tctttaactg | ctttttgtta | ctgtaattct | 4020 |
| gttcactaga | ataaaatgca | gagccacacc | tggtgagggc | | | 4060 |

```
<210> SEQ ID NO 51
<211> LENGTH: 4076
<212> TYPE: DNA
<213> ORGANISM: human

<400> SEQUENCE: 51
```

| | | | | | | |
|---|---|---|---|---|---|---|
| atgagcaaac | tcagaatggt | gctacttgaa | gactctggat | ctgctgactt | cagaagacat | 60 |
| tttgtcaact | tgagtcccctt | caccattact | gtggtcttac | ttctcagtgc | ctgttttgtc | 120 |
| accagttctc | ttggaggaac | agacaaggag | ctgaggctag | tggatggtga | aaacaagtgt | 180 |
| agcgggagag | tggaagtgaa | agtccaggag | gagtggggaa | cggtgtgtaa | taatggctgg | 240 |
| agcatggaag | cggtctctgt | gatttgtaac | cagctgggat | gtccaactgc | tatcaaagcc | 300 |
| cctggatggg | ctaattccag | tgcaggttct | ggacgcattt | ggatggatca | tgtttcttgt | 360 |
| cgtgggaatg | agtcagctct | ttgggattgc | aaacatgatg | gatggggaaa | gcatagtaac | 420 |
| tgtactcacc | aacaagatgc | tggagtgacc | tgctcagatg | gatccaattt | ggaaatgagg | 480 |
| ctgacgcgtg | gagggaatat | gtgttctgga | agaatagaga | tcaaattcca | aggacggtgg | 540 |
| ggaacagtgt | gtgatgataa | cttcaacata | gatcatgcat | ctgtcatttg | tagacaactt | 600 |
| gaatgtggaa | gtgctgtcag | tttctctggt | tcatctaatt | ttgagaagg | ctctggacca | 660 |
| atctggtttg | atgatcttat | atgcaacgga | aatgagtcag | ctctctggaa | ctgcaaacat | 720 |

```
caaggatggg gaaagcataa ctgtgatcat gctgaggatg ctggagtgat tgctcaaag      780 ggagcagatc tgagcctgag actggtagat ggagtcactg aatgttcagg aagattagaa      840
gtgagattcc aaggagaatg ggggacaata tgtgatgacg ctgggacag ttacgatgct       900 gctgtggcat gcaagcaact gggatgtcca actgccgtca cagccattgg tcgagttaac      960
gccagtaagg gatttggaca catctggctt gacagcgttt cttgccaggg acatgaacct     1020
gctatctggc aatgtaaaca ccatgaatgg ggaaagcatt attgcaatca caatgaagat     1080
gctggcgtga catgttctga tggatcagat ctggagctaa acttagagg tggaggcagc      1140 cgctgtgctg ggacagttga ggtggagatt cagagactgt tagggaaggt gtgtgacaga     1200
ggctggggac tgaaagaagc tgatgtggtt tgcaggcagc tgggatgtgg atctgcactc     1260
aaaacatctt atcaagtgta ctccaaaatc caggcaacaa acacatggct gtttctaagt     1320
agctgtaacg gaaatgaaac ttctcttttgg gactgcaaga actggcaatg gggtggactt    1380
acctgtgatc actatgaaga agccaaaatt acctgctcag cccacaggga acccagactg     1440
gttggagggg acattccctg ttctggacgt gttgaagtga agcatggtga cacgtggggc     1500
tccatctgtg attcggactt ctctctggaa gctgccagcg ttctatgcag ggaattacag     1560
tgtggcacag ttgtctctat cctgggggga gctcactttg gagagggaaa tggacagatc     1620
tgggctgaag aattccagtg tgagggacat gagtcccatc tttcactctg cccagtagca     1680
ccccgcccag aaggaacttg tagccacagc agggatgttg gagtagtctg ctcaagtaag     1740
acccagaaaa catctttaat tggttctcat actgtgaaag ggacagggtt agggagtcat     1800
agctgtcttt ttctaaagcc ctgtctcctt ccaggataca cagaaattcg cttggtgaat     1860
ggcaagaccc cgtgtgaggg cagagtggag ctcaaaacgc ttggtgcctg gggatccctc     1920
tgtaactctc actgggacat agaagatgcc catgttcttt gccagcagct taaatgtgga     1980
gttgcccttt ctaccccagg aggagcacgt tttggaaaag gaatggtca gatctggagg     2040 catatgtttc actgcactgg gactgagcag cacatgggag attgtcctgt aactgctcta     2100
ggtgcttcat tatgtccttc agagcaagtg gcctctgtaa tctgctcagg aaaccagtcc     2160
caaacactgt cctcgtgcaa ttcatcgtct ttgggcccaa caaggcctac cattccagaa     2220
gaaagtgctg tggcctgcat agagagtggt caacttcgcc tggtaaatgg aggaggtcgc     2280
tgtgctggga gagtagagat ctatcatgag ggctcctggg gcaccatctg tgatgacagc     2340
tgggacctga gtgatgccca cgtggtttgc agacagctgg gctgtggaga ggccattaat     2400
gccactggtt ctgctcattt tggggaagga acagggccca tctggctgga tgagatgaaa     2460
tgcaatggaa aagaatcccg catttggcag tgccattcac acggctgggg gcagcaaaat     2520
tgcaggcaca aggaggatgc gggagttatc tgctcagaat tcatgtctct gagactgacc     2580
agtgaagcca gcagagaggc ctgtgcaggg cgtctggaag tttttttacaa tggagcttgg     2640 ggcactgttg gcaagagtag catgtctgaa accactgtgg gtgtggtgtg caggcagctg     2700
ggctgtgcag acaaagggaa aatcaaccct gcatctttag acaaggccat gtccattccc     2760
atgtgggtgg acaatgttca gtgtccaaaa ggacctgaca cgctgtggca gtgcccatca     2820
tctccatggg agaagagact ggccagcccc tcggaggaga cctggatcac atgtgacaac     2880
aagataagac ttcaggaagg acccacttcc tgttctggac gtgtggagat ctggcatgga     2940
ggttcctggg ggacagtgtg tgatgactct tgggacttgg acgatgctca ggtggtgtgt     3000
caacaacttg gctgtggtcc agctttgaaa gcattcaaag aagcagagtt tggtcagggg     3060
```

```
actggaccga tatggctcaa tgaagtgaag tgcaaaggga atgagtcttc cttgtgggat    3120
tgtcctgcca gacgctgggg ccatagtgag tgtgggcaca aggaagacgc tgcagtgaat    3180
tgcacagata tttcagtgca gaaaacccca caaaaagcca caacaggtcg ctcatcccgt    3240
cagtcatcct ttattgcagt cgggatcctt ggggttgttc tgttggccat tttcgtcgca    3300
ttattcttct tgactaaaaa gcgaagacag agacagcggc ttgcagtttc ctcaagagga    3360
gagaacttag tccaccaaat tcaataccgg gagatgaatt cttgcctgaa tgcagatgat    3420
ctggacctaa tgaattcctc aggaggccat tctgagccac actgaaaagg aaaatgggaa    3480
tttataaccc agtgagttca gcctttaaga taccttgatg aagacctgga ctattgaatg    3540
gagcagaaat tcacctctct cactgactat tacagttgca ttttttatgga gttcttcttc    3600 tcctaggatt cctaagactg ctgctgaatt tataaaaatt aagtttgtga atgtgactac    3660
ttagtggtgt atatgagact ttcaagggaa ttaaataaat aaataagaat gttattgatt    3720
tgagtttgct ttaattactt gtccttaatt ctattaattt ctaaatgggc ttcctaattt    3780
tttgtagagt ttcctagatg tattataatg tgttttattt gacagtgttt caatttgcat    3840
atacagtact gtatatttttt tcttatttgg tttgaataat tttcctatta ccaaataaaa    3900
ataaatttat ttttactttta gttttttctaa gacaggaaaa gttaatgata ttgaagggtc    3960
tgtaaataat atatggctaa ctttataagg catgactcac aacgattctt taactgcttt    4020
ttgttactgt aattctgttc actagaataa aatgcagagc cacacctggt gagggc         4076

<210> SEQ ID NO 52
<211> LENGTH: 1714
<212> TYPE: DNA
<213> ORGANISM: human

<400> SEQUENCE: 52
tgccgccaga gtaaagcttt ctacccttta ctccctgcaa agaaacaaga gtgcttatcc      60
cagctaagct ccagggtaat gttatcatga cagcttcaac ttttagacca caggcaaatg     120
ctttgttaaa actctatgct ggtcattccc ttcaggattt ggcactcacc aacataccct     180
tctttcaagt gaaaaggcat ctctttttaat ggtcctgacc tttggaatag aagcatgta     240 ccctggacag agcacttcaa actagaggaa ccataaatcc atggctaacc ttgacaaata     300
cactgaaaca ttcaagatgg gtagcaacag taccagcact gctgagattt actgtaatgt     360
cactaatgtg aaatttcaat actccctcta tgcaaccacc tatatcctca tattcattcc     420
tggtcttctg gctaacagtg cagccttgtg ggttctgtgc cgcttcatca gcaagaaaaa     480
taaagccatc attttcatga tcaacctctc tgtggctgac cttgctcatg tattatcttt     540 accccctccgg atttactatt acatcagcca ccactggcct ttccagagag ccctttgcct     600
gctctgcttc tacctgaagt atctcaacat gtatgccagc atttgtttcc tgacgtgcat     660
cagtcttcaa aggtgctttt ttctcctcaa gcccttcagg ccagagact ggaagcgtag      720 gtacgatgtg ggcatcagtg ctgccatctg gatcgttgtg gggactgcct gtttgccatt     780
tcccatcctg agaagcacag acttaaacaa caacaagtcc tgctttgctg atcttggata     840
caagcaaatg aatgcagttg cgttggtcgg gatgattaca gttgctgagc ttgcaggatt     900
tgtgatccca gtgatcatca tcgcatggtg tacctggaaa actactatat ccttgagaca     960
gccaccaatg gctttccaag ggatcagtga gaggcagaaa gcactgcgga tggtgttcat    1020
gtgtgctgca gtcttcttca tctgcttcac tccctatcat attaacttta ttttttacac    1080
catggtaaag gaaaccatca ttagcagttg tcccgttgtc cgaatcgcac tgtatttcca    1140
```

-continued

```
ccctttttgc ctgtgccttg caagtctctg ctgcctttg gatccaattc tttattactt    1200
tatggcttca gagtttcgtg accaactatc ccgccatggc agttctgtga cccgctcccg    1260
cctcatgagc aaggagagtg gttcatcaat gattggctaa aattaagata tctctttaat    1320
tacgcctttg tttacctacg ttccttgtct ttttccaaag gccagaattg tcaaccaatt    1380
tctttaattg aacattgtaa aaaacaggaa taagtacttt tgtgtaatat tcacagtcaa    1440
caggggtgtg atggtgaagg cagagtgtga aaaacgtgag agaggaagag aaaatagatt    1500
tacctgattc ctctttaaaa ttcaagccac tttcttattt aagaaaccta gatcaagttt    1560
ttacagatgt aaataaaagt tgaatagttt accttaaatt tttttcaata agtaagttat    1620
tgttaataat gcacagtaaa tatgtgaatt tttcctagat gtaaaaaaaa aaatctttca    1680
tataaagacc ttaaattctg agtgagagta aaaa                               1714
```

<210> SEQ ID NO 53
<211> LENGTH: 1597
<212> TYPE: DNA
<213> ORGANISM: human

<400> SEQUENCE: 53

```
tttgtgcaaa taaggtttct gtggtgagac accagataaa ctcaacttcc tctttcaaca     60
acaaatgtgt cagttatcag caggatccat gccgccagag taaagctttc tacccttta    120 tccctgcaaa gaaacaagag tgcttatccc agctaagctc cagggaacca taaatccatg    180
gctaaccttg acaaatacac tgaaacattc aagatgggta gcaacagtac cagcactgct    240
gagatttact gtaatgtcac taatgtgaaa tttcaatact ccctctatgc aaccacctat    300
atcctcatat tcattcctgg tcttctggct aacagtgcag ccttgtgggt tctgtgccgc    360
ttcatcagca agaaaaataa agccatcatt ttcatgatca acctctctgt ggctgacctt    420
gctcatgtat tatctttacc cctccggatt tactattaca tcagccacca ctggcctttc    480
cagagagccc tttgcctgct ctgcttctac ctgaagtatc tcaacatgta tgccagcatt    540
tgtttcctga cgtgcatcag tcttcaaagg tgctttttc tcctcaagcc cttcagggcc    600
agagactgga agcgtaggta cgatgtgggc atcagtgctg ccatctggat cgttgtgggg    660
actgcctgtt tgccatttcc catcctgaga agcacagact aaacaacaa caagtcctgc    720 tttgctgatc ttggatacaa gcaaatgaat gcagttgcgt tggtcgggat gattacagtt    780
gctgagcttg caggatttgt gatcccagtg atcatcatcg catggtgtac ctggaaaact    840
actatatcct tgagacagcc accaatggct ttccaaggga tcagtgagag gcagaaagca    900
ctgcggatgg tgttcatgtg tgctgcagtc ttcttcatct gcttcactcc ctatcatatt    960
aactttattt tttacaccat ggtaaaggaa accatcatta gcagttgtcc cgttgtccga   1020
atcgcactgt atttccaccc ttttttgcctg tgccttgcaa gtctctgctg ccttttggat   1080
ccaattcttt attactttat ggcttcagag tttcgtgacc aactatcccg ccatggcagt   1140
tctgtgaccc gctcccgcct catgagcaag gagagtggtt catcaatgat tggctaaaat   1200
taagatatct ctttaattac gcctttgttt acctacgttc cttgtctttt tccaaaggcc   1260
agaattgtca accaatttct taattgaac attgtaaaaa acaggaataa gtacttttgt    1320
gtaatattca cagtcaacag gggtgtgatg gtgaaggcag agtgtgaaaa acgtgagaga   1380
ggaagagaaa atagatttac ctgattcctc tttaaaattc aagccacttt cttatttaag   1440
aaacctagat caagtttta cagatgtaaa taaaagttga atagtttacc ttaaattttt   1500
```

```
ttcaataagt aagttattgt taataatgca cagtaaatat gtgaattttt cctagatgta    1560
aaaaaaaaaa tctttcatat aaagaccta  aattctg                             1597

<210> SEQ ID NO 54
<211> LENGTH: 4661
<212> TYPE: DNA
<213> ORGANISM: human

<400> SEQUENCE: 54
cgctcccctc agctcctgca gtgctaatta agggagggag cagcggggag cttgcagtga      60
ccaagagggt gttgaggcta ggaggccacg ataaacagga tacgataaaa gtccttaacc    120
aagacgcaga tgggaagaag cgttagagcg agcagcactc acatctcaag aaccagcctt    180
tcaaacagtt tccagagatg gattatccta ctttactttt ggctcttctt catgtataca    240
gagctctatg tgaagaggtg cttggcata  catcagttcc ctttgccgag aacatgtctc    300
tagaatgtgt gtatccatca atgggcatct taacacaggt ggagtggttc aagatcggga    360
cccagcagga ttccatagcc attttcagcc ctactcatgg catggtcata aggaagccct    420
atgctgagag ggtttacttt ttgaattcaa cgatggcttc caataacatg actcttttct    480
ttcggaatgc ctctgaagat gatgttggct actattcctg ctctctttac acttacccac    540
agggaacttg gcagaaggtg atacaggtgg ttcagtcaga tagttttgag gcagctgtgc    600
catcaaatag ccacattgtt tcggaacctg gaaagaatgt cacactcact tgtcagcctc    660
agatgacgtg gcctgtgcag gcagtgaggt gggaaaagat ccagccccgt cagatcgacc    720
tcttaactta ctgcaacttg gtccatggca gaaatttcac ctccaagttc caagacaaa     780 tagtgagcaa ctgcagccac ggaaggtgga gcgtcatcgt catccccgat gtcacagtct    840
cagactcggg gctttaccgc tgctacttgc aggccagcgc aggagaaaac gaaaccttcg    900
tgatgagatt gactgtagcc gagggtaaaa ccgataacca atatacccctc tttgtggctg    960 gagggacagt tttattgttg ttgtttgtta tctcaattac caccatcatt gtcattttcc   1020
ttaacagaag gagaaggaga gagagaagag atctatttac agagtcctgg gatacacaga   1080
aggcacccaa taactataga agtcccatct ctaccagtca acctaccaat caatccatgg   1140
atgatacaag agaggatatt tatgtcaact atccaacctt ctctcgcaga ccaaagacta   1200
gagtttaagc ttattcttga catgagtgca ttagtaatga ctcttatgta ctcatgcatg   1260
gatctttatg caattttttt ccactaccca aggtctacct tagatactag ttgtctgaat   1320
tgagttactt tgataggaaa aatacttcat tacctaaaat cattttccat agaactgttt   1380
cagaaaacct gactctaact ggtttatata caaaagaaaa cttactgtat catataacag   1440
aatgatccag gggagattaa gctttgggca agggctattt accagggctt aaatgttgtg   1500
tctagaatta agtatgggca taaactggct tctgaatccc tttccagagt gttggatcca   1560
tttccctggt cttggcctca ctctcatgca ggctttcctc ttgtgttggc aagatggctg   1620
ccaactcttg gcaattcata catccttgtt tctgtctggt agagagtttg cttctcaaat   1680
ggagcaaaca aatttgatta ttttttcatt gttaaatagg caacatgacc agaaaggatg   1740
gaatggctta agtaaactaa gggttcactt ctagagctga gaagcagggt caaagcacaa   1800
tactgggcaa ttcagagcat ggttagaaga ggaaagggga gtctcaaagc tggagagttt   1860
accaacaaat attgactgca gtgattaacc aagacatttt tgttaactaa aaagtgaaat   1920
atgggatgga ttctagaaat gggggtatctc tgtccatact tctagaatcc actctatcag   1980
catagtccag aagaataacct ggcagtagaa gaaatgaata ttcaagagga agataaatgc   2040
```

```
gagagggcaa tcctttacta ttctcatatt tatttatctc tcattctgta tagaattctt    2100
gccgccatcc caggtctagc cttaggagca aatgtagtag atagtcgaat aataaataac    2160
ttaatgtttt ggacatattt tgtctacttt tgagaattat ttttaatatg taaattctct    2220
caaaagggtc aggcacctag ttattatttt ttaatgatta tgtgaaagtt gaatataata    2280
taccactaaa agtgacagtt gaaagtggtg gcataggacg gtagggtaga aatttgggag    2340
ggaaaaaaga aattgggagg gtacaggcaa caggagaaag gaatcaaacc acagaaaaat    2400
acaaagggaa acttctgctt cactattcag acaaagacag ccctaatgac atcaccaaca    2460
gtcaaagcaa ttagagacca tacctaatat tgtttaaatt ctagatgtag gctaacaatg    2520
aaaagtattt gccaaactga ataaaactgt catggttacc ttgaaaggac aatggttatt    2580
gttaaatata gtgatcattc atgtctaaaa gattcattat ttatctctaa agatttctaa    2640
agaccaccat ctagaaaaga ttcattatga aggctgtatt taaatatcaa agttgtggac    2700
ttcatgataa tcttaaataa agcaaatcca aattctcctg ttgcctagac agattctaag    2760
atgtaattta cacttttaag ctaattagtg agtatttat gattttagcc ttaaacacca     2820
tgtatgccaa ataatgcact tgttttgtga attacagaaa tggtaagtgc ccacatttct    2880
gtgaattata aaatttgtga gtttctttta acccttttca ggagtgaaaa aataaaaacg    2940
accatttcct ggttgtgctt aagtatatgc aagaagggta aactctcatt tttattatgt    3000
ttgcttaaag atcttttat acctggattc atgaaatgtt tccacaaata tattagtgta     3060
acaaacttga aaggcagttt acaagaaagc actctactat cagatcaatc aaagattctg    3120
tgagtgaatt tattggtttg catggtgaag caagcttagc atcaattaaa aggtaaataa    3180
tttcttttct gaatggtaaa gacaatcaaa atattacttt ctggaaaact ccaataacca    3240
aattctcaat gattagtgta tgtgagcagg aaaacatttt tacagttgta gtatggggaa    3300
atataaatcc aattttaaga gagaaaatta tgactgggtg tggaagggac agtatagtca    3360
gataccattg tcatggtggt ttttactggg aacttcatga aagactttg tagcaaacca     3420
ctgcagtatt gcaaagcctc cagaacattt ggaacttgtc tcttttttcct tgtgtgtgtt    3480
tgtgtttttg gtctctcatt caaaatattg atgagaacta tttactctgt cctttcttct    3540
ctatatattc ttcctctaca gagtgtaggg ttttttcagg aatttggagc catctgaagt    3600
cctcccaaaa attctctgac gtcttctgat gctcctgtta taccctcagg ggtaatgctt    3660
gtgaaattcc attcattcat tttctttctc tggacatctt tacttaccaa agcactttca    3720
ttgtcatctt tttaacatca ttcttaattc gtgatagttt tgggactctc cctagtgtat    3780
gtttctcccc ctctactctt ttgcacctat gattctgatt gttactaaga aagcagatga    3840
aaaacagatc cacagaataa acgatcagaa ttccagtaaa ttctatttta aatacagata    3900
cttttttacaa gttgctgctt tggaagcaaa atgcttctta agttttacat atatatatat   3960
atatatacat atatatatac acatataatt tatatcgatg gataatacat taagaatcta    4020
tgcttccttt gaatgccatt aatatttatg ttaaagtaac caatgaaagg aaattacttt    4080
gttataataa gataggaaga cttgttaatg gagtacacag ttttgtcagg gaaagaacac    4140
atcttattga actatgatga ctatgcattg actatattat tataagagat accttcaaac    4200
tttatttaaa gaactttagg tataatatgt tgagaaaata aaatagaaat ttcatttact    4260
tgtaatcatg cttaaaatgg gaggcaggta ggtgaagata taattttag taaaaactcc     4320
aatttatgtt ttaagtaatt cagtgtatta ctaaaatact atatatataa acttaaaata    4380
```

```
catgggttat caatttaaaa gacaaagtaa gtaaaaatac ttttagtagg cattcgtgga    4440
ttgtgaacat ccaagttata ttggtttgta tagaatggca ttaagtaaaa attacagctg    4500
tataacagta gttttctaaa ttgagagagt ccacattgta attagagatc actgtgacca    4560
aaatgcttct ccttgattta taatgatgta ctgtattttg tactgcttat atgaaatttc    4620
agcaagattg acgatattat aaagatgctt ataaagtgta a                       4661
```

<210> SEQ ID NO 55
<211> LENGTH: 2013
<212> TYPE: DNA
<213> ORGANISM: human

<400> SEQUENCE: 55

```
caagtgagct gcccaccttg gcctcccaaa gtgttgggat tacaggcgtg agccaccaca      60
cccagcaaaa tttctaacaa gctctcaaat gatgctgatg ttgctggttg gggtggaggt     120
ggggcatacc ttgagagcca ctagattaga ccaggggttg gcgtattatg gcagggccag     180
tcactgtgtt ttataaaatt ctattggtac atagtttctg ctgtctcttt aaatattgtc     240
tgtggctgct tttggcagag ttgagcatta gagacagatt acatgggccc caaacttaaa     300
atatttactg tttgaccatt ttaagaaaaa gtttatttaa ccttatcccc ttttttcttt     360
tctctctctc tctctctttc cttccttcct tccttccttc tttttttttc tgagacggag     420
tcttactctg tgcccaggct agagtgcagt ggcatgatct cggctcactg caacctccac     480
ctcccgggtt caagcgattc tcctgcctca gcctctcaag tagctgggat tacaggccgg     540
ctgcctaccc tccagactgt ccgctatggc tccaaggctg ttacccgcca ccgtcgtgtg     600
atgcactttc agcggcagaa gctgatggct gtgactgaat atatccccccc gaaaccagcc     660
atccacccat catgcctgcc atctcctccc agcccccac aggaggagat aggcctcatc      720
aggcttctcc gccgggagat agcagcagtt ttccaggaca accgaatgat agccgtctgc     780
cagaatgtgg ctctgagtgc agaggacaag cttcttatgc acaccagct gcggaaacac      840
aagatcctga tgaaggtctt ccccaaccag gtcctgaagc ccttcctgga ggattccaag     900
taccaaaatc tgctgcccct ttttgtgggg cacaacatgc tgctggtcag tgaagagccc     960
aaggtcaagg agatggtacg gatcttaagg actgtgccat tcctgccgct gctaggtggc    1020
tgcattgatg acaccatcct cagcaggcag ggctttatca actactccaa gctccccagc    1080
ctgccctgg tgcaggggga gcttgtagga ggcctcacct gcctcacagc ccagacccac    1140
tccctgctcc agcaccagcc cctccagctg accaccctgt tggaccagta catcagagag    1200
caacgcgaga aggattctgt catgtcggcc aatgggaagc cagatcctga cactgttccg    1260
gactcgtagc cagcctgttt agccagccct gcgcataaat acactctgcg ttattggctg    1320
tgctctcctc aatgggacat gtggaagaac ttggggtcgg ggagtgtgtt tgtcacttgg    1380
ttttcactag taatgatatt gtcaggtata gggccacttg gagatgcaga ggattccatt    1440
tcagatgtca gtcaccggct tcgtccttag ttttcccaac ttgggacgtg ataggagcaa    1500
agtctctcca ttctccaggt ccaaggcaga gatcctgaaa agatagggct attgtcccct    1560
gcctccttgg tcactgcctc ttgctgcacg ggctcctgag cccacccctt tggggcacaa    1620
cctgccactg ccacagtagc tcaaccaagc agttgtgctg agaatggcac ctggtgagag    1680
cctgctgtgt gccaggcttt gtgctgagtg ctgtacatgt attagttcct ttactgctga    1740
ccacattgta cccatttcac agagaaggag cagagaaatt aagtggcttg ctcaaggtca    1800
tgcagttagt aagtggcaga acagggactt gaaccaagcc ctctgctctg aagaccgcgt    1860
```

```
cctgaatttc ttcactagag cttcctcatc aggttaccca gaagtgggtc ccatccacca    1920
tccaggtgtg cttggatgtt agttctccac cctcgaggtg tacgctgtga aaagtttggg    1980
agcactgctt tataataaaa tgaaatatat tct                                 2013
```

```
<210> SEQ ID NO 56
<211> LENGTH: 1725
<212> TYPE: DNA
<213> ORGANISM: human

<400> SEQUENCE: 56
gtggagatgg ctgcggccgt ggcggggatg ctgcgagggg gtctcctgcc ccaggcgggc      60
cggctgccta ccctccagac tgtccgctat ggctccaagg ctgttacccg ccaccgtcgt     120
gtgatgcact tcagcggca gaagctgatg gctgtgactg aatatatccc cccgaaacca      180
gccatccacc catcatgcct gccatctcct cccagccccc cacaggagga gataggcctc     240
atcaggcttc tccgccggga gatagcagca gttttccagg acaaccgaat gatagccgtc     300
tgccagaatg tggctctgag tgcagaggac aagcttctta tgcgacacca gctgcggaaa     360
cacaagatcc tgatgaaggt cttccccaac caggtcctga gcccttcct ggaggattcc      420 aagtaccaaa atctgctgcc ccttttgtg gggcacaaca tgctgctggt cagtgaagag      480
cccaaggtca aggagatggt acggatctta aggactgtgc cattcctgcc gctgctaggt     540
ggctgcattg atgacaccat cctcagcagg cagggcttta tcaactactc caagctcccc     600
agcctgcccc tggtgcaggg ggagcttgta ggaggcctca cctgcctcac agcccagacc     660
cactccctgc tccagcacca gcccctccag ctgaccaccc tgttggacca gtacatcaga     720
gagcaacgcg agaaggattc tgtcatgtcg gccaatggga agccagatcc tgacactgtt     780
ccggactcgt agccagcctg tttagccagc cctgcgcata aatacactct gcgttattgg     840
ctgtgctctc ctcaatggga catgtggaag aacttgggt cggggagtgt gtttgtcact      900
tggttttcac tagtaatgat attgtcaggt atagggccac ttggagatgc agaggattcc     960
atttcagatg tcagtcaccg gcttcgtcct tagttttccc aacttgggac gtgataggag    1020
caaagtctct ccattctcca ggtccaaggc agagatcctg aaaagatagg gctattgtcc    1080
cctgcctcct tggtcactgc ctcttgctgc acgggctcct gagcccaccc ccttggggca    1140
caacctgcca ctgccacagt agctcaacca agcagttgtg ctgagaatgg cacctggtga    1200
gagcctgctg tgtgccaggc tttgtgctga gtgctgtaca tgtattagtt cctttactgc    1260
tgaccacatt gtacccattt cacagagaag gagcagagaa attaagtggc ttgctcaagg    1320
tcatgcagtt agtaagtggc agaacaggga cttgaaccaa gccctctgct ctgaagaccg    1380
cgtcctgaat tcttcacta gagcttcctc atcaggttac ccagaagtgg gtcccatcca     1440
ccatccaggt gtgcttggat gttagttctc caccctcgag gtgtacgctg tgaaaagttt    1500
gggagcactg ctttataata aaatgaaata tattctactt cctttatttt gtggtttaca    1560
cggttgtcct ccctctaaac ttactctcag gggcttctct gtcatctgac tttcctcact    1620
cttgcttccc ttcctaggaa aatcctcttc ccctatacct gttcccacaa atggcatccc    1680
gcgcatgctt gccctattaa aggcagctga cagctgtacc cacta                    1725
```

```
<210> SEQ ID NO 57
<211> LENGTH: 7665
<212> TYPE: DNA
<213> ORGANISM: human
```

<400> SEQUENCE: 57

```
ggccgacccg gctcgccagc tccacgctcg gctccagact ccggcatttc ctccccgcta      60
gctggcgcgg cctcgcctcc ccctcggaag aggaaactcc cggggtccga gtaacagggt     120
caggcgcgga gaggagcggc gggagagcca ggagggccgc ccagggtagg aggcgagcca     180
ggccgggcca gaagctggcc gacggcggcg cgcggggggcg ccggccgggg agggccgctg     240
ggccggactc agcgcgcagc cggggcaggg cgcggcccgg ggcccgagag cgcagggcgg     300
gccgcagctg gaaggaacac ttgagctggg agaggaggcc gagctggagg gcggcctccc     360
tcgggcctgc gttcgggaag ccgccgcgga ggaggagacg gggacagcgg ggctgcccgg     420
gcgctgtgcg catgctgggc ttgggtcgcc gccggggctt gccccctggg ctgctcggcc     480
accgccgccc cggcgcccg gcatgtcggt gcactacacc ctcaatctac gcgtcttctg     540
gcccctggtg accggcctgt gcaccgccct ggtgtgcctc taccatgtcc tgcggggaag     600
cgggggcgcc cgggccgagc ccgccgacgg cgtggatggc ggcttcccgt tgcttaaggt     660
ggccgtcctg ctcctcctca gctatgtcct cctgcgctgt cgccacgctg tccggcagcg     720
cttcctgccc gggtctcccc gtctggaggg tcacgccgcc ttctcctcga gacacttccg     780
agagccgggc ctcagcatcc tgctggagag ttactacgag catgaggtgc gcctgtctcc     840
gcacgtgttg ggccacagca aggcgcacgt gagccggatc gtgggcgagc tggtgcgggc     900
tggccgcgcc cggggtccc ccggtctcat tcctggggga gcgctggcct tggccttccg     960
cggagacttc atccaggtgg gcagcgccta cgagcaacat aaaatccgcc ggcccgacag    1020
cttcgacgtg ctggtgccac tgcgcctccc gccgcttgtg gcgctggagc cacggagcct    1080
gggcgaggag ccagcgctgg ccccggcctt ccgcggctgc ttcttgtgcg ccctcaaggc    1140
accaccctca ccatcggggg cctcgggggg ccactggctt cgggactgca aaccctttgc    1200
tgatgccttc tgcgtggatg tgcgcgggcg gcgtcacctc tctgctactc tggtgctgcg    1260
ctggttccag tcgcatctgc agcgctcctt ggccactgtg cgttacagcc tggaggggcg    1320
ctgtcgggtc accttgaccc caggtggcct ggaacagccc cccaccttac acatcttgcc    1380
ctgccgcact gactacggct gctgccgcct ttctatggct gtgcgtctca tccccgctgt    1440
ccatctggga gatgggtct tccttgtggc gccaccaccg ccaccctttgc ccagcgcgcc    1500
cctgttggag ctccctgagg gcctgcgtgc ggaggcactg tggggtgtga acacagcacg    1560
ccaggagcag aagctgctga gttggctgca ggaacgggca gctccaggtg cctgctacct    1620
caagtgcctg cagttgctta aggctctgcg cgatctgggg gcccgtgggc tggactcagc    1680
ggccgccacc cagtggggac gcatcctatc ctcatatgtg ctcaagacag tgctgctggc    1740
agtgctgctg cgcaaggggg cccctgggca aggctgggac gaggagcacc tgggaaggtg    1800
tttggaggag ttggtgcagt tccttaggga ctgcctgctg cgacgccata cgctcttcca    1860
ctgcgtcctg ggcctggtg gggcggctgc cgaggtgggt cccctgccca aggcactgag    1920
ggaagccgcc ccagttgacc tcctggccgc tttcgacggg cacgcccggg aacttgcagc    1980
agcgcggttg ctgtccacgt ggcaaaggct gccccagctt ctccgggcct acggggtcc    2040
ccgctaccttt gccaggtgcc ccccaccccg gagtcagcgc acccagggct tccttgaagg    2100
tgaaccgtaa accctgacag cacccccacc tgaccaaatg ctcctaaagc ctttcccact    2160
gggtgggggt gggaatggcg gtgaagccag ttaaatgcaa gattgcagaa ggcattggaa    2220
aatttggtgg ctgccacaag ctttagtggc ttaaatatca ccttctcgct tcacagtcca    2280
gtataatatg acatcttcac acccactaga gtgtcctggg caaaccatgg gaagacatcc    2340
```

-continued

```
aacaggagac ccaagaattg gttcaaatat tgttctgtgt agacggattc tgtagaagga    2400
tgtggctttt agagaagtcc agtagaagaa gcaagaacta gctgcaggga aagttccttc    2460
tgtcggtttt tagacacaga tctctctgcc caaattaaaa aaaaacaaaa caaaacacta    2520 aagttttga cacaattact tgctaggtac tgggttcctg attgtcttta aaagaaaaa     2580 tctgaatctt tatttgcaac tggaattgaa gttctatttt aggggctaat gtttagagga    2640
acataatttc cactgttcaa attaatatta atgtatttt aaaatggtgc aatcacaggt     2700
gtttgacaag attgtcaaca agttaagtca catgatgga aaggcaatcg agagttggtt     2760
agagaagctt ccagagaaaa tagcactta tattgatcaa ttcactcatt ttgtggtaat     2820
tgctagcacc aagcattgca tctgaaaggg aagccagtta tatttattat taaatgtaca   2880
accttgaaaa gcagccagca tgcttgccta actaacatcg ccgcaggcca caagctggga   2940
tatgtacctg tccgtcaaca tccattcatt aaactaccta ctaccagcca gagatgtctg   3000
gaaccaaagt agcaaccaaa tacatattca agacaacact ggtgaaggca taaacatgt    3060 tggcttgga gaaagatgtg ttttaggctt tgcctgtaaa ggtgtttctc caaggctggc    3120
tgctggctgg agacagaaaa ctttttttgtt ttaaggtttt tagcaaactc cttcacaaag  3180
agatttcttt ctgagcttaa tgagctaatg aagaggaaat gcctgctgct tagcatgtgg   3240
tttgtgctgg gtctctaacc attgatggtt cttccttgtc caggcagtct tacgtggtcc   3300
aagagacctg ttgattcagc acaggtcttg caaaacattt cacttatagt tcagtatctt   3360
gggctctgtg cttgaagatc agttactccc tggtcgtggg cagaggagac aaattaggaa   3420
aagagcaagg gagacagccc ttgacggcag tctgtctctt ttctctttag gtgtcagtat   3480
caccaggttg ggtgtatttt gcagctggga ggagccggtc ctggaattct tccttgttct   3540
cccaaattta taacagtcct caattgcagt ttaagttcag catggcccct catctgcttg   3600
cctgattgga aatgcagcca gtccaagtgt tacaaattgg gattttttg ttttctaaat    3660 aaaaacatgt acttcctcag actcttaaag ctaaaatttg gaagacagaa atgcctatgt   3720
gaatagaatc attgttgaag ttctgagctc ttttgaggga actctataag ccttcttct    3780 ttaggggatc cacttgcctg ctgtgggaaa tcatagtgag tgatttacag gaatccttct   3840
cctccaagct gcattggctt cttatatcct ttgcgacctt gggctgaaag agaaacagct   3900
gcaaatgttg tgctgtctct ttgaggttgt cttgggggaca gttccccgca aaggtcattc   3960
ctagcttttg aggtcaatgt tgggtcataa ggtactgcat tgtgcaaaga agtcagtctg   4020
ctaactttat gcaaagatag aaactgcacg gtatttttta aaattagttt ttaaaataaa   4080
tgccaagagt agatcttata tatatatata tgtatacata ttttatatat atatatattt   4140
ccatactcaa ccacaacttc ctctgtactc attgtttact acagtggggg acatcaaggg   4200
ttggaaggat tataaagctt taaggctggg cgtggtggct cacgcctgta atcccagcac   4260
tttgggaggc gaggtgggcg gatcacctga ggtcaggagt tcaagaccag cctagccaac   4320
atagtgaaac tctgtctcta ctaaaaaata caaaaattag ctgggcgtgg tggcgggcgc   4380
ctgtaatccc agatactcgg gaggctaagg caggagaatc acttgaaccc gggaggtgaa   4440
ggttgcagag agccaagatc acaccactgc actccagcct gggtgaccga gcagactcc   4500 gtctcaaaaa aaaaaaaaaa aagctttaaa aagctgaatt ttagaaatat ttctagcagt   4560
gtcagtgagt tcctcttta atagtgtttt aaagtataaa tctggtaaca tactgttctt    4620 gtagttttt gttagttttg ttttcaggt taattaccca aagcctcatc catcctcaag     4680
```

```
gttttttaaat ttttatttttt taaaataaat tgtgcattgt atttgtgaat ttttaaaata    4740
ttactgtttt atttaaatgc catgctgagc aattgttctc tgtacatggt aaccaaaact     4800
tagagatttc gatcaatttt gatcaatgtt tagtaaacca aaacatgtac tgtgtacaac     4860
ggaaataata tggcatatta gccaggcatg atggttgccc aagacagtta aattaagctc     4920
aattctgtat tttattaggg ctctgttatg tccttcatct gaaatgtaca cattttggt     4980
gtatgcttgg tactggagat tcatatatgc aaatattctc atgcaagaag ttccacagta     5040
acaacagcaa aaagaaaaaa ttagttgtcc agccagtgct ggaggaaaat gtttctgggg     5100
aagatgactc agtcattttg tggcgagaca ccctttggta actcccactg accagtcttg     5160
ggagccttcc tggaatgatc gtgggctgag cggagatgtt ttttgcaaaa tgaaactgaa     5220
gctgaaagaa aggagaattc gagtgaacca agagaaatcc aaagacctgg gaaggagga     5280
cttaagatga aagtgaagca agagagggaa ggggaaatga agtgaaaatg gcgtgagggt     5340
gtgagagagg tttgggttag gaaacatgtt tttagtgcta tttccaacca ggggtcgcaa     5400
actcagcagc ctgtagaaac aggggtggga ggtgggggg aagctgtgcc cacctttaaa      5460
gaggggggcca ttgctcagcc atgcagaaaa aaatggggca acaagctgga aatcaggttt    5520
tttttttttta aagtgaaact tgatgatttt taaacaagta attaaaaaaa tgtccaaaac    5580
accatgtggg ccaaacattt gttgagcct gggggccacc agtttgcgac cactgccta      5640
cgtagttaac accctgagta tgtatacagt catattttt gttttggata tggtagtgtt      5700
atatatactt gggggcgtga tatttgaagt catctttatc tctcagagtt aagctttatt    5760
gtagaagaaa aaaaaaaag ttaacacagc catagataac acttaactca cagttcccag       5820
gaggacactt gatctcgaag ctgctctttt tgagtcagat cctacatcaa accacttagg      5880
gccagttttt ggcatttcct tcctggtgat ttgggggtaaa cttctttgct ctgtcggagt     5940
ttgcagatga gtaatcagaa ggattgcaga ataacttgtt tctttgtatt ttattcttac      6000
atttaaatta attttggggg gttagtggta tcctagctcg tgcctttaca gggatgattg      6060
gtggctagat ttgggtgca agcttcttag gctcatacca tttcaactac caagaacaca      6120
ggttttttgtt tttgttttt gagacaggg ctcagtctgt tgcccaggct ggagtgcagt       6180
ggcaagattg cagctcattg cagccttgac ctcctgggct caagcgatcc tcctgcctcg     6240
gcctcccaac tagctgggac cacaggtatg tgccactaca cccagcgaat ttttaaatta     6300
tttgtagagt cagggtctcc ctatgttgcc caggctggtc ttgaactact ggactcaagc     6360
catcctccca cctcggcctc ccaaagtgtt gggattatag gcgcgagcca ccacacctgg    6420
cctaaaagcg tcgttctgat cagacttcac ccctgaatgt ttctatcatt ttcttttctt     6480
tttttttttt tttcgagaca gagttttgct cttgttttac aggctgggt gcggtgggat      6540
gatcttggct cactgcaatc tcctcctccc aggttcaagt gattcttggg ccttagcctc     6600
ccgagtagct gggattacag gcacctgcca ccacgcctgg ctaatatata tatatatata    6660
tatatatttt tttttttttt ttttagtaga gatgggtttt catcatgttg gccaggctgg     6720
tctcgaactc ctgacctcag gtgatctacc tgcctcggcc tcccaaagtg cagggattac    6780
aggtgtgagt gagccaccgc ggccggcctc tatcattttc tgactcagca gctccaccaa    6840
aattgacatc ctagcaaaca ctgtgaagga attaacctaa gtgcttccag agcatctcat     6900
gtaacctcta tggagtaagt cacttttttct gtaacatgtg gctttgacc ttgatgaaga     6960
ctttgacttc tcatccctgt ctacatggag gaagatgatt cagtggtggg gaaaatgaac    7020
ctcggtaaca tttccaatgt ccttcaagag ggaaacaagt tcagtgttat catcgtggca    7080
```
ttcgttagtt ttttttttt taaatcactt gtttagatac aactttattt ttttatacct      7140
acatagcaca tgactggggg gataaagcat gtataagttg ggagagggta aagaatgtgt      7200
gactatgtat acagaaaata gactaaaatg tgcagcaaaa tgatatatac tgtaatctgg      7260
tttttgaagt atctactatt ctggaatatt gttaaacaac ttttgcttt tgaaaaaaaa      7320 aggtgccttg attcagttgc gtgacttaga acattcatcc tattttattg tgattttaa      7380 tgtcttctga ccccaaactg tgttttggt tgcagtctgg cggctgcagg catagcgtcg      7440
gttttgttcc aataacagag accaaagagt taatcagata tggttcagct gctacaattg      7500
tatgattcaa aggcaattta atcaccccaa atttccatgg cccccacagt caagacctgc      7560
cattcgtttt ctcttgcagg ttggagtaaa tttgcacttt gaatcatgtg ggtcatttgg      7620
ggaccttgtt cttttctatt ttgctttatt aataaaggaa cttgt                    7665

<210> SEQ ID NO 58
<211> LENGTH: 1609
<212> TYPE: DNA
<213> ORGANISM: human

<400> SEQUENCE: 58
gtaaagagag gcacgtggtt aagctctcgg ggtgtggact ccaccagtct cacttcagtt       60 cctttttgcat gaagagctca gaatcaaaag aggaaaccaa cccctaagat gagctttcca      120
tgtaaatttg tagccagctt ccttctgatt ttcaatgttt cttccaaagg tgcagtctcc      180
aaagagatta cgaatgcctt ggaaacctgg ggtgccttgg gtcaggacat caacttggac      240
attcctagtt ttcaaatgag tgatgatatt gacgatataa aatgggaaaa aacttcagac      300
aagaaaaaga ttgcacaatt cagaaaagag aaagagactt tcaaggaaaa agatacatat      360 aagctatttta aaaatggaac tctgaaaatt aagcatctga agaccgatga tcaggatatc      420
tacaaggtat caatatatga tacaaaagga aaaaatgtgt tggaaaaaat atttgatttg      480
aagattcaag agagggtctc aaaaccaaag atctcctgga cttgtatcaa cacaaccctg      540
acctgtgagg taatgaatgg aactgacccc gaattaaacc tgtatcaaga tgggaaacat      600
ctaaaacttt ctcagagggt catcacacac aagtggacca ccagcctgag tgcaaaattc      660
aagtgcacag cagggaacaa agtcagcaag gaatccagtg tcgagcctgt cagctgtcca      720
gagaaaggtc tggacatcta tctcatcatt ggcatatgtg gaggaggcag cctcttgatg      780
gtctttgtgg cactgctcgt tttctatatc accaaaagga aaaacagag gagtcggaga      840 aatgatgagg agctggagac aagagcccac agagtagcta ctgaagaaag gggccggaag      900
ccccaccaaa ttccagcttc aaccccctcag aatccagcaa cttcccaaca tcctcctcca      960
ccacctggtc atcgttccca ggcacctagt catcgtcccc cgcctcctgg acaccgtgtt     1020
cagcaccagc ctcagaagag gcctcctgct ccgtcgggca caagttcca ccagcagaaa     1080 ggcccgcccc tccccagacc tcgagttcag ccaaaacctc cccatgggc agcagaaaac     1140 tcattgtccc cttcctctaa ttaaaaaaga tagaaactgt ctttttcaat aaaaagcact     1200
gtggatttct gccctcctga tgtgcatatc cgtacttcca tgaggtgttt tctgtgtgca     1260
gaacattgtc acctcctgag gctgtgggcc acagccacct ctgcatcttc gaactcagcc     1320
atgtggtcaa catctggagt ttttggtctc ctcagagagc tccatcacac cagtaaggag     1380
aagcaatata agtgtgattg caagaatggt agaggaccga gcacagaaat cttagagatt     1440
tcttgtcccc tctcaggtca tgtgtagatg cgataaatca agtgattggt gtgcctgggt     1500

```
ctcactacaa gcagcctatc tgcttaagag actctggagt ttcttatgtg ccctggtgga    1560
cacttgccca ccatcctgtg agtaaaagtg aaataaaagc tttgactag               1609

<210> SEQ ID NO 59
<211> LENGTH: 3274
<212> TYPE: DNA
<213> ORGANISM: human

<400> SEQUENCE: 59
gtcatgcgtg ccacgctctc ctctacgcgc cggaccctgg gatgctcttc ggccgcatcc      60
cgctgcgcta cgccatactg atgcagatgc gcttcgatgg acgcctgggc ttccccggcg     120
gattcgtgga cacgcaggac agaagcctag aggacgggct gaaccgcgag ctgcgcgagg     180
agctgggcga agcggctgcc gctttccgcg tggagcgcac tgactaccgc agctcccacg     240
tcgggtcagg gccacgcgtt gtgcccact tctatgccaa gcgtctgacg ctcgaggagc      300
tgttggctgt ggaggccggc gcaacacgcg ccaaggacca cgggctggag gtgctgggcc     360
tggtgcgagt gccctgtat accctgcggg atggtgtagg aggcctgcct accttcctgg     420
agaattcctt tattggctct gcgcgggagc agttacttga agctctccag gacttgggac     480
tgctgcagtc tggctctatt tcaggcctta agattccagc tcatcactag aggcagccct     540
ccatggaccc atgaaaactg agatgaggac cttggtacta gggagggagg gaaggacgtg     600
ggaatgtttt cttattggat ctgagagatg atacatgata ccagatgaaa agaaggagaa     660
gtgtgtacca tatgttttga gcagaggacc ctccaactta tggcatcagg ggcaaaaagt     720
cacagcttat cccaggcacc ctggcaggtt ctcagagcct gcctcctccc tgtttatatg     780
cgtacagcct ggtaaccccc aggcatgcaa atatacaatc tgtaacaaca cacagcctga     840
caccttcccc tggtcatgtc cagtttaacc ttgaagtggc atttgtcaca ctaccctggt     900
ccctgattgc aaggagcttc tgaagcaagg gtgaatcctt cccacactcc tccatggttg     960
ccctccaggg tctagcccag cctatttgtt agggaggata gagaaacaga gcacccctg    1020 tgctttctga aaatagactt gctcttgtct tgagtggtga ccaaagcagt tggctcttaa    1080
aaggtgggag agcagcccaa ccaatcccca atccttttct tctgaaactg agcaggaagg    1140
gtaaggaagt ggctaggtct ccttggactg agcatggaca tgagtcctgt gaggactggt    1200
gtctctcctc tagagctttc atctttggga tgcctgagac tccgagacta tcagaaggga    1260
attgacccac cccagtctag caccaccctg ccttcacttc atctacataa aggtggtata    1320
aaaacataga ctggaggagg taatccatgg agagagaaaa agaagagggc tcaggacaag    1380
gccctgagga ggcccaatcc taaaagtttg gcagaggga accaggcacg ttaaagaaga     1440
cagaaagcgg actatgcaga gtgcttgtga gggtttcact aaaacagagg caaaactgtc    1500
cattgaattc agtaacatga agtgtttgat gactatgatg gcagcagttt caggaagggc    1560
ggtatggaag gcaggctgta ctggttgagt gaatggaaag ttggggagta aacgtgtga    1620 gaagttggcc ttcaagggc tcaggttaat aatagagagc tatggagtca aggcatgttt    1680
aagatgggag gtagagcatg ccaatattga tggcaacagt caagatggtg tgatgagaga    1740
gatgggaggg gcacaaagag gaggacccct gaaggagcag agtccatgag aaagaaggag    1800
ggatgggacc tttgtaggaa gagacacagt cctgcagcct catatggctc aataaaacag    1860
aaaggggcaa gtatagaaga ttaggatgac taaattaatg gggaaatgat gaaggagttt    1920
gaatctcttc tttgtgaaat gaagtgagac tatcagctag ttgtgggtgg agtgtgttct    1980
cagaaggtat gaagtagatg ttttcctagg tgttggaaaa caggttgatt aaggcaacag    2040
```

```
cagaagggca gggcaaggct gagctctgag atggtcagtt tagagtagga tgctgggcac    2100
tcaggtgtgt gtgtgttgag tggggctctg cacacacctg tcttcccctc atcaggattc    2160
aggagctggg atgggtacac ttactgcagt gttggggttt tgccagggaa gtaaaaggag    2220
ttgagagaaa gatgggtcag ttcagaagac atacacagga gaaattgtag tgatgaaatg    2280
tgcagtctaa ggtttaatct gaccaagaaa ttggaattga aaacaggagg tgactaggga    2340
gggattagga aattagaggt cttgacaaga tagaaactcc agcatggtga ggggttgggc    2400
agggaggtat atttgagcca gacaggagtg ctttggaaat tgagaggtgg agcaatctca    2460
ggtaaaggca aaatagaggg tatgacctgg ggttgctggc cagagccagg gaggagcctt    2520
aagaagtgaa atctagggtt ggcgaggctg gagggcaggg tgagcctcca catgggtgct    2580
gaagcaagaa accgacagat gttgaggaga atggtgtgac ctaggagtca gcatccttgg    2640
tgaacaagag gagtggccac aaggccagtg gcacctgcca gaggggaaag caggcatgac    2700
aggatagcat ctcccaggtg agagcctttt gaggaaggga gggtgggcag tggtctggaa    2760
gcttgatgca gagcagtgtg ggtcccactg gcagcccttg gtcttagaag aatgggagta    2820
cccagtgggg gagcagctgt acaatgaggt agactcctag aggttaatta tcatctccta    2880
atcttaccct gaccctttg tcaaacgtta tctagattaa acctcagtat aggcaggctg     2940
caggaaatgg acattccagt ggcccctggg gttccagcct gtagcagctt catctgtgct    3000
ttgtgcactt ggttctcagt catctctgca agggaccctg acgcctggga gatcagagcc    3060
actgaccctt tatggcactg ctaacagacc ccttccctca ggtaattctg gatccagaac    3120
tcattatggg atgtaatcca ggtcaacact aataccactt ggaaggttcc gctctgtctc    3180
actctgcttg agtatcccac tgatcagtct ctcagtgcct gcctactggg cagctcatct    3240
gtccacttat tcgtattaaa tttgcttttt attt                                3274
```

METHOD AND KIT FOR PERFORMING A COLORECTAL CANCER ASSAY

This is a Division of application Ser. No. 13/698,219 filed on Nov. 15, 2012, which in turn is a National Phase of Application PCT/EP2010/057843 filed on Jun. 4, 2010. The disclosure of the prior applications is hereby incorporated by reference herein in its entirety.

FIELD OF THE INVENTION

The present invention relates to the prognosis of a colorectal cancer, especially to a method and kit for prognosis such a cancer.

BACKGROUND

Colorectal cancer (CRC), also called colon cancer or large bowel cancer is the fifth most common form of cancer in the United States, the fourth common cancer in China and the third leading cause of cancer-related death in Europe. The early detection of CRC remains a major public health challenge. Indeed, CRC is often curable particularly when diagnosed at early stages. Several screening strategies are already in place in various countries. Conventional CRC screening tests include fecal occult blood test (FOBT), sigmoidoscopy, colonoscopy, double contrast barium enema, or digital rectal examination. All of them have advantages and limitations, but compliance remains less than expected mainly due to logistics or discomfort for the patients.

Search for blood biomarkers aimed at early detection of CRC became a focus since several years, especially for its convenience. Meantime, blood-based test feasibility was supported by very few studies, which have shown that gene biomarkers in blood could differentiate CRC patients from controls. These studies were based on the flow cytometry that is a technique for counting and examining microscopic particles, such as cells by suspending them in a stream of fluid and passing them by an electronic detection apparatus.

The present inventors have found that differentially expressed genes were mostly associated to immune cell activation and trafficking. Especially, they have shown that Natural Killer cells (NK cells) represent important biomarkers in peripheral blood samples. They did not used classical technique of flow cytometry but the determination of differential expression of genes from whole blood. It is non usual to determine an expression level of genes via the analysis of transcripts in whole blood, because it is commonly admitted by the persons skilled in the art that it is very difficult to retrieve a specific information when it is diluted in a complex mixture of RNAs (total RNA) without a step of specific purification. An advantage of the present method is also to avoid the step of purification of RNA.

Accordingly, the present invention relates to a method for determining the prognosis of a colorectal cancer in a peripheral blood sample from a patient, the method comprising:
a) obtaining the peripheral blood sample and extracting total RNA from the blood sample,
b) contacting the total RNA with at least one reagent that is specific for at least one NK cell gene and no more than 25 specific reagents for 25 NK cell genes,
c) determining the expression level of the at least one NK cell gene and of the most 25 NK cell genes to obtain an expression profile for the patient,
d) performing analysis of the expression profile of the patient with expression profiles of NK cell genes from patients previously clinically classified as a good prognosis and expression profiles of NK cell genes from patients previously classified as a poor prognosis, wherein
if the expression profile for the patient is clustered with the expression profiles from patients previously clinically classified as a poor prognosis, then the patient is determined to have a poor prognosis, and
if the expression profile for the patient is clustered with the expression profiles from patients previously clinically classified as a good prognosis, then the patient is determined to have a good prognosis.

Especially in the above step b) the total RNA is brought into contact with at least one reagent is specific for at least one NK cell gene and no more than 25 specific reagents for 25 NK cell genes, said NK cell gene comprising the nucleic acid sequences set forth in SEQ ID NOs: 1 to 12, wherein the at least one reagent is specific for at least one NK cell gene selected from the group consisting of:
(i) KLRB1 gene comprising a full length sequence such as identified in SEQ ID NO: 1,
(ii) KLRC2 gene comprising a full length sequence such as identified in SEQ ID NOs: 2, 3 or 4,
(iii) KLRC3 gene comprising a full length sequence such as identified in SEQ ID NOs: 5, 6 or 7,
(iv) KLRD1 gene comprising a full length sequence such as identified in SEQ ID NOs: 8, 9, 10, 11, or 12, and
(v) KLRK1 gene comprising a full length sequence such as identified in SEQ ID NO: 13, and
the expression level of the at least one NK cell gene is determined in step c) to obtain the expression profile for the patient.

The expression level of at least one of the above genes is a sufficient information for predicting a risk of CRC, as detailed in the experimental data.

In one embodiment in step b) the total RNA is brought into contact with reagents specific for a combination of least 5 NK cell genes and no more than 25 NK cell genes, wherein the reagents include at least reagents specific for the NK cell genes consisting of:
(i) KLRE1 gene comprising a full length sequence such as identified in SEQ ID NO: 1,
(ii) KLRC2 gene comprising a full length sequence such as identified in SEQ ID NOs: 2, 3 or 4,
(iii) KLRC3 gene comprising a full length sequence such as identified in SEQ ID NOs: 5, 6 or 7,
(iv) KLRD1 gene comprising a full length sequence such as identified in SEQ ID NOs: 8, 9, 10, 11, or 12, and
(v) KLRK1 comprising a full length sequence such as identified in SEQ ID NO: 13,
the expression level of at least said 4 NK cell genes is determined in step c) to obtain the expression profile for the patient.

Furthermore, in step b) the total RNA can be brought into contact with at least one reagent specific for at least one target cell gene and no more than 5 specific reagents for 5 target cell genes, said target cell gene comprising the nucleic acid sequences set forth in SEQ ID NOs: 12 to 24, wherein the at least one reagent is specific for at least one target cell gene selected from the group consisting of:
(i) GZMB gene comprising a full length sequence such as identified in SEQ ID NO: 14, 15, 16 or 17,
(ii) CD247 gene comprising a full length sequence such as identified in SEQ ID NO: 18, 19 or 20,
(iii) RRAS2 gene comprising a full length sequence such as identified in SEQ ID NO: 21 or 22, and
(iv) SH2D1B gene comprising a full length sequence such as identified in SEQ ID NO: 23 or 24, and (v) LCK gene comprising a full length sequence such as identified in SEQ ID NO: 25, 26, 27, 28, 29 or 30, and
the expression level of the at least one cell gene is determined in step c) to obtain the expression profile for the patient; and in one embodiment the total RNA is brought into contact with reagents specific for a combination 5 target cell genes, wherein the reagents are specific for the target cell genes consisting of:
(i) GZMB gene comprising a full length sequence such as identified in SEQ ID NO: 14, 15, 16 or 17,
(ii) CD247 gene comprising a full length sequence such as identified in SEQ ID NO: 18, 19 or 20,
(iii) RRAS2 gene comprising a full length sequence such as identified in SEQ ID NO: 21 or 22, and
(iv) SH2D1B gene comprising a full length sequence such as identified in SEQ ID NO: 23 or 24, and
(v) LCK gene comprising a full length sequence such as identified in SEQ ID NO: 25, 26, 27, 28, 29 or 30, and
the expression level of the at least 5 cell gene is determined in step c) to obtain the expression profile for the patient.

In another embodiment, in step b) the total RNA is further brought into contact with at least one reagent specific for at least one target cell gene and no more than 100 specific reagents for 100 target cell genes, said target cell gene comprising the nucleic acid sequences set forth in SEQ ID NOs: 25 to 59, wherein the at least one reagent is specific for at least one target cell gene selected from the group consisting of:
(i) MRPS6 gene comprising a full length sequence such as identified in SEQ ID NO: 31, 32, or 33,
(ii) SPRY4 gene comprising a full length sequence such as identified in SEQ ID NO: 34,
(iii) NEAT1 gene comprising a full length sequence such as identified in SEQ ID NO: 35,
(iv) CYBB gene comprising a full length sequence such as identified in SEQ ID NO: 36,
(v) DUSP2 gene comprising a full length sequence such as identified in SEQ ID NO: 37,
(vi) PDEAD gene comprising a full length sequence such as identified in SEQ ID NO: 38 or 39,
(vii) SH2D2A gene comprising a full length sequence such as identified in SEQ ID NO: 40, 41 or 42,
(viii) INSR gene comprising a full length sequence such as identified in SEQ ID NO: 43 or 44,
(ix) ITGAM gene comprising a full length sequence such as identified in SEQ ID NO: 45,
(x) VCAN gene comprising a full length sequence such as identified in SEQ ID NO: 46, 47, 48 or 49,
(xi) CD 163 gene comprising a full length sequence such as identified in SEQ ID NO: 50, or 51.
(xii) P2RY10 gene comprising a full length sequence such as identified in SEQ ID NO: 52 or 53,
(xii) CD226 gene comprising a full length sequence such as identified in SEQ ID NO: 54,
(xiii) MRPL10 gene comprising a full length sequence such as identified in SEQ ID NO: 55 or 56,
(xiv) ITPRIPL2 gene comprising a full length sequence such as identified in SEQ ID NO: 57,
(xv) CD2 gene comprising a full length sequence such as identified in SEQ ID NO: 58, and
(xvi) NUDT16 gene comprising a full length sequence such as identified in SEQ ID NO: 59, and.
the expression level of the at least one cell gene is determined in step c) to obtain the expression profile for the patient.

Especially, in step b) the total RNA is brought into contact with reagents specific for a combination of least 17 target cell genes and no more than 100 target cell genes, wherein the reagents include at least reagents specific for the target cell genes consisting of:
(i) MRPS6 gene comprising a full length sequence such as identified in SEQ ID NO: 31, 32, or 33,
(ii) SPRY4 gene comprising a full length sequence such as identified in SEQ ID NO: 34,
(iii) NEAT1 gene comprising a full length sequence such as identified in SEQ ID NO: 35,
(iv) CYBB gene comprising a full length sequence such as identified in SEQ ID NO: 36,
(v) DUSP2 gene comprising a full length sequence such as identified in SEQ ID NO: 37,
(vi) PDEAD gene comprising a full length sequence such as identified in SEQ ID NO: 38 or 39,
(vii) SH2D2A gene comprising a full length sequence such as identified in SEQ ID NO: 40, 41 or 42,
(viii) INSR gene comprising a full length sequence such as identified in SEQ ID NO: 43 or 44,
(ix) ITGAM gene comprising a full length sequence such as identified in SEQ ID NO: 45,
(x) VCAN gene comprising a full length sequence such as identified in SEQ ID NO: 46, 47, 48 or 49,
(xi) CD 163 gene comprising a full length sequence such as identified in SEQ ID NO: 50, or 51.
(xii) P2RY10 gene comprising a full length sequence such as identified in SEQ ID NO: 52 or 53,
(xii) CD226 gene comprising a full length sequence such as identified in SEQ ID NO: 54,
(xiii) MRPL10 gene comprising a full length sequence such as identified in SEQ ID NO: 55 or 56,
(xiv) ITPRIPL2 gene comprising a full length sequence such as identified in SEQ ID NO: 57,
(xv) CD2 gene comprising a full length sequence such as identified in SEQ ID NO: 58, and
(xvi) NUDT16 gene comprising a full length sequence such as identified in SEQ ID NO: 59, and
the expression level of the at least 17 cell genes is determined in step c) to obtain the expression profile for the patient.

More precisely, in the methods described above the at least one specific reagent of step b) comprises at least one hybridization probe, in particular at least one hybridization probe and at least one primer and more particularly at least one hybridization probe and two primers.

Total RNA comprises transfer RNAs (tRNA), messenger RNAs (mRNAs), such as the mRNAs transcribed from the target gene, but also transcribed from any other gene, and ribosomal RNAs.

By way of indication, the extraction of total RNA can be carried out by: a step consisting of lysis of the cells present in the blood sample, in order to release the nucleic acids contained in the cells of the patient. By way of example, use may be made of the methods of lysis as described in patent applications: WO 00/05338 regarding mixed magnetic and mechanical lysis, WO 99/53304 regarding electrical lysis, WO 99/15321 regarding mechanical lysis. Those skilled in the art may use other well-known methods of lysis, such as thermal or osmotic shocks or chemical lyses using chaotropic agents such as guanidinium salts (U.S. Pat. No. 5,234,809). It is also possible to provide an additional step for separating the nucleic acids from the other cellular constituents released in the lysis step. This generally makes it possible to concentrate the nucleic acids. By way of example, use may be made of magnetic particles optionally coated with oligonucleotides, by adsorption or covalence (in this respect, see U.S. Pat. No. 4,672,040 and U.S. Pat. No.

5,750,338), and the nucleic acids which are bound to these magnetic particles can thus be purified by means of a washing step. This nucleic acid purification step is particularly advantageous if it is desired to subsequently amplify said nucleic acids. A particularly advantageous embodiment of these magnetic particles is described in patent applications: WO-A-97/45202 and WO-A-99/35500.

The term "specific reagent" is intended to mean a reagent which, when it is brought into contact with biological material as defined above, binds with the material specific for said target gene. By way of indication, when the specific reagent and the biological material are of nucleic origin, bringing the specific reagent into contact with the biological material allows the specific reagent to hybridize with the material specific for the target gene. The term "hybridization" is intended to mean the process during which, under appropriate conditions, two nucleotide fragments bind with stable and specific hydrogen bonds so as to form a double-stranded complex. These hydrogen bonds form between the complementary adenine (A) and thymine (T) (or uracile (U)) bases (this is referred to as an A-T bond) or between the complementary guanine (G) and cytosine (C) bases (this is referred to as a G-C bond). The hybridization of two nucleotide fragments may be complete (reference is then made to complementary nucleotide fragments or sequences), i.e. the double-stranded complex obtained during this hybridization comprises only A-T bonds and C-G bonds. This hybridization may be partial (reference is then made to sufficiently complementary nucleotide fragments or sequences), i.e. the double-stranded complex obtained comprises A-T bonds and C-G bonds that make it possible to form the double-stranded complex, but also bases not bound to a complementary base. The hybridization between two nucleotide fragments depends on the working conditions that are used, and in particular on the stringency. The stringency is defined in particular as a function of the base composition of the two nucleotide fragments, and also by the degree of mismatching between two nucleotide fragments. The stringency can also depend on the reaction parameters, such as the concentration and the type of ionic species present in the hybridization solution, the nature and the concentration of denaturing agents and/or the hybridization temperature. All these data are well known and the appropriate conditions can be determined by those skilled in the art. In general, depending on the length of the nucleotide fragments that it is intended to hybridize, the hybridization temperature is between approximately 20 and 70.degree.C., in particular between 35 and 65.degree.C. in a saline solution at a concentration of approximately 0.5 to 1 M. A sequence, or nucleotide fragment, or oligonucleotide, or polynucleotide, is a series of nucleotide motifs assembled together by phosphoric ester bonds, characterized by the informational sequence of the natural nucleic acids, capable of hybridizing to a nucleotide fragment, it being possible for the series to contain monomers having different structures and to be obtained from a natural nucleic acid molecule and/or by genetic recombination and/or by chemical synthesis. A motif is a derivative of a monomer which may be a natural nucleotide of nucleic acid, the constitutive elements of which are a sugar, a phosphate group and a nitrogenous base; in DNA, the sugar is deoxy-2-ribose, in RNA, the sugar is ribose; depending on whether DNA or RNA is involved, the nitrogenous base is selected from adenine, guanine, uracile, cytosine and thymine; alternatively the monomer is a nucleotide that is modified in at least one of the three constitutive elements; by way of example, the modification may occur either at the level of the bases, with modified bases such as inosine, methyl-5-deoxycytidine, deoxyuridine, dimethylamino-5-deoxyuridine, diamino-2,6-purine, bromo-5-deoxyuridine or any other modified base capable of hybridization, or at the level of the sugar, for example the replacement of at least one deoxyribose with a polyamide (P. E. Nielsen et al, Science, 254, 1497-1500 (1991) [3]), or else at the level of the phosphate group, for example its replacement with esters in particular selected from diphosphates, alkyl- and arylphosphonates and phosphorothioates.

According to a specific embodiment of the invention, the specific reagent comprises at least one hybridization probe or at least one hybridization probe and at least one primer which is specific for the target gene or at least one hybridization probe and two primers specific for the target genes.

For the purpose of the present invention, the term "amplification primer" is intended to mean a nucleotide fragment comprising from 5 to 100 nucleotides, preferably from 15 to 30 nucleotides that allow the initiation of an enzymatic polymerization, for instance an enzymatic amplification reaction. The term "enzymatic amplification reaction" is intended to mean a process which generates multiple copies of a nucleotide fragment through the action of at least one enzyme. Such amplification reactions are well known to those skilled in the art and mention may in particular be made of the following techniques: PCR (polymerase chain reaction), as described in U.S. Pat. No. 4,683,196, U.S. Pat. No. 4,683,202 and U.S. Pat. No. 4,800,159, LCR (ligase chain reaction), disclosed, for, example, in patent application EP 0 201 184, RCR (repair chain reaction), described in patent application WO 90/01069, 3SR (self sustained sequence replication) with patent application WO 90/06995, NASBA (nucleic acid sequence-based amplification) with patent application WO 91/02818, TMA (transcription mediated amplification) with U.S. Pat. No. 5,399,491 and RT-PCR.

When the enzymatic amplification is a PCR, the specific reagent comprises at least two amplification primers, specific for a target gene, that allow the amplification of the material specific for the target gene. The material specific for the target gene then preferably comprises a complementary DNA obtained by reverse transcription of messenger RNA derived from the target gene (reference is then made to target-gene-specific cDNA) or a complementary RNA obtained by transcription of the cDNAs specific for a target gene (reference is then made to target-gene-specific cRNA). When the enzymatic amplification is a PCR carried out after a reverse transcription reaction, reference is made to RT-PCR.

The term "hybridization probe" is intended to mean a nucleotide fragment comprising at least 5 nucleotides, such as from 5 to 100 nucleotides, in particular from 10 to 75 nucleotides, such as 15-35 nucleotides and 60-70 nucleotides, having a hybridization specificity under given conditions so as to form a hybridization complex with the material specific for a target gene. In the present invention, the material specific for the target gene may be a nucleotide sequence included in a messenger RNA derived from the target gene (reference is then made to target-gene-specific mRNA), a nucleotide sequence included in a complementary DNA obtained by reverse transcription of said messenger RNA (reference is then made to target-gene-specific cDNA), or else a nucleotide sequence included in a complementary RNA obtained by transcription of said cDNA as described above (reference will then be made to target-gene-specific cRNA). The hybridization probe may include a label for its detection. The term "detection" is intended to mean either a direct detection such as a counting method, or an indirect detection by a method of detection using a label. Many methods of detection exist for detecting nucleic acids (see, for example, Kricka et al., Clinical Chemistry, 1999, no 45 (4), p. 453-458 or Keller G. H. et al., DNA Probes, 2nd Ed., Stockton Press, 1993, sections 5 and 6, p. 173-249. The term "label" is intended to mean a tracer capable of generating a signal that can be detected. A non limiting list of these tracers includes enzymes which produce a signal that can be detected, for example, by colorimetry, fluorescence or luminescence, such as horseradish peroxidase, alkaline phosphatase, beta-galactosidase, glucose-6-phosphate dehydrogenase; chromophores such as fluorescent, luminescent or dye compounds; electron dense groups detectable by electron microscopy or by virtue of their electrical properties such as conductivity, by amperometry or voltametry methods, or by impedance measurement; groups that can be detected by optical methods such as diffraction, surface plasmon resonance, or contact angle variation, or by physical methods such as atomic force spectroscopy, tunnel effect, etc.; radioactive molecules such as $^{32}$P, $^{35}$S or $^{125}$I.

For the purpose of the present invention, the hybridization probe may be a "detection" probe. In this case, the "detection" probe is labeled by means of a label. The detection probe may in particular be a "molecular beacon" detection probe as described by Tyagi & Kramer (Nature biotech, 1996, 14:303-308). These "molecular beacons" become fluorescent during the hybridization. They have a stem-loop-type structure and contain a fluorophore and a "quencher" group. The binding of the specific loop sequence with its complementary target nucleic acid sequence causes the stem to unroll and the emission of a fluorescent signal during excitation at the appropriate wavelength. The detection probe in particular may be a "reporter probe" comprising a "color-coded barecode" according to NanoString™'s technology.

For the detection of the hybridization reaction, use may be made of target sequences that have been labeled, directly (in particular by the incorporation of a label within the target sequence) or indirectly (in particular using a detection probe as defined above). It is in particular possible to carry out, before the hybridization step, a step consisting in labeling and/or cleaving the target sequence, for example using a labeled deoxy-ribonucleotide triphosphate during the enzymatic amplification reaction. The cleavage may be carried out in particular by the action of imidazole or of manganese chloride. The target sequence may also be labeled after the amplification step, for example by hybridizing a detection probe according to the sandwich hybridization technique described in document WO 91/19812. Another specific preferred method of labeling nucleic acids is described in application FR 2780059.

According to a preferred embodiment of the invention, the detection probe comprises a fluorophore and a quencher. According to an even more preferred embodiment of the invention, the hybridization probe comprises an FAM (6-carboxy-fluorescein) or ROX (6-carboxy-X-rhodamine) fluorophore at its 5' end and a quencher (Dabsyl) at its 3' end.

The hybridization probe may also be a "capture" probe. In this case, the "capture" probe is immobilized or can be immobilized on a solid substrate by any appropriate means, i.e. directly or indirectly, for example by covalence or adsorption. As solid substrate, use may be made of synthetic materials or natural materials, optionally chemically modified, in particular polysaccharides such as cellulose-based materials, for example paper, cellulose derivatives such as cellulose acetate and nitrocellulose or dextran, polymers, copolymers, in particular based on styrene-type monomers, natural fibers such as cotton, and synthetic fibers such as nylon; inorganic materials such as silica, quartz, glasses or ceramics; latices; magnetic particles; metal derivatives, gels, etc. The solid substrate may be in the form of a microtitration plate, of a membrane as described in application WO-A-94/12670 or of a particle. It is also possible to immobilize on the substrate several different capture probes, each being specific for a target gene. In particular, a biochip on which a large number of probes can be immobilized may be used as substrate. The term "biochip" is intended to mean a solid substrate that is small in size, to which a multitude of capture probes are attached at predetermined positions. The biochip, or DNA chip, concept dates from the beginning of the 1990s. It is based on a multidisciplinary technology that integrates microelectronics, nucleic acid chemistry, image analysis and information technology. The operating principle is based on a foundation of molecular biology: the hybridization phenomenon, i.e. the pairing, by complementarity, of the bases of two DNA and/or RNA sequences. The biochip method is based on the use of capture probes attached to a solid substrate, on which probes a sample of target nucleotide fragments directly or indirectly labeled with fluorochromes is made to act. The capture probes are positioned specifically on the substrate or chip and each hybridization gives a specific piece of information, in relation to the target nucleotide fragment. The pieces of information obtained are cumulative, and make it possible, for example, to quantify the level of expression of one or more target genes. In order to analyze the expression of a target gene, a substrate comprising a multitude of probes, which correspond to all or part of the target gene, which is transcribed to mRNA, can then be prepared. For the purpose of the present invention, the term "low-density substrate" is intended to mean a substrate comprising fewer than 50 probes. For the purpose of the present invention, the term "medium-density substrate" is intended to mean a substrate comprising from 50 probes to 10 000 probes. For the purpose of the present invention, the term "high-density substrate" is intended to mean a substrate comprising more than 10 000 probes.

The cDNAs or cRNAs specific for a target gene that it is desired to analyze are then hybridized, for example, to specific capture probes. After hybridization, the substrate or chip is washed and the labeled cDNA or cRNA/capture probe complexes are revealed by means of a high-affinity ligand bound, for example, to a fluorochrome-type label. The fluorescence is read, for example, with a scanner and the analysis of the fluorescence is processed by information technology. By way of indication, mention may be made of the DNA chips developed by the company Affymetrix ("Accessing Genetic Information with High-Density DNA arrays", M. Chee et al., Science, 1996, 274, 610-614. "Light-generated oligonucleotide arrays for rapid DNA sequence analysis", A. Caviani Pease et al., Proc. Natl. Acad. Sci. USA, 1994, 91, 5022-5026), for molecular diagnoses. In this technology, the capture probes are generally small in size, around 25 nucleotides, Other examples of biochips are given in the publications by G. Ramsay, Nature Biotechnology, 1998, No. 16, p. 40-44; F. Ginot, Human Mutation, 1997, No. 10, p. 1-10; J. Cheng et al, Molecular diagnosis, 1996, No. 1 (3), p. 183-200; T. Livache et al, Nucleic Acids Research, 1994, No. 22 (15), p. 2915-2921 J. Cheng et al, Nature Biotechnology, 1998, No. 16, p. 541-546 or in U.S. Pat. No. 4,981,783, U.S. Pat. No. 5,700,637, U.S. Pat. No. 5,445,934, U.S. Pat. No. 5,744,305 and U.S. Pat. No. 5,807,522. The main characteristic of the solid substrate should be to conserve the hybridization characteristics of the capture probes on the target nucleotide fragments while at the same time generating a minimum background noise for the method of detection. Three main types of fabrication can be distinguished for immobilizing the probes on the substrate.

First of all, there is a first technique which consists in depositing pre-synthesized probes. The attachment of the probes is carried out by direct transfer, by means of micropipettes or of microdots or by means of an inkjet device. This technique allows the attachment of probes having a size ranging from a few bases (5 to 10) up to relatively large sizes of 60 bases (printing) to a few hundred bases (microdeposition).

Printing is an adaptation of the method used by inkjet printers. It is based on the propulsion of very small spheres of fluid (volume <1 nl) at a rate that may reach 4000 drops/second. The printing does not involve any contact between the system releasing the fluid and the surface on which it is deposited.

Microdeposition consists in attaching long probes of a few tens to several hundred bases to the surface of a glass slide. These probes are generally extracted from databases and are in the form of amplified and purified products. This technique makes it possible to produce chips called microarrays that carry approximately ten thousand spots, called recognition zones, of DNA on a surface area of a little less than 4 cm.sup.2. The use of nylon membranes, referred to as "macroarrays", which carry products that have been amplified, generally by PCR, with a diameter of 0.5 to 1 mm and the maximum density of which is 25 spots/cm.sup.2, should not however be forgotten. This very flexible technique is used by many laboratories. In the present invention, the latter technique is considered to be included among biochips. A certain volume of sample can, however, be deposited at the bottom of a microtitration plate, in each well, as in the case in patent applications WO-A-00/71750 and FR 00/14896, or a W certain number of drops that are separate from one another can be deposited at the bottom of one and the same Petri dish, according to another patent application, FR 00/14691.

The second technique for attaching the probes to the substrate or chip is called in situ synthesis. This technique results in the production of short probes directly at the surface of the chip. It is based on in situ oligonucleotide synthesis (see, in particular, patent applications WO 89/10977 and WO 90/03382) and is based on the oligonucleotide synthesizer process. It consists in moving a reaction chamber, in which the oligonucleotide extension reaction takes place, along the glass surface.

Finally, the third technique is called photolithography, which is a process that is responsible for the biochips developed by Affymetrix. It is also an in situ synthesis. Photolithography is derived from microprocessor techniques. The surface of the chip is modified by the attachment of photolabile chemical groups that can be light-activated. Once illuminated, these groups are capable of reacting with the 3' end of an oligonucleotide. By protecting this surface with masks of defined shapes, it is possible to selectively illuminate and therefore activate areas of the chip where it is desired to attach one or other of the four nucleotides. The successive use of different masks makes it possible to alternate cycles of protection/reaction and therefore to produce the oligonucleotide probes on spots of approximately a few tens of square micrometers ($\mu m^2$). This resolution makes it possible to create up to several hundred thousand spots on a surface area of a few square centimeters ($cm^2$). Photolithography has advantages: in bulk in parallel, it makes it possible to create a chip of N-mers in only 4.times.N cycles. All these techniques can be used with the present invention. According to a preferred embodiment of the invention, the at least one specific reagent of step b) defined above comprises at least one hybridization probe which is preferably immobilized on a substrate. This substrate is preferably a low-, high- or medium-density substrate as defined above.

These hybridization steps on a substrate comprising a multitude of probes may be preceded by an enzymatic amplification reaction step, as defined above, in order to increase the amount of target genetic material.

In step c), the determination of the expression level of a target gene can be carried out by any of the protocols known to those skilled in the art. In general, the expression of a target gene can be analyzed by detecting the mRNAs (messenger RNAs) that are transcribed from the target gene at a given moment.

The invention preferably relates to the determination of the expression level of a target gene by detection of the mRNAs derived from this target gene according to any of the protocols well known to those skilled in the art. According to a specific embodiment of the invention, the expression level of several target genes is determined simultaneously, by detection of several different mRNAs, each mRNA being derived from a target gene.

When the specific reagent comprises at least one amplification primer, it is possible, to determine the expression level of the target gene in the following way: 1) After having extracted the total RNA (comprising the transfer RNAs (tRNAs), the ribosomal RNAs (rRNAs) and the messenger RNAs (mRNAs)) from the whole blood, a reverse transcription step is carried out in order to obtain the complementary DNAs (or cDNAs) of said mRNAs. By way of indication, this reverse transcription reaction can be carried out using a reverse transcriptase enzyme which makes it possible to obtain, from an RNA fragment, a complementary DNA fragment. The reverse transcriptase enzyme from AMV (Avian Myoblastosis Virus) or from MMLV (Moloney Murine Leukaemia Virus) can in particular be used. When it is more particularly desired to obtain only the cDNAs of the mRNAs, this reverse transcription step is carried out in the presence of nucleotide fragments comprising only thymine bases (polyT), which hybridize by complementarity to the polyA sequence of the mRNAs so as to form a polyT-polyA complex which then serves as a starting point for the reverse transcription reaction carried out by the reverse transcriptase enzyme. cDNAs complementary to the mRNAs derived from a target gene (target-gene-specific cDNA) and cDNAs complementary to the mRNAs derived from genes other than the target gene (cDNAs not specific for the target gene) are then obtained. 2) The amplification primer(s) specific for a target gene is (are) brought into contact with the target-gene-specific cDNAs and the cDNAs not specific for the target gene. The amplification primer(s) specific for a target gene hybridize(s) with the target-gene-specific cDNAs and a predetermined region, of known length, of the cDNAs originating from the mRNAs derived from the target gene is specifically amplified. The cDNAs not specific for the target gene are not amplified, whereas a large amount of target-gene-specific cDNAs is then obtained. For the purpose of the present invention, reference is made, without distinction, to "target-gene-specific cDNAs" or to "cDNAs originating from the mRNAs derived from the target gene". This step can be carried out in particular by means of a PCR-type amplification reaction or by any other amplification technique as defined above. By PCR, it is also possible to simultaneously amplify several different cDNAs, each one being specific for different target genes, by using several pairs of different amplification primers, each one being specific for a target gene: reference is then made to multiplex amplification. 3) The expression of the target gene is determined by detecting and quantifying the target-gene-specific cDNAs obtained in step 2) above. This detection can be carried out after electrophoretic migration of the target-gene-specific cDNAs according to their size. The gel and the medium for the migration can include ethidium bromide so as to allow direct detection of the target-gene-specific cDNAs when the gel is placed, after a given migration period, on a UV (ultraviolet)-ray light table, through the emission of a light signal. The greater the amount of target-gene-specific cDNAs, the brighter this light signal. These electrophoresis techniques are well known to those skilled in the art. The target-gene-specific cDNAs can also be detected and quantified using a quantification range obtained by means of an amplification reaction carried out until saturation. In order to take into account the variability in enzymatic efficiency that may be observed during the various steps (reverse transcription, PCR, etc.), the expression of a target gene of various groups of patients can be normalized by simultaneously determining the expression of a "housekeeping" gene, the expression of which is similar in the various groups of patients. By realizing a ratio of the expression of the target gene to the expression of the housekeeping gene, i.e. by realizing a ratio of the amount of target-gene-specific cDNAs to the amount of housekeeping-gene-specific cDNAs, any variability between the various experiments is thus corrected. Those skilled in the art may refer in particular to the following publications: Bustin S A, J Mol Endocrinol, 2002, 29: 23-39; Giulietti A Methods, 2001, 25: 386-401.

When the specific reagent comprises at least one hybridization probe, the expression of a target gene can be determined in the following way: 1) After having extracted the total RNA from the whole blood, a reverse transcription step is carried out as described above in order to obtain cDNAs complementary to the mRNAs derived from a target gene (target-gene-specific cDNA) and cDNAs complementary to the mRNAs derived from genes other than the target gene (cDNA not specific for the target gene). 2) All the cDNAs are brought into contact with a substrate, on which are immobilized capture probes specific for the target gene whose expression it is desired to analyze, in order to carry out a hybridization reaction between the target-gene-specific cDNAs and the capture probes, the cDNAs not specific for the target gene not hybridizing to the capture probes. The hybridization reaction can be carried out on a solid substrate which includes all the materials as indicated above. According to a preferred embodiment, the hybridization probe is immobilized on a substrate. Preferably, the substrate is a low-, high- or medium-density substrate as defined above. The hybridization reaction may be preceded by a step consisting of enzymatic amplification of the target-gene-specific cDNAs as described above, so as to obtain a large amount of target-gene-specific cDNAs and to increase the probability of a target-gene-specific cDNA hybridizing to a capture probe specific for the target gene. The hybridization reaction may also be preceded by a step consisting in labeling and/or cleaving the target-gene-specific cDNAs as described above, for example using a labeled deoxyribonucleotide triphosphate for the amplification reaction. The cleavage can be carried out in particular by the action of imidazole and manganese chloride. The target-gene-specific cDNA can also be labeled after the amplification step, for example by hybridizing a labeled probe according to the sandwich hybridization technique described in document WO-A-91/19812. Other preferred specific methods for labeling and/or cleaving nucleic acids are described in applications WO 99/65926, WO 01/44507, WO 01/44506, WO 02/090584, WO 02/090319. 3) A step consisting of detection of the hybridization reaction is subsequently carried out. The detection can be carried out by bringing the substrate on which the capture probes specific for the target gene are hybridized with the target-gene-specific cDNAs into contact with a "detection" probe labeled with a label, and detecting the signal emitted by the label. When the target-gene-specific cDNA has been labeled beforehand with a label, the signal emitted by the label is detected directly.

When the at least one specific reagent is brought into contact in step b) comprises at least one hybridization probe, the expression of a target gene can also be determined in the following way: 1) After having extracted the total RNA from the whole blood, a reverse transcription step is carried out as described above in order to obtain the cDNAs of the mRNAs of the biological material. The polymerization of the complementary RNA of the cDNA is subsequently carried out using a T7 polymerase enzyme which functions under the control of a promoter and which makes it possible to obtain, from a DNA template, the complementary RNA. The cRNAs of the cDNAs of the mRNAs specific for the target gene (reference is then made to target-gene-specific cRNA) and the cRNAs of the cDNAs of the mRNAs not specific for the target gene are then obtained. 2) All the cRNAs are brought into contact with a substrate on which are immobilized capture probes specific for the target gene whose expression it is desired to analyze, in order to carry out a hybridization reaction between the target-gene-specific cRNAs and the capture probes, the cRNAs not specific for the target gene not hybridizing to the capture probes. When it is desired to simultaneously analyze the expression of several target genes, several different capture probes can be immobilized on the substrate, each one being specific for a target gene. The hybridization reaction may also be preceded by a step consisting in labeling and/or cleaving the target-gene-specific cRNAs as described above. 3) A step consisting of detection of the hybridization reaction is subsequently carried out. The detection can be carried out by bringing the substrate on which the capture probes specific for the target gene are hybridized with the target-gene-specific cRNA into contact with a "detection" probe labeled with a label, and detecting the signal emitted by the label. When the target-gene-specific cRNA has been labeled beforehand with a label, the signal emitted by the label is detected directly. The use of cRNA is particularly advantageous when a substrate of biochip type on which a large number of probes are hybridized is used.

The present invention also includes a kit for the prognosis of a colorectal cancer in a peripheral blood sample from a patient comprising at least one specific reagent for at least one NK cell gene and no more than 25 specific reagents for 25 NK cell genes comprising at least the nucleic acid sequences set forth in SEQ NOs 1 to 13, wherein the at least one reagent is specific for at least one NK cell gene selected from the group consisting of:
(i) KLRB1 gene comprising a full length sequence such as identified in SEQ ID NO: 1,
(ii) KLRC2 gene comprising a full length sequence such as identified in SEQ ID NOs: 2, 3 or 4,
(iii) KLRC3 gene comprising a full length sequence such as identified in SEQ ID NOs: 5, 6 or 7, (iv) KLRD1 gene comprising a full length sequence such as identified in SEQ ID NOs: 8, 9, 10, 11, or 12, and
(v) KLRK1 gene comprising a full length sequence such as identified in SEQ ID NO: 13.

In one embodiment, the kit comprises a combination of reagents that are specific for the NK cell genes consisting of:
(i) KLRB1 gene comprising a full length sequence such as identified in SEQ ID NO: 1,
(ii) KLRC2 gene comprising a full length sequence such as identified in SEQ ID NOs: 2, 3 or 4,
(iii) KLRC3 gene comprising a full length sequence such as identified in SEQ ID NOs: 5, 6 or 7,
(iv) KLRD1 gene comprising a full length sequence such as identified in SEQ ID NOs: 8, 9, 10, 11, or 12, and
(v) KLRK1 gene comprising a full length sequence such as identified in SEQ ID NO: 13.

In such an embodiment, the specific reagents can targeted a combination of several NK cell genes but no more than 25 NK genes.

Furthermore, the kit can comprise at least one reagent that is specific for at least one target cell gene and no more than 5 target cell genes, said at least one target cell gene being selected from the group consisting of:
(i) GZMB gene comprising a full length sequence such as identified in SEQ ID NO: 14, 15, 16 or 17,
(ii) CD247 gene comprising a full length sequence such as identified in SEQ ID NO: 18, 19 or 20,
(iii) RRAS2 gene comprising a full length sequence such as identified in SEQ ID NO: 21 or 22, and
(iv) SH2D1B gene comprising a full length sequence such as identified in SEQ ID NO: 23 or 24, and
(v) LCK gene comprising a full length sequence such as identified in SEQ ID NO: 25, 26, 27, 28, 29 or 30.

In particular, it comprises 5 reagents that are specific for the target cell genes consisting of:
(i) GZMB gene comprising a full length sequence such as identified in SEQ ID NO: 14, 15, 16 or 17,
(ii) CD247 gene comprising a full length sequence such as identified in SEQ ID NO: 18, 19 or 20,
(iii) RRAS2 gene comprising a full length sequence such as identified in SEQ ID NO: 21 or 22, and
(iv) SH2D1B gene comprising a full length sequence such as identified in SEQ ID NO: 23 or 24, and
(v) LCK gene comprising a full length sequence such as identified in SEQ ID NO: 25, 26, 27, 28, 29 or 30.

In such an embodiment, the specific reagents can targeted a combination of several target cell genes, such as described above but no more than 5 target cell genes.

In another embodiment, the kit such as defined above can comprise at least one reagent that is specific for at least one target cell gene and at the most 100 reagents that are specific for 100 target cell genes, said at least target cell gene being selected from the group consisting of:
(i) MRPS6 gene comprising a full length sequence such as identified in SEQ ID NO: 31, 32, or 33,
(ii) SPRY4 gene comprising a full length sequence such as identified in SEQ ID NO: 34,
(iii) NEAT1 gene comprising a full length sequence such as identified in SEQ ID NO: 35,
(iv) CYBB gene comprising a full length sequence such as identified in SEQ ID NO: 36,
(v) DUSP2 gene comprising a full length sequence such as identified in SEQ ID NO: 37,
(vi) PDEAD gene comprising a full length sequence such as identified in SEQ ID NO: 38 or 39,
(vii) SH2D2A gene comprising a full length sequence such as identified in SEQ ID NO: 40, 41 or 42,
(viii) INSR gene comprising a full length sequence such as identified in SEQ ID NO: 43 or 44,
(ix) ITGAM gene comprising a full length sequence such as identified in SEQ ID NO: 45,
(x) VCAN gene comprising a full length sequence such as identified in SEQ ID NO: 46, 47, 48 or 49,
(xi) CD 163 gene comprising a full length sequence such as identified in SEQ ID NO: 50, or 51.
(xii) P2RY10 gene comprising a full length sequence such as identified in SEQ ID NO: 52 or 53,
(xii) CD226 gene comprising a full length sequence such as identified in SEQ ID NO: 54,
(xiii) MRPL10 gene comprising a full length sequence such as identified in SEQ ID NO: 55 or 56,
(xiv) ITPRIPL2 gene comprising a full length sequence such as identified in SEQ ID NO: 57,
(xv) CD2 gene comprising a full length sequence such as identified in SEQ ID NO: 58, and
(xvi) NUDT16 gene comprising a full length sequence such as identified in SEQ ID NO: 59.

And especially, it comprises 17 reagents that are specific for 17 target cell genes consisting of:
(i) MRPS6 gene comprising a full length sequence such as identified in SEQ ID NO: 31, 32, or 33,
(ii) SPRY4 gene comprising a full length sequence such as identified in SEQ ID NO: 34,
(iii) NEAT1 gene comprising a full length sequence such as identified in SEQ ID NO: 35,
(iv) CYBB gene comprising a full length sequence such as identified in SEQ ID NO: 36,
(v) DUSP2 gene comprising a full length sequence such as identified in SEQ ID NO: 37,
(vi) PDEAD gene comprising a full length sequence such as identified in SEQ ID NO: 38 or 39,
(vii) SH2D2A gene comprising a full length sequence such as identified in SEQ ID NO: 40, 41 or 42,
(viii) INSR gene comprising a full length sequence such as identified in SEQ ID NO: 43 or 44,
(ix) ITGAM gene comprising a full length sequence such as identified in SEQ ID NO: 45,
(x) VCAN gene comprising a full length sequence such as identified in SEQ ID NO: 46, 47, 48 or 49,
(xi) CD 163 gene comprising a full length sequence such as identified in SEQ ID NO: 50, or 51.
(xii) P2RY10 gene comprising a full length sequence such as identified in SEQ ID NO: 52 or 53,
(xii) CD226 gene comprising a full length sequence such as identified in SEQ ID NO: 54,
(xiii) MRPL10 gene comprising a full length sequence such as identified in SEQ ID NO: 55 or 56,
(xiv) ITPRIPL2 gene comprising a full length sequence such as identified in SEQ ID NO: 57,
(xv) CD2 gene comprising a full length sequence such as identified in SEQ ID NO; 58, and
(xvi) NUDT16 gene comprising a full length sequence such as identified in SEQ ID NO: 59.

In such an embodiment, the specific reagents can targeted a combination of several target cell genes, such as described above but no more than 100 target cell genes.

As explained above the at least one specific reagent comprises at least one hybridization probe, in particular at least one hybridization probe and at least one primer and more particularly at least one hybridization probe and two primers.

Finally, the invention concerns the use of at least one specific reagent for at least one NK cell genes and no more than 25 specific reagents for 25 NK cell genes comprising the nucleic acid sequences set forth in SEQ ID NOs 1 to 12 in the manufacture of a composition for the prognosis of colorectal cancer in a biological sample from a patient, wherein the at least one reagent is specific for at least one NK cell gene comprising a nucleic acid sequence selected from the nucleic acid sequences set forth in anyone of SEQ ID NOs: 1 to 12;

especially the use of reagents specific for a combination of at least 5 NK cell genes and no more than 25 NK cell genes in the manufacture of a composition for the prognosis of colorectal cancer in a biological sample from a patient, wherein the reagents are specific for at least 5 NK cell genes comprising a nucleic acid sequence selected from the nucleic acid sequences set forth in SEQ ID NOs: 1, 2 to 4, 5 to 7 and 8 to 12, respectively;

in particular, the use of reagents specific for a combination of 10 target cell genes in the manufacture of a composition for the prognosis of colorectal cancer in a biological sample from a patient, wherein the reagents are specific for target cell genes comprising a nucleic acid sequence selected from the nucleic acid sequences set forth in SEQ ID NOs: 1, 2 to 4, 5 to 7, 8 to 12, 13, 14 to 17, 18 to 20, 21-22, 23-24, and 25 to 30, respectively; and more particularly the use of reagents specific for a combination of 10 target cell genes and no more than 100 target genes in the manufacture of a composition for the prognosis of colorectal cancer in a biological sample from a patient, wherein the reagents are specific for target cell genes comprising a nucleic acid sequence selected from the nucleic acid sequences set forth in SEQ ID NOs: 1, 2 to 4, 5 to 7, 8 to 12, 13, 14 to 17, 18 to 20, 21-22, 23-24, 25 to 30, 31 to 33, 34, 35, 36, 37, 38-39, 40 to 42, 43-44, 45, 46-49, 50-51, 52-53, 54, 55-56, 57, 58 and 59 respectively;

wherein the at least one specific reagent comprises at least one hybridization probe, at least one hybridization probe and at least one primer or at least one hybridization probe and two primers.

FIGURE

NK Cell Score in colonoscopy negative control (CNC) and colorectal cancer (CRC) patient blood samples, with distribution for CRC samples according to the cancer stage. Circles represent CNC; squares, up triangles, down triangle and lozenges represent CRC, Stage I, II, III and IV, respectively.

EXAMPLES

I) Materials and Methods

1. Patients and Sample Collection

The study was approved by the local Ethical Committee for Clinical Research. Written informed consent was obtained for all participants.

For the CRC group, 119 colorectal patients were consecutively recruited for the study, between July 2006 and March 2008 at the Department of Colorectal Surgery, Fudan University Cancer Hospital (FUCH), China. The tumors were staged according to the International Union Against Cancer (UICC) recommended tumor-node-metastasis (TNM) system. No patient received preoperative radiotherapy or chemotherapy. Patients suffering from hereditary colorectal cancer or inflammatory bowel disease (Crohn's disease or ulcerative colitis) were excluded from this study. For each patient, 2.5 ml of peripheral blood were collected into PAXgene™ Blood RNA tubes (PreAnalytiX GmbH, Hombrechtikon, CH) at least one week after colonoscopy, before surgery, and processed according to manufacturer's guidelines. For the control group, 101 FOBT test-positive participants without carrying any symptom of polyps or colorectal cancer, which had been confirmed by colonoscopy, were enrolled from the Community Hospital in Shanghai area. The peripheral blood samples were collected into PAXgene tubes one week before colonoscopy examination. A detailed characterization of all participants included in this study is given in Table 1.

TABLE 1

Characteristics of the Patients

| Category | Colorectal cancer (CRC) n = 119 | Colonoscopy negative controls (CNC) n = 101 |
|---|---|---|
| Age (y) | | |
| Average | 57.6 | 54.9 |
| Max | 82 | 71 |
| Min | 27 | 38 |
| Gender | | |
| Male | 59 | 42 |
| Female | 60 | 59 |
| Site | | |
| Colon | 60 | — |
| Rectal | 59 | |
| Cancer UICC Stage | | |
| Stage I | 17 | — |
| Stage II | 44 | |
| Stage III | 26 | |
| Stage IV | 32 | |

2. RNA Extraction and Microarray Experiments

Total RNA was extracted with the PAXgene™ Blood RNA System (PreAnalytix) following manufacturer's instructions. The quantity of total RNA was measured by spectrophotometer at optical density 260 nanometers and the quality was assessed using the RNA 6000 Nano LabChip® Kit on a BioAnalyzer Agilent 2100 (Agilent Technologies, Palo Alto, Calif., U.S.A.). Only samples with RNA Integrity Number between 7 and 10 were analyzed. 50 nanograms of total RNA was then reversely transcripted and linearly amplified to single strand cDNA using Ribo-SPIA™ technology with WT-Ovation™ RNA Amplification System (NuGEN Technologies Inc., San Carlos, Calif., U.S.A.) according to the manufacturer's standard protocol, and the products were purified with QIAquick™ PCR purification kit (QIAGEN GmbH, Hilden, Germany). 2 micro grams of amplified and purified cDNA were subsequently fragmented with RQ1 RNase-Free DNase (Promega Corp., Fitchburg, Wis., U.S.A.) and labeled with biotinylated deoxynucleoside triphosphates by Terminal Transferase (Roche Diagnostics Corp., Indianapolis, Ind., U.S.A.) and GeneChip® DNA Labeling Reagent (Affymetrix Inc., Santa Clara, Calif., U.S.A). The labeled cDNA was hybridized onto HG U133 Plus 2.0 Array (Affymetrix) in a Hybridization Oven 640 (Agilent Technologies) at 60 rotations per minute, 50° C. for 18 hours. The HG U133 Plus 2.0 Array contains 54,675 probe sets representing approximately 39,000 best-characterized human genes. After hybridization, the arrays were washed and stained according to the Affymetrix protocol EukGE-WS2v4 using a GeneChip® Fluidics Station 450 (Affymetrix). The arrays were scanned with the GeneChip® Scanner 3000 (Affymetrix).

3. Microarray Data Analysis

Quality control analyses were done according to the suggestions of standard Affymetrix quality control parameters. Based on the evaluation criteria, all our experiments fulfilled the minimal quality requirements. The Affymetrix expression arrays were preprocessed by RMA (Robust Multi-chip M Average) with background correction, quantile normalization and median polish summarization [1]. The probe sets with extreme signal intensity (lower than 50 or higher than $2 \cdot 10^{14}$) were filtered out. To reduce the likelihood of batch effect, a normalization algorithm, Combat was applied to the filtered expression data[11]. The ComBat method (http://statistics.byu.edu/johnson/ComBat/) applies either parametric or nonparametric empirical Bayes framework for adjusting batch effects in a given data set. Differential expressed genes (DEG) were identified by Significance Analysis of Microarrays (SAM) at False Discovery Rate (FDR) equals 0.05[12]. The preprocessing and statistical steps were executed using R-environment with Bioconductor libraries[13, 14]. Gene Ontology and Canonical Pathways analysis were conducted by using Ingenuity Pathway Analysis software version 8.5 (Ingenuity Systems, Redwood City, Calif., U.S.A).

II) Results

1. Characteristics of the Colorectal Cancer and Control Patient Populations

Clinical and demographic variables for the 119 colorectal cancer (CRC) patients and the 101 colonoscopy-negative controls (CNC) are summarized in Table 1. For the CRC, the diagnosis of colorectal cancer has been confirmed by the pathologist following the colonoscopy. The controls have been selected among FOBT positive patients enrolled in the Community Hospital, for whom the colonoscopy performed at Fudan University Cancer Hospital (FUCH) was finally negative. The age and the gender were well balanced between the CRC and the CNC groups.

2. Identification of Genes Whose Expression in Peripheral Blood is Different for Colorectal Cancer Patients and Colonoscopy-Negative Controls The inventors looked for differentially expressed genes (DEG) between the 119 CRC and the 101 CNC, with the highest differences between the two groups, considering the CRC group as a whole (Stage I, II, III and IV). After appropriate preprocessing, 20,169 probe sets were retained to perform DEG analysis. Using SAM, 327 DEGs were identified at FDR equal to 0.05, with fold change (FC) higher than 1.2.

Among these 327 DEG, 195 (59.6%) and 132 (40.36%) were found to be expressed at higher and lower levels in CRC samples respectively. The t-test p-values ranged from $1.43 \cdot 10^{-25}$ to $1.51 \cdot 10^{-01}$, with 18 DEG having t-test p-values lower than $6.27 \cdot 10^{-15}$ and all corresponding to well-annotated genes: MRPS6, SPRY4, NEAT1, CYBB, DUSP2, PDE4D, SH2D2A, G(1-2)NSR, ITGAM, VCAN, CD163, P2RY10, CD226, MRPL10, ITPRIPL2, CD2 and NUDT16 (Table 2). The highest fold change (FC) values were 1.83 (NEAT1 with higher level for CRC) and 1.71 (HBG2 with lower level for CRC), while 26 (8%) out of the 327 DEG have a FC value higher than 1.40.

As illustration, the results observed for SPRY4 (first ranked with higher expression level in CRC, t-test p-value $4.04 \cdot 10^{-23}$, FC 1.79) and MRPS6 (first ranked with lower expression level in CRC, t-test p-value $1.43 \cdot 10^{-25}$, FC 1.27). Such examples illustrate genes significantly differentially expressed between CRC and CNC patients. For SPRY4, rather homogenous hybridization signal values were observed for the 101 CNC, while the values for the CRC were more heterogeneous but with a mean value significantly (p-value $4.04 \cdot 10^{-23}$) increased compared to CNC (FC 1.78). For MRPS6, both populations presented a similar dispersion, with a significant (p-value $1.43 \cdot 10^{-25}$) mean decrease for CRC (FC 1.27).

Among the Top 18 DEG, four membrane leukocyte markers were observed, indicating different levels of expression in the peripheral blood of CRC patients compared to CNC: lower levels for CD2 and CD226 expressed by T cells and mainly NK cells respectively; higher levels for CD163 and CD11B (ITGAM) expressed mainly expressed by monocytes and in many leukocytes involved in the innate immune system, respectively. Also interesting is the lower expression of granzyme B encoded by the GZMB gene in cytotoxic T lymphocytes and Natural Killer (NK) cells, in CRC samples. The other genes like INSR, SPRY4, DUSP2, PDE4D, and ITPRIPL2 are reported to be part of various signaling pathways, SH2D2A reported to be T-cell specific. VCAN has been reported to be expressed in monocytes, and its higher expression levels in CRC samples, together with CD163 and ITGAM, would be associated with some activation of circulating monocytes in the peripheral blood of these patients compared to CNC.

Analysis of the 327 DEG has been performed by using Ingenuity Pathway Analysis (IPA), which returned 321 mapped IDs suitable for interpretation of associated Bio Functions and Canonical Pathways. For Physiological System Development and Function, a high score was observed for Immune Cell Trafficking (p-value from $1.44 \cdot 10^{-12}$ to $1.57 \cdot 10^{-02}$, with 50 molecules), covering activation, migration, accumulation, influx, chemotaxis, cell spreading, cell movement, chemoattraction, priming and adhesion of various immune cells. Interestingly for Canonical Pathways, Natural Killer Cell Signaling was the one with the lowest p-value ($2.55 \cdot 10^{-05}$), with 10 genes: CD247, KLRB1, KLRC2, KLRC3, KLRD1, KLRK1, LCK, PRKCH, RRAS2 and SH2D1D. The implication of five membrane receptors specific to NK cells (KLRB1, KLRC2, KLRC3, KLRD1, KLRK1), very strongly suggests a particular NK cells component in the differences at the gene expression level in the peripheral blood of CRC patients. All NK cell genes are down-expressed in CRC. The results are summarized in the following tables 2 and 3.

TABLE 2

TOP 18 differentially expressed genes (DEGs) between colorectal cancer (CRC) and colonoscopy negative control (CNC) patient samples; Gene description, T-test p-value and fold change-related information

| Affymetrix Probeset ID | SEQ ID NOs: | Gene Name | Gene Description* | T-test p-value | Fold Change | Direction (in CRC) |
|---|---|---|---|---|---|---|
| 224919_at | 31, 32, 33 | MRPS6 | Mitochondrial ribosomal protein S6 | $1.43 \cdot 10^{-25}$ | 1.27 | Down |

TABLE 2-continued

TOP 18 differentially expressed genes (DEGs) between colorectal cancer (CRC) and colonoscopy negative control (CNC) patient samples; Gene description, T-test p-value and fold change-related information

| Affymetrix Probeset ID | SEQ ID NOs: | Gene Name | Gene Description* | T-test p-value | Fold Change | Direction (in CRC) |
|---|---|---|---|---|---|---|
| 220983_s_at | 34 | SPRY4 | Sprouty homolog 4 | $4.04\ 10^{-23}$ | 1.79 | Up |
| 227062_at | 35 | NEAT1 | Nuclear paraspeckle assembly transcript 1 | $7.62\ 10^{-22}$ | 1.83 | Up |
| 203922_s_at | 36 | CYBB | Cytochrome b-245, beta polypeptide | $4.36\ 10^{-21}$ | 1.31 | Up |
| 204794_at | 37 | DUSP2 | Dual specificity phosphatase 2 | $1.44\ 10^{-20}$ | 1.49 | Down |
| 204491_at | 38, 39 | PDE4D | Phosphodiesterase 4D, cAMP-specific | $7.83\ 10^{-20}$ | 1.49 | Down |
| 207351_s_at | 40, 41, 42 | SH2D2A | SH2 domain protein 2A | $1.28\ 10^{-19}$ | 1.47 | Down |
| 210164_at | 14, 15, 16, 17 | GZMB | Granzyme B | $3.75\ 10^{-18}$ | 1.62 | Down |
| 213792_s_at | 43, 44 | INSR | Insulin receptor | $4.24\ 10^{-18}$ | 1.35 | Up |
| 205785_at | 45 | ITGAM | Integrin alpha M | $5.43\ 10^{-18}$ | 1.32 | Up |
| 215646_s_at | 46, 47, 48, 49 | VCAN | Versican | $6.03\ 10^{-18}$ | 1.49 | Up |
| 203645_s_at | 50, 51 | CD163 | CD163 | $3.78\ 10^{-17}$ | 1.44 | Up |
| 1553856_s_at | 52, 53 | P2RY10 | Purinergic receptor P2Y, G-protein coupled, 10 | $4.19\ 10^{-17}$ | 1.26 | Down |
| 207315_at | 54 | CD226 | CD226 | $1.14\ 10^{-16}$ | 1.29 | Down |
| 224671_at | 55, 56 | MRPL10 | Mitochondrial ribosomal protein L10 | $1.68\ 10^{-16}$ | 1.21 | Down |
| 227954_at | 57 | ITPRIPL2 | Inositol 1,4,5-triphosphate receptor interacting protein-like 2 | $8.71\ 10^{-16}$ | 1.26 | Up |
| 205831_at | 58 | CD2 | CD2 | $5.96\ 10^{-15}$ | 1.28 | Down |
| 235002_at | 59 | NUDT16 | Nudix (nucleoside diphosphate linked moiety X)-type motif 16 | $6.27\ 10^{-15}$ | 1.21 | Up |

*Gene description from NetAffx ™ and from Ingenuity Pathway Analysis ® version 8.5

TABLE 3

NK cell score: Selected genes, T-test p-value and fold change-related information

| Affymetrix Probeset ID | SEQ ID Nos: | Gene Name | Gene Description* | T-test p-value | Fold change CNC/CRC |
|---|---|---|---|---|---|
| 214470_at | 1 | KLRB1 | Killer cell lectin-like receptor subfamily B, member 1 | $2.67\ 10^{-04}$ | 1.23 |
| 206785_s_at | 2, 3, 4 | KLRC2 | Killer cell lectin-like receptor subfamily C, member 2 | $3.02\ 10^{-05}$ | 1.40 |
| 207723_s_at | 5, 6, 7 | KLRC3 (NKG2E) | Killer cell lectin-like receptor subfamily C, member 3 | $4.42\ 10^{-05}$ | 1.36 |
| 210606_x_at | 8, 9, 10, 11, 12 | KLRD1 | Killer cell lectin-like receptor subfamily D, member 1 | $1.57\ 10^{-05}$ | 1.23 |

TABLE 3-continued

NK cell score: Selected genes, T-test p-value and fold change-related information

| Affymetrix Probeset ID | SEQ ID Nos: | Gene Name | Gene Description* | T-test p-value | Fold change CNC/CRC |
|---|---|---|---|---|---|
| 205821_at | 13 | KLRK1 (NKG2D) | Killer cell lectin-like receptor subfamily K, member 1 | $5.22\ 10^{-06}$ | 1.22 |
| 210164_at | 14, 15, 16, 17 | GZMB | Granzyme B | $3.75\ 10^{-18}$ | 1.62 |
| 210031_at | 18, 19, 20 | CD247 (CD3-zeta) | CD247 molecule | $2.82\ 10^{-10}$ | 1.27 |
| 212589_at | 21, 22 | RRAS2 | Related RAS viral(r-ras) oncogene homolog 2 | $7.17\ 10^{-04}$ | 1.20 |
| 1553176_at | 23, 24 | SH2D1B | SH2 domain containing 1B | $2.11\ 10^{-10}$ | 1.47 |
| 204891_s_at | 25, 26, 27, 28, 29, 30 | LCK | Lymphocyte-specific protein tyrosine kinase | $1.93\ 10^{-11}$ | 1.22 |

*Gene description from NetAffx ™ and from Ingenuity Pathway Analysis ® version 8.5

For these 10 NK cell-related genes, lower expression levels have been observed in the CRC group, suggesting either a decrease in the number of circulating NK cells, or an efflux of such cells towards other organ/tissue compartments and particularly the tumor sites. The lower expression levels observed for GZMB is also remarkable, evocative of a major event occurring at the level of cellular cytotoxicity in CRC patients.

The top canonical pathways were related to T Cell Receptor Signaling, Communication between Innate and Adaptive Immune Cells, and iCOS-iCOSL Signaling in T Helper Cells, with p-values equal to $9.08\ 10^{-05}$, $2.85\ 10^{-04}$ and $5.78\ 10^{-04}$ respectively.

Interestingly, a low NK Cell Score under the first quarter, was observed for 51 out of the 119 CRC patients samples, and in only 4 out of the 101 CNC patients samples. Using such a straightforward cut-off, the performance of this discrimination can be expressed as 43% sensitivity and 96% specificity. Furthermore, when stratifying the CRC patients samples according to their tumor TNM staging (Stage I, II, III or IV), we observed that this NK Cell Score gradually decreased in CRC patients from Stage I to Stage IV (FIG. 1). Statistically significant differences were mainly observed between CNC and CRC Stage II, III and IV, and between CRC Stage I and CRC Stage II-III and IV.

This study shows the potential of transcriptomics in peripheral blood, to discover biomarkers, and provide new insight on immune response in colorectal cancer. In addition to prepare possible alternative/complement to current screening modalities, these results also show that the expression analysis of genes like those related to NK cells should allow to stratify patients with colorectal cancer, opening the door to personalized medicine.

REFERENCES

1. Irizarry R A, Hobbs B, Collin F, Beazer-Barclay Y D, Antonellis K J, Scherf U, Speed T P. Exploration, normalization, and summaries of high density oligonucleotide array probe level data. Biostatistics 2003; 4:249-64)
2. Johnson W E, Li C, Rabinovic A. Adjusting batch effects in microarray expression data using empirical Bayes methods. Biostatistics 2007; 8:118-27.
3. Tusher V G, Tibshirani R, Chu G. Significance analysis of microarrays applied to the ionizing radiation response. Proc Natl Acad Sci USA 2001; 98:5116-21.
4. Team RDC. R: A Language and Environment for Statistical Computing. Vienna, Austria, 2009.

The invention claimed is:

1. A method comprising:
   extracting total RNA from a peripheral blood sample obtained from a patient suspected of having or having colorectal cancer;
   contacting the total RNA, or cDNA or cRNA obtained from the total RNA, with reagents specific for at least five and no more than 100 target genes; and
   measuring the expression level of the at least five and no more than 100 target genes,
   wherein the at least five and no more than 100 target genes includes the CD247, RRAS2, SH2D1B, LCK, and GZMB genes.

2. The method as claimed in claim 1, wherein the reagents each comprise at least one hybridization probe.

3. The method as claimed in claim 1, wherein the reagents each comprise at least one hybridization probe and at least one primer.

4. The method as claimed in claim 1, wherein the reagents each comprise at least one hybridization probe and at least one pair of primers.

5. The method as claimed in claim 1, wherein:
   the reagents further include at least one reagent selected from the group consisting of reagents specific for the DUSP2, PDE4D, SH2D2A, ITGAM, P2RY10, ITPRIPL2, and NUDT16 genes; and
   the expression level of at least one of the DUSP2, PDE4D, SH2D2A, ITGAM, P2RY10, ITPRIPL2, or NUDT16 genes is measured.

6. The method as claimed in claim 1, wherein:
   the reagents further include reagents specific for the DUSP2, PDE4D, SH2D2A, ITGAM, P2RY10, ITPRIPL2, and NUDT16 genes; and
   the expression levels of the DUSP2, PDE4D, SH2D2A, ITGAM, P2RY10, ITPRIPL2, and NUDT16 genes are measured.

7. The method as claimed in claim 1, wherein:
   the reagents further include at least one reagent selected from the group consisting of reagents specific for the MRPS6, SPRY4, CYBB, DUSP2, PDE4D, SH2D2A, INSR, ITGAM, VCAN, CD163, P2RY10, CD226, MRPL10, ITPRIPL2, CD2, and NUDT16 genes; and
   the expression level of at least one of the MRPS6, SPRY4, CYBB, DUSP2, PDE4D, SH2D2A, INSR, ITGAM, VCAN, CD163, P2RY10, CD226, MRPL10, ITPRIPL2, CD2, or NUDT16 genes is measured.

8. The method as claimed in claim 1, wherein:
   the reagents further include at least one reagent selected from the group consisting of reagents specific for the KLRB1, KLRC2, KLRC3, KLRD1, and KLRK1 genes; and
   the expression level of at least one of the KLRB1, KLRC2, KLRC3, KLRD1, or KLRK1 genes is measured.

9. The method as claimed in claim 1, wherein:
   the reagents further include reagents specific for the KLRB1, KLRC2, KLRC3, KLRD1, and KLRK1 genes; and
   the expression levels of the KLRB1, KLRC2, KLRC3, KLRD1, and KLRK1 genes are measured.

* * * * *